(12) United States Patent
Feldmann

(10) Patent No.: US 8,481,814 B2
(45) Date of Patent: Jul. 9, 2013

(54) NUCLEOTIDE SEQUENCES AND POLYPEPTIDES ENCODED THEREBY USEFUL FOR MODIFYING PLANT CHARACTERISTICS

(75) Inventor: Kenneth A. Feldmann, Newbury Park, CA (US)

(73) Assignee: Ceres, Inc., Thousand Oaks, CA (US)

( * ) Notice: Subject to any disclaimer, the term of this patent is extended or adjusted under 35 U.S.C. 154(b) by 168 days.

(21) Appl. No.: 11/241,685

(22) Filed: Sep. 30, 2005

(65) Prior Publication Data

US 2007/0061914 A1  Mar. 15, 2007

Related U.S. Application Data

(60) Provisional application No. 60/615,080, filed on Sep. 30, 2004.

(51) Int. Cl.
| | |
|---|---|
| *A01H 1/00* | (2006.01) |
| *C12N 15/00* | (2006.01) |
| *C12N 15/63* | (2006.01) |
| *C12N 15/82* | (2006.01) |
| *C07H 21/04* | (2006.01) |
| *C12N 15/29* | (2006.01) |

(52) U.S. Cl.
USPC ............ 800/295; 435/6.1; 435/468; 435/419; 435/320.1; 530/370; 536/23.6; 800/278; 800/289

(58) Field of Classification Search
USPC .............. 435/6, 69.1, 468, 419, 252.3, 320.1; 530/370; 536/23.6; 800/278
See application file for complete search history.

(56) References Cited

U.S. PATENT DOCUMENTS

| | | |
|---|---|---|
| 7,151,202 B1 | 12/2006 | Yamada et al. |
| 2007/0061914 A1 | 3/2007 | Feldmann |

FOREIGN PATENT DOCUMENTS

EP  1033405 A2 *  9/2000

OTHER PUBLICATIONS

Alexanderov et al. GenEmbl Acc. No. AAC40534, EP1033405-A2, Sep. 6, 2000, Result 1.*
Database EMBL [Online] Nov. 14, 2006, "drought-induced protein like [*Arabidopsis thaliana*],"Accession CAB78633, embl accession AL161542.2.
Database EMBL [Online] Nov. 14, 2006, "drought-induced protein like [*Arabidopsis thaliana*]," Accession CAB10370, EMBL accession Z97339.2.
Database REFSEQ [Online] Apr. 20, 2007, "ATDI21 (*Arabidopsis thalinan* drough-induced 21)," REFSEQ accession NP_193326.
Database NCBI [Online] Jan. 21, 2007, "At4g15910 [*Arabidopsis thaliana*],"NCBI accession AAO24597, accession BT003165.1.
Database EMBL [Online] May 2, 1995, "Di21 [*Arabidopsis thaliana*]," Accession CAA55322, EMBL Accession X78585.1.

* cited by examiner

*Primary Examiner* — Phuong Bui
(74) *Attorney, Agent, or Firm* — Birch, Stewart, Kolasch & Birch, LLP

(57) ABSTRACT

Isolated polynucleotides and polypeptides encoded thereby are described, together with the use of those products for making transgenic plants.

8 Claims, No Drawings

NUCLEOTIDE SEQUENCES AND POLYPEPTIDES ENCODED THEREBY USEFUL FOR MODIFYING PLANT CHARACTERISTICS

This Nonprovisional application claims priority under 35 U.S.C. §119(e) on U.S. Provisional Application No(s). 60/615,080 filed on Sep. 30, 2004, the entire contents of which are hereby incorporated by reference.

This application contains a CDR, the entire contents of which are hereby incorporated by reference. The CDR contains the following files:

| File Name | File Size | File Date |
| --- | --- | --- |
| Table 1 - sequences.doc | 608 KB | Sep. 30, 2005 |
| Table 2 - reference.doc | 524 KB | Sep. 30, 2005 |
| Table 3 - microarray data.doc | 497 KB | Sep. 30, 2005 |
| Table 4 - Ortholog Reports.doc | 112 KB | Sep. 30, 2005 |
| Table 5 - utility discovery.doc | 32 KB | Sep. 30, 2005 |

FIELD OF THE INVENTION

The present invention relates to isolated polynucleotides, polypeptides encoded thereby, and the use of those products for making transgenic plants with improved water use efficiency.

BACKGROUND OF THE INVENTION

Plants are constantly exposed to a variety of biotic (i.e., pathogen infection and insect herbivory) and abiotic (i.e., high or low temperature, drought, and salinity) stresses. To survive these challenges, plants have developed elaborate mechanisms to perceive external signals and to manifest adaptive responses with proper physiological and morphological changes (Bohnert et al., 1995). Plants exposed to low water or drought conditions typically have low yields of plant material, seeds, fruit and other edible products. Some countries of the world consistently have very low rainfall and therefore have problems growing sufficient food crops for their population. Yet it has been observed that some plants survive and thrive in low water environments. It would, therefore, be of great interest and importance to be able to identify genes that confer improved water efficiency characteristics to thereby enable one to create transformed plants (such as crop plants) with improved water efficiency characteristics to, thereby better survive low water and drought conditions.

Exogenous application of high concentrations of PEG and/or mannitol to plants is known to produce osmotic stress resulting in the retardation of growth and vigor and is used to assess drought responses. Exogenous application of ABA stimulates drought-responses in plants and can, therefore also be an important screen to identify genes that confer improved water efficiency.

In the field of agriculture and forestry efforts are constantly being made to produce plants with an increased growth potential in order to feed the ever-increasing world population and to guarantee the supply of reproducible raw materials. This is done conventionally through plant breeding. The breeding process is, however, both time-consuming and labor-intensive. Furthermore, appropriate breeding programs must be performed for each relevant plant species.

Progress has been made in part by the genetic manipulation of plants; that is by introducing and expressing recombinant nucleic acid molecules in plants. Such approaches have the advantage of not usually being limited to one plant species, but instead being transferable among plant species. For example, EP-A 0 511 979 describes the expression of a prokaryotic asparagine synthetase gene in plant cells that leads to increased biomass production. Likewise, WO 96/21737 describes plants with increased yield (growth potential) arising from an increase in the photosynthesis rate and the expression of deregulated or unregulated fructose-1, 6-bisphosphatase. Nevertheless, there still is a need for generally applicable processes that improve forest or agricultural plant growth potential. Therefore, the present invention relates to a process for increasing the growth potential in plants, characterized by expression of the recombinant DNA molecules of the invention stably integrated into the plant genome.

SUMMARY OF THE INVENTION

The present invention, therefore, relates to isolated polynucleotides, polypeptides encoded thereby, and the use of those products for making transgenic plants with improved water use efficiency.

The present invention also relates to processes for increasing the growth in plants due to water use efficiency, recombinant nucleic acid molecules and polypeptides used for these processes and their uses, as well as to plants with an increased growth potential due to improved water use efficiency.

BRIEF DESCRIPTION OF THE INDIVIDUAL TABLES

1. Sequence Table

The Sequence Table sets forth the specific polynucleotide and polypeptide sequence of the invention. Each sequence is provided a number that directly follows a ">" symbol, and the description of the sequence directly follows on the next line in the Table. It will be noted that a polynuceotide sequence is directly followed by the encoded.

2. Reference Table

The Reference Table refers to a number of "Maximum Length Sequences" or "MLS." Each MLS corresponds to the longest cDNA obtained, either by cloning or by the prediction from genomic sequence. The sequence of the MLS is the cDNA sequence as described in the Av subsection of the Reference Table.

The Reference Table includes the following information relating to each MLS:
I. cDNA Sequence
  A. 5' UTR
  B. Coding Sequence
  C. 3' UTR
II. Genomic Sequence
  A. Exons
  B. Introns
  C. Promoters
III. Link of cDNA Sequences to Clone IDs
IV. Multiple Transcription Start Sites
V. Polypeptide Sequences
  A. Signal Peptide
  B. Domains
  C. Related Polypeptides
VI. Related Polynucleotide Sequences
  I. cDNA Sequence The Reference Table indicates which sequence in the Sequence Table represents the sequence of each MLS. The MLS sequence can comprise 5' and 3' UTR as well as coding sequences. In addition, specific cDNA clone numbers also are included in the Reference Table when the MLS sequence relates to a specific cDNA clone.

A. 5' UTR

The location of the 5' UTR can be determined by comparing the most 5' MLS sequence with the corresponding genomic sequence as indicated in the Reference Table. The sequence that matches, beginning at any of the transcriptional start sites and ending at the last nucleotide before any of the translational start sites corresponds to the 5' UTR.

B. Coding Region

The coding region is the sequence in any open reading frame found in the MLS. Coding regions of interest are indicated in the PolyP SEQ subsection of the Reference Table.

C. 3' UTR

The location of the 3' UTR can be determined by comparing the most 3' MLS sequence with the corresponding genomic sequence as indicated in the Reference Table. The sequence that matches, beginning at the translational stop site and ending at the last nucleotide of the MLS corresponds to the 3' UTR.

II. Genomic Sequence

Further, the Reference Table indicates the specific "gi" number of the genomic sequence if the sequence resides in a public databank. For each genomic sequence, Reference tables indicate which regions are included in the MLS. These regions can include the 5' and 3' UTRs as well as the coding sequence of the MLS. See, for example, the scheme below:

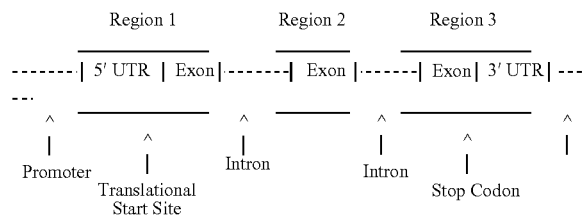

The Reference Table reports the first and last base of each region that is included in an MLS sequence. An example is shown below:

gi No. 47000:

37102 . . . 37497

37593 . . . 37925

The numbers indicate that the MLS contains the following sequences from two regions of gi No. 47000; a first region including bases 37102-37497, and a second region including bases 37593-37925.

A. Exon Sequences

The location of the exons can be determined by comparing the sequence of the regions from the genomic sequences with the corresponding MLS sequence as indicated by the Reference Table.

i. Initial Exon

To determine the location of the initial exon, information from the (1) polypeptide sequence section;

(2) cDNA polynucleotide section; and (3) the genomic sequence section of the Reference Table is used. First, the polypeptide section indicates where the translational start site is located in the MLS sequence. The MLS sequence can be matched to the genomic sequence that corresponds to the MLS. Based on the match between the MLS and corresponding genomic sequences, the location of the translational start site can be determined in one of the regions of the genomic sequence. The location of this translational start site is the start of the first exon.

Generally, the last base of the exon of the corresponding genomic region, in which the translational start site is located, will represent the end of the initial exon. In some cases, the initial exon ends with a stop codon, when the initial exon is the only exon.

In the case when sequences representing the MLS are in the positive strand of the corresponding genomic sequence, the last base will be a larger number than the first base. When the sequences representing the MLS are in the negative strand of the corresponding genomic sequence, then the last base will be a smaller number than the first base.

ii. Internal Exons

Except for the regions that comprise the 5' and 3' UTRs, initial exon, and terminal exon, the remaining genomic regions that match the MLS sequence are the internal exons. Specifically, the bases defining the boundaries of the remaining regions also define the intron/exon junctions of the internal exons.

iii. Terminal Exon

As with the initial exon, the location of the terminal exon is determined with information from the (1) polypeptide sequence section;

(2) cDNA polynucleotide section; and (3) the genomic sequence section of the Reference Table. The polypeptide section will indicate where the stop codon is located in the MLS sequence. The MLS sequence can be matched to the corresponding genomic sequence. Based on the match between MLS and corresponding genomic sequences, the location of the stop codon can be determined in one of the regions of the genomic sequence. The location of this stop codon is the end of the terminal exon. Generally, the first base of the exon of the corresponding genomic region that matches the cDNA sequence, in which the stop codon is located, will represent the beginning of the terminal exon. In some cases, the translational start site represents the start of the terminal exon, which is the only exon.

In the case when the MLS sequences are in the positive strand of the corresponding genomic sequence, the last base will be a larger number than the first base. When the MLS sequences are in the negative strand of the corresponding genomic sequence, then the last base will be a smaller number than the first base.

B. Intron Sequences

In addition, the introns corresponding to the MLS are defined by identifying the genomic sequence located between the regions where the genomic sequence comprises exons. Thus, introns are defined as starting one base downstream of a genomic region comprising an exon, and end one base upstream from a genomic region comprising an exon.

C. Promoter Sequences

As indicated below, promoter sequences corresponding to the MLS are defined as sequences upstream of the first exon; more usually, as sequences upstream of the first of multiple transcription start sites; even more usually as sequences about 2,000 nucleotides upstream of the first of multiple transcription start sites.

III. Link of cDNA Sequences to Clone Ids

As noted above, the Reference Table identifies the cDNA clone(s) that relate to each MLS. The MLS sequence can be longer than the sequences included in the cDNA clones. In such a case, the Reference Table indicates the region of the MLS that is included in the clone. If either the 5' or 3' termini of the cDNA clone sequence is the same as the MLS sequence, no mention will be made.

IV. Multiple Transcription Start Sites

Initiation of transcription can occur at a number of sites of the gene. The Reference Table indicates the possible multiple transcription sites for each gene. In the Reference Table, the location of the transcription start sites can be either a positive or negative number.

The positions indicated by positive numbers refer to the transcription start sites as located in the MLS sequence. The negative numbers indicate the transcription start site within the genomic sequence that corresponds to the MLS.

To determine the location of the transcription start sites with the negative numbers, the MLS sequence is aligned with the corresponding genomic sequence. In the instances when a public genomic sequence is referenced, the relevant corresponding genomic sequence can be found by direct reference to the nucleotide sequence indicated by the "gi" number shown in the public genomic DNA section of the Reference Table. When the position is a negative number, the transcription start site is located in the corresponding genomic sequence upstream of the base that matches the beginning of the MLS sequence in the alignment. The negative number is relative to the first base of the MLS sequence that matches the genomic sequence corresponding to the relevant "gi" number.

In the instances when no public genomic DNA is referenced, the relevant nucleotide sequence for alignment is the nucleotide sequence associated with the amino acid sequence designated by "gi" number of the later PolyP SEQ subsection.

V. Polypeptide Sequences

The PolyP SEQ subsection lists SEQ ID NOs and Ceres SEQ ID NO for polypeptide sequences corresponding to the coding sequence of the MLS sequence and the location of the translational start site with the coding sequence of the MLS sequence.

The MLS sequence can have multiple translational start sites and can be capable of producing more than one polypeptide sequence.

A. Signal Peptide

The Reference tables also indicate in subsection (B) the cleavage site of the putative signal peptide of the polypeptide corresponding to the coding sequence of the MLS sequence. Typically, signal peptide coding sequences comprise a sequence encoding the first residue of the polypeptide to the cleavage site residue.

B. Domains

Subsection (C) provides information regarding identified domains (where present) within the polypeptide and (where present) a name for the polypeptide domain.

C. Related Polypeptides

Subsection (Dp) provides (where present) information concerning amino acid sequences that are found to be related and have some percentage of sequence identity to the polypeptide sequences of the Reference and Sequence Tables. Each of these related sequences is identified by a "gi" number.

VI. Related Polynucleotide Sequences

Subsection (Dn) provides polynucleotide sequences (where present) that are related to and have some percentage of sequence identity to the MLS or corresponding genomic sequence.

| Abbreviation | Description |
|---|---|
| Max Len Seq. | Maximum Length Sequence |
| rel to | Related to |
| Clones Ids | Clone ID numbers |

-continued

| Abbreviation | Description |
|---|---|
| Pub gDNA | Public Genomic DNA |
| gi No. | gi number |
| Gen. Seq. in Cdna | Genomic Sequence in cDNA (Each region for a single gene prediction is listed on a separate line. In the case of multiple gene predictions, the group of regions relating to a single prediction are separated by a blank line) |
| (Ac) cDNA SEQ | cDNA sequence |
| Pat. Appln. SEQ ID NO | Patent Application SEQ ID NO: |
| Ceres SEQ ID NO: 1673877 | Ceres SEQ ID NO: |
| SEQ # w. TSS | Location within the cDNA sequence, SEQ ID NO:, of Transcription Start Sites which are listed below |
| Clone ID #: # -> # | Clone ID comprises bases # to # of the cDNA Sequence |
| PolyP SEQ | Polypeptide Sequence |
| Pat. Appln. SEQ ID NO: | Patent Application SEQ ID NO: |
| Ceres SEQ ID NO | Ceres SEQ ID NO: |
| Loc. SEQ ID NO: @ nt. | Location of translational start site in cDNA of SEQ ID NO: at nucleotide number |
| (C) Pred. PP Nom. & Annot. (Title) | Nomination and Annotation of Domains within Predicted Polypeptide(s) Name of Domain |
| Loc. SEQ ID NO #: # -> # aa. | Location of the domain within the polypeptide of SEQ ID NO: from # to # amino acid residues. |
| (Dp) Rel. AA SEQ | Related Amino Acid Sequences |
| Align. NO | Alignment number |
| gi No | Gi number |
| Desp. | Description |
| % Idnt. | Percent identity |
| Align. Len. | Alignment Length |
| Loc. SEQ ID NO: # -> # aa | Location within SEQ ID NO: from # to # amino acid residue. |

3. MA Table

The MA Table presents the results of the differential expression experiments for the mRNAs, as reported by their corresponding cDNA ID number, that were differentially transcribed under a particular set of conditions as compared to a control sample. The cDNA ID numbers correspond to those utilized in the Reference and Sequence Tables. Increases in mRNA abundance levels in experimental plants versus the controls are denoted with the plus sign (+). Likewise, reductions in mRNA abundance levels in the experimental plants are denoted with the minus (−) sign.

The "cDNA_ID" provides the identifier number for the cDNA tracked in the experiment. The column headed "SHORT_NAME" (e.g. At_0.001%_MeJA_cDNA_P) provides a short description of the experimental conditions used. The column headed "EXPT_REP_ID" provides an identifier number for the particular experiment conducted. The values in the column headed "Differential" indicate whether expression of the cDNA was increased (+) or decreased (−) compared to the control.

The data following the expression results provides the experimental parameters used in conducting the microarray experiment. Again, the "SHORT_NAME" identifies the experiment (e.g. At_0.001%_MeJA_cDNA_P). The first column, "EXPT_REP_ID," indicates the individual experiment. (e.g. 108569). The second column, "PARAM_NAME," identifies the parameter used(e.g. Timepoint (hr)), while the third column, "VALUE" provides the descriptor for the particular parameter (e.g. "6"). As an example, when read together one understands that the "Methyl Jasmonate" section of the Specification provides information pertinent to the 0.001% MeJA (methyl jasmonate) experiment 108569, which contains data taken from a 6 hr Timepoint.

4. Ortholog Report (Table 4)

This table contains three types of sequence information. First, it identifies protein sequences that have similar activities to the sequence of the "query" protein. The query sequence is identified by the cDNA_ID, a taxon ID and the organism from which it originated.

The sequences that follow are orthologous to the query sequence. These sequences, denoted as "Hit," are identified either by the Ceres clone ID, the Ceres cDNA ID or a "gi" number. When possible, a nucleotide sequence that encodes the protein is included. Note that a particular protein can be identified by more than one "gi" number. In these cases, only one nucleotide sequence corresponding to one of the "gi" numbers in included. Other nucleotide sequences corresponding to the remaining "gi" number(s) can be found on the internet at the NCBI website.

The second type of information presented is a consensus sequence derived from the ortholog sequences previously listed. This consensus sequence indicates which amino acid(s) appear at each position. The following Legend applies:

"t" refers to tiny amino acids, which are specifically alanine, glycine, serine and threonine.

"p" refers to polar amino acids, which are specifically, asparagine and glutamine "n" refers to negatively charged amino acids, which are specifically, aspartic acid and glutamic acid "+" refers to positively charged residues, which are specifically, lysine, arginine, and histidine "r" refers to aromatic residues, which are specifically, phenylalanine, tyrosine, and tryptophan, "a" refers to aliphatic residues, which are specifically, isoleucine, valine, leucine, and methonine "<>" refers to an insertion of residues of any identity, the number of which is specified within the brackets The third type of information presented is in the form of a matrix. This matrix indicates the specific amino acid(s) found at each residue position when the ortholog sequences are aligned in a multiple alignment. Each row of the matrix contains 60 positions (e.g. 1-60, 61-120, etc.) In order to accommodate legible font, the values of each row wrap such that positions 1-60, for example, appear on lines 1-7 in this section of the table even though they represent a single row. The first row of each matrix indicates the residue position in the consensus sequence. The matrix reports the number of occurrences of all the amino acids that were found in the group members for every residue position of the signature sequence in the next row. For each residue position the matrix also indicates how many different organisms were found to have a polypeptide in the group that included a residue at the relevant position indicates for each residue position (third row). Note that this number can be greater than the number of different organisms due to sequence differences found in mutants, etc. The last row of the matrix indicates all the amino acids that were found at each position of the consensus.

5. Utility Discovery (Table 5)

The Utility Discovery Table presents the results of experiments wherein plants are grown from tissues transformed with a marker gene-containing insert and phenotypes are ascertained from the transformed plants. Each section of the Table relating to information on a new transformant begins with a heading "Utility discovery for cDNA_id:" followed by a number which represents the Ceres internal code for a proprietary cDNA sequence. The transformant described is prepared by procedures described herein and the marker gene-containing insert interrupts the Ceres proprietary cDNA_id (corresponding to the cDNA_id in the Reference and Sequence Tables) identified. The following information is presented for each section.

Construct Name—represents an internal identification code.

Event ID—presents the recombinant plant number of the Ceres proprietary plant that exhibits the phenotype Assay—presents the type of growth analyzed (e.g. soil gross morphology), followed by the assay name which corresponds to the type/location of the tissue that was observed, the name of the assay conducted for which the result provided the identified phenotype.

Tissue—identifies the tissue observed

Phenotype ID—represents an internal identification code.

Phenotype—describes the phenotype noted for the F1 generation transformant.

Notes—provide additional information on the described phenotype for the transformant.

Each entry in the Utility Discovery report represents a transformant with an interruption in the identified cDNA_id, which may be correlated with more than one identified phenotype.

DETAILED DESCRIPTION OF THE INVENTION

1. Definitions

The following terms are utilized throughout this application:

Allelic variant: An "allelic variant" is an alternative form of the same SDF, which resides at the same chromosomal locus in the organism. Allelic variations can occur in any portion of the gene sequence, including regulatory regions. Allelic variants can arise by normal genetic variation in a population. Allelic variants can also be produced by genetic engineering methods. An allelic variant can be one that is found in a naturally occurring plant, including a cultivar or ecotype. An allelic variant may or may not give rise to a phenotypic change, and may or may not be expressed. An allele can result in a detectable change in the phenotype of the trait represented by the locus. A phenotypically silent allele can give rise to a product.

Chimeric: The term "chimeric" is used to describe genes, as defined supra, or contructs wherein at least two of the elements of the gene or construct, such as the promoter and the coding sequence and/or other regulatory sequences and/or filler sequences and/or complements thereof, are heterologous to each other.

Constitutive Promoter: Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region and the 1' or 2' promoter derived from T-DNA of *Agrobacterium tumefaciens*, and other transcription initiation regions from various plant genes, such as the maize ubiquitin-1 promoter, known to those of skill.

Coordinately Expressed: The term "coordinately expressed," as used in the current invention, refers to genes that are expressed at the same or a similar time and/or stage and/or under the same or similar environmental conditions.

Domain: Domains are fingerprints or signatures that can be used to characterize protein families and/or parts of proteins. Such fingerprints or signatures can comprise conserved (1) primary sequence, (2) secondary structure, and/or (3) three-dimensional conformation. Generally, each domain has been associated with either a family of proteins or motifs. Typically, these families and/or motifs have been correlated with specific in-vitro and/or in-vivo activities. A domain can be any length, including the entirety of the sequence of a protein. Detailed descriptions of the domains, associated families and motifs, and correlated activities of the polypeptides of the instant invention are described below. Usually, the polypeptides with designated domain(s) can exhibit at least one activity that is exhibited by any polypeptide that comprises the same domain(s).

Endogenous: The term "endogenous," within the context of the current invention refers to any polynucleotide, polypeptide or protein sequence which is a natural part of a cell or organisms regenerated from said cell.

Exogenous: "Exogenous," as referred to within, is any polynucleotide, polypeptide or protein sequence, whether chimeric or not, that is initially or subsequently introduced into the genome of an individual host cell or the organism regenerated from said host cell by any means other than by a sexual cross. Examples of means by which this can be accomplished are described below, and include *Agrobacterium*-mediated transformation (of dicots—e.g. Salomon et al. *EMBO J.* 3:141 (1984); Herrera-Estrella et al. *EMBO J.* 2:987 (1983); of monocots, representative papers are those by Escudero et al., *Plant J.* 10:355 (1996), Ishida et al., *Nature Biotechnology* 14:745 (1996), May et al., *Bio/Technology* 13:486 (1995)), biolistic methods (Armaleo et al., *Current Genetics* 17:97 1990)), electroporation, in planta techniques, and the like. Such a plant containing the exogenous nucleic acid is referred to here as a $T_0$ for the primary transgenic plant and $T_1$ for the first generation. The term "exogenous" as used herein is also intended to encompass inserting a naturally found element into a non-naturally found location.

Gene: The term "gene," as used in the context of the current invention, encompasses all regulatory and coding sequence contiguously associated with a single hereditary unit with a genetic function. Genes can include non-coding sequences that modulate the genetic function that include, but are not limited to, those that specify polyadenylation, transcriptional regulation, DNA conformation, chromatin conformation, extent and position of base methylation and binding sites of proteins that control all of these. Genes comprised of "exons" (coding sequences), which may be interrupted by "introns" (non-coding sequences), encode proteins. A gene's genetic function may require only RNA expression or protein production, or may only require binding of proteins and/or nucleic acids without associated expression. In certain cases, genes adjacent to one another may share sequence in such a way that one gene will overlap the other. A gene can be found within the genome of an organism, artificial chromosome, plasmid, vector, etc., or as a separate isolated entity.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence originates from, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

Homologous gene: In the current invention, "homologous gene" refers to a gene that shares sequence similarity with the gene of interest. This similarity may be in only a fragment of the sequence and often represents a functional domain such as, examples including without limitation a DNA binding domain, a domain with tyrosine kinase activity, or the like. The functional activities of homologous genes are not necessarily the same.

Inducible Promoter: An "inducible promoter" in the context of the current invention refers to a promoter which is regulated under certain conditions, such as light, chemical concentration, protein concentration, conditions in an organism, cell, or organelle, etc. A typical example of an inducible promoter, which can be utilized with the polynucleotides of the present invention, is PARSK1, the promoter from the *Arabidopsis* gene encoding a serine-threonine kinase enzyme, and which promoter is induced by dehydration, abscissic acid and sodium chloride (Wang and Goodman, *Plant J.* 8:37 (1995)). Examples of environmental conditions that may affect transcription by inducible promoters include anaerobic conditions, elevated temperature, or the presence of light.

Masterpool: The term "masterpool" as used in these experiments is a pool of seeds from five different plants. Each of these plants has been transformed with the same promoter/cDNA combination. An equal number of seeds from each plant is used to make up the pool.

Misexpression: The term "misexpression" refers to an increase or a decrease in the transcription of a coding region into a complementary RNA sequence as compared to the wild-type. This term also encompasses expression of a gene or coding region for a different time period as compared to the wild-type and/or from a non-natural location within the plant genome.

Orthologous Gene: In the current invention "orthologous gene" refers to a second gene that encodes a gene product that performs a similar function as the product of a first gene. The orthologous gene may also have a degree of sequence similarity to the first gene. The orthologous gene may encode a polypeptide that exhibits a degree of sequence similarity to a polypeptide corresponding to a first gene. The sequence similarity can be found within a functional domain or along the entire length of the coding sequence of the genes and/or their corresponding polypeptides.

Percentage of sequence identity: "Percentage of sequence identity," as used herein, is determined by comparing two optimally aligned sequences over a comparison window, where the fragment of the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman *Add. APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (USA) 85: 2444 (1988), by computerized implementations of these algorithms (GAP, BEST-FIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Plant Promoter: A "plant promoter" is a promoter capable of initiating transcription in plant cells and can drive or facilitate transcription of a fragment of the SDF of the instant invention or a coding sequence of the SDF of the instant invention. Such promoters need not be of plant origin. For example, promoters derived from plant viruses, such as the CaMV35S promoter or from *Agrobacterium tumefaciens* such as the T-DNA promoters, can be plant promoters. A typical example of a plant promoter of plant origin is the maize ubiquitin-1 (ubi-1)promoter known to those of skill.

Promoter: The term "promoter," as used herein, refers to a region of sequence determinants located upstream from the start of transcription of a gene and which are involved in recognition and binding of RNA polymerase and other proteins to initiate and modulate transcription. A basal promoter is the minimal sequence necessary for assembly of a transcription complex required for transcription initiation. Basal promoters frequently include a "TATA box" element usually located between 15 and 35 nucleotides upstream from the site of initiation of transcription. Basal promoters also sometimes include a "CCAAT box" element (typically a sequence CCAAT) and/or a GGGCG sequence, usually located between 40 and 200 nucleotides, preferably 60 to 120 nucleotides, upstream from the start site of transcription.

Regulatory Sequence: The term "regulatory sequence," as used in the current invention, refers to any nucleotide sequence that influences transcription or translation initiation and rate, and stability and/or mobility of the transcript or polypeptide product. Regulatory sequences include, but are not limited to, promoters, promoter control elements, protein binding sequences, 5' and 3' UTRs, transcriptional start site, termination sequence, polyadenylation sequence, introns, certain sequences within a coding sequence, etc.

Signal Peptide: A "signal peptide" as used in the current invention is an amino acid sequence that targets the protein for secretion, for transport to an intracellular compartment or organelle or for incorporation into a membrane. Signal peptides are indicated in the tables and a more detailed description located below.

Specific Promoter: In the context of the current invention, "specific promoters" refers to a subset of inducible promoters that have a high preference for being induced in a specific tissue or cell and/or at a specific time during development of an organism. By "high preference" is meant at least 3-fold, preferably 5-fold, more preferably at least 10-fold still more preferably at least 20-fold, 50-fold or 100-fold increase in transcription in the desired tissue over the transcription in any other tissue. Typical examples of temporal and/or tissue specific promoters of plant origin that can be used with the polynucleotides of the present invention, are: PTA29, a promoter which is capable of driving gene transcription specifically in tapetum and only during anther development (Koltonow et al., *Plant Cell* 2:1201 (1990); RCc2 and RCc3, promoters that direct root-specific gene transcription in rice (Xu et al., *Plant Mol. Biol.* 27:237 (1995); TobRB27, a root-specific promoter from tobacco (Yamamoto et al., *Plant Cell* 3:371 (1991)). Examples of tissue-specific promoters under developmental control include promoters that initiate transcription only in certain tissues or organs, such as root, ovule, fruit, seeds, or flowers. Other suitable promoters include those from genes encoding storage proteins or the lipid body membrane protein, oleosin. A few root-specific promoters are noted above.

Stringency: "Stringency" as used herein is a function of probe length, probe composition (G+C content), and salt concentration, organic solvent concentration, and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m-5°$ C. to $T_m-10°$ C. Medium or moderate stringency conditions are those providing $T_m-20°$ C. to $T_m-29°$ C. Low stringency conditions are those providing a condition of $T_m-40°$ C. to $T_m-48°$ C. The relationship of hybridization conditions to $T_m$ (in ° C.) is expressed in the mathematical equation $$T_m = 81.5 - 16.6(\log_{10}[Na^+]) + 0.41(\% G+C) - (600/N) \qquad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m = 81.5 + 16.6 \log\{[Na^+]/(1+0.7[Na^+])\} + 0.41(\% G+C) - 500/L \; 0.63(\% \text{ formamide}) \qquad (2)$$

where L is the length of the probe in the hybrid. (P. Tijessen, "Hybridization with Nucleic Acid Probes" in Laboratory Techniques in Biochemistry and Molecular Biology, P. C. vand der Vliet, ed., c. 1993 by Elsevier, Amsterdam.) The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al., *J. Mol. Biol.* 81:123 (1973)), stringency conditions can be adjusted to favor detection of identical genes or related family members.

Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

Substantially free of: A composition containing A is "substantially free of" B when at least 85% by weight of the total A+B in the composition is A. Preferably, A comprises at least about 90% by weight of the total of A+B in the composition, more preferably at least about 95% or even 99% by weight. For example, a plant gene or DNA sequence can be considered substantially free of other plant genes or DNA sequences.

Substantially free of: A composition containing A is "substantially free of" B when at least 85% by weight of the total A+B in the composition is A. Preferably, A comprises at least about 90% by weight of the total of A+B in the composition, more preferably at least about 95% or even 99% by weight. For example, a plant gene or DNA sequence can be considered substantially free of other plant genes or DNA sequences.

$T_1$: As used in the current application, the term $T_1$ refers to the cell or plant that is the direct result of a transformation experiment $T_2$: As used in the current application, the term T2 refers to the progeny of the cell or plant that is the direct result of a transformation experiment.

$T_3$: As used in the current application, the term $T_3$ refers to second generation progeny of the cell or plant that is the direct result of a transformation experiment.

Translational start site: In the context of the current invention, a "translational start site" is usually an ATG in the cDNA transcript, more usually the first ATG. A single cDNA, however, may have multiple translational start sites.

Transcription start site: "Transcription start site" is used in the current invention to describe the point at which transcription is initiated. This point is typically located about 25 nucleotides downstream from a TFIID binding site, such as a TATA box. Transcription can initiate at one or more sites within the gene, and a single gene may have multiple transcriptional start sites, some of which may be specific for transcription in a particular cell-type or tissue.

Untranslated region (UTR): A "UTR" is any contiguous series of nucleotide bases that is transcribed, but is not translated. These untranslated regions may be associated with particular functions such as increasing mRNA message stability. Examples of UTRs include, but are not limited to polyadenylation signals, terminations sequences, sequences located between the transcriptional start site and the first exon (5' UTR) and sequences located between the last exon and the end of the mRNA (3' UTR).

Variant: The term "variant" is used herein to denote a polypeptide or protein or polynucleotide molecule that differs from others of its kind in some way. For example, polypeptide and protein variants can consist of changes in amino acid sequence and/or charge and/or post-translational modifications (such as glycosylation, etc).

2. Important Characteristics of the Polynucleotides of the Invention

The genes and polynucleotides of the present invention are of interest because when they are misexpressed (i.e. when expressed at a non-natural location or in an increased amount) they produce plants with modified water use characteristics as discussed below and as evidenced by the results of differential expression experiments. These traits can be used to exploit or maximize plant products or to minimize undesirable characteristics. For example, an increase in water use efficiency allows growth under drought or low water availability conditions. Another example of a characteristic that may be modified is an increase in plant height, which is beneficial in species grown or harvested for their main stem or trunk, such as ornamental cut flowers, fiber crops (e.g. flax, kenaf, hesperaloe, hemp) and wood producing trees. Increase in inflorescence thickness is also desirable for some ornamentals, while increases in the number, shape and size of leaves can lead to increased production/ harvest from leaf crops such as lettuce, spinach, cabbage and tobacco. Likewise, a decrease in plant height is beneficial in species that are particularly susceptible to lodging or uprooting due to wind stress.

In addition to modified water use efficiency, the polynucleotides of the invention may also have some particular characteristics and uses as discussed below.

Organ-Affecting Genes, Gene Components and Products (Including Differentiation and Function)

Root Genes, Gene Components and Products

The economic values of roots arise not only from harvested adventitious roots or tubers, but also from the ability of roots to funnel nutrients to support growth of all plants and increase their vegetative material, seeds, fruits, etc. Roots have four main functions. First, they anchor the plant in the soil. Second, they facilitate and regulate the molecular signals and molecular traffic between the plant, soil, and soil fauna. Third, the root provides a plant with nutrients gained from the soil or growth medium. Fourth, they condition local soil chemical and physical properties.

Root genes are active or potentially active to a greater extent in roots than in most other organs of the plant. These genes and gene products regulate many plant traits from yield to stress tolerance. Root genes are used to modulate root growth and development.

Root Hair Genes, Gene Components and Products

Root hairs are specialized outgrowths of single epidermal cells termed trichoblasts. In many and perhaps all species of plants, the trichoblasts are regularly arranged around the perimeter of the root. In *Arabidopsis*, for example, trichoblasts tend to alternate with non-hair cells or atrichoblasts. This spatial patterning of the root epidermis is under genetic control, and a variety of mutants have been isolated in which this spacing is altered or in which root hairs are completely absent, such as the rhl mutant. Some surface cells of roots develop into single epidermal cells termed trichoblasts or root hairs. Some of the root hairs persist for the life of the plant; others gradually die back and some cease to function due to external influences.

Root hairs are also sites of intense chemical and biological activity and as a result strongly modify the soil they contact. Some roots hairs are coated with surfactants and/or mucilage to facilitate these activities. Specifically, roots hairs are responsible for nutrient uptake by mobilizing and assimilating water, reluctant ions, organic and inorganic compounds and chemicals. In addition, they attract and interact with beneficial microfauna and flora. Root hairs also help to mitigate the effects of toxic ions, pathogens and stress. Examples of root hair properties and activities that root hairs modulate include root hair surfactant and mucilage, nutrient uptake, microbe and nematode associations, oxygen transpiration; detoxification effects of iron, aluminum, cadium, mercury, salt, and other soil constituents, pathogens, glucosinolates, changes in soil and rhizosheath.

The root and root hairs uptake of the nutrients contributes to a source-sink effect in a plant. The greater the source of nutrients, the more sinks, such as stems, leaves, flowers, seeds, fruits, etc. can draw sustenance to grow. Thus, root hair genes modulate the vigor and yield of the plant overall, as well as of distinct cells, organs, or tissues of a plant.

Leaf Genes, Gene Components and Products

Leaves are responsible for producing most of the fixed carbon in a plant and are critical to plant productivity and survival. Great variability in leaf shapes and sizes is observed in nature. Leaves also exhibit varying degrees of complexity, ranging from simple to multi-compound. Leaf genes, as defined here, not only modulate leaf morphology, but also influence the shoot apical meristem, thereby affecting leaf arrangement on the shoot, internodes, nodes, axillary buds, photosynthetic capacity, carbon fixation, photorespiration and starch synthesis. Leaf genes elucidated here are used to modify a number of traits of economic interest including leaf shape, plant yield, stress tolerance, and to modify both the efficiency of synthesis and accumulation of specific metabolites and macromolecules (including carbohydrates, proteins, oils, waxes, etc).

Trichome Genes and Gene Components

Trichomes, defined as hair-like structures that extend from the epidermis of aerial tissues, are present on the surface of most terrestrial plants. Plant trichomes display a diverse set of structures, and many plants contain several types of trichomes on a single leaf. The presence of trichomes increases the boundary layer thickness between the epidermal tissue and the environment, and reduce heat and water loss. In many species, trichomes protect the plant against insect or pathogen attack, either by secreting chemical components or by physically limiting insect access to or mobility on vegetative tissues. The stellate trichomes of *Arabidopsis* do not have a secretory anatomy, but at a functional level they limit herbivore access to the leaf in the field. In addition, trichomes are known to secrete economically valuable substances, such as menthol in mint plants.

Trichome differentiation is integrated with leaf development, hormone levels and the vegetative development phase. The first trichome at the leaf tip appears only after the leaf grows to ~100 µm in length. Subsequent events proceed basipetally as the leaf grows. As leaf development progresses, cell division patterns become less regular and islands of dividing cells are observed among differentiated pavement cells with their characteristic lobed morphology. Trichome initiation in the expanding leaf occurs within these islands of cells and often defines points along the perimeter of a circle, with an existing trichome defining the center.

Once a cell enters the trichome pathway it undergoes an elaborate morphogenesis program that has been divided into different stages based on specific morphological hallmarks. In addition, the glandular trichomes from various species secrete and, sometimes locally synthesize, a number of substances including salt, monoterpenes and sesquiterpenes, terpenoids, exudate, insect entrapping substances, antifeedants and pheromones.

The trichome genes are used to modulate the number, structure and biochemistry of trichomes.

Chloroplast Genes, Gene Components and Products

The chloroplast is a complex and specialized organelle in plant cells. Its complexity comes from the fact that it has at least six suborganellar compartments subdivided by double-membrane envelopes and internal thylakoid membranes. It is specialized to carry out different biologically important processes including photosynthesis and amino acid and fatty acid biosynthesis. The biogenesis and development of the chloroplast from its progenitor (the proplasptid) and the conversion of one form of plastid to another (e.g., from chloroplast to amyloplast) depends on several factors that include the developmental and physiological states of the cells.

One of the contributing problems that complicates the biogenesis of the chloroplast is the fact that some, if not most, of its components must come from outside of the organelle itself. The import mechanisms must take into account what part within the different sub-compartments the proteins are being targeted; hence the proteins being imported from the cytoplasm must be able to cross the different internal membrane barriers before they can reach their destinations. The import mechanism must also take into account how to tightly coordinate the interaction between the plastid and the nucleus such that both nuclear and plastidic components are expressed in a synchronous and orchestrated manner. As a consequence, changes in the developmental and physiological conditions within or surrounding plant cells change this tight coordination and therefore also change how import mechanisms are regulated. Manipulation of these conditions and modulation of expression of the import components and their functions have critical and global consequences to the development of the plant and to several biochemical pathways occurring outside the chloroplast.

Chloroplast genes are useful to modulate growth and development, including plastid biogenesis, plastid division, plastid development and thylakoid membrane structures. They are also useful for altering differentiation including plastid/chloroplast differentiation, photosynthesis, transport, phosphate translocation, targeted starch deposition and accumulation, and biosynthesis of essential compounds such as lipid biosynthesis, riboflavin biosynthesis, carotenoid biosynthesis, and aminoacid biosynthesis.

Guard Cell Genes, Gene Components and Products

Scattered throughout the epidermis of the shoot are minute pores called stomata. Each stomal pore is surrounded by two guard cells. The guard cells control the size of the stomal pore, which is critical since the stomata control the exchange of carbon dioxide, oxygen, and water vapor between the interior of the plant and the outside atmosphere. Stomata open and close through turgor changes driven by ion fluxes, which occur mainly through the guard cell plasma membrane and tonoplast. Guard cells are known to respond to a number of external stimuli such as changes in light intensity, carbon dioxide and water vapor, for example. Guard cells can also sense and rapidly respond to internal stimuli including changes in ABA, auxin and calcium ion flux. Thus, guard cell genes are useful to modulate ABA responses, drought tolerance, respiration, water potential, and water management. All of which in turn affect plant yield including seed yield, harvest index, fruit yield, etc.

Reproduction Genes, Gene Components and Products

Reproduction genes are defined as genes or components of genes capable of modulating any aspect of sexual reproduction from flowering time and inflorescence development to fertilization and finally seed and fruit development. These genes are of great economic interest as well as biological importance. The fruit and vegetable industry grosses over $1 billion USD a year. The seed market, valued at approximately $15 billion USD annually, is even more lucrative.

Inflorescence and Floral Development Genes, Gene Components and Products

During reproductive growth the plant enters a program of floral development that culminates in fertilization, followed by the production of seeds. Senescence may or may not follow. Flower formation is a precondition for the sexual propagation of plants and is therefore essential for propagation of plants that cannot be propagated vegetatively, as well as for the formation of seeds and fruits. The point of time at which the vegetative growth of plants changes into flower formation is of vital importance in agriculture, horticulture and plant breeding. Also, the number of flowers is often of economic importance, for example in the case of various useful plants (tomato, cucumber, zucchini, cotton etc.) where an increased number of flowers leads to an increased yield, or in the case of ornamental plants and cut flowers.

Flowering plants exhibit one of two types of inflorescence architecture: (1) indeterminate, in which the inflorescence grows indefinitely, or (2) determinate, in which a terminal flower is produced. Adult organs of flowering plants develop from groups of stem cells called meristems. The identity of a meristem is inferred from structures it produces: vegetative meristems give rise to roots and leaves, inflorescence meristems give rise to flower meristems, and flower meristems give rise to floral organs such as sepals and petals. Not only are meristems capable of generating new meristems of a different identity, but their own identity can change during development. For example, a vegetative shoot meristem can be transformed into an inflorescence meristem upon floral induction, and in some species, the inflorescence meristem itself will eventually become a flower meristem. Despite the importance of meristem transitions in plant development, little is known about the underlying mechanisms.

Following germination, the shoot meristem produces a series of leaf meristems on its flanks. However, once floral induction has occurred, the shoot meristem switches to the production of flower meristems. Flower meristems produce floral organ primordia, which individually develop into sepals, petals, stamens or carpels. Thus, flower formation can be thought of as a series of distinct developmental steps, i.e. floral induction, the formation of flower primordia and the production of flower organs. Mutations disrupting each of the steps have been isolated in a variety of species, suggesting that a genetic hierarchy directs the flowering process (see for review, Weigel and Meyerowitz, In Molecular Basis of Morphogenesis (ed. M. Bemfield). 51st Annual Symposium of the Society for Developmental Biology, pp. 93-107, New York, 1993).

Expression of many reproduction genes and gene products is orchestrated by internal programs or the surrounding environment of a plant. These genes used to modulate traits such as fruit and seed yield Seed and Fruit Development Genes, Gene Components and Products The ovule is the primary female sexual reproductive organ of flowering plants. At maturity it contains the egg cell and one large central cell containing two polar nuclei encased by two integuments that, after fertilization, develop into the embryo, endosperm and seed coat of the mature seed, respectively. As the ovule develops into the seed, the ovary matures into the fruit or silique. As such, seed and fruit development requires the orchestrated transcription of numerous polynucleotides, some of which are ubiquitous, others that are embryo-specific and still others that are expressed only in the endosperm, seed coat or fruit. Such genes are termed fruit development responsive genes and are used to modulate seed and fruit growth and development such as seed size, seed yield, seed composition and seed dormancy.

Ovule Genes, Gene Components and Products

The ovule is the primary female sexual reproductive organ of flowering plants. It contains the egg cell and, after fertilization occurs, contains the developing seed. Consequently, the ovule is at times comprised of haploid, diploid and triploid tissue. As such, ovule development requires the orchestrated transcription of numerous polynucleotides, some of which are ubiquitous, others that are ovule-specific and still others that are expressed only in the haploid, diploid or triploid cells of the ovule.

Although the morphology of the ovule is well known, little is known of these polynucleotides and polynucleotide products. Mutants allow identification of genes that participate in ovule development. As an example, the pistillata (PI) mutant replaces stamens with carpels, thereby increasing the number of ovules present in the flower. Accordingly, comparison of transcription levels between the wild-type and PI mutants allows identification of ovule-specific developmental polynucleotides.

Ovule genes are useful to modulate egg cell development, ovule maturation, metabolism, polar nuclei, fusion, central cell, maturation, metabolism, synergids, maturation, programmed cell death, nucellus, maturation, integuments, maturation, funiculus, extension, cuticle, maturation, tensile properties, ovule, modulation of ovule senescence and shaping.

Seed and Fruit Development Genes, Gene Components and Products

The ovule is the primary female sexual reproductive organ of flowering plants. At maturity it contains the egg cell and one large central cell containing two polar nuclei encased by two integuments that, after fertilization, develop into the embryo, endosperm and seed coat of the mature seed, respectively. As the ovule develops into the seed, the ovary matures into the fruit or silique. As such, seed and fruit development requires the orchestrated transcription of numerous polynucleotides, some of which are ubiquitous, others that are embryo-specific and still others that are expressed only in the endosperm, seed coat or fruit. Such genes are termed fruit development responsive genes and are used to modulate seed and fruit growth and development such as seed size, seed yield, seed composition and seed dormancy.

Development Genes, Gene Components and Products
Imbibition and Germination Responsive Genes, Gene Components and Products Seeds are a vital component of the world's diet. Cereal grains alone, which comprise ~90% of all cultivated seeds, contribute up to half of the global per capita energy intake. The primary organ system for seed production in flowering plants is the ovule. At maturity, the ovule consists of a haploid female gametophyte or embryo sac surrounded by several layers of maternal tissue including the nucellous and the integuments. The embryo sac typically contains seven cells including the egg cell, two synergids, a large central cell containing two polar nuclei, and three antipodal cells. Pollination results in the fertilization of both egg and central cell. The fertilized egg develops into the embryo. The fertilized central cell develops into the endosperm. And the integuments mature into the seed coat. As the ovule develops into the seed, the ovary matures into the fruit or silique. Late in development, the developing seed ends a period of extensive biosynthetic and cellular activity and begins to desiccate to complete its development and enter a dormant, metabolically quiescent state. Seed dormancy is generally an undesirable characteristic in agricultural crops, where rapid germination and growth are required. Some degree of dormancy is advantageous, however, at least during seed development. This is particularly true for cereal crops because it prevents germination of grains while still on the ear of the parent plant (preharvest sprouting), a phenomenon that results in major losses to the agricultural industry. Extensive domestication and breeding of crop species have ostensibly reduced the level of dormancy mechanisms present in the seeds of their wild ancestors, although under some adverse environmental conditions, dormancy may reappear. By contrast, weed seeds frequently mature with inherent dormancy mechanisms that allow some seeds to persist in the soil for many years before completing germination.

Germination commences with imbibition, the uptake of water by the dry seed, and the activation of the quiescent embryo and endosperm. The result is a burst of intense metabolic activity. At the cellular level, the genome is transformed from an inactive state to one of intense transcriptional activity. Stored lipids, carbohydrates and proteins are catabolized fueling seedling growth and development. DNA and organelles are repaired, replicated and begin functioning. Cell expansion and cell division are triggered. The shoot and root apical meristems are activated and begin growth and organogenesis. Germination is complete when a part of the embryo, the radicle, extends to penetrate the structures that surround it. In *Arabidopsis*, seed germination takes place within twenty-four (24) hours after imbibition. As such, germination requires the rapid and orchestrated transcription of numerous polynucleotides. Germination is followed by expansion of the hypocotyl and opening of the cotyledons. Meristem development continues to promote root growth and shoot growth, which is followed by early leaf formation.

The germination period exists from imbibition to when part of the embryo, usually the radicle, extends to penetrate the seed coat that surrounds it. Imbibition and germination genes are defined as genes, gene components and products that modulate one or more processes of imbibition and germination described above. They are useful to modulate many plant traits from early vigor to yield to stress tolerance.

Early Seedling-Phase Specific Responsive Genes, Gene Components and Products

A few days after germination is complete, which is also referred to as the early seedling phase, is one of the more active stages of the plant life cycle. During this period the plant begins development and growth of the first leaves, roots, and other organs not found in the embryo. Generally this stage begins when germination ends. The first sign that germination has been completed is usually an increase in length and fresh weight of the radicle. Such genes and gene products can regulate a number of plant traits to modulate yield. For example, these genes are active or potentially active to a greater extent in developing and rapidly growing cells, tissues and organs, as exemplified by development and growth of a seedling 3 or 4 days after planting a seed.

Rapid, efficient establishment of a seedling is very important in commercial agriculture and horticulture. It is also vital that resources are approximately partitioned between shoot and root to facilitate adaptive growth. Phototropism and geotropism need to be established. All these require post-germination process to be sustained to ensure that vigorous seedlings are produced. Early seedling phase genes, gene components and products are useful to manipulate these and other processes.

Size and Stature Genes, Gene Components and Products

Great agronomic value results from modulating the size of a plant as a whole or of any of its organs. For example, the "Green Revolution" came about as a result of creating dwarf wheat plants, which produced a higher seed yield than taller plants because they could withstand higher levels and inputs of fertilizer and water. Size and stature genes elucidated here modify the growth of either an organism as a whole or of localized organs or cells. Manipulation of such genes, gene components and products enhances many traits of economic interest from increased seed and fruit size to increased lodging resistance. Many kinds of genes control the height attained by a plant and the size of the organs. For genes additional to the ones in this section other sections of the Application should be consulted.

These genes can be divided into three classes. One class of genes acts during cytokinesis and/or karyokinesis, such as mitosis and/or meiosis. A second class is involved in cell growth. Examples include genes regulating metabolism and nutrient uptake pathways. A third class includes genes that control pathways that regulate or constrain cell division and growth. Examples of these pathways include those genes specifying hormone biosynthesis, hormone sensing and pathways activated by hormones.

Size and stature genes are useful to selectively alter the size of organs and stems and so make plants specifically improved for agriculture, horticulture and other industries Shoot-Apical Meristem Genes, Gene Components and Products New organs, stems, leaves, branches and inflorescences develop from the stem apical meristem (SAM). The growth structure and architecture of the plant therefore depends on the behavior of SAMs. SAMs are comprised of a number of morphologically undifferentiated, dividing cells located at the tips of shoots. SAM genes elucidated here modify the activity of SAMs and thereby many traits of economic interest from ornamental leaf shape to organ number to responses to plant density.

In addition, a key attribute of the SAM is its capacity for self-renewal. Thus, SAM genes of the instant invention are useful for modulating one or more processes of SAM structure and/or function including (I) cell size and division; (II) cell differentiation and organ primordia. The genes and gene components of this invention are useful for modulating any one or all of these cell division processes generally, as in timing and rate, for example. In addition, the polynucleotides and polypeptides of the invention can control the response of these processes to the internal plant programs associated with embryogenesis, and hormone responses, for example.

Because SAMs determine the architecture of the plant, modified plants are useful in many agricultural, horticultural, forestry and other industrial sectors. Plants with a different shape, numbers of flowers and seed and fruits have altered yields of plant parts. For example, plants with more branches produce more flowers, seed or fruits. Trees without lateral branches produce long lengths of clean timber. Plants with greater yields of specific plant parts are useful sources of constituent chemicals.

Vegetative-Phase Specific Responsive Genes, Gene Components and Products

Often growth and yield are limited by the ability of a plant to tolerate stress conditions, including water loss. To combat such conditions, plant cells deploy a battery of responses that are controlled by a phase shift, from so called juvenile to adult. These changes at distinct times involve, for example, cotyledons and leaves, guard cells in stomata, and biochemical activities involved with sugar and nitrogen metabolism. These responses depend on the functioning of an internal clock that becomes entrained to plant development, and a series of downstream signaling events leading to transcription-independent and transcription-dependent stress responses. These responses involve changes in gene expression.

Phase responsive genes are useful to modulate timing, dormancy, germination, cotyledon opening, appearance of first leaves, juvenile to adult transition, bolting, flowering, pollination, fertilization, seed development, seed set, fruit drop, senescence and epinasty.

Hormone Responsive Genes, Gene Components and Products

Absissic Acid Responsive Genes, Gene Components and Products

Plant hormones are naturally occurring substances, effective in very small amounts, which act as signals to stimulate or inhibit growth or regulate developmental processes in plants. Abscisic acid (ABA) is a ubiquitous hormone in vascular plants that has been detected in every major organ or living tissue from the root to the apical bud. The major physiological responses affected by ABA are dormancy, stress stomatal closure, water uptake, abscission and senescence. In contrast to Auxins, cytokinins and gibberellins, which are principally growth promoters, ABA primarily acts as an inhibitor of growth and metabolic processes.

Changes in ABA concentration internally or in the surrounding environment in contact with a plant results in modulation of many genes and gene products. These genes and/or products are responsible for effects on traits such as plant vigor and seed yield.

While ABA responsive polynucleotides and gene products can act alone, combinations of these polynucleotides also affect growth and development. Useful combinations include different ABA responsive polynucleotides and/or gene products that have similar transcription profiles or similar biological activities, and members of the same or similar biochemical pathways. Whole pathways or segments of pathways are controlled by transcription factor proteins and proteins controlling the activity of signal transduction pathways. Therefore, manipulation of such protein levels is especially useful for altering phenotypes and biochemical activities of plants. In addition, the combination of an ABA responsive polynucleotide and/or gene product with another environmentally responsive polynucleotide is also useful because of the interactions that exist between hormone-regulated pathways, stress and defence induced pathways, nutritional pathways and development.

Auxin Responsive Genes, Gene Components and Products

Plant hormones are naturally occurring substances, effective in very small amounts that stimulate or inhibit growth or regulate developmental processes in plants. One of the plant hormones is indole-3-acetic acid (IAA), often referred to as Auxin.

Changes in Auxin concentration in the surrounding environment in contact with a plant or in a plant results in modulation of the activities of many genes and hence levels of gene products. Auxin is known to influence and/or regulate growth, apical dominance, vascular growth, roots, inhibition of primary root elongation, increased lateral root formation, stems, lateral buds, lateral branching, reduction of branching, organ formation, fruit number in tomatoes, leaves, height/stature, regeneration and differentiation of cultured cells or plantlets, biomass, number of flowers; number of seeds; starch content, fruit yield, orienting cell growth, establishment and maintenance of plant axis, cell plate placement, polarised growth, initiation and/or development of embryo morphogenic progression, differentiation of cells into morphologically different cell layers, cotyledon separation, fruit development, abscission, parthenocarpy, and modulation of phototropic sensitivity, e.g. increase growth under a reduced light spectrum.

Brassinosteroid Responsive Genes, Gene Components and Products

Plant hormones are naturally occurring substances, effective in very small amounts, which act as signals to stimulate or inhibit growth or regulate developmental processes in plants. Brassinosteroids (BRs) are the most recently discovered, and least studied, class of plant hormones. The major physiological response affected by BRs is the longitudinal growth of young tissue via cell elongation and cell division. Consequently, disruptions in BR metabolism, perception and activity result in a dwarf phenotype. In addition, because BRs are derived from the sterol metabolic pathway, any perturbations to the sterol pathway affect the BR pathway. In the same way, perturbations in the BR pathway have effects on the later part of the sterol pathway and thus the sterol composition of membranes.

Changes in BR concentration in the surrounding environment or in contact with a plant result in modulation of many genes and gene products.

While BR responsive polynucleotides and gene products can act alone, combinations of these polynucleotides also affect growth and development. Useful combinations include different BR responsive polynucleotides and/or gene products that have similar transcription profiles or similar biological activities, and members of the same or functionally related biochemical pathways. Whole pathways or segments of pathways are controlled by transcription factors and proteins controlling the activity of signal transduction pathways. Therefore, manipulation of such protein levels is especially useful for altering phenotypes and biochemical activities of plants. In addition, the combination of a BR responsive polynucleotide and/or gene product with another environmentally responsive polynucleotide is useful because of the interactions that exist between hormone-regulated pathways, stress pathways, nutritional pathways and development. Here, in addition to polynucleotides having similar transcription profiles and/or biological activities, useful combinations include polynucleotides that may have different transcription profiles but which participate in common or overlapping pathways.

Cytokinin Responsive Genes, Gene Components and Products

Plant hormones are naturally occurring substances, effective in very small amounts, which act as signals to stimulate or inhibit growth or regulate developmental processes in plants. Cytokinins (BA) are a group of hormones that are best known for their stimulatory effect on cell division, although they also participate in many other processes and pathways. All naturally occurring BAs are aminopurine derivatives, while nearly all synthetic compounds with BA activity are 6-substituted aminopurine derivatives. One of the most common synthetic BAs used in agriculture is benzylaminopurine (BAP).

BA responsive genes are useful to modulate plant growth, emergence of lateral buds, cotyledon expansion, senescence, differentiation, nutrient metabolism, control of fruit ripening, and parthenocarpy.

Gibberellic Acid Responsive Genes, Gene Components and Products

Plant hormones are naturally occurring substances, effective in very small amounts, which act as signals to stimulate or inhibit growth or regulate developmental processes in plants. Gibberellic acid (GA) is a hormone in vascular plants that is synthesized in proplastids (which give rise to chloroplasts or leucoplasts) and vascular tissues. The major physiological responses affected by GA are seed germination, stem elongation, flower induction, anther development, seed and pericarp growth. GA is similar to auxins, cytokinins and gibberellins, in that they are principally growth promoters.

GA responsive genes are useful to modulate one or more phenotypes including promoting leaf and root growth, promoting cell division, promoting stem elongation and secondary (woody) growth, increasing xylem fiber length and biomass production. In addition, GA responsive genes are used to alter fruit and seed development, breaking dormancy in seeds and buds, decreasing senescence and regulating stress responses, fertility and flowering time.

Metabolism Affecting Genes, Gene Components and Products

Nitrogen Responsive Genes, Gene Components and Products

Nitrogen is often the rate-limiting element in plant growth, and all field crops have a fundamental dependence on exogenous nitrogen sources. Nitrogenous fertilizer, which is usually supplied as ammonium nitrate, potassium nitrate, or urea, typically accounts for 40% of the costs associated with crops in intensive agriculture,. such as corn and wheat. Increased efficiency of nitrogen use by plants enables the production of higher yields with existing fertilizer inputs and/or enable existing yields of crops to be obtained with lower fertilizer input, or better yields from growth on soils of poorer quality. Also, higher amounts of proteins in the crops are produced more cost-effectively. "Nitrogen responsive" genes and gene products are used to alter or modulate plant growth and development.

Circadian Rhythm (Clock) Responsive Genes, Gene Components and Products

Often growth and yield are limited by the ability of a plant to tolerate stress conditions, including water loss. To combat such conditions, plant cells deploy a battery of responses that are controlled by an internal circadian clock, including the timed movement of cotyledons and leaves, timed movements in guard cells in stomata, and timed biochemical activities involved with sugar and nitrogen metabolism. These responses depend on the functioning of an internal circadian clock, that becomes entrained to the ambient light/dark cycle, and a series of downstream signaling events leading to transcription independent and transcription dependent stress responses.

A functioning circadian clock anticipates dark/light transitions and prepares the physiology and biochemistry of a plant accordingly. For example, expression of a chlorophyll a/b binding protein (CAB) is elevated before daybreak so that photosynthesis can operate maximally as soon as there is light to drive it. Similar considerations apply to light/dark transitions and to many areas of plant physiology such as sugar metabolism, nitrogen metabolism, water uptake, water loss, flowering, flower opening, epinasty, germination, perception of season and senescence.

Clock responsive genes and gene products are useful to modulate timing, dormancy, germination, cotyledon opening, appearance of first leaves, juvenile to adult transition, bolting, flowering, pollination, fertilization, seed development, seed set, fruit drop, senescence, epinasty and biomass.

Blue Light (Phototropism) Responsive Genes, Gene Components and Products

Phototropism is the orientation or growth of a cell, an organism or part of an organism in relation to a source of light. Plants can sense red (R), far-red (FR) and blue light in their environment and respond differently to particular ratios of these. For example, a low R:FR ratio enhances cell elongation and favors flowering over leaf production, but blue light regulated cryptochromes also appear to be involved in determining hypocotyl growth and flowering time.

Phototropism of Arabidopsis thaliana seedlings in response to a blue light source is initiated by nonphototropic hypocotyl 1 (NPH1), a blue light-activated serine-threonine protein kinase, but the downstream signaling events are not entirely known. Blue light treatment leads to changes in gene expression. These genes are identified by comparing the levels of mRNAs of individual genes in dark-grown seedlings compared with dark grown seedlings treated with 1 hour of blue light.

Auxin also affects blue light phototropism. The effect of Auxin on gene expression stimulated by blue light is found by comparing mRNA levels in a mutant of Arabidopsis thaliana nph4-2 grown in the dark and treated with blue light for 1 hour with wild type seedlings treated similarly. This mutant is disrupted for Auxin-related growth and Auxin-induced gene transcription.

Blue light responsive genes are used to alter or modulate growth, roots (elongation or gravitropism), stems (such as elongation), cell development, flower, seedling, plant yield, and seed and fruit yield.

Carbon Dioxide Responsive Genes, Gene Components and Products

There has been a recent and significant increase in the level of atmospheric carbon dioxide. This rise in level is projected to continue over the next 50 years. The effects of the increased level of carbon dioxide on vegetation are just now being examined, generally in large scale, whole plant experiments often conducted with trees. Some researchers have initiated physiological experiments in attempts to define the biochemical pathways that are either affected by and/or are activated to allow the plant to avert damage from elevated carbon dioxide levels.

$CO_2$ responsive genes are useful to modulate catabolism, energy generation, metabolism, carbohydrate synthesis, growth rate and photosynthesis (such as carbon dioxide fixation).

Mitochondiria Electron Transport (Respiration) Genes, Gene Components and Products One means to alter flux through metabolic pathways is to alter the levels of proteins in the pathways. Plant mitochondria contain many proteins involved in various metabolic processes, including the TCA cycle, respiration, and photorespiration and particularly the electron transport chain (mtETC). Most mtETC complexes consist of nuclearly-encoded mitochondrial proteins (NEMPs) and mitochondrially-encoded mitochondrial proteins (MEMPs). NEMPs are produced in coordination with MEMPs of the same complex and pathway and with other proteins in multi- organelle pathways. Enzymes involved in photorespiration, for example, are located in chloroplasts, mitochondria, and peroxisomes and many of the proteins are nuclearly-encoded. Manipulation of the coordination of protein levels within and between organelles have critical and global consequences to the growth and yield of a plant Respiration responsive genes are useful to modulate catabolism; energy generation, growth rate; water usage and photosynthesis.

Protein Degradation Genes, Gene Components and Products

One of the components of molecular mechanisms that operate to support plant development is the "removal" of a gene product from a particular developmental circuit once the substrate protein is no longer functionally relevant in temporal and/or spatial contexts. The "removal" mechanisms can be accomplished either by protein inactivation (e.g., phosphorylation or protein-protein interaction) or protein degradation, most notably via the ubiquitination-proteasome pathway. The ubiquitination-proteasome pathway is responsible for the degradation of a plethora of proteins involved in cell cycle, cell division, transcription and signal transduction, all of which are required for normal cellular functions. Ubiquitination occurs through the activity of ubiquitin-activating enzymes (E1), ubiquitin-conjugating enzymes (E2), and ubiquitin-protein ligases (E3), which act sequentially to catalyze the attachment of ubiquitin (or other modifying molecules that are related to ubiquitin) to substrate proteins (Hochstrasser 2000, Science 289: 563). Ubiquitinated proteins are then routed to proteasomes for degradation processing [2000, Biochemistry and Molecular Biology of Plants, Buchanan, Gruissem, and Russel (eds), Amer. Soc. of Plant Physiologists, Rockville, Md.]. The degradation mechanism can be selective and specific to the concerned target protein (Joazeiro and Hunter 2001, Science 289: 2061; Sakamoto et al., 2001, PNAS Online 141230798). This selectivity and specificity is believed to be one of the ways that the activity of gene products is modulated.

Protein degradation genes are useful for used promoting/controlling cell death and for altering developmental and growth processes.

Carotenogenesis Responsive Genes, Gene Components and Products

Carotenoids serve important biochemical functions in both plants and animals. In plants, carotenoids function as accessory light harvesting pigments for photosynthesis and to protect chloroplasts and photosystem II from heat and oxidative damage by dissipating energy and scavenging oxygen radicals produced by high light intensities and other oxidative stresses. Decreases in yield frequently occur as a result of light stress and oxidative stress in the normal growth ranges of crop species. In addition light stress limits the geographic range of many crop species. Modest increases in oxidative stress tolerance greatly improve the performance and growth range of many crop species. The development of genotypes with increased tolerance to light and oxidative stress provides a more reliable means to minimize crop losses and diminish the use of energy-costly practices to modify the soil environment.

In animals carotenoids such as beta-carotene are essential provitamins required for proper visual development and function. In addition, their antioxidative properties are also thought to provide valuable protection from diseases such as cancer. Modest increases in carotenoid levels in crop species produce a dramatic effect on plant nutritional quality. The development of genotypes with increased carotenoid content provides a more reliable and effective nutritional source of Vitamin A and other carotenoid derived antioxidants than through the use of costly nutritional supplements.

Viability Genes, Gene Components and Products

Plants contain many proteins and pathways that when blocked or induced lead to cell, organ or whole plant death. Gene variants that influence these pathways have profound effects on plant survival, vigor and performance. The critical pathways include those concerned with metabolism and development or protection against stresses, diseases and pests. They also include those involved in apoptosis and necrosis. Viability genes are modulated to affect cell or plant death.

Herbicides are, by definition, chemicals that cause death of tissues, organs and whole plants. The genes and pathways that are activated or inactivated by herbicides include those that cause cell death as well as those that function to provide protection.

Histone Deacetylase (Axel) Responsive Genes, Gene Components and Products

The deacetylation of histones is known to play an important role in regulating gene expression at the chromatin level in eukaryotic cells. Histone deacetylation is catalyzed by proteins known as histone deacetylases (hdacs). Hdacs are found in multisubunit complexes that are recruited to specific sites on nuclear DNA thereby affecting chromatin architecture and target gene transcription. Mutations in plant hdac genes cause alterations in vegetative and reproductive growth that result from changes in the expression and activities of hdac target genes or genes whose expression is governed by hdac target genes. For example, transcription factor proteins control whole pathways or segments of pathways and proteins also control the activity of signal transduction pathways.

HDAc genes are useful to modulate growth rate and development.

Stress Responsive Genes, Gene Components and Products
Cold Responsive Genes, Gene Components and Products The ability to endure low temperatures and freezing is a major determinant of the geographical distribution and productivity of agricultural crops. Even areas considered suiTable for the cultivation of a given species or cultivar can give rise to yield decreases and crop failures as a result of aberrant freezing temperatures. Even modest increases (1-2° C.) in the freezing tolerance of certain crop species have a dramatic impact on agricultural productivity in some areas. The development of genotypes with increased freezing tolerance provide a more reliable means to minimize crop losses and diminish the use of energy-costly practices to modify the microclimate.

Sudden cold temperatures result in modulation of many genes and gene products. These genes and/or products are responsible for effects on traits such as plant vigor and seed yield.

Manipulation of one or more cold responsive gene activities is useful to modulate growth and development.

Heat Responsive Genes, Gene Components and Products

The ability to endure high temperatures is a major determinant of the geographical distribution and productivity of agricultural crops. Decreases in yield and crop failure frequently occur as a result of aberrant hot conditions even in areas considered suitable for the cultivation of a given species or cultivar. Only modest increases in the heat tolerance of crop species have a dramatic impact on agricultural productivity. The development of genotypes with increased heat tolerance provide a more reliable means to minimize crop losses and diminish the use of energy-costly practices to modify the microclimate.

Drought Responsive Genes, Gene Components and Products

The ability to endure drought conditions is a major determinant of the geographical distribution and productivity of agricultural crops. Decreases in yield and crop failure frequently occur as a result of aberrant drought conditions even in areas considered suitable for the cultivation of a given species or cultivar. Only modest increases in the drought tolerance of crop species have a dramatic impact on agricultural productivity. The development of genotypes with increased drought tolerance provide a more reliable means to minimize crop losses and diminish the use of energy-costly practices to modify the microclimate.

Wounding Responding Genes, Gene Components and Products

Plants are continuously subjected to various forms of wounding from physical attacks including the damage created by pathogens and pests, wind, and contact with other objects. Therefore, survival and agricultural yields depend on constraining the damage created by the wounding process and inducing defense mechanisms against future damage.

Plants have evolved complex systems to minimize and/or repair local damage and to minimize subsequent attacks by pathogens or pests or their effects. These involve stimulation of cell division and cell elongation to repair tissues, induction of programmed cell death to isolate damage caused mechanically and by invading pests and pathogens, and induction of long-range signaling systems to induce protecting molecules in case of future attack. The genetic and biochemical systems associated with responses to wounding are connected with those associated with other stresses such as pathogen attack and drought.

Wounding results in the modulation of activities of specific genes and, as a consequence, of the levels of key proteins and metabolites. These genes, called here wounding responsive genes, are important for minimizing the damage induced by wounding from pests, pathogens and other objects.

Methyl Jasmonate (Jasmonate) Responsive Genes, Gene Components and Products

Jasmonic acid and its derivatives, collectively referred to as jasmonates, are naturally occurring derivatives of plant lipids. These substances are synthesized from linolenic acid in a lipoxygenase-dependent biosynthetic pathway. Jasmonates are signalling molecules which are growth regulators as well as regulators of defense and stress responses. As such, jasmonates represent a separate class of plant hormones. Jasmonate responsive genes can be used to modulate plant growth and development.

Reactive Oxygen Responsive Genes, Gene Components and $H_2O_2$ Products

Often growth and yield are limited by the ability of a plant to tolerate stress conditions, including pathogen attack, wounding, extreme temperatures and various other factors. To combat such conditions, plant cells deploy a battery of inducible defense responses, including triggering an oxidative burst. The burst of reactive oxygen intermediates occurs in time, place and it plays a key role in either pathogen elimination and/or subsequent signaling of downstream defense functions. For example, $H_2O_2$ plays a key role in the pathogen resistance response, including initiating the hypersensitive response (HR). HR is correlated with the onset of systemic acquired resistance (SAR) to secondary infection in distal tissues and organs.

Reactive oxygen responsive genes are useful to modulate pathogen tolerance and/or resistance, Avr/R locus sensitivity, non-host sensitivity; HR, SAR, bacterial resistance, fungal resistance, virus or viroid resistance, insect resistance, nematodes, heavy metal tolerance and treatment of indications modulated by free radicals and cancer.

Salicylic Acid Responsive Genes, Gene Components and Products

Plant defense responses can be divided into two groups: constitutive and induced. Salicylic acid (SA) is a signaling molecule necessary for activation of the plant induced defense system known as systemic acquired resistance or SAR. This response, which is triggered by prior exposure to avirulent pathogens, is long lasting and provides protection against a broad spectrum of pathogens. Another induced defense system is the hypersensitive response (HR). HR is far more rapid, occurs at the sites of pathogen (avirulent pathogens) entry and precedes SAR. SA is also the key signaling molecule for this defense pathway.

SA genes are useful to modulate plant defense systems.

Nitric Oxide Responsive Genes, Gene Components and Products

The rate-limiting element in plant growth and yield is often its ability to tolerate suboptimal or stress conditions, including pathogen attack conditions, wounding and the presence of various other factors. To combat such conditions, plant cells deploy a battery of inducible defense responses, including synergistic interactions between nitric oxide (NO), reactive oxygen intermediates (ROS), and salicylic acid (SA). NO plays a critical role in the activation of innate immune and inflammatory responses in animals. At least part of this mammalian signaling pathway is present in plants, where NO potentiates the hypersensitive response (HR). In addition, NO is a stimulator molecule in plant photomorphogenesis.

Changes in nitric oxide concentration in the internal or surrounding environment, or in contact with a plant, results in modulation of many genes and gene products.

In addition, the combination of a nitric oxide responsive polynucleotide and/or gene product with other environmentally responsive polynucleotides is also useful because of the interactions that exist between hormone regulated pathways, stress pathways, pathogen stimulated pathways, nutritional pathways and development.

Nitric oxide responsive genes and gene products function either to increase or dampen the above phenotypes or activities either in response to changes in nitric oxide concentration or in the absence of nitric oxide fluctuations. More specifically, these genes and gene products modulate stress responses in an organism. In plants, these genes and gene products are useful for modulating yield under stress conditions. Measurements of yield include seed yield, seed size, fruit yield, fruit size, etc.

Osmotic Stress Responsive Genes, Gene Components and Products

The ability to endure and recover from osmotic and salt related stress is a major determinant of the geographical distribution and productivity of agricultural crops. Osmotic stress is a major component of stress imposed by saline soil and water deficit. Decreases in yield and crop failure frequently occur as a result of aberrant or transient environmental stress conditions even in areas considered suitable for the cultivation of a given species or cultivar. Only modest increases in the osmotic and salt tolerance of a crop species have a dramatic impact on agricultural productivity. The development of genotypes with increased osmotic tolerance provides a more reliable means to minimize crop losses and diminish the use of energy-costly practices to modify the soil environment. Thus, osmotic stress responsive genes are used to modulate plant growth and development.

Aluminum Responsive Genes, Gene Components and Products

Aluminum is toxic to plants in soluble form ($Al^{3+}$). Plants grown under aluminum stress have inhibited root growth and function due to reduced cell elongation, inhibited cell division and metabolic interference. As an example, protein inactivation frequently results from displacement of the $Mg^{2+}$ cofactor with aluminum. These types of consequences result in poor nutrient and water uptake. In addition, because stress perception and response occur in the root apex, aluminum exposure leads to the release of organic acids, such as citrate, from the root as the plant attempts to prevent aluminum uptake.

The ability to endure soluble aluminum is a major determinant of the geographical distribution and productivity of agricultural crops. Decreases in yield and crop failure frequently occur as a result of aberrant aluminum conditions even in areas considered suitable for the cultivation of a given species or cultivar. Only modest increases in the aluminum tolerance of crop species have a dramatic impact on agricultural productivity. The development of genotypes with increased aluminum tolerance provides a more reliable means to minimize crop losses and diminish the use of costly practices to modify the environment.

Cadium Responsive Genes, Gene Components and Products

Cadmium (Cd) has both toxic and non-toxic effects on plants. Plants exposed to non-toxic concentrations of cadmium are blocked for viral disease due to the inhibition of systemic movement of the virus. Surprisingly, higher toxic levels of Cd do not inhibit viral systemic movement, so that cellular factors that interfere with the viral movement are triggered by non-toxic Cd concentrations but repressed in high Cd concentrations. Furthermore, exposure to non-toxic Cd levels reverses posttranslational gene silencing, an inherent plant defense mechanism. Consequently, Cd responsive genes are useful for altering plant disease control in addition to improving soil bio-remediation and plant performance.

Disease Responsive Genes, Gene Components and Products

Often growth and yield are limited by the ability of a plant to tolerate stress conditions, including pathogen attack. To combat such conditions, plant cells deploy a battery of inducible defense responses, including the triggering of an oxidative burst and the transcription of pathogenesis-related protein (PR protein) genes. These responses depend on the recognition of a microbial avirulence gene product (avr) by a plant resistance gene product (R), and a series of downstream signaling events leading to transcription-independent and transcription-dependent disease resistance responses. Reactive oxygen species (ROS) such as $H_2O_2$ and NO from the oxidative burst play a signaling role, including initiation of the hypersensitive response (HR) and induction of systemic acquired resistance (SAR) to secondary infection by unrelated pathogens. PR proteins are able to degrade the cell walls of invading microorganisms, and phytoalexins are directly microbicidal.

Disease responsive genes and gene products are useful to modulate plant response to pathogen attack including bacteria, fungi, virus, insects and nematodes.

Defense (LOL2) Responsive Genes, Gene Components and Products

Often growth and yield are limited by the ability of a plant to tolerate stress conditions, including pathogen attack. To combat such conditions, plant cells deploy a battery of inducible defense responses, including the triggering of an oxidative burst and the transcription of pathogenesis-related protein (PR protein) genes. Reactive oxygen species (ROS) such as $H_2O_2$ and NO from the oxidative burst play a signaling role, including initiation of the hypersensitive response (HR) and induction of systemic acquired resistance (SAR) to secondary infection by unrelated pathogens. Some PR proteins are able to degrade the cell walls of invading microorganisms, and phytoalexins are directly microbicidal. Other defense related pathways are regulated by salicylic acid (SA) or methyl jasmonate (MeJ).

These responses depend on the recognition of a microbial avirulence gene product (avr) by a plant resistance gene product (R), and a series of downstream signaling events leading to transcription- independent and transcription-dependent disease resistance responses. R- gene-encoded receptors specifically interact with pathogen-encoded ligands to trigger a signal transduction cascade. Several components include ndr1 and eds1 loci. NDR1, EDS1, PR1, as well as PDF1.2, a MeJ regulated gene and Nim1, a SA regulated gene, are differentially regulated in plants with mutations in the LOL2 gene.

LOL2 shares a novel zinc finger motif with LSD1, a negative regulator of cell death and defense response. Due to an alternative splice site, the LOL2 gene encodes two different proteins, one of which contains an additional, putative DNA binding motif. Northern analysis demonstrates that LOL2 transcripts containing the additional DNA binding motif are predominantly upregulated after treatment with both virulent and avirulent *Pseudomonas syringae* pv maculicola strains. Modulation of this gene confers enhanced resistance to virulent and avirulent *Peronospora parasitica* isolates.

LOL2 responsive genes and gene products are useful to alter pathogen tolerance and/or resistance, including bacteria, fungus, virus, insects and nematodes.

Iron Responsive Genes, Gene Components and Products

Iron (Fe) deficiency in humans is the most prevalent nutritional problem worldwide today. Increasing iron availability via diet is a sustainable malnutrition solution for many of the world's nations. One-third of the world's soils, however, are iron deficient. Consequently, to form a food-based solution to iron malnutrition we need a better understanding of iron uptake, storage and utilization by plants. Furthermore, exposure to non-toxic Fe levels affects inherent plant defense mechanisms. Consequently, altering the expression of Fe response genes leads to an increase in plant disease resistance, in addition to improvements in human nutrition.

Shade Responsive Genes, Gene Components and Products

Plants sense the ratio of Red (R): Far Red (FR) light in their environment and respond differently to particular ratios. A low R:FR ratio, for example, enhances cell elongation and favors flowering over leaf production. The changes in R:FR ratios mimic and cause the shading response effects in plants. The response of a plant to shade in the canopy structures of agricultural crop fields influences crop yields significantly. Therefore manipulation of genes regulating the shade avoidance responses can improve crop yields.

While phytochromes mediate the shade avoidance response, the down-stream factors participating in this pathway are largely unknown. One potential downstream participant, ATHB-2, is a member of the HD-Zip class of transcription factors and shows a strong and rapid response to changes in the R:FR ratio. ATHB-2 overexpressors have a thinner root mass, smaller and fewer leaves and longer hypocotyls and petioles. This elongation arises from longer epidermal and cortical cells, and a decrease in secondary vascular tissues, paralleling the changes observed in wild-type seedlings grown under conditions simulating canopy shade.

On the other hand, plants with reduced ATHB-2 expression have a thick root mass and many larger leaves and shorter hypocotyls and petioles. Here, the changes in the hypocotyl result from shorter epidermal and cortical cells and increased proliferation of vascular tissue. Interestingly, application of Auxin is able to reverse the root phenotypic consequences of high ATHB-2 levels, restoring the wild-type phenotype. Consequently, given that ATHB-2 is tightly regulated by phytochrome, these data indicate that ATHB-2 links the Auxin and phytochrome pathways in the shade avoidance response pathway.

Shade responsive genes can be used to modulate plant growth and development.

Sulfur Responsive Genes, Gene Components and Products

Sulfur is one of the important macronutrients required by plants. It is taken up from the soil solution by roots as in the form of sulfate anion which higher plants are dependent on to fulfill their nutritional sulfur requirement. After uptake from the soil, sulfate is either accumulated and stored in vacuole or it is assimilated into various organic compounds, e.g. cysteine, glutathione, methionine, etc. Thus, plants also serve as nutritional sulfur sources for animals. Sulfur can be assimilated in one of two ways: it is either incorporated as sulfate in a reaction called sulfation, or it is first reduced to sulfide, the substrate for cysteine synthesis. In plants, majority of sulfur is assimilated in reduced form.

Sulfur comprises a small but vital fraction of the atoms in many protein molecules. As disulfide bridges, the sulfur atoms aid in stabilizing the folded proteins. Cys is the first sulfur-containing amino acid, which forms disulfide bonds that affects the tertiary structures in proteins and enzyme activities. This redox balance is mediated by the disulfide/thiol interchange of thioredoxin or glutaredoxin using NADPH as an electron donor. Sulfur can also become sulfhydryl (SH) groups participating in the active sites of some enzymes and some enzymes require the aid of small molecules that contain sulfur. In addition, the machinery of photosynthesis includes some sulfur-containing compounds, such as ferrodoxin. Thus, sulfate assimilation plays important roles not only in the sulfur nutrition but also in the ubiquitous process that may regulate the biochemical reactions of various metabolic pathways.

Sulfur deficiency leads to a marked chlorosis in younger leaves, which may become white in color. Other symptoms of sulfur deficiency includes weak stems and reduced growth. Adding sulfur fertilizer to plants can increase root development and a deeper green color of the leaves in sulfur-deficient plants. Sulfur, however, is generally sufficient in soils for two reasons: (1) it is a contaminant in potassium and other fertilizers and (2) is a product of industrial combustion. Sulfur limitation in plants is thus likely due to the limitation in uptake and distribution in plants.

Seven cell type specific sulfate transporter genes have been isolated from *Arabidopsis*. In sulfate-starved plants, expression of the high-affinity transporter, AtST1-1, is induced in root epidermis and cortex for acquisition of sulfur. The low affinity transporter, AtST2-1 (AST68), accumulates in the root vascular tissue by sulfate starvation for root-to-shoot transport of sulfate. These studies show that the whole-plant process of sulfate transport is coordinately regulated by the expression of these 2 sulfate transporter genes under sulfur limited conditions. Recent studies propose that feeding of O-acetylserine, GSH and selenate regulates the expression of AtST1-1 and AtST2-1 (AST68) in roots either positively or negatively. There are regulatory interactions between assimilatory sulfate and nitrate reduction in plants. The two assimilatory pathways are very similar and well coordinated; deficiency for one element represses the other pathway.

Manipulation of sulfur responsive genes improves plant nutrition, growth and development.

Zinc Responsive Genes, Gene Components and Products

Phytoremediation of soils contaminated with toxic levels of heavy metals requires the understanding of plant metal transport and tolerance. The numerous *Arabidopsis thaliana* studies give scientists the potential for dissection and elucidation of plant micronutrient/heavy metal uptake and accumulation pathways. Altered regulation of ZNT1, a Zn/Cd transporter, contributes to high Zn uptake. Isolation and characterization of Zn/Cd hyperaccumulation genes allows expression in higher biomass plant species for efficient contaminated soil clean up. Identification of additional Zn transport, tolerance and nutrition-related genes involved in heavy metal accumulation enables manipulation of increased uptake (for phytoremediation) as well as limitation of uptake or leak pathways that contribute to toxicity in crop plants. Additionally, Zn-binding ligands involved in Zn homeostasis or tolerance are identified, as well as factors affecting the activity or expression of Zn binding transcription factors.

Vigor Genes, Gene Components and Products

Great agronomic value can result from modulating the vigor of a plant as a whole, or of any one of a plants' organs.

Manipulation of genes, gene components and gene products that modulate plant vigor results in many traits of economic interest including increases in seed and fruit size and increases in lodging resistance.

Sterol Genes, Gene Components and Products

Sterols are essential for all eukaryotes. In contrast to animal and fungal cells which contain only one major sterol, plant cells synthesize a complex array of different sterol compounds in which sitosterol, stigmasterol and 24-methylcholesterol are the major constituents. Sitosterol and 24-methylcholesterol affect membrane fluidity and permeability in plant cell membranes in a similar manner to the way cholesterol affects membrane fluidity and permeability in mammalian cell membranes. Plant sterols can also modulate the activity of membrane-bound enzymes. Stigmasterol is required for cell proliferation. Sterols are synthesized from the isoprenoid pathway originating with mevalonate. The branch point into sterols occurs via squalene.

Sterol genes are useful to modulate plant growth and development.

Branching Genes, Gene Components and Products

Modulating the amount of branches in a plant is useful to alter the plant architecture for ornamental or economic reasons.

The branching genes elucidated here increase or decrease the number of branches in a plant and thereby regulate many traits from ornamental plant shape to increased yield, including biomass, fruit or seed yield.

Brittle-Snap Responsive Genes, Gene Components and Products

Brittle-snap is a phenomenon also referred to as greensnap or mid-season stalk breakage. This phenomenon is exemplified when rapidly growing corn stalks that are bent by a low tool bar become subject to breakage from wind as well as other physical phenomenon such as cultivation, tilling, or anhydrous N application. Corn is most vulnerable during the seven- to ten-day period prior to tasseling. Preliminary data based on laboratory analyses indicate that plant hybrids with either higher rates of lignification or higher lignin content as mature plants are more prone to brittle-snap. Economic consequences can be severe. For example, severe thunderstorms on Jul. 8, 1993, and Jul. 1, 1994 resulted in brittle-snap over a large portion of Nebraska's corn production area. Estimated losses were $200 million in Nebraska from the 1993 storm alone.

Brittle snap genes are useful to modulate plant yield.

pH Stress Responsive Genes, Gene Components and Products

Extreme soil pH conditions have a major influence on mineral nutrient uptake that is required to sustain plant growth and maximize plant yields. Plants exposed to low pH soil conditions develop deficiencies in nutrients such as phosphate, copper, molybdenum, potassium, sulfur, and nitrogen. Plants exposed to high pH soil conditions develop phosphate, iron, copper, manganese, and zinc deficiencies. Phosphate is the only nutrient that becomes limiting in both acidic and alkaline soils. Phosphate is a critical nutrient not just for plants, but for all organisms. Phosphorous is necessary for life-dependent molecules such as ATP, nucleic acids, and phospholipids and it also regulates carbon-amino acid metabolic function.

pH Stress genes are useful to modulate plant growth and development.

3. The Genes of the Invention

The sequences of the invention were isolated from *Arabidopsis thaliana*, corn, soybean, wheat, *Brassica* and others as noted in the Tables.

4. Use of the Genes to make Transgenic Plants

To use the sequences of the present invention or a combination of them or parts and/or mutants and/or fusions and/or variants of them, recombinant DNA constructs are prepared which comprise the polynucleotide sequences of the invention inserted into a vector, and which are suitable for transformation of plant cells. The construct is made using standard recombinant DNA techniques (Sambrook et al. 1989) and is introduced to the species of interest by *Agrobacterium*-mediated transformation or by other means of transformation as referenced below.

The vector backbone is any of those typical in the art such as plasmids, viruses, artificial chromosomes, BACs, YACs and PACs and vectors of the sort described by
(a) BAC: Shizuya et al., Proc. Natl. Acad. Sci. USA 89: 8794-8797 (1992); Hamilton et al., Proc. Natl. Acad. Sci. USA 93: 9975-9979 (1996);
(b) YAC: Burke et al., Science 236:806-812 (1987);
(c) PAC: Stemberg N. et al., Proc Natl Acad Sci U S A. Jan;87(1):103-7 (1990);
(d) Bacteria-Yeast Shuttle Vectors: Bradshaw et al., Nucl Acids Res 23: 4850-4856 (1995);
(e) Lambda Phage Vectors: Replacement Vector, e.g., Frischauf et al., J. Mol Biol 170: 827-842 (1983); or Insertion vector, e.g., Huynh et al., In: Glover NM (ed) DNA Cloning: A practical Approach, Vol.1 Oxford: IRL Press (1985); T-DNA gene fusion vectors :Walden et al., Mol Cell Biol 1: 175-194 (1990); and
(g) Plasmid vectors: Sambrook et al., infra.

Typically, the construct comprises a vector containing a sequence of the present invention with any desired transcriptional and/or translational regulatory sequences, such as promoters, UTRs, and 3' end termination sequences. Vectors can also include origins of replication, scaffold attachment regions (SARs), markers, homologous sequences, introns, etc. The vector may also comprise a marker gene that confers a selectable phenotype on plant cells. The marker may encode biocide resistance, particularly antibiotic resistance, such as resistance to kanamycin, G418, bleomycin, hygromycin, or herbicide resistance, such as resistance to chlorosulfuron or phosphinotricin.

A plant promoter fragment is used that directs transcription of the gene in all tissues of a regenerated plant and/or is a constitutive promoter, such as 35S. Alternatively, the plant promoter directs transcription of a sequence of the invention in a specific tissue (tissue-specific promoter) or is otherwise under more precise environmental control (inducible promoter).

If proper polypeptide production is desired, a polyadenylation region at the 3'-end of the coding region is typically included. The polyadenylation region is derived from the natural gene, from a variety of other plant genes, or from T-DNA.

Knock-In Constructs

Ectopic expression of the sequences of the invention is also accomplished using a "knock-in" approach. Here, the first component, an "activator line," is created by generating a transgenic plant comprising a transcriptional activator operatively linked to a promoter. The second component comprises the desired cDNA sequence operatively linked to the target binding sequence/region of the transcriptional activator. The second component is transformed into the "activator line" or is used to transform a host plant to produce a "target" line that is crossed with the "activator line" by ordinary breeding methods. In either case, the result is the same. That is, the promoter drives production of the transcriptional activator protein that then binds to the target binding region to facilitate expression of the desired cDNA.

Any promoter that functions in plants is used in the first component, such as the 35S Cauliflower Mosaic Virus promoter or a tissue or organ specific promoter. Suitable transcriptional activator polypeptides include, but are not limited to, those encoding HAP 1 and GAL4. The binding sequence recognized and targeted by the selected transcriptional activator protein is used in the second component.

Transformation

Techniques for transforming a wide variety of higher plant species are well known and described in the technical and scientific literature. See, e.g. Weising et al., *Ann. Rev. Genet.* 22:421 (1988); and Christou, Euphytica, v. 85, n.1-3:13-27, (1995).

The person skilled in the art knows processes for the transformation of monocotyledonous and dicotyledonous plants. A variety of techniques are available for introducing DNA into a plant host cell. These techniques comprise transformation of plant cells by DNA injection, DNA electroporation, use of bolistics methods, protoplast fusion and via T-DNA using *Agrobacterium tumefaciens* or *Agrobacterium rhizogenes*, as well as further possibilities.

DNA constructs of the invention are introduced into the genome of the desired plant host by a variety of conventional techniques. For example, the DNA construct is introduced directly into the genomic DNA of the plant cell using techniques such as electroporation, microinjection and polyethylene glycol precipitation of plant cell protoplasts or protoplast fusion. Electroporation techniques are described in Fromm et al. *Proc. Natl Acad. Sci.* USA 82:5824 (1985). Microinjection techniques are known in the art and well described in the scientific and patent literature. The plasmids do not have to fulfill specific requirements for use in DNA electroporation or DNA injection into plant cells. Simple plasmids such as pUC derivatives can be used.

The introduction of DNA constructs using polyethylene glycol precipitation is described in Paszkowski et al. *EMBO J.* 3:2717 (1984). Introduction of foreign DNA using protoplast fusion is described by Willmitzer (Willmitzer, L., 1993 Transgenic plants. In: Biotechnology, A Multi-Volume Comprehensive Treatise (H. J. Rehm, G. Reed, A. Pühler, P. Stadler, eds.), Vol. 2, 627-659, VCH Weinheim-New York-Basel-Cambridge).

Alternatively, the DNA constructs of the invention are introduced directly into plant tissue using ballistic methods, such as DNA particle bombardment. Ballistic transformation techniques are described in Klein et al. *Nature* 327:773 (1987). Introduction of foreign DNA using ballistics is described by Willmitzer (Willmitzer, L., 1993 Transgenic plants. In: Biotechnology, A Multi-Volume Comprehensive Treatise (H. J. Rehm, G. Reed, A. Pühler, P. Stadler, eds.), Vol. 2, 627-659, VCH Weinheim-New York-Basel-Cambridge).

DNA constructs are also introduced with the help of *Agrobacteria*. The use of *Agrobacteria* for plant cell transformation is extensively examined and sufficiently disclosed in the specification of EP-A 120 516, and in Hoekema (In: The Binary Plant Vector System Offsetdrukkerij Kanters B. V., Alblasserdam (1985), Chapter V), Fraley et al. (Crit. Rev. Plant. Sci. 4, 1-46) and An et al. (EMBO J. 4 (1985), 277-287). Using this technique, the DNA constructs of the invention are combined with suitable T-DNA flanking regions and introduced into a conventional *Agrobacterium tumefaciens* host vector. The virulence functions of the *Agrobacterium tumefaciens* host direct the insertion of the construct and adjacent marker(s) into the plant cell DNA when the cell is infected by the bacteria (McCormac et al., 1997, *Mol. Biotechnol.* 8:199; Hamilton, 1997, *Gene* 200:107; Salomon et al., 1984 *EMBO J.* 3:141; Herrera-Estrella et al., 1983 *EMBO J.* 2:987). *Agrobacterium tumefaciens*-mediated transformation techniques, including disarming and use of binary or co-integrate vectors, are well described in the scientific literature. See, for example Hamilton, CM., *Gene* 200:107 (1997); Müller et al. *Mol. Gen. Genet.* 207:171 (1987); Komari et al. *Plant J.* 10:165 (1996); Venkateswarlu et al. *Biotechnology* 9:1103 (1991) and Gleave, A P., *Plant Mol.*

Biol. 20:1203 (1992); Graves and Goldman, *Plant Mol. Biol.* 7:34 (1986) and Gould et al., *Plant Physiology* 95:426 (1991).

For plant cell T-DNA transfer of DNA, plant explants, plant cells that have been cultured in suspension or protoplasts are co-cultivated with *Agrobacterium tumefaciens* or *Agrobacterium rhizogenes*. Whole plants are regenerated from the infected plant material using a suitable medium that contains antibiotics or biocides for the selection of transformed cells. . Plants obtained in this way are then examined for the presence of the DNA introduced. The transformation of dicotyledonous plants via Ti-plasmid-vector systems and *Agrobacterium tumefaciens* is well established.

Monocotyledonous plants are also transformed by means of *Agrobacterium* based vectors (See Chan et al., Plant Mol. Biol. 22 (1993), 491-506; Hiei et al., Plant J. 6 (1994), 271-282; Deng et al., Science in China 33 (1990), 28-34; Wilmink et al., Plant Cell Reports 11 (1992), 76-80; May et al., Bio/Technology 13 (1995), 486-492; Conner and Domisse; Int. J. Plant Sci. 153 (1992), 550-555; Ritchie et al., Transgenic Res. 2 (1993), 252-265). Maize transformation in particular is described in the literature (see, for example, WO95/06128, EP 0 513 849; EP 0 465 875; Fromm et al., Biotechnology 8 (1990), 833-844; Gordon-Kamm et al., Plant Cell 2 (1990), 603-618; Koziel et al., Biotechnology 11 (1993), 194-200). In EP 292 435 and in Shillito et al. (1989, Bio/Technology 7, 581) fertile plants are obtained from a mucus-free, soft (friable) maize callus. Prioli and Sondahl (1989, Bio/Technology 7, 589) also report regenerating fertile plants from maize protoplasts of the maize Cateto inbred line, Cat 100-1.

Other cereal species have also been successfully transformed, such as barley (Wan and Lemaux, see above; Ritala et al., see above) and wheat (Nehra et al., 1994, Plant J. 5, 285-297).

Alternatives to *Agrobacterium* transformation for monocotyledonous plants are ballistics, protoplast fusion, electroporation of partially permeabilized cells and use of glass fibers (See Wan and Lemaux, Plant Physiol. 104 (1994), 37-48; Vasil et al., Bio/Technology 11 (1993), 1553-1558; Ritala et al., Plant Mol. Biol. 24 (1994), 317-325; Spencer et al., Theor. Appl. Genet. 79 (1990), 625-631)).

Introduced DNA is usually stable after integration into the plant genome and is transmitted to the progeny of the transformed cell or plant. Generally the transformed plant cell contains a selectable marker that makes the transformed cells resistant to a biocide or an antibiotic such as kanamycin, G 418, bleomycin, hygromycin, phosphinotricin or others. Therefore, the individually chosen marker should allow the selection of transformed cells from cells lacking the introduced DNA.

The transformed cells grow within the plant in the usual way (McCormick et al., 1986, Plant Cell Reports 5 , 81-84) and the resulting plants are cultured normally. Transformed plant cells obtained by any of the above transformation techniques are cultured to regenerate a whole plant that possesses the transformed genotype and thus the desired phenotype. Such regeneration techniques rely on manipulation of certain phytohormones in a tissue culture growth medium, typically relying on a biocide and/or herbicide marker that has been introduced together with the desired nucleotide sequences.

Plant regeneration from cultured protoplasts is described in Evans et al., *Protoplasts Isolation and Culture* in "Handbook of Plant Cell Culture," pp. 124-176, MacMillan Publishing Company, New York, 1983; and Binding, *Regeneration of Plants, Plant Protoplasts*, pp. 21-73, CRC Press, Boca Raton, 1988. Regeneration also occurs from plant callus, explants, organs, or parts thereof. Such regeneration techniques are described generally in Klee et al. *Ann. Rev. of plant Phys.* 38:467 (1987). Regeneration of monocots (rice) is described by Hosoyama et al. (*Biosci. Biotechnol. Biochem.* 58:1500 (1994)) and by Ghosh et al. (*J. Biotechnol.* 32:1 (1994)).

Seeds are obtained from the plants and used for testing stability and inheritance. Generally, two or more generations are cultivated to ensure that the phenotypic feature is stably maintained and transmitted.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The nucleic acids of the invention are used to confer the trait of increased yield, on essentially any plant.

The nucleotide sequences according to the invention generally encode an appropriate protein from any organism, in particular from plants, fungi, bacteria or animals. The sequences preferably encode proteins from plants or fungi. Preferably, the plants are higher plants, in particular starch or oil storing useful plants, such as potato or cereals such as rice, maize, wheat, barley, rye, triticale, oat, millet, etc., as well as spinach, tobacco, sugar beet, soya, cotton etc.

In principle, the process according to the invention can be applied to any plant. Therefore, monocotyledonous as well as dicotyledonous plant species are particularly suitable. The process is preferably used with plants that are interesting for agriculture, horticulture and/or forestry. Examples are vegetable plants such as cucumber, melon, pumpkin, eggplant, zucchini, tomato, spinach, cabbage species, peas, beans, etc., as well as fruits such as pears, apples, etc.

Thus, the invention has use over a broad range of plants, including species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna*, and, *Zea*.

Microarray Analysis

A major way that a cell controls its response to internal or external stimuli is by regulating the rate of transcription of specific genes. For example, the differentiation of cells during organogenensis into forms characteristic of the organ is associated with the selective activation and repression of large numbers of genes. Thus, specific organs, tissues and cells are functionally distinct due to the different populations of mRNAs and protein products they possess. Internal signals program the selective activation and repression programs. For example, internally synthesized hormones produce such signals. The level of hormone is raised by increasing the level of transcription of genes encoding proteins concerned with hormone synthesis.

To measure how a cell reacts to internal and/or external stimuli, individual mRNA levels are measured and used as an indicator for the extent of transcription of the gene. Cells are exposed to a stimulus, and mRNA isolated and assayed at different time points after stimulation. The mRNA from the stimulated cells is compared to control cells that are not stimulated. The mRNA levels that are higher in the stimulated cell versus the control indicate a stimulus-specific response of the cell. The same is true of mRNA levels that are lower in stimulated cells versus the control condition.

Similar studies are performed with cells taken from an organism with a defined mutation in its genome as compared with cells without the mutation. Altered mRNA levels in the mutated cells indicate how the mutation causes transcriptional changes. These transcriptional changes are associated with the phenotype that the mutated cells exhibit that is different from the phenotype exhibited by the control cells.

Applicants use microarray techniques to measure the levels of mRNAs in cells from mutant plants, stimulated plants, and/or cells selected from specific organs. Microarray techniques are also used to measure the levels of mRNAs in cells from plants transformed with the polynucleotides of the invention. In this case, transformants with the genes of the invention are grown to an appropriate stage, and tissue samples prepared for the microarray differential expression analysis.

Microarray Experimental Procedure and Results
Procedures
1. Sample Tissue Preparation Tissue samples for each of the expression analysis experiments are prepared as follows:

(a) Abscissic acid (ABA)

Seeds of *Arabidopsis thaliana* (ecotype Wassilewskija) are sown in trays and left at 4° C. for 4 days to vernalize. They are then transferred to a growth chamber having grown 16 hr light/8 hr dark, 13,000 LUX, 70% humidity, and 20° C. and watered twice a week with 1 L of 1× Hoagland's solution. Approximately 1,000 14 day old plants are sprayed with 200-250 mls of 100 µM ABA in a 0.02% solution of the detergent Silwet L-77. Whole seedlings, including roots, are harvested within a 15 to 20 minute time period at 1 hr and 6 hr after treatment, flash-frozen in liquid nitrogen and stored at −80° C.

Seeds of maize hybrid 35A (Pioneer) are sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats are watered every three days for 7 days. Seedlings are carefully removed from the sand and placed in 1-liter beakers with 100 µM ABA for treatment. Control plants are treated with water. After 6 hr and 24 hr, aerial and root tissues are separated and flash frozen in liquid nitrogen prior to storage at −80° C.

(b) Ap2

Seeds of *Arabidopsis thaliana* (ecotype Landesberg erecta) and floral mutant apetala2 (Jofuku et al., 1994, Plant Cell 6:1211-1225) are sown in pots and left at 4° C. for two to three days to vernalize. They are then transferred to a growth chamber. Plants are grown under long-day (16 hr light, 8 hr dark) conditions 7000-8000 LUX light intensity, 70% humidity and 22° C. temperature. Inflorescences containing immature floral buds (stages 1-7; Bowman, 1994) as well as the inflorescence meristem are harvested and flashfrozen. Polysomal polyA+RNA is isolated from tissue according to Cox and Goldberg, 1988).

(c) *Arabidopsis* Endosperm mea/mea Fruits 0-10 mm

Seeds of *Arabidopsis thaliana* heterozygous for the fertilization-independent endosperm1(fie1) [Ohad et al., 1996; ecotype Landsberg erecta (Ler)] are sown in pots and left at 4° C. for two to three days to vernalize. Kiyosue et al. (1999) subsequently determined that fie1 was allelic to the gametophytic maternal effect mutant medea (Grossniklaus et al., 1998). Imbibed seeds are then transferred to a growth chamber. Plants are grown under long-day (16 hr light: 8 hr dark) conditions, 7000-8000 LUX light intensity, 70% humidity, and 22° C. temperature. 1-2 siliques (fruits) bearing developing seeds just prior to dessication [9 days after flowering (DAF)] are selected from each plant and are hand-dissected to identify wild-type, mea/+ heterozygotes, and mea/mea homozygous mutant plants. At this stage, homozygous mea/mea plants produce short siliques that contain >70% aborted seed and can be distinguished from those produced by wild-type (100% viable seed) and mea/+ heterozygous (50% viable seed) plants (Ohad et al., 1996; Grossniklaus et al., 1998; Kiyosue et al., 1999). Siliques 0-10 mm in length containing developing seeds 0-9 DAF produced by homozygous mea/mea plants are harvested and flash frozen in liquid nitrogen.

Pods 0-10 mm (Control Tissue for Sample 70)

Seeds of *Arabidopsis thaliana* heterozygous for the fertilization-independent endosperm1 (fie1) [Ohad et al., 1996; ecotype Landsberg erecta (Ler)] are sown in pots and left at 4° C. for two to three days to vernalize. Kiyosue et al. (1999) subsequently determined that fie1 was allelic to the gametophytic maternal effect mutant medea (Grossniklaus et al., 1998). Imbibed seeds are then transferred to a growth chamber. Plants are grown under long-day (16 hr light: 8 hr dark) conditions, 7000-8000 LUX light intensity, 70% humidity, and 22° C. temperature. 1-2 siliques (fruits) bearing developing seeds just prior to dessication [9 days after flowering (DAF)] are selected from each plant and are hand-dissected to identify wild-type, mea/+ heterozygotes, and mea/mea homozygous mutant plants. At this stage, homozygous mea/mea plants produce short siliques that contain >70% aborted seed and can be distinguished from those produced by wild-type (100% viable seed) and mea/+ heterozygous (50% viable seed) plants (Ohad et al., 1996; Grossniklaus et al., 1998; Kiyosue et al., 1999). Siliques 0-10 mm in length containing developing seeds 0-9 DAF produced by segregating wild-type plants are opened and the seeds removed. The remaining tissues (pods minus seed) are harvested and flash frozen in liquid nitrogen.

(d) *Arabidopsis* Seeds

Fruits (pod+seed) 0-5 mm

Seeds of *Arabidopsis thaliana* (ecotype Wassilewskija) are sown in pots and left at 4° C. for two to three days to vernalize. They are then transferred to a growth chamber. Plants are grown under long-day (16 hr light: 8 hr dark) conditions, 7000-8000 LUX light intensity, 70% humidity, and 22° C. temperature. 3-4 siliques (fruits) bearing developing seeds are selected from at least 3 plants and are hand-dissected to determine what developmental stage(s) is represented by the enclosed embryos. Description of the stages of *Arabidopsis* embryogenesis used in this determination were summarized by Bowman (1994). Silique lengths are then determined and used as an approximate determinant for embryonic stage. Siliques 0-5 mm in length containing post fertilization through pre-heart stage [0-72 hours after fertilization (HAF)] embryos are harvested and flash frozen in liquid nitrogen.

Fruits(pod+seed) 5-10 mm

Seeds of *Arabidopsis thaliana* (ecotype Wassilewskija) are sown in pots and left at 4° C. for two to three days to vernalize. They are then transferred to a growth chamber. Plants are grown under long-day (16 hr light: 8 hr dark) conditions, 7000-8000 LUX light intensity, 70% humidity, and 22° C. temperature. 3-4 siliques (fruits) bearing developing seeds were selected from at least 3 plants and are hand-dissected to determine what developmental stage(s) are represented by the enclosed embryos. Description of the stages of *Arabidopsis* embryogenesis used in this determination are summarized by Bowman (1994). Silique lengths are then determined and used as an approximate determinant for embryonic stage. Siliques 5-10 mm in length containing heart—through early upturned-U-stage [72-120 hours after fertilization (HAF)] embryos are harvested and flash frozen in liquid nitrogen.

Fruits(pod+seed) >10 mm

Seeds of *Arabidopsis thaliana* (ecotype Wassilewskija) are sown in pots and left at 4° C. for two to three days to vernalize. They are then transferred to a growth chamber. Plants are grown under long-day (16 hr light: 8 hr dark) conditions, 7000-8000 LUX light intensity, 70% humidity, and 22° C. temperature. 3-4 siliques (fruits) bearing developing seeds are selected from at least 3 plants and were hand-dissected to determine what developmental stage(s) are represented by the enclosed embryos. Description of the stages of *Arabidopsis* embryogenesis used in this determination were summarized by Bowman (1994). Silique lengths are then determined and used as an approximate determinant for embryonic stage. Siliques >10 mm in length containing green, late upturned-U-stage [>120 hours after fertilization (HAF)-9 days after flowering (DAF)] embryos are harvested and flash frozen in liquid nitrogen.

Green Pods 5-10 mm (Control Tissue for Samples 72-74)

Seeds of *Arabidopsis thaliana* (ecotype Wassilewskija) are sown in pots and left at 4° C. for two to three days to vernalize. They are then transferred to a growth chamber. Plants are grown under long-day (16 hr light: 8 hr dark) conditions, 7000-8000 LUX light intensity, 70% humidity, and 22° C. temperature. 3-4 siliques (fruits) bearing developing seeds are selected from at least 3 plants and are hand-dissected to determine what developmental stage(s) are represented by the enclosed embryos. Description of the stages of *Arabidopsis* embryogenesis used in this determination are summarized by Bowman (1994). Silique lengths are then determined and used as an approximate determinant for embryonic stage. Green siliques 5-10 mm in length containing developing seeds 72-120 hours after fertilization (HAF)] are opened and the seeds removed. The remaining tissues (green pods minus seed) were harvested and flash frozen in liquid nitrogen.

Green Seeds from Fruits >10 mm

Seeds of *Arabidopsis thaliana* (ecotype Wassilewskija) are sown in pots and left at 4° C. for two to three days to vernalize. They are then transferred to a growth chamber. Plants are grown under long-day (16 hr light: 8 hr dark) conditions, 7000-8000 LUX light intensity, 70% humidity, and 22° C. temperature. 3-4 siliques (fruits) bearing developing seeds are selected from at least 3 plants and are hand-dissected to determine what developmental stage(s) are represented by the enclosed embryos. Description of the stages of *Arabidopsis* embryogenesis used in this determination were summarized by Bowman (1994). Silique lengths are then determined and used as an approximate determinant for embryonic stage. Green siliques >10 mm in length containing developing seeds up to 9 days after flowering (DAF)] are opened and the seeds removed and harvested and flash frozen in liquid nitrogen.

Brown Seeds from Fruits >10 mm

Seeds of *Arabidopsis thaliana* (ecotype Wassilewskija) are sown in pots and left at 4° C. for two to three days to vernalize. They are then transferred to a growth chamber. Plants are grown under long-day (16 hr light: 8 hr dark) conditions, 7000-8000 LUX light intensity, 70% humidity, and 22° C. temperature. 3-4 siliques (fruits) bearing developing seeds are selected from at least 3 plants and are hand-dissected to determine what developmental stage(s) are represented by the enclosed embryos. Description of the stages of *Arabidopsis* embryogenesis used in this determination were summarized by Bowman (1994). Silique lengths are then determined and used as an approximate determinant for embryonic stage. Yellowing siliques >10 mm in length containing brown, desiccating seeds >11 days after flowering (DAF)] are opened and the seeds removed and harvested and flash frozen in liquid nitrogen.

Green/Brown Seeds from Fruits >10 mm

Seeds of *Arabidopsis thaliana* (ecotype Wassilewskija) are sown in pots and left at 4° C. for two to three days to vernalize. They were then transferred to a growth chamber. Plants are grown under long-day (16 hr light: 8 hr dark) conditions, 7000-8000 LUX light intensity, 70% humidity, and 22° C. temperature. 3-4 siliques (fruits) bearing developing seeds are selected from at least 3 plants and are hand-dissected to determine what developmental stage(s) are represented by the enclosed embryos. Description of the stages of *Arabidopsis* embryogenesis used in this determination were summarized by Bowman (1994). Silique lengths are then determined and used as an approximate determinant for embryonic stage. Green siliques >10 mm in length containing both green and brown seeds >9 days after flowering (DAF)] are opened and the seeds removed and harvested and flash frozen in liquid nitrogen.

Mature Seeds (24 hours after imbibition)

Mature dry seeds of *Arabidopsis thaliana* (ecotype Wassilewskija) are sown onto moistened filter paper and left at 4° C. for two to three days to vernalize. Imbibed seeds are then transferred to a growth chamber [16 hr light: 8 hr dark conditions, 7000-8000 LUX light intensity, 70% humidity, and 22° C. temperature], the emerging seedlings harvested after 48 hours and flash frozen in liquid nitrogen.

Mature Seeds (Dry)

Seeds of *Arabidopsis thaliana* (ecotype Wassilewskija) are sown in pots and left at 4° C. for two to three days to vernalize. They are then transferred to a growth chamber. Plants are grown under long-day (16 hr light: 8 hr dark) conditions, 7000-8000 LUX light intensity, 70% humidity, and 22° C. temperature and taken to maturity. Mature dry seeds are collected, dried for one week at 28° C., and vernalized for one week at 4° C. before use as a source of RNA.

Ovules(Ler-pi)

Seeds of *Arabidopsis thaliana* heterozygous for pistillata (pi) (ecotype Landsberg erecta (Ler)) are sown in pots and left at 4° C. for two to three days to vernalize. They are then transferred to a growth chamber. Plants are grown under long-day (16 hr light: 8 hr dark) conditions, 7000-8000 LUX light intensity, 76% humidity, and 24° C. temperature. Inflorescences are harvested from seedlings about 40 days old. The inflorescences are cut into small pieces and incubated in the following enzyme solution (pH 5) at room temperature for 0.5-1 hr.: 0.2% pectolyase Y-23, 0.04% pectinase, 5 mM MES, 3% Sucrose and MS salts (1900 mg/l $KNO_3$, 1650 mg/l $NH_4NO_3$, 370 mg/l $MgSO_4$. 7 $H_2O$, 170 mg/l $KH_2PO_4$, 440 mg/l $CaCl_2$. 2 $H_2O$, 6.2 mg/l $H_3BO_3$, 15.6 mg/l $MnSO_4$. 4 $H_2O$, 8.6 mg/l $ZnSO_4$. 7 $H_2O$, 0.25 mg/l $NaMoO_4$. 2 $H_2O$, 0.025 mg/l $CuCO_4$. 5 $H_2O$, 0.025 mg/l $CoCl_2$. 6 $H_2O$, 0.83 mg/l KI, 27.8 mg/l $FeSO_4$. 7 $H_2O$, 37.3 mg/l Disodium EDTA, pH 5.8). At the end of the incubation the mixture of inflorescence material and enzyme solution is passed through a size 60 sieve and then through a sieve with a pore size of 125 μm. Ovules greater than 125 μm in diameter are collected, rinsed twice in B5 liquid medium (2500 mg/l $KNO_3$, 250 mg/l $MgSO_4$. 7 $H_2O$, 150 mg/l $NaH2PO4$. $H_2O$, 150 mg/l $CaCl_2$. 2 $H_2O$, 134 mg/l $(NH4)2$ $CaCl_2$. $SO_4$, 3 mg/l $H_3BO_3$, 10 mg/l $MnSO_4$. 4 $H_2O$, 2 $ZnSO_4$. 7 $H_2O$, 0.25 mg/l $NaMoO_4$. 2 $H_2O$, 0.025 mg/l $CuCO_4$. 5 $H_2O$, 0.025 mg/l $CoCl_2$. 6 $H_2O$, 0.75 mg/l KI, 40 mg/l EDTA sodium ferric salt, 20 g/l sucrose, 10 mg/l Thiamine hydrochloride, 1 mg/l Pyridoxine hydrochloride, 1 mg/l Nicotinic acid, 100 mg/l myo-inositol, pH 5.5)), rinsed once in deionized water and flash frozen in liquid nitrogen. The supernatant from the 125 gm sieving is passed through subsequent sieves of 50 μm and 32 μm. The tissue retained in the 32 μm sieve is collected and mRNA prepared for use as a control.

(e) Auxin Responsive (NAA)

Seeds of *Arabidopsis thaliana* (ecotype Wassilewskija) are sown in trays and left at 4° C. for 4 days to vernalize. They are then transferred to a growth chamber having 16 hr light/8 hr dark, 13,000 LUX, 70% humidity, 20° C. and watered twice a week with 1 L of 1× Hoagland's solution (recipe recited in Feldmann et al., (1987) Mol. Gen. Genet. 208: 1-9 and described as complete nutrient solution). Approximately 1,000 14 day old plants are spayed with 200-250 mls of 100 μM NAA in a 0.02% solution of the detergent Silwet L-77. Aerial tissues (everything above the soil line) are harvested within a 15 to 20 minute time period 1 hr and 6 hrs after treatment, flash-frozen in liquid nitrogen and stored at −80° C.

Seeds of maize hybrid 35A (Pioneer) are sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats are watered every three days for 7 days. Seedlings are carefully removed from the sand and placed in 1-liter beakers with 100 μM NAA for treatment. Control plants are treated with water. After 6 hr and 24 hr, aerial and root tissues are separated and flash frozen in liquid nitrogen prior to storage at −80° C.

(f) Brassinosteroid Responsive (Br, Bz)

Two separate experiments are performed, one with epi-brassinolide and one with the brassinosteroid biosynthetic inhibitor brassinazole. In the epi-brassinolide experiments, seeds of wild-type *Arabidopsis thaliana* (ecotype Wassilewskija) and the brassinosteroid biosynthetic mutant dwf4-1 are sown in trays and left at 4° C. for 4 days to vernalize. They are then transferred to a growth chamber having 16 hr light/8 hr dark, 11,000 LUX, 70% humidity and 22° C. temperature. Four week old plants are spayed with a 1 lM solution of epi-brassinolide and shoot parts (unopened floral primordia and shoot apical meristems) harvested three hours later. Tissue is flash-frozen in liquid nitrogen and stored at −80° C.

In the brassinazole experiments, seeds of wild-type *Arabidopsis thaliana* (ecotype Wassilewskija) are grown as described above. Four week old plants are sprayed with a 1 μM solution of brassinazole and shoot parts (unopened floral primordia and shoot apical meristems) harvested three hours later. Tissue is flash-frozen in liquid nitrogen and stored at −80° C.

In addition to the spray experiments, tissue is prepared from two different mutants; (1) a dwf4-1 knock out mutant and (2) a mutant overexpressing the dwf4-1 gene Seeds of wild-type *Arabidopsis thaliana* (ecotype Wassilewskija) and of the dwf4-1 knock out and overexpressor mutants are sown in trays and left at 4° C. for 4 days to vernalize. They are then transferred to a growth chamber having 16 hr light/8 hr dark, 11,000 LUX, 70% humidity and 22° C. temperature. Tissue from shoot parts (unopened floral primordia and shoot apical meristems) is flash-frozen in liquid nitrogen and stored at −80° C.

Another experiment is completed with seeds of *Arabidopsis thaliana* (ecotype Wassilewskija) that are sown in trays and left at 4° C. for 4 days to vernalize. They are then transferred to a growth chamber. Plants are grown under long-day (16 hr light: 8 hr. dark) conditions, 13,000 LUX light intensity, 70% humidity, 20° C. temperature and watered twice a week with 1 L 1× Hoagland's solution (recipe recited in Feldmann et al., (1987) Mol. Gen. Genet. 208: 1-9 and described as complete nutrient solution). Approximately 1,000 14 day old plants are spayed with 200-250 mls of 0.1 μM Epi-Brassinolite in 0.02% solution of the detergent Silwet L-77. At 1 hr. and 6 hrs. after treatment aerial tissues are harvested within a 15 to 20 minute time period and flash-frozen in liquid nitrogen.

Seeds of maize hybrid 35A (Pioneer) are sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats are watered every three days for 7 days. Seedlings are carefully removed from the sand and placed in 1-liter beakers with 0.1 μM epi-brassinolide for treatment. Control plants are treated with distilled deionized water. After 24 hr, aerial and root tissues are separated and flash frozen in liquid nitrogen prior to storage at −80° C.

(g) CS237

CS237 is an ethylene triple response mutant that is insensitive to ethylene and which has an etr1-1 phenotype. *Arabidopsis thaliana* CS237 seeds are vernalized at 4° C. for 3 days before sowing. Aerial tissue is collected from mutants and wild-type Columbia ecotype plants, flash frozen in liquid nitrogen and stored at −80° C.

(h) CS6630

*Arabidopsis thaliana* (ecotype Wassilewskija) seeds are vernalized at 4° C. for 3 days before sowing on MS media (1%) sucrose on bactor-agar. Roots and shoots are separated 14 days after germination, flash frozen in liquid nitrogen and stored at −80° C.

(i) CS6632

Seedlings are grown on regular MS (1% sucrose) bacto-agar. 14 day old seedlings (days after germination) roots and shoots are separated and flash frozen in liquid N2.

(j) CS6632 Shoots-Roots

Seedlings are grown on regular MS (1% sucrose) bacto-agar.14 day old seedlings (days after germination) roots and shoots were separated and flash frozen in liquid N2.

(k) CS6879-Shoots-Roots

Seedlings are grown vertically on regular MS (1% sucrose) bacto agar plates for 14 days. The roots are then isolated, flash frozen and RNA isolated.

(l) CS8548

RNA from wild-type and mutant whole plants is prepared and compared.

(m) Caf

Carple factory (Caf) is a double-stranded RNAse protein that is hypothesized to process small RNAs in *Arabidopsis*. The protein is closely related to a Drosophila protein named DICER that functions in the RNA degradation steps of RNA interference. *Arabidopsis thaliana* Caf mutant seeds are vernalized at 4° C. for 3 days before sowing in flats of MetroMix 200. Flats are placed in the greenhouse, watered and grown to the 8 leaf, pre-flower stage. Stems and rosette leaves are harvested from the mutants and the wild-type segregants, flash frozen and stored at −80° C.

(n) Cold (8 deg)

Sterilized *Arabidopsis thaliana* (ecotype Wassilewskija) seeds are kept at 4° C. in dark for three days and carefully spread on 0.5×MS plates by dispersing ~300-500 seeds on agar surface. Plates are left to dry in the hood for 15-20 min. and then sealed with micropore tape. Plates are placed in a Percival growth chamber set at 22C, 16 h light/8 h dark. By day 7 (9AM), half of plates are moved into another Percival growth chamber whose setting is identical to the previous one except that the temperature is set to 8° C. Plants are gently pulled out from plates and harvested/frozen at 2 hrs, 4 hrs, 8 hrs, 2 days, 4 days, 7 days, 9 days and 11 days after transfer. Samples kept in the 22° C. chamber are harvested at the same time as the cold-treated samples.

(o) Cold Shock Treatment

Seeds of *Arabidopsis thaliana* (ecotype Wassilewskija) are sown in trays and left at 4° C. for three days to vernalize before being transferred to a growth chamber having 16 hr light/8 hr dark, 12,000-14,000 LUX, 20° C. and 70% humidity. Fourteen day old plants are transferred to a 4° C. dark growth chamber and aerial tissues are harvested 1 hour and 6 hours later. Control plants are maintained at 20° C. and covered with foil to avoid exposure to light. Tissues are flash-frozen in liquid nitrogen and stored at 80° C.

Seeds of maize hybrid 35A (Pioneer) are sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats are watered every three days for 7 days. Seedlings are carefully removed from the sand and placed in 1-liter beakers containing 4° C. water for treatment. Control plants are treated with water at 25° C. After 1 hr and 6 hr aerial and root tissues are separated and flash frozen in liquid nitrogen prior to storage at −80° C.

(p) Cytokinin (BA)

Seeds of *Arabidopsis thaliana* (ecotype Wassilewskija) are sown in trays and left at 4° C. for 4 days to vernalize. They are then transferred to a growth chamber having 16 hr light/8 hr dark, 13,000 LUX, 70% humidity, 20° C. temperature and watered twice a week with 1 L of 1× Hoagland's solution. Approximately 1,000 14 day old plants are spayed with 200-250 mls of 100 tM BA in a 0.02% solution of the detergent Silwet L-77. Aerial tissues (everything above the soil line) are harvested within a 15 to 20 minute time period 1 hr and 6 hrs after treatment, flash-frozen in liquid nitrogen and stored at −80° C.

Seeds of maize hybrid 35A (Pioneer) are sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings are carefully removed from the sand and placed in 1-liter beakers with 100 μM BA for treatment. Control plants are treated with water. After 6 hr, aerial and root tissues are separated and flash frozen in liquid nitrogen prior to storage at −80° C.

(q) Diversity Expt

Sterilized and wild-type *Arabidopsis thaliana* seeds (ecotype Wassilewskija) and wild-type *Arabis holboellii* seeds are sown in MS boxes (0.5% sucrose, 1.5% agar) after 3day-cold treatment. The boxes are placed horizontally in a Percival growth chamber (16:8 light cycles, 22° C.) so that hypocotyls grow upward. The hypocotyls are harvested after 7 d in the chamber, flash-frozen in liquid nitrogen and stored at −80° C.

(r) DMT-II

Demeter (dmt) is a mutant of a methyl transferase gene and is similar to fie. *Arabidopsis thaliana* (ecotype Wassilewskija) seeds are vernalized at 4° C. for 3 days before sowing. Cauline leaves and closed flowers are isolated from 35S::DMT and dmt −/− plant lines, flash frozen in liquid nitrogen and stored at −80° C.

(s) Drought Reproduction

*Arabidopsis thaliana* (ecotype Wassilewskija) seeds are kept at 4° C. in dark for three days and then sown in soil mix (Metromix 200) with a regular watering schedule (1.5-2 L per flat per week). Drought treatment by withholding water starts when plants are 30-days-old. The control samples are watered as before. Rosettes, flowers (with siliques less than 5 mm) and siliques (>5 mm) are harvested separately on day 5, 7 and 10 post-drought-treatment (PDT). By day 10 PDT, the majority of drought plants are wilted and unable to recover after re-watering and the experiment is terminated. The samples are harvested between 2-5 PM. Plants are grown in a walk-in growth chamber under these conditions: 16 h light/8 hr dark, 70% relative humidity, 20° C. light/18° C. dark for the first 10 days, and under 22° C. light/20° C. dark for the following days.

(t) Drought Stress

Seeds of *Arabidopsis thaliana* (ecotype Wassilewskija) are sown in pots and left at 4° C. for three days to vernalize before being transferred to a growth chamber having 16 hr light/8 hr dark, 150,000-160,000 LUX, 20° C. and 70% humidity. After 14 days, aerial tissues are cut and left to dry on 3 MM Whatman paper in a petri-plate for 1 hour and 6 hours. Aerial tissues exposed for 1 hour and 6 hours to 3 MM Whatman paper wetted with 1× Hoagland's solution serve as controls. Tissues are harvested, flash-frozen in liquid nitrogen and stored at −80° C.

Alternatively, *Arabidopsis thaliana* (ecotype Wassilewskija) seed is vernalized at 4° C. for 3 days before sowing in Metromix soil type 350. Flats are placed in a growth chamber with 23° C., 16 hr light/8 hr. dark, 80% relative humidity, ~13,000 LUX for germination and growth. Plants are watered with 1-1.5 L of water every four days. Watering is stopped 16 days after germination for the treated samples, but continues for the control samples. Rosette leaves and stems, flowers and siliques are harvested 2 d, 3 d, 4 d, 5 d, 6 d and 7 d after watering is stopped. Tissue is flash frozen in liquid nitrogen and kept at −80° C. until RNA is isolated. Flowers and siliques are also harvested on day 8 from plants that had undergone a 7 d drought treatment followed by 1 day of watering. Control plants (whole plants) are harvested after 5 weeks, flash frozen in liquid nitrogen and stored as above.

Seeds of maize hybrid 35A (Pioneer) are sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats are watered every three days for 7 days. Seedlings are carefully removed from the sand and placed in empty 1-liter beakers at room temperature for treatment. Control plants are placed in water. After 1 hr, 6 hr, 12 hr and 24 hr aerial and root tissues are separated and flash frozen in liquid nitrogen prior to storage at −80° C.

(u) Far-Red-Enriched-Adult

Wildtype *Arabidopsis thaliana* (ecotype Columbia) seeds are planted on soil and vernalized for 4 days at 4° C. Soil sown plants are grown in a growth room (16 h light/8 h dark, 22° C.; 4 bulbs total alternating Gro-Lux and cool whites); light measurements are as follows: Red=330.9 μW/cm$^2$, Blue=267 μW/cm$^2$, Far Red=56.1 μW/cm$^2$. At 4 weeks after germination, the soil pots are transferred to shade environment (16 h light/8 h dark; Red=376 μW/cm$^2$, Blue=266 μW/cm$^2$, Far Red=552 μW/cm$^2$) for various durations of exposure time (1, 4, 8, 16, 24, 48, and 72 hrs). After timed exposure, above ground tissue is flash frozen with liquid nitrogen and stored at −80° C. Control seedlings are not transferred, but are collected at the same time as corresponding shade-exposed experimental samples.

(v) Far-Red-Induction

Seeds from wildtype *Arabidopsis thaliana* (ecotype Columbia) are vernalized in sterile water for 4 days at 4° C. prior to planting. Seeds are then sterilized and evenly planted on 0.5% sucrose MS media plates. Plates are sealed with Scotch micropore tape to allow for gas exchange and prevent contamination. Plates are grown in a growth room (16 h light/8 h dark, 22° C.; 6 bulbs total Gro-Lux); light measurements are as follows: Red=646.4 µW/cm², Blue=387 µW/cm², Far Red=158.7 µW/cm². At 7 days after germination, the plates containing the seedlings are transferred to Far Red light only (Far Red=525 µW/cm²) for various durations of exposure time (1, 4, 8, and 24 hrs). After timed exposure, tissue is flash frozen with liquid nitrogen and stored at −80° C. Control seedlings are not transferred, but are collected at same time as the corresponding far-red exposed experimental samples.

(w) Far-Red-Induction-Adult

Wildtype *Arabidopsis thaliana* (ecotype Columbia) seeds are planted on soil and vernalized for 4 days at 4° C. Soil sown plants are grown in a growth room (16 h light/8 h dark, 22° C.; 4 bulbs total alternating Gro-Lux and cool whites); light measurements are as follows: Red=330.9 µW/cm², Blue=267 µW/cm², Far Red=56.1 µW/cm². At 4 weeks after germination, the soil pots are transferred to shade environment (16h light/8 h dark; Red=376 µW/cm², Blue=266 µW/cm², Far Red=552 µW/cm²) for various durations of exposure time (1, 4, 8, 16, 24, 48, and 72 hrs). After timed exposure, above ground tissue is flash frozen with liquid nitrogen and stored at −80° C. Control seedlings are not transferred, but are collected at same time as the corresponding shade-exposed experimental samples.

(x) Flowers (Green, White or Buds)

Approximately 10 µl of *Arabidopsis thaliana* seeds (ecotype Wassilewskija) are sown on 350 soil (containing 0.03% marathon) and vernalized at 4C for 3 days. Plants are then grown at room temperature under fluorescent lighting until flowering. Flowers are harvested after 28 days in three different categories. Buds that had not opened at all and are completely green are categorized as "flower buds" (also referred to as green buds by the investigator). Buds that had started to open, with white petals emerging slightly are categorized as "green flowers" (also referred to as white buds by the investigator). Flowers that are mostly opened (with no silique elongation) with white petals completely visible are categorized as "white flowers" (also referred to as open flowers by the investigator). Buds and flowers are harvested with forceps, flash frozen in liquid nitrogen and stored at −80° C. until RNA is isolated.

(y) Germination

*Arabidopsis thaliana* seeds (ecotype Wassilewskija) is sterilized in bleach and rinsed with sterile water. The seeds are placed in 100 mm petri plates containing soaked autoclaved filter paper. Plates are foil-wrapped and left at 4° C. for 3 nights to vernalize. After cold treatment, the foil is removed and plates are placed into a growth chamber having 16 hr light/8 hr dark cycles, 23° C., 70% relative humidity and ~11,000 lux. Seeds are collected 1 d, 2 d, 3 d and 4 d later, flash frozen in liquid nitrogen and stored at −80° C. until RNA is isolated.

(z) Gibberillic Acid (GA)

Seeds of *Arabidopsis thaliana* (ecotype Wassilewskija) are sown in trays and left at 4° C. for 4 days to vernalize. They are then transferred to a growth chamber having 16 hr light/8 hr. dark, 13,000 LUX, 70% humidity, 20° C. and watered twice a week with 1 L of 1× Hoagland's solution. Approximately 1,000 14 day old plants are sprayed with 200-250 mls of 100 µM gibberillic acid in a 0.02% solution of the detergent Silwet L-77. At 1 hr. and 6 hrs. after treatment, aerial tissues (everything above the soil line) are harvested within a 15 to 20 minute time period, flash-frozen in liquid nitrogen and stored at 80° C.

Alternatively, seeds of *Arabidopsis thaliana* (ecotype Ws) are sown in Metro-mix soil type 350 and left at 4° C. for 3 days to vernalize. They are then transferred to a growth chamber having 16 hr light/8 hr dark, 13,000 LUX, 80% humidity, 20° C. temperature and watered every four days with 1.5 L water. Fourteen (14) days after germination, plants are sprayed with 100 µM gibberillic acid or with water. Aerial tissues are harvested 1 hr 6 hrs 12 hrs and 24 hrs post-treatment, flash frozen and stored at −80° C.

Seeds of maize hybrid 35A (Pioneer) are sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats are watered every three days for 7 days. Seedlings are carefully removed from the sand and placed in 1-liter beakers with 100 µM gibberillic acid for treatment. Control plants are treated with water. After 1 hr, 6 hr and 12 hr, aerial and root tissues were separated and flash frozen in liquid nitrogen prior to storage at −80° C.

(aa) Guard Cells

*Arabidopsis thaliana* (ecotype Wassilewskija) seeds are vernalized at 4° C. for 3 days before sowing. Leaves are harvested, homogenized and centrifuged to isolate the guard cell containing fraction. Homogenate from leaves served as the control. Samples are flash frozen in liquid nitrogen and stored at −80° C. Identical experiments using leaf tissue from canola are performed.

(bb) Heat Shock Treatment

Seeds of *Arabidopsis thaliana* (ecotype Wassilewskija) are sown in trays and left at 4° C. for three days to vernalize before being transferred to a growth chamber with 16 hr light/8 hr dark, 12,000-14,000 LUX, 70% humidity and 20° C., fourteen day old plants are transferred to a 42° C. growth chamber and aerial tissues are harvested 1 hr and 6 hr after transfer. Control plants are left at 20° C. and aerial tissues are harvested. Tissues are flash-frozen in liquid nitrogen and stored at −80° C.

Seeds of maize hybrid 35A (Pioneer) are sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats are watered every three days for 7 days. Seedlings are carefully removed from the sand and placed in 1-liter beakers containing 42° C. water for treatment. Control plants are treated with water at 25° C. After 1 hr and 6 hr aerial and root tissues are separated and flash frozen in liquid nitrogen prior to storage at −80° C.

(cc) Herbicide Treatment

*Arabidopsis thaliana* (ecotype Wassilewskija) seeds are sterilized for 5 min. with 30% bleach, 50 µl Triton in a total volume of 50 ml. Seeds are vernalized at 4° C. for 3 days before being plated onto GM agar plates at a density of about 144 seeds per plate. Plates are incubated in a Percival growth chamber having 16 hr light/8 hr dark, 80% relative humidity, 22° C. and 11,000 LUX for 14 days.

Plates are sprayed (~0.5 mls/plate) with water, Finale (1.128 g/L), Glean (1.88 g/L), RoundUp (0.01 g/L) or Trimec (0.08 g/L). Tissue is collected and flash frozen in liquid nitrogen at the following time points: 0, 1, 2, 4, 8, 12, and 24 hours. Frozen tissue is stored at −80° C. prior to RNA isolation.

(dd) Imbibed Seed

Seeds of maize hybrid 35A (Pioneer) are sown in water-moistened sand in covered flats (10 rows, 5-6 seed/row) and covered with clear, plastic lids before being placed in a growth chamber having 16 hr light (25° C.)/8 hr dark (20° C.), 75% relative humidity and 13,000-14,000 LUX. One day after sowing, whole seeds are flash frozen in liquid nitrogen prior to storage at −80° C. Two days after sowing, embryos and endosperm are isolated and flash frozen in liquid nitrogen prior to storage at −80° C. On days 3-6, aerial tissues, roots and endosperm are isolated and flash frozen in liquid nitrogen prior to storage at −80° C.

(ee) Interploidy Crosses

Interploidy crosses involving a 6x parent are lethal. Crosses involving a 4x parent are complete and analyzed. The imbalance in the maternal/paternal ratio produced from the cross can lead to big seeds. *Arabidopsis thaliana* (ecotype Wassilewskija) seeds are vernalized at 4° C. for 3 days before sowing. Small siliques are harvested at 5 days after pollination, flash frozen in liquid nitrogen and stored at −80° C.

(ff) Leaf Mutant 3642:

Mutant 3642 is a recessive mutation that causes abnormal leaf development. The leaves of mutant 3642 plants are characterized by leaf twisting and irregular leaf shape. Mutant 3642 plants also exhibit abnormally shaped floral organs which results in reduced fertility.

Seed segregating for the mutant phenotype are sown in Metro-mix 350 soil and grown in a Conviron growth chamber with watering by sub-irrigation twice a week. Environmental conditions are set at 20 degrees Celsius, 70% humidity with an 8 hour day, 16 hour night light regime. Plants are harvested after 4 weeks of growth and the entire aerial portion of the plant is harvested and immediately frozen in liquid nitrogen and stored at −80° C. Mutant phenotype plants are harvested separately from normal phenotype plants, which serve as the control tissue.

(gg) Line Comparisons

Alkaloid 35S over-expressing lines are used to monitor the expression levels of terpenoid/alkaloid biosynthetic and P450 genes to identify the transcriptional regulatory points in the biosynthesis pathway and the related P450 genes. *Arabidopsis thaliana* (ecotype Wassilewskija) seeds are vernalized at 4° C. for 3 days before sowing in vermiculite soil (Zonolite) supplemented by Hoagland solution. Flats are placed in Conviron growth chambers under long day conditions (16 hr light, 23° C. /8 hr dark, 20° C.). Basta spray and selection of the overexpressing lines is conducted about 2 weeks after germination. Approximately 2-3 weeks after bolting (approximately 5-6 weeks after germination), aerial portions (e.g. stem and siliques) from the over-expressing lines and from wild-type plants are harvested, flash frozen in liquid nitrogen and stored at −80° C.

(hh) Methyl Jasmonate (MeJ)

Seeds of *Arabidopsis thaliana* (ecotype Wassilewskija) are sown in trays and left at 4° C. for 4 days to vernalize before being transferred to a growth chamber having 16 hr light/8 hr. dark, 13,000 LUX, 70% humidity, 20° C. temperature and watered twice a week with 1 L of a 1× Hoagland's solution. Approximately 1,000 14 day old plants are sprayed with 200-250 mls of 0.001% methyl jasmonate in a 0.02% solution of the detergent Silwet L-77. At 1 hr and 6 hrs after treatment, whole seedlings, including roots, are harvested within a 15 to 20 minute time period, flash-frozen in liquid nitrogen and stored at −80° C.

Seeds of maize hybrid 35A (Pioneer) are sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats are watered every three days for 7 days. Seedlings are carefully removed from the sand and placed in 1-liter beakers with 0.001% methyl jasmonate for treatment. Control plants are treated with water. After 24 hr, aerial and root tissues are separated and flash frozen in liquid nitrogen prior to storage at −80° C.

(ii) Nitric Oxide Treatment (NaNP)

Seeds of *Arabidopsis thaliana* (ecotype Wassilewskija) are sown in trays and left at 4° C. for three days to vernalize before being transferred to a growth chamber having 16 hr light/8 hr dark, 12,000-14,000 LUX, 20° C. and 70% humidity. Fourteen day old plants are sprayed with 5 mM sodium nitroprusside in a 0.02% Silwett L-77 solution. Control plants are sprayed with a 0.02% Silwett L-77 solution. Aerial tissues are harvested 1 hour and 6 hours after spraying, flash-frozen in liquid nitrogen and stored at −80° C.

Seeds of maize hybrid 35A (Pioneer) are sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats are watered every three days for 7 days. Seedlings are carefully removed from the sand and placed in 1-liter beakers with 5 mM nitroprusside for treatment. Control plants are treated with water. After 1 hr, 6 hr and 12 hr, aerial and root tissues are separated and flash frozen in liquid nitrogen prior to storage at −80° C.

(jj) Nitrogen: Low to High

*Arabidopsis thaliana* (ecotype Wassilewskija) seeds are sown on flats containing 4 L of a 1:2 mixture of Grace Zonolite vermiculite and soil. Flats are watered with 3 L of water and vernalized at 4° C. for five days. Flats are placed in a Conviron growth chamber having 16 hr light/8 hr dark at 20° C., 80% humidity and 17,450 LUX. Flats are watered with approximately 1.5 L of water every four days. Mature, bolting plants (24 days after germination) are bottom treated with 2 L of either a control (100 mM mannitol pH 5.5) or an experimental (50 mM ammonium nitrate, pH 5.5) solution. Roots, leaves and siliques are harvested separately 30, 120 and 240 minutes after treatment, flash frozen in liquid nitrogen and stored at −80° C.

Hybrid maize seed (Pioneer hybrid 35A19) are aerated overnight in deionized water. Thirty seeds are plated in each flat, which contained 4 liters of Grace zonolite vermiculite. Two liters of water are bottom fed and flats were kept in a Conviron growth chamber with 16 hr light/8 hr dark at 20° C. and 80% humidity. Flats are watered with 1 L of tap water every three days. Five day old seedlings are treated as described above with 2 L of either a control (100 mM mannitol pH 6.5) solution or 1 L of an experimental (50 mM ammonium nitrate, pH 6.8) solution. Fifteen shoots per time point per treatment are harvested 10, 90 and 180 minutes after treatment, flash frozen in liquid nitrogen and stored at −80° C.

Alternatively, seeds of *Arabidopsis thaliana* (ecotype Wassilewskija) are left at 4° C. for 3 days to vernalize. They are then sown on vermiculite in a growth chamber having 16 hours light/8 hours dark, 12,000-14,000 LUX, 70% humidity, and 20° C. They are bottom-watered with tap water, twice weekly. Twenty-four days old plants are sprayed with either water (control) or 0.6% ammonium nitrate at 4 µL/cm² of tray surface. Total shoots and some primary roots are cleaned of vermiculite, flash-frozen in liquid nitrogen and stored at −80° C.

(kk) Nitrogen High to Low

Wild type *Arabidopsis thaliana* seeds (ecotype Wassilewskija) are surface sterilized with 30% Clorox, 0.1% Triton X-100 for 5 minutes. Seeds are then rinsed with 4-5 exchanges of sterile double distilled deionized water. Seeds are vernalized at 4° C. for 2-4 days in darkness. After cold treatment, seeds are plated on modified 1× MS media (without $NH_4NO_3$ or $KNO_3$), 0.5% sucrose, 0.5 g/L MES pH5.7, 1% phytagar and supplemented with KNO3 to a final concentration of 60 mM (high nitrate modified 1× MS media). Plates are then grown for 7 days in a Percival growth chamber at 22° C. with 16 hr. light/8 hr dark.

Germinated seedlings are then transferred to a sterile flask containing 50 mL of high nitrate modified 1× MS liquid media. Seedlings are grown with mild shaking for 3 additional days at 22° C. in 16 hr. light/8 hr dark (in a Percival growth chamber) on the high nitrate modified 1× MS liquid media.

After three days of growth on high nitrate modified 1× MS liquid media, seedlings are transferred either to a new sterile flask containing 50 mL of high nitrate modified 1× MS liquid media or to low nitrate modified 1× MS liquid media (containing 20 μM $KNO_3$). Seedlings are grown in these media conditions with mild shaking at 22° C. in 16 hr light/8 hr dark for the appropriate time points and whole seedlings harvested for total RNA isolation via the Trizol method (LifeTech.). The time points used for the microarray experiments are 10 min. and 1 hour time points for both the high and low nitrate modified 1× MS media.

Alternatively, seeds that are surface sterilized in 30% bleach containing 0.1% Triton X-100 and further rinsed in sterile water, are planted on MS agar, (0.5% sucrose) plates containing 50 mM $KNO_3$ (potassium nitrate). The seedlings are grown under constant light (3500 LUX) at 22° C. After 12 days, seedlings are transferred to MS agar plates containing either 1 mM $KNO_3$ or 50 mM $KNO_3$. Seedlings transferred to agar plates containing 50 mM $KNO_3$ are treated as controls in the experiment. Seedlings transferred to plates with 1 mM $KNO_3$ are rinsed thoroughly with sterile MS solution containing 1 mM $KNO_3$. There are ten plates per transfer. Root tissue was collected and frozen in 15 mL Falcon tubes at various time points which included 1 hour, 2 hours, 3 hours, 4 hours, 6 hours, 9 hours, 12 hours, 16 hours, and 24 hours.

Maize 35A19 Pioneer hybrid seeds are sown on flats containing sand and grown in a Conviron growth chamber at 25° C., 16 hr light/8 hr dark, ~13,000 LUX and 80% relative humidity. Plants are watered every three days with double distilled deionized water. Germinated seedlings are allowed to grow for 10 days and are watered with high nitrate modified 1× MS liquid media (see above). On day 11, young corn seedlings are removed from the sand (with their roots intact) and rinsed briefly in high nitrate modified 1× MS liquid media. The equivalent of half a flat of seedlings is then submerged (up to their roots) in a beaker containing either 500 mL of high or low nitrate modified 1× MS liquid media (see above for details).

At appropriate time points, seedlings are removed from their respective liquid media, the roots separated from the shoots and each tissue type flash frozen in liquid nitrogen and stored at −80° C. This is repeated for each time point. Total RNA is isolated using the Trizol method (see above) with root tissues only.

Corn root tissues isolated at the 4 hr and 16 hr time points are used for the microarray experiments. Both the high and low nitrate modified 1× MS media are used.

(ll) Osmotic Stress (PEG)

Seeds of *Arabidopsis thaliana* (ecotype Wassilewskija) are sown in trays and left at 4° C. for three days to vernalize before being transferred to a growth chamber having 16 hr light/8 hr dark, 12,000-14,000 LUX, 20° C., and 70% humidity. After 14 days, the aerial tissues are cut and placed on 3 MM Whatman paper in a petri-plate wetted with 20% PEG (polyethylene glycol-Mr 8,000) in 1× Hoagland's solution. Aerial tissues on 3 MM Whatman paper containing 1× Hoagland's solution alone serve as the control. Aerial tissues are harvested at 1 hour and 6 hours after treatment, flash-frozen in liquid nitrogen and stored at −80° C.

Seeds of maize hybrid 35A (Pioneer) are sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats are watered every three days for 7 days. Seedlings are carefully removed from the sand and placed in 1-liter beakers with 20% PEG (polyethylene glycol-Mr 8,000) for treatment. Control plants are treated with water. After 1 hr and 6 hr aerial and root tissues are separated and flash frozen in liquid nitrogen prior to storage at −80° C.

Seeds of maize hybrid 35A (Pioneer) are sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats are watered every three days for 7 days. Seedlings are carefully removed from the sand and placed in 1-liter beakers with 150 mM NaCl for treatment. Control plants were treated with water. After 1 hr, 6hr, and 24 hr aerial and root tissues are separated and flash frozen in liquid nitrogen prior to storage at −80° C.

(mm) Oxidative Stress—Hydrogen Peroxide Treatment ($H_2O_2$)

Seeds of *Arabidopsis thaliana* (ecotype Wassilewskija) are sown in trays and left at 4° C. for three days to vernalize before being transferred to a growth chamber having 16 hr light/8 hr dark, 12,000-14,000 LUX, 20° C. and 70% humidity. Fourteen day old plants are sprayed with 5 mM $H_2O_2$ (hydrogen peroxide) in a 0.02% Silwett L-77 solution. Control plants are sprayed with a 0.02% Silwett L-77 solution. Aerial tissues are harvested 1 hour and 6 hours after spraying, flash-frozen in liquid nitrogen and stored at −80° C.

Seeds of maize hybrid 35A (Pioneer) are sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats are watered every three days for 7 days. Seedlings are carefully removed from the sand and placed in 1-liter beakers with 5 mM $H_2O_2$ for treatment. Control plants are treated with water. After 1 hr, 6 hr and 24 hr, aerial and root tissues are separated and flash frozen in liquid nitrogen prior to storage at −80° C.

(nn) Petals

*Arabidopsis thaliana* (ecotype Wassilewskija) seeds are vernalized at 4° C. for 3 days before sowing in flats containing vermiculite soil. Flats are watered placed at 20° C. in a Conviron growth chamber having 16 hr light/8 hr dark. Whole plants (used as the control) and petals from inflorescences 23-25 days after germination are harvested, flash frozen in liquid nitrogen and stored at −80° C.

(oo) Pollen

*Arabidopsis thaliana* (ecotype Wassilewskija) seeds are vernalized at 4° C. for 3 days before sowing in flats containing vermiculite soil. Flats are watered and placed at 20° C. in a Conviron growth chamber having 16 hr light/8 hr dark. Whole plants (used as controls) and pollen from plants 38 dap is harvested, flash frozen in liquid nitrogen and stored at −80° C.

(pp) Protein Degradation

*Arabidopsis thaliana* (ecotype Wassilewskija) wild-type and 13B12-1 (homozygous) mutant seed are sown in pots containing Metro-mix 350 soil and incubated at 4° C. for four days. Vernalized seeds are germinated in the greenhouse (16 hr light/8 hr dark) over a 7 day period. Mutant seedlings are sprayed with 0.02% (active ingredient) Finale to confirm their transgenic standing. Plants were grown until the mutant phenotype (either multiple pistils in a single flower and/or multiple branching per node) is apparent. Young inflorescences immediately forming from the multiple-branched stems are cut and flash frozen in liquid nitrogen. Young inflorescences from wild-type plants grown in parallel and under identical conditions are collected as controls. All collected tissue is stored at −80° C. until RNA isolation.

(qq) Roots

Seeds of *Arabidopsis thaliana* (ecotype Wassilewskija) are sterilized in full strength bleach for less than 5 min., washed more than 3 times in sterile distilled deionized water and plated on MS agar plates. The plates are placed at 4° C. for 3 nights and then placed vertically into a growth chamber having 16 hr light/8 hr dark cycles, 23° C., 70% relative humidity and ~11,000 LUX. After 2 weeks, the roots are cut from the agar, flash frozen in liquid nitrogen and stored at −80° C.

(rr) Root Hairless Mutants

Plants mutant at the rhl gene locus lack root hairs. This mutation is maintained as a heterozygote.

Seeds of *Arabidopsis thaliana* (ecotype Landsberg erecta) mutated at the rhl gene locus are sterilized using 30% bleach with 1 ul/ml 20% Triton −X 100 and then vernalized at 4° C. for 3 days before being plated onto GM agar plates. Plates are placed in growth chamber with 16 hr light/8 hr. dark, 23° C., 14,500-15,900 LUX, and 70% relative humidity for germination and growth.

After 7 days, seedlings are inspected for root hairs using a dissecting microscope. Mutants are harvested and the cotyledons removed so that only root tissue remained. Tissue is then flash frozen in liquid nitrogen and stored at −80C.

*Arabidopsis thaliana* (Landsberg erecta) seedlings grown and prepared as above are used as controls.

Alternatively, seeds of *Arabidopsis thaliana* (ecotype Landsberg erecta), heterozygous for the rhl1 (root hairless) mutation, are surface-sterilized in 30% bleach containing 0.1% Triton X-100 and further rinsed in sterile water. They are then vernalized at 4° C. for 4 days before being plated onto MS agar plates. The plates are maintained in a growth chamber at 24° C. with 16 hr light/8 hr dark for germination and growth. After 10 days, seedling roots that expressed the phenotype (i.e. lacking root hairs) are cut below the hypocotyl junction, frozen in liquid nitrogen and stored at −80° C. Those seedlings with the normal root phenotype (heterozygous or wt) are collected as described for the mutant and used as controls.

(ss) Root Tips

Seeds of *Arabidopsis thaliana* (ecotype Wassilewskija) are placed on MS plates and vernalized at 4° C. for 3 days before being placed in a 25° C. growth chamber having 16 hr light/8 hr dark, 70% relative humidity and about 3 W/m$^2$. After 6 days, young seedlings are transferred to flasks containing B5 liquid medium, 1% sucrose and 0.05 mg/l indole-3-butyric acid. Flasks are incubated at room temperature with 100 rpm agitation. Media is replaced weekly. After three weeks, roots are harvested and incubated for 1 hr with 2% pectinase, 0.2% cellulase, pH 7 before straining through a #80 (Sigma) sieve. The root body material remaining on the sieve (used as the control) is flash frozen and stored at −80° C. until use. The material that passes through the #80 sieve is strained through a #200 (Sigma) sieve and the material remaining on the sieve (root tips) is flash frozen and stored at −80° C. until use. Approximately 10 mg of root tips are collected from one flask of root culture.

Seeds of maize hybrid 35A (Pioneer) are sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats are watered every three days for 8 days. Seedlings are carefully removed from the sand and the root tips (~2 mm long) are removed and flash frozen in liquid nitrogen prior to storage at −80° C. The tissues above the root tips (~1 cm long) are cut, treated as above and used as control tissue.

(tt) Rosette Leaves, Stems and Siliques

*Arabidopsis thaliana* (ecotype Wassilewskija) seed was vernalized at 4° C. for 3 days before sowing in Metro-mix soil type 350. Flats are placed in a growth chamber having 16 hr light/8 hr dark, 80% relative humidity, 23° C. and 13,000 LUX for germination and growth. After 3 weeks, rosette leaves, stems, and siliques are harvested, flash frozen in liquid nitrogen and stored at −80° C. until use. After 4 weeks, siliques (<5 mm, 5-10 mm and >10 mm) are harvested, flash frozen in liquid nitrogen and stored at −80° C. until use. Five week old whole plants (used as controls) are harvested, flash frozen in liquid nitrogen and kept at −80° C. until RNA is isolated.

(uu) Rough Sheath2-R (rs2-R) Mutants (1400-6/S-17)

This experiment is conducted to identify abnormally expressed genes in the shoot apex of rough sheath2-R (rs2-R) mutant plants. rs2 encodes a myb domain DNA binding protein that functions in repression of several shoot apical meristem expressed homeobox genes. Two homeobox gene targets are known for rs2 repression, rough sheath1, liguleless 3. The recessive loss of function phenotype of rs2-R homozygous plants is described in Schneeberger et al. 1998, *Development* 125: 2857-2865.

The seed stock genetically segregates 1:1 for rs2-R/rs2-R : rs2-R/+

Preparation of tissue samples: 160 seedlings pooled from 2 and 3 week old plants grown in sand. Growth conditions; Conviron #107 at 12 hr days/12 hr night, 25° C., 75% humidity. Shoot apex was dissected to include leaf three and older.

1) rough sheath2-R homozygous (mutant) shoot apex
2) rough sheath2-R heterozygous (wild-type, control) shoot apex.

(vv) rt1

The rt1 allele is a variation of rt1 rootless1 and is recessive. Plants displaying the rt1 phenotype have few or no secondary roots.

Seed from plants segregating for rt1 are sown on sand and placed in a growth chamber having 16 hr light/8 hr dark, 13,000 LUX, 70% humidity and 20° C. temperature. Plants are watered every three days with tap water. Eleven (11) day old seedlings are carefully removed from the sand, keeping the roots intact. rt1-type seedlings are separated from their wild-type counterparts and the root tissue isolated. Root tissue from normal seedlings (control) and rt1 mutants is flash frozen in liquid nitrogen and stored at −80° C. until use.

(ww) S4 Immature Buds Inflorescence Meristem

Seeds of *Arabidopsis thaliana* (ecotype Wassilewskija) are sown in pots and left at 4° C. for two to three days to vernalize. They are then transferred to a growth chamber. Plants are grown under long-day (16 hr light: 8 hr dark) conditions, 7000-8000 LUX light intensity, 70% humidity, and 22° C. temperature. Inflorescences containing immature floral buds [stages 1-12; Smyth et al., 1990] as well as the inflorescence meristem are harvested and flash frozen in liquid nitrogen (xx) S5 Flowers (Opened)

Seeds of *Arabidopsis thaliana* (ecotype Wassilewskija) are sown in pots and left at 4° C. for two to three days to vernalize. They are then transferred to a growth chamber. Plants are grown under long-day (16 hr light: 8 hr dark) conditions, 7000-8000 LUX light intensity, 70% humidity, and 22° C.

temperature. Mature, unpollinated flowers [stages 12-14; Smyth et al. 1990] are harvested and flash frozen in liquid nitrogen.

(yy) S6 Siliques (All Stages)

Seeds of *Arabidopsis thaliana* (ecotype Wassilewskija) are sown in pots and left at 4° C. for two to three days to vernalize. They are then transferred to a growth chamber. Plants are grown under long-day (16 hr light: 8 hr dark) conditions, 7000-8000 LUX light intensity, 70% humidity, and 22° C. temperature. Siliques bearing developing seeds containing post fertilization through pre-heart stage [0-72 hours after fertilization (HAF)], heart-through early curled cotyledon stage [72-120 HAF] and late-curled cotyledon stage [>120 HAF] embryos are harvested separately and pooled prior to RNA isolation in a mass ratio of 1:1:1. The tissues are then flash frozen in liquid nitrogen. Bowman (1994) reviews and provides a description of the stages of *Arabidopsis* embryogenesis used.

(zz) Salicylic Acid (SA)

Seeds of *Arabidopsis thaliana* (ecotype Wassilewskija) are sown in trays and left at 4° C. for 4 days to vernalize before being transferred to a growth chamber having 16 hr light/8 hr. dark, 13,000 LUX, 70% humidity, 20° C. temperature and watered twice a week with 1 L of a 1× Hoagland's solution. Approximately 1,000 14 day old plants are sprayed with 200-250 mls of 5 mM salicylic acid (solubilized in 70% ethanol) in a 0.02% solution of the detergent Silwet L-77. At 1 hr and 6 hrs after treatment, whole seedlings, including roots, are harvested within a 15 to 20 minute time period flash-frozen in liquid nitrogen and stored at −80° C.

Alternatively, seeds of wild-type *Arabidopsis thaliana* (ecotype Columbia) and mutant CS3726 are sown in soil type 200 mixed with osmocote fertilizer and Marathon insecticide and left at 4° C. for 3 days to vernalize. Flats are incubated at room temperature with continuous light. Sixteen days post germination plants are sprayed with 2 mM SA, 0.02% SilwettL-77 or control solution (0.02% SilwettL-77. Aerial parts or flowers were harvested 1 hr, 4 hr, 6 hr, 24 hr and 3 weeks post-treatment flash frozen and stored at −80° C.

Seeds of maize hybrid 35A (Pioneer) are sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats are watered every three days for 7 days. Seedlings are carefully removed from the sand and placed in 1-liter beakers with 2 mM SA for treatment. Control plants are treated with water. After 12 hr and 24 hr, aerial and root tissues are separated and flash frozen in liquid nitrogen prior to storage at −80° C.

(aaa) Salt

*Arabidopsis thaliana* (ecotype Wassilewskija) seeds are vernalized at 4° C. for 3 days before sowing in flats containing vermiculite soil. Flats are placed at 20° C. in a conviron growth chamber having 16 hr light/8 hr dark. Whole plants (used as controls) receive water. Other plants are treated with 100 mm nacl. After 6 hr and 72 hr, aerial and root tissues are harvested and flash frozen in liquid nitrogen prior to storage at −80° C.

(bbb) Shoots

Sterilized wild-type *Arabidopsis thaliana* seeds (ecotype Wassilewskija) are sown on MS plates (0.5% sucrose, 1.5% agar) after 3day-cold treatment. The plates are placed vertically in a Percival growth chamber (16:8 light cycles, 22° C.) so that roots grow vertically on the agar surface. The shoots or aerials, harvested after 7 d- and 14d-growth in the chamber, are used as the experimental samples. The control sample is derived from tissues harvested from 3 week-old plants that are grown in soil in a Conviron chamber (16:8 light cycles, 22° C.), including rosettes, roots, stems, flowers, and siliques.

(ccc) Shoot Apical Meristem (stm)

*Arabidopsis thaliana* (ecotype Landsberg erecta) plants mutant at the stm gene locus lack shoot meristems, produce aerial rosettes, have a reduced number of flowers per inflorescence, as well as a reduced number of petals, stamens and carpels, and is female sterile. This mutation is maintained as a heterozygote.

Seeds of *Arabidopsis thaliana* (ecotype Landsberg erecta) mutated at the stm locus are sterilized using 30% bleach with 1 ul/ml 20% Triton −X100. The seeds are vernalized at 4° C. for 3 days before being plated onto GM agar plates. Half are then put into a 22° C., 24 hr light growth chamber and half in a 24° C. 16 hr light/8 hr dark growth chamber having 14,500-15,900 LUX, and 70% relative humidity for germination and growth.

After 7 days, seedlings are examined for leaf primordia using a dissecting microscope. Presence of leaf primordia indicated a wild type phenotype. Mutants are selected based on lack of leaf primordia. Mutants are then harvested and hypocotyls removed leaving only tissue in the shoot region. Tissue is then flash frozen in liquid nitrogen and stored at −80° C.

Control tissue is isolated from 5 day old Landsberg erecta seedlings grown in the same manner as above. Tissue from the shoot region is harvested in the same manner as the stm tissue, but only contains material from the 24° C., 16 hr light/8 hr dark long day cycle growth chamber.

Seeds of maize hybrid 35A (Pioneer) are sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats are watered every three days for 8 days. Seedlings are carefully removed from the sand and the outer layers of leaf shealth removed. About 2 mm sections are cut and flash frozen in liquid nitrogen prior to storage at −80° C. The tissues above the shoot apices (~1 cm long) are cut, treated as above and used as control tissue.

(ddd) Siliques

Wild type *Arabidopsis thaliana* (ecotype Wassilewskija) seeds are sown in moistened soil mix, metromix 200 with osmocote, and stratified at 4° C. for 3 days in dark. Flats are placed in a Conviron growth chamber maintained at 16 h light (22° C.), 8 h dark (20° C.) and 70% humidity. After 3 weeks, siliques (<5 mm long) are collected in liquid nitrogen. The control samples are 3-week old whole plants (including all tissue types) grown in the same Conviron growth chamber.

(eee) Trichomes

*Arabidopsis thaliana* (Colombia glabrous) inflorescences are used as a control and CS8143 (hairy inflorescence ecotype) inflorescences, having increased trichomes, are used as the experimental sample.

Approximately 10 μl of each type of seed is sown on a flat of 350 soil (containing 0.03% marathon) and vernalized at 4° C. for 3 days. Plants are then grown at room temperature under florescent lighting. Young inflorescences are collected at 30 days for the control plants and 37 days for the experimental plants. Each inflorescence is cut into one-half inch (½") pieces, flash frozen in liquid nitrogen and stored at −80° C. until RNA is isolated.

(fff) Wounding

Seeds of *Arabidopsis thaliana* (Wassilewskija) are sown in trays and left at 4° C. for three days to vernalize before being transferred to a growth chamber having 16 hr light/8 hr dark, 12,000-14,000 LUX, 70% humidity and 20° C. After 14 days, the leaves are wounded with forceps. Aerial tissues are harvested 1 hour and 6 hours after wounding. Aerial tissues from unwounded plants serve as controls. Tissues are flash-frozen in liquid nitrogen and stored at −80° C.

Seeds of maize hybrid 35A (Pioneer) are sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats are watered every three days for 7 days. Seedlings are wounded (one leaf nicked by scissors) and placed in 1-liter beakers of water for treatment. Control plants are treated not wounded. After 1 hr and 6 hr aerial and root tissues are separated and flash frozen in liquid nitrogen prior to storage at −80° C.

(ggg) 3642-1

3642-1 is a T-DNA mutant that affects leaf development. This mutant segregates 3:1, wild-type:mutant. *Arabidopsis thaliana* 3642-1 mutant seeds are vernalized at 4° C. for 3 days before sowing in flats of MetroMix 200. Flats are placed in the greenhouse, watered and grown to the 8 leaf, pre-flower stage. Stems and rosette leaves are harvested from the mutants and the wild-type segregants, flash frozen and stored at −80° C.

2. Microarray Hybridization Procedures

Microarray technology provides the ability to monitor mRNA transcript levels of thousands of genes in a single experiment. These experiments simultaneously hybridize two differentially labeled fluorescent cDNA pools to glass slides that have been previously spotted with cDNA clones of the same species. Each arrayed cDNA spot has a corresponding ratio of fluorescence that represents the level of disparity between the respective mRNA species in the two sample pools. Thousands of polynucleotides are spotted on one slide, and each experiment generates a global expression pattern.

Coating Slides

The microarray consists of a chemically coated microscope slide, referred to herein as a "chip" with numerous polynucleotide samples arrayed at a high density. The poly-L-lysine coating allows for this spotting at high density by providing a hydrophobic surface, reducing the spreading of spots of DNA solution arrayed on the slides. Glass microscope slides (Gold Seal #3010 manufactured by Gold Seal Products, Portsmouth, N.H. USA) are coated with a 0.1% WNV solution of Poly-L-lysine (Sigma, St. Louis, Mo.) using the following protocol:

1. Slides are placed in slide racks (Shandon Lipshaw #121). The racks are then put in chambers (Shandon Lipshaw #121).
2. Cleaning solution is prepared: 70 g NaOH is dissolved in 280 mL ddH2O. 420 mL 95% ethanol is added. The total volume is 700 mL (=2×350 mL); it is stirred until completely mixed. If the solution remains cloudy, ddH$_2$O is added until clear.
3. The solution is poured into chambers with slides; the chambers are covered with glass lids. The solution is mixed on an orbital shaker for 2 hr.
4. The racks are quickly transferred to fresh chambers filled with ddH$_2$O. They are rinsed vigorously by plunging racks up and down. Rinses are repeated 4× with fresh ddH$_2$O each time, to remove all traces of NaOH-ethanol.
5. Polylysine solution is prepared: 0 mL poly-L-lysine+70 mL tissue culture PBS in 560 mL water, using plastic graduated cylinder and beaker.
6. Slides are transferred to polylysine solution and shaken for 1 hr.
7. The rack is transferred to a fresh chambers filled with ddH$_2$O. It is plunged up and down 5× to rinse.
8. The slides are centrifuged on microtiter plate carriers (paper towels are placed below the rack to absorb liquid) for 5 min. @ 500 rpm. The slide racks are transferred to empty chambers with covers.
9. Slide racks are dried in a 45C oven for 10 min.
10. The slides are stored in a closed plastic slide box.
    1. Normally, the surface of lysine coated slides is not very hydrophobic immediately after this process, but becomes increasingly hydrophobic with storage. A hydrophobic surface helps ensure that spots do not run together while printing at high densities. After they age for 10 days to a month, the slides are ready to use. However, coated slides that have been sitting around for long periods of time are usually too old to be used. This is because they develop opaque patches, visible when held to the light, and these result in high background hybridization from the fluorescent probe. Alternatively, pre-coated glass slides are purchased from TeleChem International, Inc. (Sunnyvale, Calif., 94089; catalog number SMM-25, Superamine substrates).

PCR Amplification of cDNA Clone Inserts

Polynucleotides are amplified from *Arabidopsis* cDNA clones using insert specific probes. The resulting 100 µL PCR reactions are purified with Qiaquick 96 PCR purification columns (Qiagen, Valencia, Calif., USA) and eluted in 30 uL of 5 mM Tris. 8.5 uL of the elution are mixed with 1.5 uL of 20× SSC to give a final spotting solution of DNA in 3× SSC. The concentrations of DNA generated from each clone vary between 10-100 ng/ul, but are usually about 50 ng/ul.

Arraying of PCR Products on Glass Slides

PCR products from cDNA clones are spotted onto the poly-L-Lysine coated glass slides using an arrangement of quill-tip pins (ChipMaker 3 spotting pins; Telechem, International, Inc., Sunnyvale, Calif., USA) and a robotic arrayer (PixSys 3500, Cartesian Technologies, Irvine, Calif., USA). Around 0.5 nl of a prepared PCR product is spotted at each location to produce spots with approximately 100 um diameters. Spot center-to-center spacing is from 180 um to 210 um depending on the array. Printing is conducted in a chamber with relative humidity set at 50%.

Slides containing maize sequences are purchased from Agilent Technology (Palo Alto, Calif. 94304).

Post-Processing of Slides

After arraying, slides are processed through a series of steps—rehydration, UV cross-linking, blocking and denaturation—required prior to hybridization. Slides are rehydrated by placing them over a beaker of warm water (DNA face down), for 2-3 sec, to distribute the DNA more evenly within the spots, and then snap dried on a hot plate (DNA side, face up). The DNA is then cross-linked to the slides by UV irradiation (60-65 mJ; 2400 Stratalinker, Stratagene, La Jolla, Calif., USA).

Following this, a blocking step is performed to modify remaining free lysine groups, and hence minimize their ability to bind labeled probe DNA. To achieve this the arrays are placed in a slide rack. An empty slide chamber is left ready on an orbital shaker. The rack is bent slightly inwards in the middle, to ensure the slides do not run into each other while shaking. The blocking solution is prepared as follows: 3×350-ml glass chambers (with metal tops) are set to one side, and a large round Pyrex dish with dH$_2$O is placed ready in the microwave. At this time, 15 ml sodium borate is prepared in a 50 ml conical tube.

6-g succinic anhydride is dissolved in approx. 325-350 mL 1-methyl-2-pyrrolidinone. Rapid addition of reagent is crucial.

a. Immediately after the last flake of the succinic anhydride dissolves, the 15-mL sodium borate is added.

b. Immediately after the sodium borate solution is mixed in, the solution is poured into an empty slide chamber.

c. The slide rack is plunged rapidly and evenly in the solution. It is vigorously shaken up and down for a few seconds, making sure slides never leave the solution.

d. It is mixed on an orbital shaker for 15-20 min. Meanwhile, the water in the Pyrex dish (enough to cover slide rack) is heated to boiling.

Following this, the slide rack is gently plunged in the 95C water Oust stopped boiling) for 2 min. Then the slide rack is plunged 5× in 95% ethanol. The slides and rack are centrifuged for 5 min. @ 500 rpm. The slides are loaded quickly and evenly onto the carriers to avoid streaking. The arrays are used immediately or stored in a slide box.

The Hybridization process begins with the isolation of mRNA from the two tissues in question (see "*Isolation of total RNA*" and "*Isolation of mRNA*", below) followed by their conversion to single stranded cDNA (see "*Generation of probes for hybridization*", below). The cDNA from each tissue is independently labeled with a different fluorescent dye and then both samples are pooled together. This final differentially labeled cDNA pool is then placed on a processed microarray and allowed to hybridize (see "*Hybridization and wash conditions*", below).

Isolation of Total RNA

Approximately 1 g of plant tissue is ground in liquid nitrogen to a fine powder and transferred into a 50-ml centrifuge tube containing 10 ml of Trizol reagent. The tube is vigorously vortexed for 1 min and then incubated at room temperature for 10-20 min. on an orbital shaker at 220 rpm. Two ml of chloroform are added to the tube and the solution vortexed vigorously for at least 30-sec before again incubating at room temperature with shaking. The sample is then centrifuged at 12,000 ×g (10,000 rpm) for 15-20 min at 4° C. The aqueous layer is removed and mixed by inversion with 2.5 ml of 1.2 M NaCl/0.8 M Sodium Citrate and 2.5 ml of isopropyl alcohol added. After a 10 min. incubation at room temperature, the sample is centrifuged at 12,000 ×g (10,000 rpm) for 15 min at 4° C. The pellet is washed with 70% ethanol, re-centrifuged at 8,000 rpm for 5 min and then air dried at room temperature for 10 min. The resulting total RNA is dissolved in either TE (10 mM Tris-HCl, 1 mM EDTA, pH 8.0) or DEPC (diethylpyrocarbonate) treated deionized water (RNAse-free water). For subsequent isolation of MRNA using the Qiagen kit, the total RNA pellet is dissolved in RNAse-free water.

Isolation of mRNA mRNA is isolated using the Qiagen Oligotex mRNA Spin-Column protocol (Qiagen, Valencia, Calif.). Briefly, 500 µl OBB buffer (20 mM Tris-Ci, pH 7.5, 1 M NaCl, 2 mM EDTA, 0.2% SDS) is added to 500 µl of total RNA (0.5-0.75 mg) and mixed thoroughly. The sample is first incubated at 70° C. for 3 min, then at room temperature for 10 minutes and finally centrifuged for 2 min at 14,000-18,000 ×g. The pellet is resuspended in 400 µl OW2 buffer (10 mM Tris-Cl, pH 7.5, 150 mM NaCl, 1 mM EDTA) by vortexing, the resulting solution placed on a small spin column in a 1.5 ml RNase-free microcentrifuge tube and centrifuged for 1 min at 14,000-18,000 ×g. The spin column is transferred to a new 1.5 ml RNase-free microcentrifuge tube and washed with 400 µl of OW2 buffer. To release the isolated mRNA from the resin, the spin column is again transferred to a new RNase-free 1.5 ml microcentrifuge tube, 20-100 gl 70° C. OEB buffer (5 mM Tris-Cl, pH 7.5) added and the resin resuspended in the resulting solution via pipeting. The mRNA solution is collected after centrifuging for 1 min at 14,000-18,000 ×g.

Alternatively, mRNA is isolated using the Stratagene Poly (A) Quik mRNA Isolation Kit (Startagene, La Jolla, Calif.). Here, up to 0.5 mg of total RNA (maximum volume of 1 ml) are incubated at 65° C. for 5 minutes, snap cooled on ice and 0.1× volumes of 10× sample buffer (10 mM Tris-HCl (pH 7.5), 1 mM EDTA (pH 8.0) 5 M NaCl) added. The RNA sample is applied to a prepared push column and passed through the column at a rate of ~1 drop every 2 sec. The solution collected is reapplied to the column and collected as above. 200 µl of high salt buffer (10 mM Tris-HCl (pH 7.5), 1 mM EDTA, 0.5 NaCl) are applied to the column and passed through the column at a rate of ~1 drop every 2 sec. This step is repeated and followed by three low salt buffer (10 mM Tris-HCl (pH 7.5), 1 mM EDTA, 0.1 M NaCl) washes preformed in a similar manner. mRNA is eluted by applying to the column four separate 200 µl aliquots of elution buffer (10 mM Tris-HCl (pH 7.5), 1 mM EDTA) preheated to 65° C. Here, the elution buffer is passed through the column at a rate of 1 drop/sec. The resulting mRNA solution is precipitated by adding 0.1×volumes of 10× sample buffer, 2,5 volumes of ice-cold 100% ethanol, incubating overnight at −20° C. and centrifuging at 14,000-18,000 ×g for 20-30 min at 4° C. The pellet is washed with 70% ethanol and air dried for 10 min. at room temperature before resuspension in RNase-free deionized water.

Preparation of Yeast Controls

Plasmid DNA is isolated from the following yeast clones using Qiagen filtered maxiprep kits (Qiagen, Valencia, Calif.): YAL022c(Fun26), YAL031c(Fun21), YBR032w, YDL131w, YDL182w, YDL194w, YDL196w, YDRO5Oc and YDR116c. Plasmid DNA is linearized with either BsrBI (YAL022c(Fun26), YAL031c(Fun21), YDL131w, YDL182w, YDL194w, YDL196w, YDR050c) or AflIII (YBR032w, YDR116c) and isolated.

In Vitro Transcription of Yeast Clones

The following solution is incubated at 37° C. for 2 hours: 17 III of isolated yeast insert DNA (1 µg), 20 µl 5× buffer, 10 µl 100 mM DTT, 2.5 µl (100 U) RNasin, 20 µl 2.5 mM (ea.) rNTPs, 2.7 µl (40U) SP6 polymerase and 27.8 µl RNase-free deionized water. 2 µl (2 U) Ampli DNase I is added and the incubation continued for another 15 min. 10 µl SM $NH_4OAC$ and 100 µl phenol:chloroform:isoamyl alcohol (25:24:1) are added, the solution vortexed and then centrifuged to separate the phases. To precipitate the RNA, 250 µl ethanol is added and the solution incubated at −20° C. for at least one hour. The sample is then centrifuged for 20 min at 4° C. at 14,000-18,000 ×g, the pellet washed with 500 µl of 70% ethanol, air dried at room temperature for 10 min and resuspended in 100 µl of RNase-free deionized water. The precipitation procedure is then repeated.

Alternatively, after the two-hour incubation, the solution is extracted with phenol/chloroform once before adding 0.1 volume 3M sodium acetate and 2.5 volumes of 100% ethanol. The solution is centrifuged at 15,000rpm, 4° C. for 20 minutes and the pellet resuspended in RNase-free deionized water. The DNase I treatment is carried out at 37° C. for 30 minutes using 2 U of Ampli DNase I in the following reaction condition: 50 mM Tris-HCl (pH 7.5), 10 mM $MgCl_2$. The DNase I reaction is then stopped with the addition of $NH_4OAC$ and phenol:chloroform:isoamyl alcohol (25:24:1), and RNA isolated as described above.

0.15-2.5 ng of the in vitro transcript RNA from each yeast clone are added to each plant mRNA sample prior to labeling to serve as positive (internal) probe controls.

Generation of Probes for Hybridization
Generation of Labeled Probes for Hybridization from First-Strand cDNA Hybridization probes are generated from isolated mRNA using an Atlas™ Glass Fluorescent Labeling Kit (Clontech Laboratories, Inc., Palo Alto, Calif., USA). This entails a two step labeling procedure that first incorporates primary aliphatic amino groups during cDNA synthesis and then couples fluorescent dye to the cDNA by reaction with the amino functional groups. Briefly, 5 µg of oligo(dT)$_{18}$ primer d(TTTTTTTTTTTTTTTTTTV) (SEQ ID No. 148) is mixed with Poly A+mRNA (1.5-2 µg mRNA isolated using the Qiagen Oligotex mRNA Spin-Column protocol or-the Stratagene Poly(A) Quik mRNA Isolation protocol (Stratagene, La Jolla, Calif., USA)) in a total volume of 25 µl. The sample is incubated in a thermocycler at 70° C. for 5 min, cooled to 48° C. and 10 µl of 5×cDNA Synthesis Buffer (kit supplied), 5µl 10 ×dNTP mix (dATP, dCTP, dGTP, dTTP and aminoallyl-dUTP; kit supplied), 7.5 µl deionized water and 2.5 µl MMLV Reverse Transcriptase (500U) added. The reaction is then incubated at 48° C. for 30 minutes, followed by 1 hr incubation at 42° C. At the end of the incubation the reaction is heated to 70° C. for 10 min, cooled to 37° C. and 0.5 µl (5 U) RNase H added, before incubating for 15 min at 37° C. The solution is vortexed for 1 min after the addition of 0.5 µl 0.5 M EDTA and 5 µl of QuickClean Resin (kit supplied) then centrifuged at 14,000-18,000 ×g for 1 min. After removing the supernatant to a 0.45 µm spin filter (kit supplied), the sample is again centrifuged at 14,000-18,000 ×g for 1 min, and 5.5 µl 3 M sodium acetate and 137.5 µl of 100% ethanol added to the sample before incubating at –20° C. for at least 1 hr. The sample is then centrifuged at 14,000-18,000 ×g at 4° C. for 20 min, the resulting pellet washed with 500 µl 70% ethanol, air-dried at room temperature for 10 min and resuspended in 10 µl of 2× fluorescent labeling buffer (kit provided). 10 µl each of the fluorescent dyes Cy3 and Cy5 (Amersham Pharmacia (Piscataway, N.J., USA); prepared according to Atlas™ kit directions of Clontech) are added and the sample incubated in the dark at room temperature for 30 min.

The fluorescently labeled first strand cDNA is precipitated by adding 2 µl 3M sodium acetate and 50 µl 100% ethanol, incubated at –20° C. for at least 2 hrs, centrifuged at 14,000-18,000 ×g for 20 min, washed with 70% ethanol, air-dried for 10 min and dissolved in 100 µl of water.

Alternatively, 3-4 µg mRNA, 2.5 (~8.9 ng of in vitro translated mRNA) µl yeast control and 3 µg oligo dTV (TTTTTTTTTTTTTTTTTTT(A/C/G)(SEQ ID No. 149) are mixed in a total volume of 24.7 µl. The sample is incubated in a thermocycler at 70° C. for 10 min. before chilling on ice. To this, 8 µl of 5× first strand buffer (*SuperScript II RNase H-Reverse Transcriptase kit* from Invitrogen (Carlsbad, Calif. 92008); cat no. 18064022), 0.8° C. of aa-dUTP/dNTP mix (50×; 25 mM DATP, 25 mM dGTP, 25 mM dCTP, 15 mM dTTP, 10 mM aminoallyl-dUTP), 4 µl of 0.1 M DTT and 2.5 µl (500 units) of Superscript R.T.II enzyme (Stratagene) are added. The sample is incubated at 42° C. for 2 hours before a mixture of 10 µl of 1M NaOH and 10° C. of 0.5 M EDTA are added. After a 15 minute incubation at 65° C., 25 µl of 1 M Tris pH 7.4 is added. This is mixed with 450 µl of water in a Microcon 30 column before centrifugation at 11,000 ×g for 12 min. The column is washed twice with 450 µl (centrifugation at 11,000 g, 12 min.) before eluting the sample by inverting the Microcon column and centrifuging at 11,000×g for 20 seconds. Sample is dehydrated by centrifugation under vacuum and stored at –20° C.

Each reaction pellet is dissolved in 9 µl of 0.1 M carbonate buffer (0.1M sodium carbonate and sodium bicarbonate, pH=8.5-9) and 4.5 µl of this placed in two microfuge tubes. 4.5 µl of each dye (in DMSO) are added and the mixture incubated in the dark for 1 hour. 4.5 µl of 4 M hydroxylamine is added and again incubated in the dark for 15 minutes.

Regardless of the method used for probe generation, the probe is purified using a Qiagen PCR cleanup kit (Qiagen, Valencia, Calif., USA), and eluted with 100 ul EB (kit provided). The sample is loaded on a Microcon YM-30 (Millipore, Bedford, Mass., USA) spin column and concentrated to 4-5 ul in volume.

Probes for maize microarrays are generated using the Fluorescent Linear Amplification Kit (cat. No. G2556A) from Agilent Technologies (Palo Alto, Calif.).

Hybridization and Wash Conditions

The following Hybridization and Washing Condition are used:

Hybridization Conditions:

Labeled probe is heated at 95° C. for 3 min and chilled on ice. Then 25 µL of the hybridization buffer which is warmed at 42C is added to the probe, mixing by pipeting, to give a final concentration of:

50% formamide
4× SSC
0.03% SDS
5× Denhardt's solution
0.1 µg/ml single-stranded salmon sperm DNA The probe is kept at 42C. Prior to the hybridization, the probe is heated for 1 more min., added to the array, and then covered with a glass cover slip. Slides are placed in hybridization chambers (Telechem, Sunnyvale, Calif.) and incubated at 42° C. overnight.

Washing Conditions:
A. Slides are washed in 1× SSC+0.03% SDS solution at room temperature for 5 minutes,
B. Slides are washed in 0.2× SSC at room temperature for 5 minutes,
C. Slides are washed in 0.05× SSC at room temperature for 5 minutes.

After A, B, and C, slides are spun at 800 ×g for 2 min. to dry. They are then scanned.

Maize microarrays are hybridized according to the instructions included Fluorescent Linear Amplification Kit (cat. No. G2556A) from Agilent Technologies (Palo Alto, Calif.).

Scanning of Slides

The chips are scanned using a ScanArray 3000 or 5000 (General Scanning, Watertown, Mass., USA). The chips are scanned at 543 and 633 nm, at 10 um resolution to measure the intensity of the two fluorescent dyes incorporated into the samples hybridized to the chips.

Data Extraction and Analysis

The images generated by scanning slides consiste of two 16-bit TIFF images representing the fluorescent emissions of the two samples at each arrayed spot. These images are then quantified and processed for expression analysis using the data extraction software Imagene™ (Biodiscovery, Los Angeles, Calif., USA). Imagene output is subsequently analyzed using the analysis program Genespring™ (Silicon Genetics, San Carlos, Calif., USA). In Genespring, the data is imported using median pixel intensity measurements derived from Imagene output. Background subtraction, ratio calculation and normalization are all conducted in Genespring. Normalization is achieved by breaking the data in to 32 groups, each of which represented one of the 32 pin printing regions on the microarray. Groups consist of 360 to 550 spots. Each group is independently normalized by setting the median of ratios to one and multiplying ratios by the appropriate factor.

Results

The MA Table presents the results of the differential expression experiments for the mRNAs, as reported by their corresponding cDNA ID number, that are differentially transcribed under a particular set of conditions as compared to a control sample. The cDNA ID numbers correspond to those used in the Sequence and Reference Tables. Increases in mRNA abundance levels in experimental plants versus the controls are denoted with the plus sign (+). Likewise, reductions in MRNA abundance levels in the experimental plants are denoted with the minus (−) sign.

The Table is organized according to the clone number with each set of experimental conditions being denoted by a "short name" followed by the term "Expt Rep ID." The table also provides the parameters for the experimental treatment associated with each "Expt Rep ID."

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

What is claimed is:

1. A transgenic plant, plant cell, plant material or plant seed which comprises a nucleic acid molecule comprising
a nucleic acid having a nucleotide sequence which encodes an amino acid sequence exhibiting at least 95% sequence identity to SEQ ID NO: 21
which is exogenous or heterologous to said plant or plant cell wherein said nucleic acid molecule is expressed and wherein said transgenic plant, plant cell, plant material or plant seed is selected from a plurality of transformed plants as having improved drought tolerance compared to a non-transformed plant of the same species cultivated under the same conditions.

2. A transgenic plant, plant cell, plant material or plant seed which comprises a nucleic acid molecule comprising
a nucleic acid having a nucleotide sequence which encodes the amino acid sequence of SEQ ID NO: 21
which is exogenous or heterologous to said plant or plant cell wherein said nucleic acid molecule is expressed, and wherein said transgenic plant, plant cell, plant material or plant seed is selected from a plurality of transformed plants as having improved drought tolerance compared to a non-transformed plant of the same species cultivated under the same conditions.

3. A transgenic plant, plant cell, plant material or plant seed which comprises a vector construct comprising a first nucleic acid having a regulatory sequence capable of causing transcription and/or translation in a plant; and a second nucleic acid comprising:
a nucleic acid having a nucleotide sequence which encodes an amino acid sequence exhibiting at least 95% sequence identity to the amino acid sequence according to SEQ ID NO:21
wherein said first and second nucleic acids are operably linked and said second nucleic acid is heterologous to any element in said vector construct and is expressed, and wherein said transgenic plant, plant cell, plant material or plant seed is selected from a plurality of transformed plants as having improved drought tolerance compared to a non-transformed plant of the same species cultivated under the same conditions.

4. A transgenic plant, plant cell, plant material or plant seed which comprises a vector construct comprising a first nucleic acid having a regulatory sequence capable of causing transcription and/or translation in a plant; and a second nucleic acid comprising
a nucleic acid having a nucleotide sequence which encodes the amino acid sequence of SEQ ID NO:21
wherein said first and second nucleic acids are operably linked and
said second nucleic acid is heterologous to any element in said vector construct and is expressed, and wherein said transgenic plant, plant cell, plant material or plant seed is selected from a plurality of transformed plants as having improved drought tolerance compared to a non-transformed plant of the same species cultivated under the same conditions.

5. A plant which has been regenerated from the plant cell or seed according to claim 2 which has improved drought tolerance compared to a non-transformed plant of the same species cultivated under the same conditions.

6. A transgenic plant which has been regenerated from the plant cell or seed according to claim 1.

7. A method of producing a plant having increased drought tolerance, said method comprising:
a) transforming a plant, plant cell, plant material or seed of a plant which comprises contacting a host cell by contacting said plant, plant cell, plant material or seed of a plant with a vector construct, said vector construct comprising:
a first nucleic acid sequence that is a regulatory sequence which causes transcription in a plant; and
a second nucleic acid sequence that encodes an amino acid sequence which is at least 95% identical to SEQ ID NO: 21, wherein said first and second nucleic acid sequences are operably linked,
b) overexpressing said second nucleic acid sequence in said transformed plant, plant cell, plant material or seed of a plant; and
c) selecting from a plurality of said transformed plants a plant having increased drought tolerance as compared to a non-transformed plant of the same species cultivated under the same conditions.

8. A method of producing a plant having increased drought tolerance, said method comprising:
a) transforming a plant, plant cell, plant material or seed of a plant which comprises contacting a host cell by contacting said plant, plant cell, plant material or seed of a plant with a vector construct, said vector construct comprising:
a first nucleic acid sequence that is a regulatory sequence which causes transcription in a plant; and
a second nucleic acid sequence that encodes the amino acid sequence of SEQ ID NO: 21, wherein said first and second nucleic acid sequences are operably linked,
b) overexpressing said second nucleic acid sequence in said transformed plant, plant cell, plant material or seed of a plant; and
c) selecting from a plurality of said transformed plants a plant having increased drought tolerance as compared to a non-transformed plant of the same species cultivated under the same conditions.

* * * * *

```
                              SEQUENCE LISTING

<160> NUMBER OF SEQ ID NOS: 149

<210> SEQ ID NO 1
<211> LENGTH: 704
<212> TYPE: DNA
<213> ORGANISM: Brassica napus
<220> FEATURE:
<221> NAME/KEY: misc_feature
<222> LOCATION: (1)..(704)
<223> OTHER INFORMATION: Ceres Seq. ID no. 12475607
<220> FEATURE:
<221> NAME/KEY: misc_feature
<222> LOCATION: (485)..(485)
<223> OTHER INFORMATION: n is a, c, t, g, unknown, or other
<220> FEATURE:
<221> NAME/KEY: misc_feature
<222> LOCATION: (511)..(511)
<223> OTHER INFORMATION: n is a, c, t, g, unknown, or other

<400> SEQUENCE: 1
accaaaaaca tcaccggaga atctgacggc ggcttagcag cgactgctac tgcaaaaaga      60
ttgtttatct tcttggggta ttttacttac ctttggaaga aacataacgt cttttgcggt     120
agctaaaagc taagctcggt cgttatatat acatatttta taagtactgc actatttaaa    180
ataacacaat ggcagctgct cgttcactct ccggcgccgt taaatctctt tgctccgccg    240
catcccacaa catttctggt tccattgtct tgaggaggag ttacgttgcg acagtaccag    300
gatttggtaa gggaggttcc acaagagtta cggtggggaa gatggaacaa agagcaaatc    360
aagaggcaga gtctgcgtgg gccccggatc cagttacggg atactacagg ccatctaatc    420
gtgcggatga gattgatcca gcggagctgc gtgagatgct tttgaaaaac aaagccaagc    480
ctttntgagg atttcaattt ggttggttcc nctagactat gttgtaaggg attcctgttt    540
gttatgttcg tcttaaatat ctatcttttg gagtttaaag taaaataaag atactatata    600
tttcagttcg tatgagttca cgtttcttgt agttaaatct cgacagcatg aaaaacaaca    660
aagatcccat actgccacga ttagcttggt ggcttttcct acct                     704

<210> SEQ ID NO 2
<211> LENGTH: 99
<212> TYPE: PRT
<213> ORGANISM: Brassica napus
<220> FEATURE:
<221> NAME/KEY: misc_feature
<222> LOCATION: (1)..(99)
<223> OTHER INFORMATION: Ceres Seq. ID no. 12475608
<220> FEATURE:
<221> NAME/KEY: misc_feature
<222> LOCATION: (3)..(93)
<223> OTHER INFORMATION: PFAM Description: Late embryogenesis abundant
      protein
<220> FEATURE:
```

```
<221> NAME/KEY: misc_feature
<222> LOCATION: (4)..(96)
<223> OTHER INFORMATION: GI NO: 1370589
      NR DESCRIPTION: protein induced upon tuberization
<220> FEATURE:
<221> NAME/KEY: misc_feature
<222> LOCATION: (4)..(96)
<223> OTHER INFORMATION: GI NO: 7489029
      NR DESCRIPTION: late-embryogenesis protein homolog
<220> FEATURE:
<221> NAME/KEY: misc_feature
<222> LOCATION: (29)..(95)
<223> OTHER INFORMATION: GI NO: 25044821
      NR DESCRIPTION: late-embryogenesis abundant protein-like protein
<220> FEATURE:
<221> NAME/KEY: misc_feature
<222> LOCATION: (29)..(97)
<223> OTHER INFORMATION: GI NO: 34894580
      NR DESCRIPTION: zinc-induced protein-like
<220> FEATURE:
<221> NAME/KEY: misc_feature
<222> LOCATION: (99)..(99)
<223> OTHER INFORMATION: Xaa is any aa, unknown or other

<400> SEQUENCE: 2

Met Ala Ala Ala Arg Ser Leu Ser Gly Ala Val Lys Ser Leu Cys Ser
1               5                   10                  15

Ala Ala Ser His Asn Ile Ser Gly Ser Ile Val Leu Arg Arg Ser Tyr
            20                  25                  30

Val Ala Thr Val Pro Gly Phe Gly Lys Gly Gly Ser Thr Arg Val Thr
        35                  40                  45

Val Gly Lys Met Glu Gln Arg Ala Asn Gln Glu Ala Glu Ser Ala Trp
    50                  55                  60

Ala Pro Asp Pro Val Thr Gly Tyr Tyr Arg Pro Ser Asn Arg Ala Asp
65                  70                  75                  80

Glu Ile Asp Pro Ala Glu Leu Arg Glu Met Leu Leu Lys Asn Lys Ala
                85                  90                  95

Lys Pro Xaa

<210> SEQ ID NO 3
<211> LENGTH: 438
<212> TYPE: DNA
<213> ORGANISM: Brassica napus
<220> FEATURE:
<221> NAME/KEY: misc_feature
<222> LOCATION: (1)..(438)
<223> OTHER INFORMATION: Ceres Seq. ID no. 6421618

<400> SEQUENCE: 3 attgttctttt tggaaaataa actgaagaac tagtaacaga aggctgacgc gctgacgtat      60
cggcatttag agagagagaa aatctctttta tatatgttgt gtggtgtcgg tctgtgagga    120
gtaggaaata atatacaaaa tcaaaggtta agaaaaaaaa tgggtgagga aagaatcag      180 cagcacttcg tgctagtaca tggtgcatgc cacggcgcgt ggtgctggaa caaggttaag    240
ccgcttctcg aggcctccgg ccaccgcgta accgcttag acctagctgc ttcgggtata     300
gacacaacca ggtctatcac tgagatctcc acatgcgaac aatactctga gccattgata    360
cagctaatcg cctcattacc aagtgatgag aaggttgtgc tcgttggtca tagctttgga    420
gggttcagct tagccatg                                                  438

<210> SEQ ID NO 4
<211> LENGTH: 93
<212> TYPE: PRT
<213> ORGANISM: Brassica napus
<220> FEATURE:
```

```
<221> NAME/KEY: misc_feature
<222> LOCATION: (1)..(93)
<223> OTHER INFORMATION: Ceres Seq. ID no. 6421619
<220> FEATURE:
<221> NAME/KEY: misc_feature
<222> LOCATION: (35)..(92)
<223> OTHER INFORMATION: PFAM Description: alpha/beta hydrolase fold
<220> FEATURE:
<221> NAME/KEY: misc_feature
<222> LOCATION: (1)..(92)
<223> OTHER INFORMATION: GI NO: 21554666
      NR DESCRIPTION: putative acetone-cyanohydrin lyase
<220> FEATURE:
<221> NAME/KEY: misc_feature
<222> LOCATION: (1)..(92)
<223> OTHER INFORMATION: GI NO: 7488034
      NR DESCRIPTION: probable (S)-acetone-cyanohydrin lyase
<220> FEATURE:
<221> NAME/KEY: misc_feature
<222> LOCATION: (1)..(92)
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (5)..(92)
<223> OTHER INFORMATION: GI NO: 40549303
      NR DESCRIPTION: salicylic acid-binding protein 2
<220> FEATURE:
<221> NAME/KEY: misc_feature
<222> LOCATION: (2)..(92)
<223> OTHER INFORMATION: GI NO: 34907174
      NR DESCRIPTION: putative pir7b (Pseudomonas inducible protein)
<220> FEATURE:
<221> NAME/KEY: misc_feature
<222> LOCATION: (7)..(92)
<223> OTHER INFORMATION: GI NO: 14279437
      NR DESCRIPTION: ethylene-induced esterase
<220> FEATURE:
<221> NAME/KEY: misc_feature
<222> LOCATION: (5)..(92)
<223> OTHER INFORMATION: GI NO: 15028131
      NR DESCRIPTION: putative alpha-hydroxynitrile lyase
<220> FEATURE:
<221> NAME/KEY: misc_feature
<222> LOCATION: (1)..(92)
<223> OTHER INFORMATION: GI NO: 28393451
      NR DESCRIPTION: putative acetone-cyanohydrin lyase
<220> FEATURE:
<221> NAME/KEY: misc_feature
<222> LOCATION: (10)..(92)
<223> OTHER INFORMATION: GI NO: 2780225
      NR DESCRIPTION: alpha-hydroxynitrile lyase
<220> FEATURE:
<221> NAME/KEY: misc_feature
<222> LOCATION: (5)..(92)
<223> OTHER INFORMATION: GI NO: 16648679
      NR DESCRIPTION: AT5g10300/F18D22_70

<400> SEQUENCE: 4

Met Gly Glu Glu Lys Asn Gln Gln His Phe Val Leu Val His Gly Ala
1               5                   10                  15

Cys His Gly Ala Trp Cys Trp Asn Lys Val Lys Pro Leu Leu Glu Ala
                20                  25                  30

Ser Gly His Arg Val Thr Ala Leu Asp Leu Ala Ala Ser Gly Ile Asp
            35                  40                  45

Thr Thr Arg Ser Ile Thr Glu Ile Ser Thr Cys Glu Gln Tyr Ser Glu
        50                  55                  60

Pro Leu Ile Gln Leu Ile Ala Ser Leu Pro Ser Asp Glu Lys Val Val
65                  70                  75                  80

Leu Val Gly His Ser Phe Gly Gly Phe Ser Leu Ala Met
                85                  90

<210> SEQ ID NO 5
```

```
<211> LENGTH: 457
<212> TYPE: DNA
<213> ORGANISM: Brassica napus
<220> FEATURE:
<221> NAME/KEY: misc_feature
<222> LOCATION: (1)..(457)
<223> OTHER INFORMATION: Ceres Seq. ID no. 6424418

<400> SEQUENCE: 5
aagaacatct caaacacttc tattcttcat tcattcaata ttttgaccaa cacacacaca      60
tataatcatt tgtcctcata accctaaac cctacctagt tccaacaact ctctagttcc     120
aaactcaaga aaaaaaaga ggttagtttc ataagcaatg ccaaagttg ggaagctgac      180
aaagctcaag tcggccataa agaaatggcc ttccttcgcc aagaatcacc accactcgtc    240
ctcctccgct gccgtctccg atgagctctc agaggacaac aatctccatg ttgtttatgt    300
tggtcagact cgaagacctt acatgcttag accggacatc atctctcacc cacttttca    360
agaactggtg gatcggtctt ctagatccgt ggaacatgat cgtgagattg ttgtatcttg    420
tgaagttgtt ttgttcgagc atttgttgtg gatgctc                             457

<210> SEQ ID NO 6
<211> LENGTH: 100
<212> TYPE: PRT
<213> ORGANISM: Brassica napus
<220> FEATURE:
<221> NAME/KEY: misc_feature
<222> LOCATION: (1)..(100)
<223> OTHER INFORMATION: Ceres Seq. ID no. 6424419
<220> FEATURE:
<221> NAME/KEY: misc_feature
<222> LOCATION: (10)..(99)
<223> OTHER INFORMATION: PFAM Description: Auxin responsive protein
<220> FEATURE:
<221> NAME/KEY: misc_feature
<222> LOCATION: (1)..(99)
<223> OTHER INFORMATION: GI NO: 21554070
    NR DESCRIPTION: unknown
<220> FEATURE:
<221> NAME/KEY: misc_feature
<222> LOCATION: (1)..(99)
<223> OTHER INFORMATION: GI NO: 15242071
    NR DESCRIPTION: putative protein; protein id: At5g20820.1
<220> FEATURE:
<221> NAME/KEY: misc_feature
<222> LOCATION: (1)..(99)
<223> OTHER INFORMATION: GI NO: 50946385
    NR DESCRIPTION: auxin-induced protein-related-like protein
<220> FEATURE:
<221> NAME/KEY: misc_feature
<222> LOCATION: (35)..(99)
<223> OTHER INFORMATION: GI NO: 21536952
    NR DESCRIPTION: unknown

<400> SEQUENCE: 6

Met Ala Lys Val Gly Lys Leu Thr Lys Leu Lys Ser Ala Ile Lys Lys
1               5                   10                  15

Trp Pro Ser Phe Ala Lys Asn His His Ser Ser Ser Ala Ala
            20                  25                  30

Val Ser Asp Glu Leu Ser Glu Asp Asn Asn Leu His Val Val Tyr Val
        35                  40                  45

Gly Gln Thr Arg Arg Pro Tyr Met Leu Arg Pro Asp Ile Ile Ser His
    50                  55                  60

Pro Leu Phe Gln Glu Leu Val Asp Arg Ser Ser Arg Ser Val Glu His
65                  70                  75                  80

Asp Arg Glu Ile Val Val Ser Cys Glu Val Val Leu Phe Glu His Leu
                85                  90                  95
```

Leu Trp Met Leu
            100

<210> SEQ ID NO 7
<211> LENGTH: 65
<212> TYPE: PRT
<213> ORGANISM: Brassica napus
<220> FEATURE:
<221> NAME/KEY: misc_feature
<222> LOCATION: (1)..(65)
<223> OTHER INFORMATION: Ceres Seq. ID no. 6424420

<400> SEQUENCE: 7

Met Ser Ser Gln Arg Thr Thr Ile Ser Met Leu Phe Met Leu Val Arg
1               5                   10                  15

Leu Glu Asp Leu Thr Cys Leu Asp Arg Thr Ser Ser Leu Thr His Phe
            20                  25                  30

Phe Lys Asn Trp Trp Ile Gly Leu Leu Asp Pro Trp Asn Met Ile Val
        35                  40                  45

Arg Leu Leu Tyr Leu Val Lys Leu Phe Cys Ser Ser Ile Cys Cys Gly
50                  55                  60

Cys
65

<210> SEQ ID NO 8
<211> LENGTH: 56
<212> TYPE: PRT
<213> ORGANISM: Brassica napus
<220> FEATURE:
<221> NAME/KEY: misc_feature
<222> LOCATION: (1)..(56)
<223> OTHER INFORMATION: Ceres Seq. ID no. 6424421

<400> SEQUENCE: 8

Met Leu Phe Met Leu Val Arg Leu Glu Asp Leu Thr Cys Leu Asp Arg
1               5                   10                  15

Thr Ser Ser Leu Thr His Phe Phe Lys Asn Trp Trp Ile Gly Leu Leu
            20                  25                  30

Asp Pro Trp Asn Met Ile Val Arg Leu Leu Tyr Leu Val Lys Leu Phe
        35                  40                  45

Cys Ser Ser Ile Cys Cys Gly Cys
    50                  55

<210> SEQ ID NO 9
<211> LENGTH: 503
<212> TYPE: DNA
<213> ORGANISM: Brassica napus
<220> FEATURE:
<221> NAME/KEY: misc_feature
<222> LOCATION: (1)..(503)
<223> OTHER INFORMATION: Ceres Seq. ID no. 6422420

<400> SEQUENCE: 9
aagaacatct caaacacttc tattcttcat tcattgaaat attttgacca acacacacac      60
atataatcat ttgtcctcat aaaccctaaa ccttacctag ttcaacaac tctctagttc     120 caaatccaag aaaaagaggt tagtttcata agcaatggcc aaagttggga agctgacaaa    180
gctcaagtcg ccataaaga atggccttc cttcgccaag aaccaccac actcatcctc      240 ctccgccgct gtatccgacg agctctcaga ggacaacaat ctccatgttg tttatgttgg    300
tcagactcga agaccttaca tgcttagacc agacatcatc tctcacccac ttttttcaaga   360 actggtcaag aaggaggatc cgttggaaca tgatcgtgag attgttgtag cttgtgaagt    420

-continued

```
tgttttgttc gagcacttgt tgtggatgct caagactggt caagaaggag gatccgttga      480
agaattggct gagttctata ctt                                             503
```

<210> SEQ ID NO 10
<211> LENGTH: 116
<212> TYPE: PRT
<213> ORGANISM: Brassica napus
<220> FEATURE:
<221> NAME/KEY: misc_feature
<222> LOCATION: (1)..(116)
<223> OTHER INFORMATION: Ceres Seq. ID no. 6422421
<220> FEATURE:
<221> NAME/KEY: misc_feature
<222> LOCATION: (10)..(100)
<223> OTHER INFORMATION: PFAM Description: Auxin responsive protein
<220> FEATURE:
<221> NAME/KEY: misc_feature
<222> LOCATION: (1)..(115)
<223> OTHER INFORMATION: GI NO: 21554070
    NR DESCRIPTION: unknown
<220> FEATURE:
<221> NAME/KEY: misc_feature
<222> LOCATION: (1)..(115)
<223> OTHER INFORMATION: GI NO: 15242071
    NR DESCRIPTION: putative protein; protein id: At5g20820.1
<220> FEATURE:
<221> NAME/KEY: misc_feature
<222> LOCATION: (1)..(115)
<223> OTHER INFORMATION: GI NO: 50946385
    NR DESCRIPTION: auxin-induced protein-related-like protein
<220> FEATURE:
<221> NAME/KEY: misc_feature
<222> LOCATION: (35)..(114)
<223> OTHER INFORMATION: GI NO: 21536952
    NR DESCRIPTION: unknown

<400> SEQUENCE: 10

Met Ala Lys Val Gly Lys Leu Thr Lys Leu Lys Ser Ala Ile Lys Lys
1               5                   10                  15

Trp Pro Ser Phe Ala Lys Asn His His His Ser Ser Ser Ala Ala
            20                  25                  30

Val Ser Asp Glu Leu Ser Glu Asp Asn Asn Leu His Val Val Tyr Val
        35                  40                  45

Gly Gln Thr Arg Arg Pro Tyr Met Leu Arg Pro Asp Ile Ile Ser His
    50                  55                  60

Pro Leu Phe Gln Glu Leu Val Lys Lys Glu Asp Pro Leu Glu His Asp
65                  70                  75                  80

Arg Glu Ile Val Val Ala Cys Glu Val Val Leu Phe Glu His Leu Leu
                85                  90                  95

Trp Met Leu Lys Thr Gly Gln Glu Gly Gly Ser Val Glu Glu Leu Ala
            100                 105                 110

Glu Phe Tyr Thr
        115

<210> SEQ ID NO 11
<211> LENGTH: 61
<212> TYPE: PRT
<213> ORGANISM: Brassica napus
<220> FEATURE:
<221> NAME/KEY: misc_feature
<222> LOCATION: (1)..(61)
<223> OTHER INFORMATION: Ceres Seq. ID no. 6422422
<220> FEATURE:
<221> NAME/KEY: misc_feature
<222> LOCATION: (1)..(60)
<223> OTHER INFORMATION: GI NO: 21554070
    NR DESCRIPTION: unknown
<220> FEATURE:
<221> NAME/KEY: misc_feature

```
<222> LOCATION: (1)..(60)
<223> OTHER INFORMATION: GI NO: 15242071
      NR DESCRIPTION: putative protein; protein id: At5g20820.1
<220> FEATURE:
<221> NAME/KEY: misc_feature
<222> LOCATION: (1)..(60)
<223> OTHER INFORMATION: GI NO: 50946385
      NR DESCRIPTION: auxin-induced protein-related-like protein
<220> FEATURE:
<221> NAME/KEY: misc_feature
<222> LOCATION: (1)..(59)
<223> OTHER INFORMATION: GI NO: 21536952
      NR DESCRIPTION: unknown

<400> SEQUENCE: 11

Met Leu Arg Pro Asp Ile Ile Ser His Pro Leu Phe Gln Glu Leu Val
1               5                   10                  15

Lys Lys Glu Asp Pro Leu Glu His Asp Arg Glu Ile Val Val Ala Cys
            20                  25                  30

Glu Val Val Leu Phe Glu His Leu Leu Trp Met Leu Lys Thr Gly Gln
        35                  40                  45

Glu Gly Gly Ser Val Glu Glu Leu Ala Glu Phe Tyr Thr
    50                  55                  60

<210> SEQ ID NO 12
<211> LENGTH: 939
<212> TYPE: DNA
<213> ORGANISM: Arabidopsis thaliana
<220> FEATURE:
<221> NAME/KEY: misc_feature
<222> LOCATION: (1)..(939)
<223> OTHER INFORMATION: Ceres Seq. ID no. 12333678
<220> FEATURE:
<221> NAME/KEY: misc_feature
<222> LOCATION:
<223> OTHER INFORMATION: Phenotype: Soil drought tolerant
      Useful for making plants with increased tolerance to drought

<400> SEQUENCE: 12
aaaaagtacg aaaggaaaat atgagtgagg agaagaggaa gcaacacttc gtgctagtac      60
atggtgcgtg ccacggcgca tggtgctggt acaaggttaa gcctcttctc gaggctttgg     120
gccatcgtgt aaccgcctta gacctagctg cttccggtat agacacaacc aggtcaatca     180
ctgacatttc tacatgtgaa caatattctg agccattgat gcagctaatg acttcattgc     240
cgaatgatga gaaggttgta ctcgttggtc atagctttgg aggtttgagt ttagccttag     300
ccatggataa gtttcccgat aaaatctctg tctctgtctt cgtgactgca ttcatgcccg     360
acaccaaaca ctcaccatcg ttcgtcgagg aaaagtttgc aagcagcatg acaccagaag     420
gatggatggg ctctgagctc gagacatatg gttcagataa ttccggcttg tctgtgttct     480
tcagcaccga cttcatgaag caccgtctct accaactttc tcctgtggag gatcttgagc     540
ttggattgct tctaaagagg cctagttcat tgtttattaa tgaattatcg aagatggaga     600
acttttctga gaagggtat ggatctgttc ctcgagctta cattgtgtgc aaagaggaca     660
acattatctc ggaagaccat caacgatgga tgatccataa ttatccggcg aatttagtga     720
ttgagatgga agagactgat catatgccaa tgttttgcaa acctcaacta ctaagtgacc     780
atctattggc aatcgctgac aatttctgtt aaataatatt ttgatgaaaa tgtatttgga     840
gtggatacaa tcaaacgtgt tctaaaatgg atccttcaaa aggttcaaac ttatttctta     900
gttcttacta tggttgaaat gagaaaccta agtcaatcg                            939

<210> SEQ ID NO 13
<211> LENGTH: 269
```

```
<212> TYPE: PRT
<213> ORGANISM: Arabidopsis thaliana
<220> FEATURE:
<221> NAME/KEY: misc_feature
<222> LOCATION: (1)..(269)
<223> OTHER INFORMATION: Ceres Seq. ID no. 12333679
<220> FEATURE:
<221> NAME/KEY: misc_feature
<222> LOCATION: (41)..(263)
<223> OTHER INFORMATION: PFAM Description: alpha/beta hydrolase fold
<220> FEATURE:
<221> NAME/KEY: misc_feature
<222> LOCATION: (7)..(268)
<223> OTHER INFORMATION: GI NO: 21554666
      NR DESCRIPTION: putative acetone-cyanohydrin lyase
<220> FEATURE:
<221> NAME/KEY: misc_feature
<222> LOCATION: (7)..(268)
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (13)..(265)
<223> OTHER INFORMATION: GI NO: 14279437
      NR DESCRIPTION: ethylene-induced esterase
<220> FEATURE:
<221> NAME/KEY: misc_feature
<222> LOCATION: (11)..(268)
<223> OTHER INFORMATION: GI NO: 40549303
      NR DESCRIPTION: salicylic acid-binding protein 2
<220> FEATURE:
<221> NAME/KEY: misc_feature
<222> LOCATION: (6)..(265)
<223> OTHER INFORMATION: GI NO: 21595837
      NR DESCRIPTION: polyneuridine aldehyde esterase
<220> FEATURE:
<221> NAME/KEY: misc_feature
<222> LOCATION: (9)..(265)
<223> OTHER INFORMATION: GI NO: 25404802
      NR DESCRIPTION: probable alpha/beta hydrolase F23O10.18
<220> FEATURE:
<221> NAME/KEY: misc_feature
<222> LOCATION: (49)..(249)
<223> OTHER INFORMATION: GI NO: 25518436
      NR DESCRIPTION: hypothetical protein T1K7.26
<220> FEATURE:
<221> NAME/KEY: misc_feature
<222> LOCATION: (16)..(124)
<223> OTHER INFORMATION: GI NO: 21222782
      NR DESCRIPTION: putative esterase
<220> FEATURE:
<221> NAME/KEY: misc_feature
<222> LOCATION: (63)..(265)
<223> OTHER INFORMATION: GI NO: 46324511
      NR DESCRIPTION: COG0596: Predicted hydrolases or acyltransferases
<220> FEATURE:
<221> NAME/KEY: misc_feature
<222> LOCATION: (6)..(54)
<223> OTHER INFORMATION: GI NO: 46324511
      NR DESCRIPTION: COG0596: Predicted hydrolases or acyltransferases

<400> SEQUENCE: 13

Lys Val Arg Lys Glu Asn Met Ser Glu Glu Lys Arg Lys Gln His Phe
1               5                   10                  15

Val Leu Val His Gly Ala Cys His Gly Ala Trp Cys Trp Tyr Lys Val
            20                  25                  30

Lys Pro Leu Leu Glu Ala Leu Gly His Arg Val Thr Ala Leu Asp Leu
        35                  40                  45

Ala Ala Ser Gly Ile Asp Thr Thr Arg Ser Ile Thr Asp Ile Ser Thr
50                  55                  60

Cys Glu Gln Tyr Ser Glu Pro Leu Met Gln Leu Met Thr Ser Leu Pro
65                  70                  75                  80

Asn Asp Glu Lys Val Val Leu Val Gly His Ser Phe Gly Gly Leu Ser
                85                  90                  95
```

```
Leu Ala Leu Ala Met Asp Lys Phe Pro Asp Lys Ile Ser Val Ser Val
            100                 105                 110

Phe Val Thr Ala Phe Met Pro Asp Thr Lys His Ser Pro Ser Phe Val
        115                 120                 125

Glu Glu Lys Phe Ala Ser Ser Met Thr Pro Glu Gly Trp Met Gly Ser
    130                 135                 140

Glu Leu Glu Thr Tyr Gly Ser Asp Asn Ser Gly Leu Ser Val Phe Phe
145                 150                 155                 160

Ser Thr Asp Phe Met Lys His Arg Leu Tyr Gln Leu Ser Pro Val Glu
                165                 170                 175

Asp Leu Glu Leu Gly Leu Leu Leu Lys Arg Pro Ser Ser Leu Phe Ile
            180                 185                 190

Asn Glu Leu Ser Lys Met Glu Asn Phe Ser Glu Lys Gly Tyr Gly Ser
        195                 200                 205

Val Pro Arg Ala Tyr Ile Val Cys Lys Glu Asp Asn Ile Ile Ser Glu
    210                 215                 220

Asp His Gln Arg Trp Met Ile His Asn Tyr Pro Ala Asn Leu Val Ile
225                 230                 235                 240

Glu Met Glu Glu Thr Asp His Met Pro Met Phe Cys Lys Pro Gln Leu
                245                 250                 255

Leu Ser Asp His Leu Leu Ala Ile Ala Asp Asn Phe Cys
            260                 265

<210> SEQ ID NO 14
<211> LENGTH: 263
<212> TYPE: PRT
<213> ORGANISM: Arabidopsis thaliana
<220> FEATURE:
<221> NAME/KEY: misc_feature
<222> LOCATION: (1)..(263)
<223> OTHER INFORMATION: Ceres Seq. ID no. 12333680
<220> FEATURE:
<221> NAME/KEY: misc_feature
<222> LOCATION: (35)..(257)
<223> OTHER INFORMATION: PFAM Description: alpha/beta hydrolase fold
<220> FEATURE:
<221> NAME/KEY: misc_feature
<222> LOCATION: (1)..(262)
<223> OTHER INFORMATION: GI NO: 21554666
    NR DESCRIPTION: putative acetone-cyanohydrin lyase
<220> FEATURE:
<221> NAME/KEY: misc_feature
<222> LOCATION: (1)..(262)
<223> OTHER INFORMATION: GI NO: 27754457
    NR DESCRIPTION: putative acetone-cyanohydrin lyase
<220> FEATURE:
<221> NAME/KEY: misc_feature
<222> LOCATION: (7)..(259)
<223> OTHER INFORMATION: GI NO: 14279437
    NR DESCRIPTION: ethylene-induced esterase
<220> FEATURE:
<221> NAME/KEY: misc_feature
<222> LOCATION: (5)..(262)
<223> OTHER INFORMATION: GI NO: 40549303
    NR DESCRIPTION: salicylic acid-binding protein 2
<220> FEATURE:
<221> NAME/KEY: misc_feature
<222> LOCATION: (1)..(259)
<223> OTHER INFORMATION: GI NO: 21595837
    NR DESCRIPTION: polyneuridine aldehyde esterase
<220> FEATURE:
<221> NAME/KEY: misc_feature
<222> LOCATION: (3)..(259)
<223> OTHER INFORMATION: GI NO: 25404802
    NR DESCRIPTION: probable alpha/beta hydrolase F23O10.18
<220> FEATURE:
<221> NAME/KEY: misc_feature
<222> LOCATION: (43)..(243)
```

```
<223> OTHER INFORMATION: GI NO: 25518436
      NR DESCRIPTION: hypothetical protein T1K7.26
<220> FEATURE:
<221> NAME/KEY: misc_feature
<222> LOCATION: (10)..(118)
<223> OTHER INFORMATION: GI NO: 21222782
      NR DESCRIPTION: putative esterase
<220> FEATURE:
<221> NAME/KEY: misc_feature
<222> LOCATION: (57)..(259)
<223> OTHER INFORMATION: GI NO: 46324511
      NR DESCRIPTION: COG0596: Predicted hydrolases or acyltransferases
<220> FEATURE:
<221> NAME/KEY: misc_feature
<222> LOCATION: (1)..(48)
<223> OTHER INFORMATION: GI NO: 46324511
      NR DESCRIPTION: COG0596: Predicted hydrolases or acyltransferases

<400> SEQUENCE: 14

Met Ser Glu Glu Lys Arg Lys Gln His Phe Val Leu Val His Gly Ala
1               5                   10                  15

Cys His Gly Ala Trp Cys Trp Tyr Lys Val Pro Leu Leu Glu Ala
            20                  25                  30

Leu Gly His Arg Val Thr Ala Leu Asp Leu Ala Ala Ser Gly Ile Asp
        35                  40                  45

Thr Thr Arg Ser Ile Thr Asp Ile Ser Thr Cys Glu Gln Tyr Ser Glu
50                  55                  60

Pro Leu Met Gln Leu Met Thr Ser Leu Pro Asn Asp Glu Lys Val Val
65                  70                  75                  80

Leu Val Gly His Ser Phe Gly Gly Leu Ser Leu Ala Leu Ala Met Asp
                85                  90                  95

Lys Phe Pro Asp Lys Ile Ser Val Ser Val Phe Val Thr Ala Phe Met
            100                 105                 110

Pro Asp Thr Lys His Ser Pro Ser Phe Val Glu Glu Lys Phe Ala Ser
        115                 120                 125

Ser Met Thr Pro Glu Gly Trp Met Gly Ser Glu Leu Glu Thr Tyr Gly
130                 135                 140

Ser Asp Asn Ser Gly Leu Ser Val Phe Phe Ser Thr Asp Phe Met Lys
145                 150                 155                 160

His Arg Leu Tyr Gln Leu Ser Pro Val Glu Asp Leu Glu Leu Gly Leu
                165                 170                 175

Leu Leu Lys Arg Pro Ser Ser Leu Phe Ile Asn Glu Leu Ser Lys Met
            180                 185                 190

Glu Asn Phe Ser Glu Lys Gly Tyr Gly Ser Val Pro Arg Ala Tyr Ile
        195                 200                 205

Val Cys Lys Glu Asp Asn Ile Ile Ser Glu Asp His Gln Arg Trp Met
210                 215                 220

Ile His Asn Tyr Pro Ala Asn Leu Val Ile Glu Met Glu Glu Thr Asp
225                 230                 235                 240

His Met Pro Met Phe Cys Lys Pro Gln Leu Leu Ser Asp His Leu Leu
                245                 250                 255

Ala Ile Ala Asp Asn Phe Cys
            260

<210> SEQ ID NO 15
<211> LENGTH: 197
<212> TYPE: PRT
<213> ORGANISM: Arabidopsis thaliana
<220> FEATURE:
<221> NAME/KEY: misc_feature
<222> LOCATION: (1)..(197)
<223> OTHER INFORMATION: Ceres Seq. ID no. 12333681
```

```
<220> FEATURE:
<221> NAME/KEY: misc_feature
<222> LOCATION: (1)..(191)
<223> OTHER INFORMATION: PFAM Description: alpha/beta hydrolase fold
<220> FEATURE:
<221> NAME/KEY: misc_feature
<222> LOCATION: (1)..(196)
<223> OTHER INFORMATION: GI NO: 21554666
      NR DESCRIPTION: putative acetone-cyanohydrin lyase
<220> FEATURE:
<221> NAME/KEY: misc_feature
<222> LOCATION: (1)..(196)
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (1)..(193)
<223> OTHER INFORMATION: GI NO: 14279437
      NR DESCRIPTION: ethylene-induced esterase
<220> FEATURE:
<221> NAME/KEY: misc_feature
<222> LOCATION: (1)..(196)
<223> OTHER INFORMATION: GI NO: 40549303
      NR DESCRIPTION: salicylic acid-binding protein 2
<220> FEATURE:
<221> NAME/KEY: misc_feature
<222> LOCATION: (1)..(193)
<223> OTHER INFORMATION: GI NO: 21595837
      NR DESCRIPTION: polyneuridine aldehyde esterase
<220> FEATURE:
<221> NAME/KEY: misc_feature
<222> LOCATION: (1)..(193)
<223> OTHER INFORMATION: GI NO: 25404802
      NR DESCRIPTION: probable alpha/beta hydrolase F23O10.18
<220> FEATURE:
<221> NAME/KEY: misc_feature
<222> LOCATION: (1)..(177)
<223> OTHER INFORMATION: GI NO: 25518436
      NR DESCRIPTION: hypothetical protein T1K7.26
<220> FEATURE:
<221> NAME/KEY: misc_feature
<222> LOCATION: (1)..(52)
<223> OTHER INFORMATION: GI NO: 21222782
      NR DESCRIPTION: putative esterase
<220> FEATURE:
<221> NAME/KEY: misc_feature
<222> LOCATION: (1)..(193)
<223> OTHER INFORMATION: GI NO: 46324511
      NR DESCRIPTION: COG0596: Predicted hydrolases or acyltransferases
<220> FEATURE:
<221> NAME/KEY: misc_feature
<222> LOCATION: (12)..(47)
<223> OTHER INFORMATION: GI NO: 7672985
      NR DESCRIPTION: EstC

<400> SEQUENCE: 15

Met Gln Leu Met Thr Ser Leu Pro Asn Asp Glu Lys Val Val Leu Val
1               5                   10                  15

Gly His Ser Phe Gly Gly Leu Ser Leu Ala Leu Ala Met Asp Lys Phe
                20                  25                  30

Pro Asp Lys Ile Ser Val Ser Val Phe Val Thr Ala Phe Met Pro Asp
            35                  40                  45

Thr Lys His Ser Pro Ser Phe Val Glu Glu Lys Phe Ala Ser Ser Met
    50                  55                  60

Thr Pro Glu Gly Trp Met Gly Ser Glu Leu Glu Thr Tyr Gly Ser Asp
65                  70                  75                  80

Asn Ser Gly Leu Ser Val Phe Phe Ser Thr Asp Phe Met Lys His Arg
                85                  90                  95

Leu Tyr Gln Leu Ser Pro Val Glu Asp Leu Glu Leu Gly Leu Leu Leu
                100                 105                 110

Lys Arg Pro Ser Ser Leu Phe Ile Asn Glu Leu Ser Lys Met Glu Asn
            115                 120                 125
```

Phe Ser Glu Lys Gly Tyr Gly Ser Val Pro Arg Ala Tyr Ile Val Cys
    130                 135                 140

Lys Glu Asp Asn Ile Ile Ser Glu Asp His Gln Arg Trp Met Ile His
145                 150                 155                 160

Asn Tyr Pro Ala Asn Leu Val Ile Glu Met Glu Thr Asp His Met
                165                 170                 175

Pro Met Phe Cys Lys Pro Gln Leu Leu Ser Asp His Leu Leu Ala Ile
            180                 185                 190

Ala Asp Asn Phe Cys
        195

<210> SEQ ID NO 16
<211> LENGTH: 586
<212> TYPE: DNA
<213> ORGANISM: Arabidopsis thaliana
<220> FEATURE:
<221> NAME/KEY: misc_feature
<222> LOCATION: (1)..(586)
<223> OTHER INFORMATION: Ceres Seq. ID no. 12393104
<220> FEATURE:
<221> NAME/KEY: misc_feature
<222> LOCATION:
<223> OTHER INFORMATION: Phenotype: Soil drought tolerant
      Useful for making plants with increased tolerance to drought

<400> SEQUENCE: 16
agtttcaaca actctcttgt tccaaccccca agaaaaaagt tcaatttcgt tagcaatggc      60
caaagttggg aagctgacaa agcttaagtc ggctatgaag aaatggcctt ctttcgccaa     120
gaaccaccac cactcaacct cctcagccgc tgtttccgac gaactctcag aagacaacaa     180
tctccatgtg gtttacgttg gtcaaactcg aagaccttac atgctagac cagacatcat      240 ctctcaccca ctcctttcaag aactcgtgga tcggtcttct tctagatcca tcgaacaaga     300
tcgtgagatt gttgtagctt gtgaagtcgt tttgttcgag cacttgctgt ggatgctcaa     360
gtctggtcaa gaaggaggat ccgttgaaga attggctgag ttctatactt attgacatcg     420
accgattgat tttatacact tatttcgtat aatatatacc ttttttgtta ttgtttgttg     480
ttgctgattt gtattttcat tcgatgcggt gtgtgatcaa aacgtgatct cgtaaaccat     540
gtcatttgct tccgttttc tgagcaattt tatgatgatg atgagc                     586

<210> SEQ ID NO 17
<211> LENGTH: 137
<212> TYPE: PRT
<213> ORGANISM: Arabidopsis thaliana
<220> FEATURE:
<221> NAME/KEY: misc_feature
<222> LOCATION: (1)..(137)
<223> OTHER INFORMATION: Ceres Seq. ID no. 12393105
<220> FEATURE:
<221> NAME/KEY: misc_feature
<222> LOCATION: (28)..(120)
<223> OTHER INFORMATION: PFAM Description: Auxin responsive protein
<220> FEATURE:
<221> NAME/KEY: misc_feature
<222> LOCATION: (19)..(135)
<223> OTHER INFORMATION: GI NO: 21554070
      NR DESCRIPTION: unknown
<220> FEATURE:
<221> NAME/KEY: misc_feature
<222> LOCATION: (19)..(135)
<223> OTHER INFORMATION: GI NO: 15242071
      NR DESCRIPTION: putative protein; protein id: At5g20820.1
<220> FEATURE:
<221> NAME/KEY: misc_feature
<222> LOCATION: (19)..(135)
<223> OTHER INFORMATION: GI NO: 50946385

```
                NR DESCRIPTION: auxin-induced protein-related-like protein
<220> FEATURE:
<221> NAME/KEY: misc_feature
<222> LOCATION: (53)..(134)
<223> OTHER INFORMATION: GI NO: 21536952
       NR DESCRIPTION: unknown

<400> SEQUENCE: 17

Val Ser Thr Thr Leu Leu Phe Gln Pro Gln Glu Lys Ser Ser Ile Ser
1               5                   10                  15

Leu Ala Met Ala Lys Val Gly Lys Leu Thr Lys Leu Lys Ser Ala Met
            20                  25                  30

Lys Lys Trp Pro Ser Phe Ala Lys Asn His His His Ser Thr Ser Ser
        35                  40                  45

Ala Ala Val Ser Asp Glu Leu Ser Glu Asp Asn Asn Leu His Val Val
    50                  55                  60

Tyr Val Gly Gln Thr Arg Arg Pro Tyr Met Leu Arg Pro Asp Ile Ile
65                  70                  75                  80

Ser His Pro Leu Phe Gln Glu Leu Val Asp Arg Ser Ser Ser Arg Ser
                85                  90                  95

Ile Glu Gln Asp Arg Glu Ile Val Val Ala Cys Glu Val Val Leu Phe
            100                 105                 110

Glu His Leu Leu Trp Met Leu Lys Ser Gly Gln Glu Gly Gly Ser Val
        115                 120                 125

Glu Glu Leu Ala Glu Phe Tyr Thr Tyr
    130                 135

<210> SEQ ID NO 18
<211> LENGTH: 119
<212> TYPE: PRT
<213> ORGANISM: Arabidopsis thaliana
<220> FEATURE:
<221> NAME/KEY: misc_feature
<222> LOCATION: (1)..(119)
<223> OTHER INFORMATION: Ceres Seq. ID no. 12393106
<220> FEATURE:
<221> NAME/KEY: misc_feature
<222> LOCATION: (10)..(102)
<223> OTHER INFORMATION: PFAM Description: Auxin responsive protein
<220> FEATURE:
<221> NAME/KEY: misc_feature
<222> LOCATION: (1)..(117)
<223> OTHER INFORMATION: GI NO: 21554070
       NR DESCRIPTION: unknown
<220> FEATURE:
<221> NAME/KEY: misc_feature
<222> LOCATION: (1)..(117)
<223> OTHER INFORMATION: GI NO: 15242071
       NR DESCRIPTION: putative protein; protein id: At5g20820.1
<220> FEATURE:
<221> NAME/KEY: misc_feature
<222> LOCATION: (1)..(117)
<223> OTHER INFORMATION: GI NO: 50946385
       NR DESCRIPTION: auxin-induced protein-related-like protein
<220> FEATURE:
<221> NAME/KEY: misc_feature
<222> LOCATION: (35)..(116)
<223> OTHER INFORMATION: GI NO: 21536952
       NR DESCRIPTION: unknown

<400> SEQUENCE: 18

Met Ala Lys Val Gly Lys Leu Thr Lys Leu Lys Ser Ala Met Lys Lys
1               5                   10                  15

Trp Pro Ser Phe Ala Lys Asn His His His Ser Thr Ser Ser Ala Ala
            20                  25                  30

Val Ser Asp Glu Leu Ser Glu Asp Asn Asn Leu His Val Val Tyr Val
        35                  40                  45
```

```
Gly Gln Thr Arg Arg Pro Tyr Met Leu Arg Pro Asp Ile Ile Ser His
    50                  55                  60

Pro Leu Phe Gln Glu Leu Val Asp Arg Ser Ser Ser Arg Ser Ile Glu
65                  70                  75                  80

Gln Asp Arg Glu Ile Val Val Ala Cys Glu Val Val Leu Phe Glu His
                85                  90                  95

Leu Leu Trp Met Leu Lys Ser Gly Gln Glu Gly Gly Ser Val Glu Glu
            100                 105                 110

Leu Ala Glu Phe Tyr Thr Tyr
            115

<210> SEQ ID NO 19
<211> LENGTH: 106
<212> TYPE: PRT
<213> ORGANISM: Arabidopsis thaliana
<220> FEATURE:
<221> NAME/KEY: misc_feature
<222> LOCATION: (1)..(106)
<223> OTHER INFORMATION: Ceres Seq. ID no. 12393107
<220> FEATURE:
<221> NAME/KEY: misc_feature
<222> LOCATION: (1)..(89)
<223> OTHER INFORMATION: PFAM Description: Auxin responsive protein
<220> FEATURE:
<221> NAME/KEY: misc_feature
<222> LOCATION: (1)..(104)
<223> OTHER INFORMATION: GI NO: 21554070
       NR DESCRIPTION: unknown
<220> FEATURE:
<221> NAME/KEY: misc_feature
<222> LOCATION: (1)..(104)
<223> OTHER INFORMATION: GI NO: 15242071
       NR DESCRIPTION: putative protein; protein id: At5g20820.1
<220> FEATURE:
<221> NAME/KEY: misc_feature
<222> LOCATION: (1)..(104)
<223> OTHER INFORMATION: GI NO: 50946385
       NR DESCRIPTION: auxin-induced protein-related-like protein
<220> FEATURE:
<221> NAME/KEY: misc_feature
<222> LOCATION: (22)..(103)
<223> OTHER INFORMATION: GI NO: 21536952
       NR DESCRIPTION: unknown

<400> SEQUENCE: 19

Met Lys Lys Trp Pro Ser Phe Ala Lys Asn His His Ser Thr Ser
1               5                   10                  15

Ser Ala Ala Val Ser Asp Glu Leu Ser Glu Asp Asn Asn Leu His Val
                20                  25                  30

Val Tyr Val Gly Gln Thr Arg Arg Pro Tyr Met Leu Arg Pro Asp Ile
            35                  40                  45

Ile Ser His Pro Leu Phe Gln Glu Leu Val Asp Arg Ser Ser Ser Arg
    50                  55                  60

Ser Ile Glu Gln Asp Arg Glu Ile Val Val Ala Cys Glu Val Val Leu
65                  70                  75                  80

Phe Glu His Leu Leu Trp Met Leu Lys Ser Gly Gln Glu Gly Gly Ser
                85                  90                  95

Val Glu Glu Leu Ala Glu Phe Tyr Thr Tyr
            100                 105

<210> SEQ ID NO 20
<211> LENGTH: 633
<212> TYPE: DNA
<213> ORGANISM: Arabidopsis thaliana
<220> FEATURE:
<221> NAME/KEY: misc_feature
```

```
<222> LOCATION: (1)..(633)
<223> OTHER INFORMATION: Ceres Seq. ID no. 12420738
<220> FEATURE:
<221> NAME/KEY: misc_feature
<222> LOCATION:
<223> OTHER INFORMATION: Phenotype: Soil drought tolerant
      Useful for making plants with increased tolerance to drought

<400> SEQUENCE: 20
tcgaaaaacc atcaccgggg aatctgacgg cggcttagta ccggcggcta ctgcaaaaag      60
gattgtgttc ttcttaggct tgatacttgc cttgggaaga atataacaat cattttttgcg   120 gtagctaaaa cgctaagctc tatcgtcata tctttatcat taatacttat ttgatatcta    180
aatatcataa aaatggccgc tcgttcactc tccggtgccg ttaaatctct ttgctccgcc    240
gcatccggaa gtctgtcttg ttccattgtc ttaaggagga gttacgttgc tacatcgcag    300
aatgtaacag cagcaggatt gagtaaggga ggttccacca gagttatggt ggggaagatg    360
gaacagagag gtttagatca agaggcagag tctgcttggg gaccagatcc agttactgga    420
tactatagac cttccaatcg tgcggctgaa attgatccag ctgagctcag agaattgctt    480
ttgaaaaaca aagcaaagtc tttctgagga ttttgattgg ttggttgact tggttccagt    540
ggaaggttgt cgtaggcgac tattatgatt atgtgtgttt atgtttgtct tgtatcaact    600
attaagtaaa aataaagatc acattaacta gtc                                 633

<210> SEQ ID NO 21
<211> LENGTH: 104
<212> TYPE: PRT
<213> ORGANISM: Arabidopsis thaliana
<220> FEATURE:
<221> NAME/KEY: misc_feature
<222> LOCATION: (1)..(104)
<223> OTHER INFORMATION: Ceres Seq. ID no. 12420739
<220> FEATURE:
<221> NAME/KEY: misc_feature
<222> LOCATION: (2)..(98)
<223> OTHER INFORMATION: PFAM Description: Late embryogenesis abundant
      protein
<220> FEATURE:
<221> NAME/KEY: misc_feature
<222> LOCATION: (3)..(103)
<223> OTHER INFORMATION: GI NO: 1370589
      NR DESCRIPTION: protein induced upon tuberization
<220> FEATURE:
<221> NAME/KEY: misc_feature
<222> LOCATION: (3)..(103)
<223> OTHER INFORMATION: GI NO: 7489029
      NR DESCRIPTION: late-embryogenesis protein homolog
<220> FEATURE:
<221> NAME/KEY: misc_feature
<222> LOCATION: (3)..(99)
<223> OTHER INFORMATION: GI NO: 7488660
      NR DESCRIPTION: desiccation protective protein LEA5
<220> FEATURE:
<221> NAME/KEY: misc_feature
<222> LOCATION: (17)..(102)
<223> OTHER INFORMATION: GI NO: 34894580
      NR DESCRIPTION: zinc-induced protein-like

<400> SEQUENCE: 21

Met Ala Ala Arg Ser Leu Ser Gly Ala Val Lys Ser Leu Cys Ser Ala
1               5                   10                  15

Ala Ser Gly Ser Leu Ser Cys Ser Ile Val Leu Arg Arg Ser Tyr Val
            20                  25                  30

Ala Thr Ser Gln Asn Val Thr Ala Ala Gly Leu Ser Lys Gly Gly Ser
        35                  40                  45

Thr Arg Val Met Val Gly Lys Met Glu Gln Arg Gly Leu Asp Gln Glu
    50                  55                  60
```

Ala Glu Ser Ala Trp Gly Pro Asp Pro Val Thr Gly Tyr Tyr Arg Pro
65                  70                  75                  80

Ser Asn Arg Ala Ala Glu Ile Asp Pro Ala Glu Leu Arg Glu Leu Leu
                85                  90                  95

Leu Lys Asn Lys Ala Lys Ser Phe
            100

<210> SEQ ID NO 22
<211> LENGTH: 53
<212> TYPE: PRT
<213> ORGANISM: Arabidopsis thaliana
<220> FEATURE:
<221> NAME/KEY: misc_feature
<222> LOCATION: (1)..(53)
<223> OTHER INFORMATION: Ceres Seq. ID no. 12420740
<220> FEATURE:
<221> NAME/KEY: misc_feature
<222> LOCATION: (1)..(52)
<223> OTHER INFORMATION: GI NO: 1370589
      NR DESCRIPTION: protein induced upon tuberization
<220> FEATURE:
<221> NAME/KEY: misc_feature
<222> LOCATION: (1)..(52)
<223> OTHER INFORMATION: GI NO: 7489029
      NR DESCRIPTION: late-embryogenesis protein homolog
<220> FEATURE:
<221> NAME/KEY: misc_feature
<222> LOCATION: (1)..(48)
<223> OTHER INFORMATION: GI NO: 7488660
      NR DESCRIPTION: desiccation protective protein LEA5
<220> FEATURE:
<221> NAME/KEY: misc_feature
<222> LOCATION: (1)..(51)
<223> OTHER INFORMATION: GI NO: 34894580
      NR DESCRIPTION: zinc-induced protein-like

<400> SEQUENCE: 22

Met Val Gly Lys Met Glu Gln Arg Gly Leu Asp Gln Glu Ala Glu Ser
1               5                   10                  15

Ala Trp Gly Pro Asp Pro Val Thr Gly Tyr Tyr Arg Pro Ser Asn Arg
            20                  25                  30

Ala Ala Glu Ile Asp Pro Ala Glu Leu Arg Glu Leu Leu Leu Lys Asn
        35                  40                  45

Lys Ala Lys Ser Phe
    50

<210> SEQ ID NO 23
<211> LENGTH: 1325
<212> TYPE: DNA
<213> ORGANISM: Arabidopsis thaliana
<220> FEATURE:
<221> NAME/KEY: misc_feature
<222> LOCATION: (1)..(1325)
<223> OTHER INFORMATION: Ceres Seq. ID no. 12562714

<400> SEQUENCE: 23
acgaaaggaa aatatgagtg aggagaagag gaagcaacac ttcgtgctag tacatggtgc     60
gtgccacggc gcatggtgct ggtacaaggt taagcctctt ctcgaggctt tgggccatcg    120
tgtaaccgcc ttagacctag ctgcttccgg tatagacaca accaggtcaa tcactgacat    180
ttctacatgt gaacaatatt ctgagccatt gatgcagcta atgacttcat tgccgaatga    240
tgagaaggtt gtactcgttg gtcatagctt tggaggtttg agtttagcct tagccatgga    300
taagtttccc gataaaatct ctgtctctgt cttcgtgact gcattcatgc ccgacaccaa    360
acactcacca tcgttcgtcg aggaaaaggt atatatctct ttttaaagca gccaaatttt    420

```
gtgttctgtt cttaaatcca ccacctggaa gtctagacgg tcaaaacaac gtggtcgtcc      480 attttagcc  aaaaccgtta caagattgta gccaaaatta ttacaaaaat tgatcaacat      540
aacggttcct tttggtctat atgtccgatt gttcagtcta gtcggacaaa atcgagattt      600
ccatttcgca gtcttttata acttgtggct tatatactat aaccaattaa ccatagatca      660
tgtgttagac aatctaatgt ccaagtagtg tcactttcgt ggtgatgagt tagtaatttg      720
ttttaacatg tttcattttc atggttgtta cttcgttaga attttaaag gtagttaatt       780 gtaataaacg tgaaaataaa tatgattttt tcgtaattac tatgaaaaag tttgcaagca      840
gcatgacacc agaaggatgg atgggctctg agctcgagac atatggttca gataattccg      900
gcttgtctgt gttcttcagc accgacttca tgaagcaccg tctctaccaa ctttctcctg      960
tggaggatct tgagcttgga ttgcttctaa agaggcctag ttcattgttt attaatgaat     1020
tatcgaagat ggagaacttt tcttagaaag ggtatggatc tgttcctcga gcttacattg     1080
tgtgcaaaga ggacaacatt atctcggaag accatcaacg atggatgatc cataattatc     1140
cggcgaattt agtgattgag atggaagaga cggatcatat gccaatgttt tgcaaacctc     1200
aagtactaag tgaccatcta ttggcaatcg ctgacaattt ctcttaaata atattttgat     1260
gaaaatgtat ttggagtgga tacaataaaa atgtgttcta aattaatgga tctttatgaa     1320
ggtcc                                                                 1325
```

```
<210> SEQ ID NO 24
<211> LENGTH: 134
<212> TYPE: PRT
<213> ORGANISM: Arabidopsis thaliana
<220> FEATURE:
<221> NAME/KEY: misc_feature
<222> LOCATION: (1)..(134)
<223> OTHER INFORMATION: Ceres Seq. ID no. 12562715
<220> FEATURE:
<221> NAME/KEY: misc_feature
<222> LOCATION: (39)..(129)
<223> OTHER INFORMATION: PFAM Description: alpha/beta hydrolase fold
<220> FEATURE:
<221> NAME/KEY: misc_feature
<222> LOCATION: (5)..(129)
<223> OTHER INFORMATION: GI NO: 21554666
      NR DESCRIPTION: putative acetone-cyanohydrin lyase
<220> FEATURE:
<221> NAME/KEY: misc_feature
<222> LOCATION: (5)..(129)
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (11)..(129)
<223> OTHER INFORMATION: GI NO: 14279437
      NR DESCRIPTION: ethylene-induced esterase
<220> FEATURE:
<221> NAME/KEY: misc_feature
<222> LOCATION: (9)..(129)
<223> OTHER INFORMATION: GI NO: 40549303
      NR DESCRIPTION: salicylic acid-binding protein 2
<220> FEATURE:
<221> NAME/KEY: misc_feature
<222> LOCATION: (4)..(128)
<223> OTHER INFORMATION: GI NO: 21595837
      NR DESCRIPTION: polyneuridine aldehyde esterase
<220> FEATURE:
<221> NAME/KEY: misc_feature
<222> LOCATION: (7)..(116)
<223> OTHER INFORMATION: GI NO: 25404802
      NR DESCRIPTION: probable alpha/beta hydrolase F23O10.18
<220> FEATURE:
<221> NAME/KEY: misc_feature
<222> LOCATION: (47)..(116)
<223> OTHER INFORMATION: GI NO: 25518436
      NR DESCRIPTION: hypothetical protein T1K7.26
```

```
<220> FEATURE:
<221> NAME/KEY: misc_feature
<222> LOCATION: (14)..(122)
<223> OTHER INFORMATION: GI NO: 21222782
      NR DESCRIPTION: putative esterase
<220> FEATURE:
<221> NAME/KEY: misc_feature
<222> LOCATION: (61)..(117)
<223> OTHER INFORMATION: GI NO: 46324511
      NR DESCRIPTION: COG0596: Predicted hydrolases or acyltransferases
<220> FEATURE:
<221> NAME/KEY: misc_feature
<222> LOCATION: (4)..(52)
<223> OTHER INFORMATION: GI NO: 46324511
      NR DESCRIPTION: COG0596: Predicted hydrolases or acyltransferases

<400> SEQUENCE: 24

Arg Lys Glu Asn Met Ser Glu Glu Lys Arg Lys Gln His Phe Val Leu
1               5                   10                  15

Val His Gly Ala Cys His Gly Ala Trp Cys Trp Tyr Lys Val Lys Pro
            20                  25                  30

Leu Leu Glu Ala Leu Gly His Arg Val Thr Ala Leu Asp Leu Ala Ala
        35                  40                  45

Ser Gly Ile Asp Thr Thr Arg Ser Ile Thr Asp Ile Ser Thr Cys Glu
50                  55                  60

Gln Tyr Ser Glu Pro Leu Met Gln Leu Met Thr Ser Leu Pro Asn Asp
65                  70                  75                  80

Glu Lys Val Val Leu Val Gly His Ser Phe Gly Gly Leu Ser Leu Ala
                85                  90                  95

Leu Ala Met Asp Lys Phe Pro Asp Lys Ile Ser Val Ser Val Phe Val
            100                 105                 110

Thr Ala Phe Met Pro Asp Thr Lys His Ser Pro Ser Phe Val Glu Glu
        115                 120                 125

Lys Val Tyr Ile Ser Phe
        130

<210> SEQ ID NO 25
<211> LENGTH: 130
<212> TYPE: PRT
<213> ORGANISM: Arabidopsis thaliana
<220> FEATURE:
<221> NAME/KEY: misc_feature
<222> LOCATION: (1)..(130)
<223> OTHER INFORMATION: Ceres Seq. ID no. 12562716
<220> FEATURE:
<221> NAME/KEY: misc_feature
<222> LOCATION: (35)..(125)
<223> OTHER INFORMATION: PFAM Description: alpha/beta hydrolase fold
<220> FEATURE:
<221> NAME/KEY: misc_feature
<222> LOCATION: (1)..(125)
<223> OTHER INFORMATION: GI NO: 21554666
      NR DESCRIPTION: putative acetone-cyanohydrin lyase
<220> FEATURE:
<221> NAME/KEY: misc_feature
<222> LOCATION: (1)..(125)
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (7)..(125)
<223> OTHER INFORMATION: GI NO: 14279437
      NR DESCRIPTION: ethylene-induced esterase
<220> FEATURE:
<221> NAME/KEY: misc_feature
<222> LOCATION: (5)..(125)
<223> OTHER INFORMATION: GI NO: 40549303
      NR DESCRIPTION: salicylic acid-binding protein 2
<220> FEATURE:
<221> NAME/KEY: misc_feature
```

```
<222> LOCATION: (1)..(124)
<223> OTHER INFORMATION: GI NO: 21595837
      NR DESCRIPTION: polyneuridine aldehyde esterase
<220> FEATURE:
<221> NAME/KEY: misc_feature
<222> LOCATION: (3)..(112)
<223> OTHER INFORMATION: GI NO: 25404802
      NR DESCRIPTION: probable alpha/beta hydrolase F23O10.18
<220> FEATURE:
<221> NAME/KEY: misc_feature
<222> LOCATION: (43)..(112)
<223> OTHER INFORMATION: GI NO: 25518436
      NR DESCRIPTION: hypothetical protein T1K7.26
<220> FEATURE:
<221> NAME/KEY: misc_feature
<222> LOCATION: (10)..(118)
<223> OTHER INFORMATION: GI NO: 21222782
      NR DESCRIPTION: putative esterase
<220> FEATURE:
<221> NAME/KEY: misc_feature
<222> LOCATION: (57)..(113)
<223> OTHER INFORMATION: GI NO: 46324511
      NR DESCRIPTION: COG0596: Predicted hydrolases or acyltransferases
<220> FEATURE:
<221> NAME/KEY: misc_feature
<222> LOCATION: (1)..(48)
<223> OTHER INFORMATION: GI NO: 46324511
      NR DESCRIPTION: COG0596: Predicted hydrolases or acyltransferases

<400> SEQUENCE: 25

Met Ser Glu Glu Lys Arg Lys Gln His Phe Val Leu Val His Gly Ala
1               5                  10                  15

Cys His Gly Ala Trp Cys Trp Tyr Lys Val Lys Pro Leu Leu Glu Ala
            20                  25                  30

Leu Gly His Arg Val Thr Ala Leu Asp Leu Ala Ala Ser Gly Ile Asp
        35                  40                  45

Thr Thr Arg Ser Ile Thr Asp Ile Ser Thr Cys Glu Gln Tyr Ser Glu
    50                  55                  60

Pro Leu Met Gln Leu Met Thr Ser Leu Pro Asn Asp Glu Lys Val Val
65                  70                  75                  80

Leu Val Gly His Ser Phe Gly Gly Leu Ser Leu Ala Leu Ala Met Asp
                85                  90                  95

Lys Phe Pro Asp Lys Ile Ser Val Ser Val Phe Val Thr Ala Phe Met
            100                 105                 110

Pro Asp Thr Lys His Ser Pro Ser Phe Val Glu Glu Lys Val Tyr Ile
        115                 120                 125

Ser Phe
    130

<210> SEQ ID NO 26
<211> LENGTH: 101
<212> TYPE: PRT
<213> ORGANISM: Arabidopsis thaliana
<220> FEATURE:
<221> NAME/KEY: misc_feature
<222> LOCATION: (1)..(101)
<223> OTHER INFORMATION: Ceres Seq. ID no. 12562717
<220> FEATURE:
<221> NAME/KEY: misc_feature
<222> LOCATION: (29)..(101)
<223> OTHER INFORMATION: PFAM Description: alpha/beta hydrolase fold
<220> FEATURE:
<221> NAME/KEY: misc_feature
<222> LOCATION: (29)..(101)
<223> OTHER INFORMATION: GI NO: 21554666
      NR DESCRIPTION: putative acetone-cyanohydrin lyase
<220> FEATURE:
<221> NAME/KEY: misc_feature
<222> LOCATION: (28)..(101)
<223> OTHER INFORMATION: GI NO: 27754457
```

NR DESCRIPTION: putative acetone-cyanohydrin lyase
<220> FEATURE:
<221> NAME/KEY: misc_feature
<222> LOCATION: (28)..(101)
<223> OTHER INFORMATION: GI NO: 14279437
      NR DESCRIPTION: ethylene-induced esterase
<220> FEATURE:
<221> NAME/KEY: misc_feature
<222> LOCATION: (36)..(101)
<223> OTHER INFORMATION: GI NO: 40549303
      NR DESCRIPTION: salicylic acid-binding protein 2
<220> FEATURE:
<221> NAME/KEY: misc_feature
<222> LOCATION: (49)..(101)
<223> OTHER INFORMATION: GI NO: 21595837
      NR DESCRIPTION: polyneuridine aldehyde esterase
<220> FEATURE:
<221> NAME/KEY: misc_feature
<222> LOCATION: (49)..(101)
<223> OTHER INFORMATION: GI NO: 25518436
      NR DESCRIPTION: hypothetical protein T1K7.26

<400> SEQUENCE: 26

Met Val Val Thr Ser Leu Glu Phe Leu Lys Val Val Asn Cys Asn Lys
1               5                   10                  15

Arg Glu Asn Lys Tyr Asp Phe Phe Val Ile Thr Met Lys Lys Phe Ala
            20                  25                  30

Ser Ser Met Thr Pro Glu Gly Trp Met Gly Ser Glu Leu Glu Thr Tyr
        35                  40                  45

Gly Ser Asp Asn Ser Gly Leu Ser Val Phe Phe Ser Thr Asp Phe Met
    50                  55                  60

Lys His Arg Leu Tyr Gln Leu Ser Pro Val Glu Asp Leu Glu Leu Gly
65                  70                  75                  80

Leu Leu Leu Lys Arg Pro Ser Ser Leu Phe Ile Asn Glu Leu Ser Lys
                85                  90                  95

Met Glu Asn Phe Ser
            100

<210> SEQ ID NO 27
<211> LENGTH: 913
<212> TYPE: DNA
<213> ORGANISM: Arabidopsis thaliana
<220> FEATURE:
<221> NAME/KEY: misc_feature
<222> LOCATION: (1)..(913)
<223> OTHER INFORMATION: Ceres Seq. ID no. 13503070

<400> SEQUENCE: 27
gtgtgacttt taggagagta agaaaatatc gaaggtcaga agaatgagtg aggaaaagag     60
gaaacaacat tttgtactag tacatggttc gtgccatggc gcgtggtgct ggtacaaggt    120
taagccgctg ctagaggcgg tgggccaccg cgtaactgct gtggacttag ctgcctccgg    180
aatagacaca acgaggtcga tcactgacat ccccacatgc gaacaatact cggagccatt    240
gacgaagctc ctgacctcat tgccaaatga tgaaaaggtt gtgctcgttg gtcacagctt    300
tggtggcttg aacttagcca tagccatgga aaagtttccc gaaaaaatct ctgtcgctgt    360
attcttgact gctttcatgc cggacaccga acactcacca tccttcgtct tggacaagtt    420
tggaagcaac atgcctcaag aagcatggat gggcaccgaa ttcgaacctt atggttcaga    480
caattccgga ctgagtatgt tttttagccc tgacttcatg aagttgggtc tctaccagct    540
ttctccagtt gaggatcttg aactgggatt acttttaatg aggccaggat cgttatttat    600
taacgattta tcgaagatga aaaacttctc ggatgaagga tatgggtctg ttcctcgagt    660
tttcatagtg tgtaaagagg acaaagcaat tccagaagaa cgccagagat ggatgattga    720

```
taattttccg gtgaatttag tgatggagat ggaggagaca gatcatatgc caatgttctg    780
caagcctcag caactcagtg attacttcct gaaaatcgcg gacaaattcg tttaatcaaa    840
tcttcatgaa actgtattgg atttgatata ataaaggttt gttgcaaatg aattaataat    900
gatgaatatt ttt                                                       913

<210> SEQ ID NO 28
<211> LENGTH: 263
<212> TYPE: PRT
<213> ORGANISM: Arabidopsis thaliana
<220> FEATURE:
<221> NAME/KEY: misc_feature
<222> LOCATION: (1)..(263)
<223> OTHER INFORMATION: Ceres Seq. ID no. 13503071
<220> FEATURE:
<221> NAME/KEY: misc_feature
<222> LOCATION: (35)..(257)
<223> OTHER INFORMATION: PFAM Description: alpha/beta hydrolase fold
<220> FEATURE:
<221> NAME/KEY: misc_feature
<222> LOCATION: (1)..(263)
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (1)..(262)
<223> OTHER INFORMATION: GI NO: 21554666
      NR DESCRIPTION: putative acetone-cyanohydrin lyase
<220> FEATURE:
<221> NAME/KEY: misc_feature
<222> LOCATION: (5)..(262)
<223> OTHER INFORMATION: GI NO: 40549303
      NR DESCRIPTION: salicylic acid-binding protein 2
<220> FEATURE:
<221> NAME/KEY: misc_feature
<222> LOCATION: (7)..(262)
<223> OTHER INFORMATION: GI NO: 14279437
      NR DESCRIPTION: ethylene-induced esterase
<220> FEATURE:
<221> NAME/KEY: misc_feature
<222> LOCATION: (132)..(263)
<223> OTHER INFORMATION: GI NO: 34914024
      NR DESCRIPTION: OJ1014_G12.27
<220> FEATURE:
<221> NAME/KEY: misc_feature
<222> LOCATION: (11)..(124)
<223> OTHER INFORMATION: GI NO: 34914024
      NR DESCRIPTION: OJ1014_G12.27
<220> FEATURE:
<221> NAME/KEY: misc_feature
<222> LOCATION: (1)..(259)
<223> OTHER INFORMATION: GI NO: 21595837
      NR DESCRIPTION: polyneuridine aldehyde esterase
<220> FEATURE:
<221> NAME/KEY: misc_feature
<222> LOCATION: (1)..(259)
<223> OTHER INFORMATION: GI NO: 42562323
      NR DESCRIPTION: hydrolase
<220> FEATURE:
<221> NAME/KEY: misc_feature
<222> LOCATION: (3)..(259)
<223> OTHER INFORMATION: GI NO: 25404802
      NR DESCRIPTION: probable alpha/beta hydrolase F23O10.18
<220> FEATURE:
<221> NAME/KEY: misc_feature
<222> LOCATION: (40)..(243)
<223> OTHER INFORMATION: GI NO: 25518436
      NR DESCRIPTION: hypothetical protein T1K7.26

<400> SEQUENCE: 28

Met Ser Glu Glu Lys Arg Lys Gln His Phe Val Leu Val His Gly Ser
1               5                   10                  15

Cys His Gly Ala Trp Cys Trp Tyr Lys Val Pro Leu Leu Glu Ala
            20                  25                  30
```

```
Val Gly His Arg Val Thr Ala Val Asp Leu Ala Ala Ser Gly Ile Asp
            35                  40                  45

Thr Thr Arg Ser Ile Thr Asp Ile Pro Thr Cys Glu Gln Tyr Ser Glu
 50                  55                  60

Pro Leu Thr Lys Leu Leu Thr Ser Leu Pro Asn Asp Glu Lys Val Val
 65                  70                  75                  80

Leu Val Gly His Ser Phe Gly Gly Leu Asn Leu Ala Ile Ala Met Glu
                85                  90                  95

Lys Phe Pro Glu Lys Ile Ser Val Ala Val Phe Leu Thr Ala Phe Met
            100                 105                 110

Pro Asp Thr Glu His Ser Pro Ser Phe Val Leu Asp Lys Phe Gly Ser
            115                 120                 125

Asn Met Pro Gln Glu Ala Trp Met Gly Thr Gly Phe Glu Pro Tyr Gly
            130                 135                 140

Ser Asp Asn Ser Gly Leu Ser Met Phe Phe Ser Pro Asp Phe Met Lys
145                 150                 155                 160

Leu Gly Leu Tyr Gln Leu Ser Pro Val Glu Asp Leu Glu Leu Gly Leu
                165                 170                 175

Leu Leu Met Arg Pro Gly Ser Leu Phe Ile Asn Asp Leu Ser Lys Met
            180                 185                 190

Lys Asn Phe Ser Asp Glu Gly Tyr Gly Ser Val Pro Arg Val Phe Ile
            195                 200                 205

Val Cys Lys Glu Asp Lys Ala Ile Pro Glu Glu Arg Gln Arg Trp Met
210                 215                 220

Ile Asp Asn Phe Pro Val Asn Leu Val Met Glu Met Glu Glu Thr Asp
225                 230                 235                 240

His Met Pro Met Phe Cys Lys Pro Gln Gln Leu Ser Asp Tyr Phe Leu
            245                 250                 255

Lys Ile Ala Asp Lys Phe Val
            260

<210> SEQ ID NO 29
<211> LENGTH: 169
<212> TYPE: PRT
<213> ORGANISM: Arabidopsis thaliana
<220> FEATURE:
<221> NAME/KEY: misc_feature
<222> LOCATION: (1)..(169)
<223> OTHER INFORMATION: Ceres Seq. ID no. 13503072
<220> FEATURE:
<221> NAME/KEY: misc_feature
<222> LOCATION: (1)..(163)
<223> OTHER INFORMATION: PFAM Description: alpha/beta hydrolase fold
<220> FEATURE:
<221> NAME/KEY: misc_feature
<222> LOCATION: (1)..(169)
<223> OTHER INFORMATION: GI NO: 27754457
    NR DESCRIPTION: putative acetone-cyanohydrin lyase
<220> FEATURE:
<221> NAME/KEY: misc_feature
<222> LOCATION: (1)..(168)
<223> OTHER INFORMATION: GI NO: 21554666
    NR DESCRIPTION: putative acetone-cyanohydrin lyase
<220> FEATURE:
<221> NAME/KEY: misc_feature
<222> LOCATION: (1)..(168)
<223> OTHER INFORMATION: GI NO: 40549303
    NR DESCRIPTION: salicylic acid-binding protein 2
<220> FEATURE:
<221> NAME/KEY: misc_feature
<222> LOCATION: (1)..(168)
<223> OTHER INFORMATION: GI NO: 14279437
    NR DESCRIPTION: ethylene-induced esterase
<220> FEATURE:
```

```
<221> NAME/KEY: misc_feature
<222> LOCATION: (38)..(169)
<223> OTHER INFORMATION: GI NO: 34914024
      NR DESCRIPTION: OJ1014_G12.27
<220> FEATURE:
<221> NAME/KEY: misc_feature
<222> LOCATION: (1)..(30)
<223> OTHER INFORMATION: GI NO: 34914024
      NR DESCRIPTION: OJ1014_G12.27
<220> FEATURE:
<221> NAME/KEY: misc_feature
<222> LOCATION: (1)..(165)
<223> OTHER INFORMATION: GI NO: 21595837
      NR DESCRIPTION: polyneuridine aldehyde esterase
<220> FEATURE:
<221> NAME/KEY: misc_feature
<222> LOCATION: (1)..(165)
<223> OTHER INFORMATION: GI NO: 42562323
      NR DESCRIPTION: hydrolase
<220> FEATURE:
<221> NAME/KEY: misc_feature
<222> LOCATION: (1)..(165)
<223> OTHER INFORMATION: GI NO: 25404802
      NR DESCRIPTION: probable alpha/beta hydrolase F23O10.18
<220> FEATURE:
<221> NAME/KEY: misc_feature
<222> LOCATION: (1)..(149)
<223> OTHER INFORMATION: GI NO: 25518436
      NR DESCRIPTION: hypothetical protein T1K7.26

<400> SEQUENCE: 29

Met Glu Lys Phe Pro Glu Lys Ile Ser Val Ala Val Phe Leu Thr Ala
1               5                   10                  15

Phe Met Pro Asp Thr Glu His Ser Pro Ser Phe Val Leu Asp Lys Phe
            20                  25                  30

Gly Ser Asn Met Pro Gln Glu Ala Trp Met Gly Thr Glu Phe Glu Pro
        35                  40                  45

Tyr Gly Ser Asp Asn Ser Gly Leu Ser Met Phe Phe Ser Pro Asp Phe
    50                  55                  60

Met Lys Leu Gly Leu Tyr Gln Leu Ser Pro Val Glu Asp Leu Glu Leu
65                  70                  75                  80

Gly Leu Leu Leu Met Arg Pro Gly Ser Leu Phe Ile Asn Asp Leu Ser
                85                  90                  95

Lys Met Lys Asn Phe Ser Asp Glu Gly Tyr Gly Ser Val Pro Arg Val
            100                 105                 110

Phe Ile Val Cys Lys Glu Asp Lys Ala Ile Pro Glu Arg Gln Arg
        115                 120                 125

Trp Met Ile Asp Asn Phe Pro Val Asn Leu Val Met Glu Met Glu Glu
130                 135                 140

Thr Asp His Met Pro Met Phe Cys Lys Pro Gln Gln Leu Ser Asp Tyr
145                 150                 155                 160

Phe Leu Lys Ile Ala Asp Lys Phe Val
                165

<210> SEQ ID NO 30
<211> LENGTH: 152
<212> TYPE: PRT
<213> ORGANISM: Arabidopsis thaliana
<220> FEATURE:
<221> NAME/KEY: misc_feature
<222> LOCATION: (1)..(152)
<223> OTHER INFORMATION: Ceres Seq. ID no. 13503073
<220> FEATURE:
<221> NAME/KEY: misc_feature
<222> LOCATION: (1)..(146)
<223> OTHER INFORMATION: PFAM Description: alpha/beta hydrolase fold
<220> FEATURE:
<221> NAME/KEY: misc_feature
```

-continued

```
<222> LOCATION: (1)..(152)
<223> OTHER INFORMATION: GI NO: 27754457
       NR DESCRIPTION: putative acetone-cyanohydrin lyase
<220> FEATURE:
<221> NAME/KEY: misc_feature
<222> LOCATION: (1)..(151)
<223> OTHER INFORMATION: GI NO: 21554666
       NR DESCRIPTION: putative acetone-cyanohydrin lyase
<220> FEATURE:
<221> NAME/KEY: misc_feature
<222> LOCATION: (1)..(151)
<223> OTHER INFORMATION: GI NO: 40549303
       NR DESCRIPTION: salicylic acid-binding protein 2
<220> FEATURE:
<221> NAME/KEY: misc_feature
<222> LOCATION: (1)..(151)
<223> OTHER INFORMATION: GI NO: 14279437
       NR DESCRIPTION: ethylene-induced esterase
<220> FEATURE:
<221> NAME/KEY: misc_feature
<222> LOCATION: (21)..(152)
<223> OTHER INFORMATION: GI NO: 34914024
       NR DESCRIPTION: OJ1014_G12.27
<220> FEATURE:
<221> NAME/KEY: misc_feature
<222> LOCATION: (1)..(13)
<223> OTHER INFORMATION: GI NO: 34914024
       NR DESCRIPTION: OJ1014_G12.27
<220> FEATURE:
<221> NAME/KEY: misc_feature
<222> LOCATION: (1)..(148)
<223> OTHER INFORMATION: GI NO: 21595837
       NR DESCRIPTION: polyneuridine aldehyde esterase
<220> FEATURE:
<221> NAME/KEY: misc_feature
<222> LOCATION: (1)..(148)
<223> OTHER INFORMATION: GI NO: 42562323
       NR DESCRIPTION: hydrolase
<220> FEATURE:
<221> NAME/KEY: misc_feature
<222> LOCATION: (1)..(148)
<223> OTHER INFORMATION: GI NO: 25404802
       NR DESCRIPTION: probable alpha/beta hydrolase F23O10.18
<220> FEATURE:
<221> NAME/KEY: misc_feature
<222> LOCATION: (1)..(132)
<223> OTHER INFORMATION: GI NO: 25518436
       NR DESCRIPTION: hypothetical protein T1K7.26

<400> SEQUENCE: 30

Met Pro Asp Thr Glu His Ser Pro Ser Phe Val Leu Asp Lys Phe Gly
 1               5                  10                  15

Ser Asn Met Pro Gln Glu Ala Trp Met Gly Thr Glu Phe Glu Pro Tyr
                20                  25                  30

Gly Ser Asp Asn Ser Gly Leu Ser Met Phe Phe Ser Pro Asp Phe Met
            35                  40                  45

Lys Leu Gly Leu Tyr Gln Leu Ser Pro Val Glu Asp Leu Glu Leu Gly
        50                  55                  60

Leu Leu Leu Met Arg Pro Gly Ser Leu Phe Ile Asn Asp Leu Ser Lys
65                  70                  75                  80

Met Lys Asn Phe Ser Asp Glu Gly Tyr Gly Ser Val Pro Arg Val Phe
                85                  90                  95

Ile Val Cys Lys Glu Asp Lys Ala Ile Pro Glu Glu Arg Gln Arg Trp
            100                 105                 110

Met Ile Asp Asn Phe Pro Val Asn Leu Val Met Glu Met Glu Glu Thr
        115                 120                 125

Asp His Met Pro Met Phe Cys Lys Pro Gln Gln Leu Ser Asp Tyr Phe
    130                 135                 140

Leu Lys Ile Ala Asp Lys Phe Val
145                 150
```

```
<210> SEQ ID NO 31
<211> LENGTH: 569
<212> TYPE: DNA
<213> ORGANISM: Glycine max
<220> FEATURE:
<221> NAME/KEY: misc_feature
<222> LOCATION: (1)..(569)
<223> OTHER INFORMATION: Ceres Seq. ID no. 12432354

<400> SEQUENCE: 31
cgtgtggtgc gcctcctcac aaatacacac agaaagttga gaggtggtag tagctgctgc      60
ggaagcgttc agcagccaat agctttcgca gcagcatcaa caacaaacca acgattcaaa     120
ttcaacctcc tcattcagat ggcacaatct ttctcaccag ccaaacgcgc ccttgccttt     180
tcccttcacc ggcgagggta cgcagtggcg tctgatgctt ctccttcggt gagaggggga     240
ttggatagca ttggaagcag gagtgcaatc gagaagggtg tgacaaaaaa caattcgggc     300
ccatcggggg cctcatcagc ttgggccccg gacccagtga cgggttacta caggcccatc     360
aatcacacca atgagattga cccggtggag cttcgaagga tgctgttgaa acacaaagtc     420
agatcatcat cctcctccta gagtggcaag gggcaccaac acccacacct tattccatca     480
aatcaagttt attttgcttt tcttgtgtgg ttttatctat ctattttttat tttattttc     540 tgaatctatc tatctttca tatctatct                                       569

<210> SEQ ID NO 32
<211> LENGTH: 146
<212> TYPE: PRT
<213> ORGANISM: Glycine max
<220> FEATURE:
<221> NAME/KEY: misc_feature
<222> LOCATION: (1)..(146)
<223> OTHER INFORMATION: Ceres Seq. ID no. 12432355
<220> FEATURE:
<221> NAME/KEY: misc_feature
<222> LOCATION: (47)..(137)
<223> OTHER INFORMATION: PFAM Description: Late embryogenesis abundant
      protein
<220> FEATURE:
<221> NAME/KEY: misc_feature
<222> LOCATION: (47)..(137)
<223> OTHER INFORMATION: GI NO: 7488660
      NR DESCRIPTION: desiccation protective protein LEA5
<220> FEATURE:
<221> NAME/KEY: misc_feature
<222> LOCATION: (47)..(143)
<223> OTHER INFORMATION: GI NO: 7489029
      NR DESCRIPTION: late-embryogenesis protein homolog
<220> FEATURE:
<221> NAME/KEY: misc_feature
<222> LOCATION: (47)..(143)
<223> OTHER INFORMATION: GI NO: 1370589
      NR DESCRIPTION: protein induced upon tuberization
<220> FEATURE:
<221> NAME/KEY: misc_feature
<222> LOCATION: (54)..(145)
<223> OTHER INFORMATION: GI NO: 34894580
      NR DESCRIPTION: zinc-induced protein-like

<400> SEQUENCE: 32

Arg Val Val Arg Leu Leu Thr Asn Thr His Arg Lys Leu Arg Gly Gly
 1               5                  10                  15

Ser Ser Cys Cys Gly Ser Val Gln Gln Pro Ile Ala Phe Ala Ala Ala
                20                  25                  30

Ser Thr Thr Asn Gln Arg Phe Lys Phe Asn Leu Leu Ile Gln Met Ala
            35                  40                  45

Gln Ser Phe Ser Pro Ala Lys Arg Ala Leu Ala Phe Ser Leu His Arg
```

-continued

```
                    50                  55                  60
Arg Gly Tyr Ala Val Ala Ser Asp Ala Ser Pro Ser Val Arg Gly Gly
 65                  70                  75                  80

Leu Asp Ser Ile Gly Ser Arg Ser Ala Ile Glu Lys Gly Val Thr Lys
                     85                  90                  95

Asn Asn Ser Gly Pro Ser Gly Ala Ser Ser Ala Trp Ala Pro Asp Pro
                100                 105                 110

Val Thr Gly Tyr Tyr Arg Pro Ile Asn His Thr Asn Glu Ile Asp Pro
                115                 120                 125

Val Glu Leu Arg Arg Met Leu Leu Lys His Lys Val Arg Ser Ser Ser
130                 135                 140

Ser Ser
145

<210> SEQ ID NO 33
<211> LENGTH: 100
<212> TYPE: PRT
<213> ORGANISM: Glycine max
<220> FEATURE:
<221> NAME/KEY: misc_feature
<222> LOCATION: (1)..(100)
<223> OTHER INFORMATION: Ceres Seq. ID no. 12432356
<220> FEATURE:
<221> NAME/KEY: misc_feature
<222> LOCATION: (1)..(91)
<223> OTHER INFORMATION: PFAM Description: Late embryogenesis abundant
      protein
<220> FEATURE:
<221> NAME/KEY: misc_feature
<222> LOCATION: (1)..(91)
<223> OTHER INFORMATION: GI NO: 7488660
      NR DESCRIPTION: desiccation protective protein LEA5
<220> FEATURE:
<221> NAME/KEY: misc_feature
<222> LOCATION: (1)..(97)
<223> OTHER INFORMATION: GI NO: 7489029
      NR DESCRIPTION: late-embryogenesis protein homolog
<220> FEATURE:
<221> NAME/KEY: misc_feature
<222> LOCATION: (1)..(97)
<223> OTHER INFORMATION: GI NO: 1370589
      NR DESCRIPTION: protein induced upon tuberization
<220> FEATURE:
<221> NAME/KEY: misc_feature
<222> LOCATION: (8)..(99)
<223> OTHER INFORMATION: GI NO: 34894580
      NR DESCRIPTION: zinc-induced protein-like

<400> SEQUENCE: 33

Met Ala Gln Ser Phe Ser Pro Ala Lys Arg Ala Leu Ala Phe Ser Leu
  1               5                  10                  15

His Arg Arg Gly Tyr Ala Val Ala Ser Asp Ala Ser Pro Ser Val Arg
                 20                  25                  30

Gly Gly Leu Asp Ser Ile Gly Ser Arg Ser Ala Ile Glu Lys Gly Val
                 35                  40                  45

Thr Lys Asn Asn Ser Gly Pro Ser Gly Ala Ser Ser Ala Trp Ala Pro
 50                  55                  60

Asp Pro Val Thr Gly Tyr Tyr Arg Pro Ile Asn His Thr Asn Glu Ile
 65                  70                  75                  80

Asp Pro Val Glu Leu Arg Arg Met Leu Leu Lys His Lys Val Arg Ser
                 85                  90                  95

Ser Ser Ser Ser
                100

<210> SEQ ID NO 34
```

```
<211> LENGTH: 625
<212> TYPE: DNA
<213> ORGANISM: Glycine max
<220> FEATURE:
<221> NAME/KEY: misc_feature
<222> LOCATION: (1)..(625)
<223> OTHER INFORMATION: Ceres Seq. ID no. 12399500

<400> SEQUENCE: 34
cacatgcact ctctttctct ctgttcttcg ttcattttca agtttgatat ttgacatcat      60
catggcaaga ggtggaaaac taatgaagct aaaatcagtg ctgaagaaat ggaactcatt     120
cggcaatggc agcaagcata gccgccacca cagcagcagc gccgtcgccg atgacgagtc     180
ctcctccaga tcagacctcc acgccgtcta cgtcggcaag tcccgccgcc tctatcgcgt     240
ctcctccgac gttgtcgacc accccgtctt ccgggaactc gtcgagagat cccgcgattc     300
tgaccaacaa caaaacgaag acactactac gatcaatgtc gtcgcatgcg aggttgtcct     360
tttcgaaaca ttgctctgga tgctcgataa cgccgaccca caacccgagt cactcaacga     420
actcgtcgac ttctacggtt gctaatgcta gctactatct atcccatacc ttccacgtgt     480
ccctatcatc ccacattatt aaaaaaaaca cgtatattat attataccac ttccgattaa     540
tttttataag aaacaagtaa ttgcagtgta ttttacacaa aaacttgttt attataaata     600
gaattggaga tatattattg ttctt                                          625

<210> SEQ ID NO 35
<211> LENGTH: 147
<212> TYPE: PRT
<213> ORGANISM: Glycine max
<220> FEATURE:
<221> NAME/KEY: misc_feature
<222> LOCATION: (1)..(147)
<223> OTHER INFORMATION: Ceres Seq. ID no. 12399501
<220> FEATURE:
<221> NAME/KEY: misc_feature
<222> LOCATION: (30)..(128)
<223> OTHER INFORMATION: PFAM Description: Auxin responsive protein
<220> FEATURE:
<221> NAME/KEY: misc_feature
<222> LOCATION: (21)..(147)
<223> OTHER INFORMATION: GI NO: 15242071
      NR DESCRIPTION: putative protein; protein id: At5g20820.1
<220> FEATURE:
<221> NAME/KEY: misc_feature
<222> LOCATION: (21)..(147)
<223> OTHER INFORMATION: GI NO: 21554070
      NR DESCRIPTION: unknown
<220> FEATURE:
<221> NAME/KEY: misc_feature
<222> LOCATION: (21)..(147)
<223> OTHER INFORMATION: GI NO: 50946385
      NR DESCRIPTION: auxin-induced protein-related-like protein
<220> FEATURE:
<221> NAME/KEY: misc_feature
<222> LOCATION: (44)..(144)
<223> OTHER INFORMATION: GI NO: 21536952
      NR DESCRIPTION: unknown

<400> SEQUENCE: 35

Thr Cys Thr Leu Phe Leu Ser Val Leu Arg Ser Phe Ser Ser Leu Ile
  1               5                  10                  15

Phe Asp Ile Ile Met Ala Arg Gly Gly Lys Leu Met Lys Leu Lys Ser
             20                  25                  30

Val Leu Lys Lys Trp Asn Ser Phe Gly Asn Gly Ser Lys His Ser Arg
         35                  40                  45

His His Ser Ser Ser Ala Val Ala Asp Asp Glu Ser Ser Ser Arg Ser
     50                  55                  60
```

```
Asp Leu His Ala Val Tyr Val Gly Lys Ser Arg Arg Leu Tyr Arg Val
 65                  70                  75                  80

Ser Ser Asp Val Val Asp His Pro Val Phe Arg Glu Leu Val Glu Arg
                 85                  90                  95

Ser Arg Asp Ser Asp Gln Gln Gln Asn Glu Asp Thr Thr Thr Ile Asn
            100                 105                 110

Val Val Ala Cys Glu Val Val Leu Phe Glu His Leu Leu Trp Met Leu
        115                 120                 125

Asp Asn Ala Asp Pro Gln Pro Glu Ser Leu Asn Glu Leu Val Asp Phe
130                 135                 140

Tyr Gly Cys
145

<210> SEQ ID NO 36
<211> LENGTH: 144
<212> TYPE: PRT
<213> ORGANISM: Glycine max
<220> FEATURE:
<221> NAME/KEY: misc_feature
<222> LOCATION: (1)..(144)
<223> OTHER INFORMATION: Ceres Seq. ID no. 12399502
<220> FEATURE:
<221> NAME/KEY: misc_feature
<222> LOCATION: (1)..(129)
<223> OTHER INFORMATION: PFAM Description: Herpes virus major outer
      envelope glycoprotein (BLLF1)

<400> SEQUENCE: 36

Met Ala Ala Ser Ile Ala Ala Thr Thr Ala Ala Pro Ser Pro Met
  1               5                  10                  15

Thr Ser Pro Pro Pro Asp Gln Thr Ser Thr Pro Ser Thr Ser Ala Ser
                 20                  25                  30

Pro Ala Ala Ser Ile Ala Ser Pro Pro Thr Leu Ser Thr Thr Pro Ser
            35                  40                  45

Ser Gly Asn Ser Ser Arg Asp Pro Ala Ile Leu Thr Asn Asn Lys Thr
 50                  55                  60

Lys Thr Leu Leu Arg Ser Met Ser Ser His Ala Arg Leu Ser Phe Ser
 65                  70                  75                  80

Asn Thr Cys Ser Gly Cys Ser Ile Thr Pro Thr His Asn Pro Ser His
                 85                  90                  95

Ser Thr Asn Ser Ser Thr Ser Thr Val Ala Asn Ala Ser Tyr Tyr Leu
            100                 105                 110

Ser His Thr Phe His Val Ser Leu Ser Ser His Ile Ile Lys Lys Asn
        115                 120                 125

Thr Tyr Ile Ile Leu Tyr His Phe Arg Leu Ile Phe Ile Arg Asn Lys
130                 135                 140

<210> SEQ ID NO 37
<211> LENGTH: 129
<212> TYPE: PRT
<213> ORGANISM: Glycine max
<220> FEATURE:
<221> NAME/KEY: misc_feature
<222> LOCATION: (1)..(129)
<223> OTHER INFORMATION: Ceres Seq. ID no. 12399503
<220> FEATURE:
<221> NAME/KEY: misc_feature
<222> LOCATION: (1)..(114)
<223> OTHER INFORMATION: PFAM Description: Herpes virus major outer
      envelope glycoprotein (BLLF1)

<400> SEQUENCE: 37

Met Thr Ser Pro Pro Pro Asp Gln Thr Ser Thr Pro Ser Thr Ser Ala
```

-continued

```
                1               5                  10                 15
            Ser Pro Ala Ala Ser Ile Ala Ser Pro Pro Thr Leu Ser Thr Thr Pro
                            20                  25                 30

Ser Ser Gly Asn Ser Ser Arg Asp Pro Ala Ile Leu Thr Asn Asn Lys
                            35                  40                 45

Thr Lys Thr Leu Leu Arg Ser Met Ser Ser His Ala Arg Leu Ser Phe
                            50                  55                 60

Ser Asn Thr Cys Ser Gly Cys Ser Ile Thr Pro Thr His Asn Pro Ser
            65                          70                  75                 80

His Ser Thr Asn Ser Ser Thr Ser Thr Val Ala Asn Ala Ser Tyr Tyr
                            85                  90                 95

Leu Ser His Thr Phe His Val Ser Leu Ser Ser His Ile Ile Lys Lys
                            100                 105                110

Asn Thr Tyr Ile Ile Leu Tyr His Phe Arg Leu Ile Phe Ile Arg Asn
                            115                 120                125

Lys

<210> SEQ ID NO 38
<211> LENGTH: 127
<212> TYPE: PRT
<213> ORGANISM: Glycine max
<220> FEATURE:
<221> NAME/KEY: misc_feature
<222> LOCATION: (1)..(127)
<223> OTHER INFORMATION: Ceres Seq. ID no. 12399504
<220> FEATURE:
<221> NAME/KEY: misc_feature
<222> LOCATION: (10)..(108)
<223> OTHER INFORMATION: PFAM Description: Auxin responsive protein
<220> FEATURE:
<221> NAME/KEY: misc_feature
<222> LOCATION: (1)..(127)
<223> OTHER INFORMATION: GI NO: 15242071
      NR DESCRIPTION: putative protein; protein id: At5g20820.1
<220> FEATURE:
<221> NAME/KEY: misc_feature
<222> LOCATION: (1)..(127)
<223> OTHER INFORMATION: GI NO: 21554070
      NR DESCRIPTION: unknown
<220> FEATURE:
<221> NAME/KEY: misc_feature
<222> LOCATION: (1)..(127)
<223> OTHER INFORMATION: GI NO: 50946385
      NR DESCRIPTION: auxin-induced protein-related-like protein
<220> FEATURE:
<221> NAME/KEY: misc_feature
<222> LOCATION: (24)..(124)
<223> OTHER INFORMATION: GI NO: 21536952
      NR DESCRIPTION: unknown

<400> SEQUENCE: 38

Met Ala Arg Gly Gly Lys Leu Met Lys Leu Lys Ser Val Leu Lys Lys
1               5                  10                 15

Trp Asn Ser Phe Gly Asn Gly Ser Lys His Ser Arg His Ser Ser
                20                  25                 30

Ser Ala Val Ala Asp Asp Glu Ser Ser Arg Ser Asp Leu His Ala
                35                  40                 45

Val Tyr Val Gly Lys Ser Arg Arg Leu Tyr Arg Val Ser Ser Asp Val
                50                  55                 60

Val Asp His Pro Val Phe Arg Glu Leu Val Glu Arg Ser Arg Asp Ser
65                          70                  75                 80

Asp Gln Gln Gln Asn Glu Asp Thr Thr Thr Ile Asn Val Val Ala Cys
                            85                  90                 95

Glu Val Val Leu Phe Glu His Leu Leu Trp Met Leu Asp Asn Ala Asp
```

Pro Gln Pro Glu Ser Leu Asn Glu Leu Val Asp Phe Tyr Gly Cys
        100             105             110
    115             120             125

<210> SEQ ID NO 39
<211> LENGTH: 540
<212> TYPE: DNA
<213> ORGANISM: Glycine max
<220> FEATURE:
<221> NAME/KEY: misc_feature
<222> LOCATION: (1)..(540)
<223> OTHER INFORMATION: Ceres Seq. ID no. 13643428
<220> FEATURE:
<221> NAME/KEY: misc_feature
<222> LOCATION: (97)..(97)
<223> OTHER INFORMATION: n is a, c, t, g, unknown, or other

<400> SEQUENCE: 39
acgttctcac aagtcacaac ataacaaaaa caacaacaaa atcatctttg ctccatcaaa      60
ttctcaagcc atatccaaca tgtccaaagc aggaaanact aacgaagctc aagtcagtgc     120
tgaggaaatg gaactcattc agcaacaaac acagtcaagt cagtgtcatc tccgccgtcg     180
cgaacgacgg aggtgacacc tcatcgctcc tcccagtgta tgttgggagg acacgtcggc     240
gttatctcgt gagcgccgat gtagtcggac accgctcttt cagggagctg gtgggccggt     300
cccgcgacgg ctccaaggat gaggacgagg acaccatcaa cgtggcgtgc gaggttgtcc     360
tattcgagca cttgctctgg atgctccaca atgccgatcc tcaacccgag tcgctcgatg     420
aactcgccga tttttacgcc tgctagctct ataattattc ctttctcgtg aacaacacag     480
tacgagtgaa agasktttaa attaattgcc gttgtaattg ttttgatgta cgtacgtgat     540

<210> SEQ ID NO 40
<211> LENGTH: 147
<212> TYPE: PRT
<213> ORGANISM: Glycine max
<220> FEATURE:
<221> NAME/KEY: misc_feature
<222> LOCATION: (1)..(147)
<223> OTHER INFORMATION: Ceres Seq. ID no. 13643429
<220> FEATURE:
<221> NAME/KEY: misc_feature
<222> LOCATION: (36)..(128)
<223> OTHER INFORMATION: PFAM Description: Auxin responsive protein
<220> FEATURE:
<221> NAME/KEY: misc_feature
<222> LOCATION: (33)..(147)
<223> OTHER INFORMATION: GI NO: 15242071
    NR DESCRIPTION: auxin-induced (indole-3-acetic acid induced)
    protein-related
<220> FEATURE:
<221> NAME/KEY: misc_feature
<222> LOCATION: (33)..(147)
<223> OTHER INFORMATION: GI NO: 21554070
    NR DESCRIPTION: unknown
<220> FEATURE:
<221> NAME/KEY: misc_feature
<222> LOCATION: (33)..(147)
<223> OTHER INFORMATION: GI NO: 50946385
    NR DESCRIPTION: auxin-induced protein-related-like protein
<220> FEATURE:
<221> NAME/KEY: misc_feature
<222> LOCATION: (62)..(145)
<223> OTHER INFORMATION: GI NO: 21536952
    NR DESCRIPTION: unknown
<220> FEATURE:
<221> NAME/KEY: misc_feature
<222> LOCATION: (32)..(32)
<223> OTHER INFORMATION: Xaa is any aa, unknown or other

<400> SEQUENCE: 40

```
Val Leu Thr Ser His Asn Ile Thr Lys Thr Thr Lys Ser Ser Leu
1               5                  10                 15

Leu His Gln Ile Leu Lys Pro Tyr Pro Thr Cys Pro Lys Gln Glu Xaa
            20                  25                  30

Leu Thr Lys Leu Lys Ser Val Leu Arg Lys Trp Asn Ser Phe Ser Asn
            35                  40                  45

Lys His Ser Gln Val Ser Val Ile Ser Ala Val Ala Asn Asp Gly Gly
        50                  55                  60

Asp Thr Ser Ser Leu Leu Pro Val Tyr Val Gly Arg Thr Arg Arg
65              70                  75                  80

Tyr Leu Val Ser Ala Asp Val Val Gly His Pro Leu Phe Arg Glu Leu
                85                  90                  95

Val Gly Arg Ser Arg Asp Gly Ser Lys Asp Glu Asp Glu Asp Thr Ile
            100                 105                 110

Asn Val Ala Cys Glu Val Val Leu Phe Glu His Leu Leu Trp Met Leu
            115                 120                 125

His Asn Ala Asp Pro Gln Pro Glu Ser Leu Asp Glu Leu Ala Asp Phe
        130                 135                 140

Tyr Ala Cys
145
```

<210> SEQ ID NO 41
<211> LENGTH: 449
<212> TYPE: DNA
<213> ORGANISM: Glycine max
<220> FEATURE:
<221> NAME/KEY: misc_feature
<222> LOCATION: (1)..(449)
<223> OTHER INFORMATION: Ceres Seq. ID no. 3456813

<400> SEQUENCE: 41

```
agtcatcaca ctctctctct ctctctttcc ttctctcttt tcaactcatt gaggcattca    60
tcaaacacct tctcaaaatg gccaaagttg gaaaactaac aaagctcaag tcagcaatca   120
agagatggcc ctcattgacc aggctcagcc gcaacagcag cagtgtctct ccaacaaag    180 gggtctctgg aaaaggaaca tcccttaatt catccaagga acacgagcat gaacaagaac   240
aacttcgtgc ggtttatgtt ggcaagtcta ggaggcggta cctcgtgaac tccgaagtga   300
tcgatcaccc cgtgtttcag gagctagtgg acaggtcttg ctcttctaat tcttcttctt   360
ctcatcatca tgacgatgat gggtggtgg tggtgtcstg cgaggtggtg ctgttcgarc    420
acttgctgtg gatgcttgag agcgaaarag                                    449
```

<210> SEQ ID NO 42
<211> LENGTH: 148
<212> TYPE: PRT
<213> ORGANISM: Glycine max
<220> FEATURE:
<221> NAME/KEY: misc_feature
<222> LOCATION: (1)..(148)
<223> OTHER INFORMATION: Ceres Seq. ID no. 3456814
<220> FEATURE:
<221> NAME/KEY: misc_feature
<222> LOCATION: (32)..(146)
<223> OTHER INFORMATION: PFAM Description: Auxin responsive protein
<220> FEATURE:
<221> NAME/KEY: misc_feature
<222> LOCATION: (26)..(147)
<223> OTHER INFORMATION: GI NO: 50946385
     NR DESCRIPTION: auxin-induced protein-related-like protein
<220> FEATURE:
<221> NAME/KEY: misc_feature
<222> LOCATION: (26)..(147)
<223> OTHER INFORMATION: GI NO: 21554070

```
      NR DESCRIPTION: unknown
<220> FEATURE:
<221> NAME/KEY: misc_feature
<222> LOCATION: (26)..(147)
<223> OTHER INFORMATION: GI NO: 15242071
      NR DESCRIPTION: putative protein; protein id: At5g20820.1
<220> FEATURE:
<221> NAME/KEY: misc_feature
<222> LOCATION: (45)..(146)
<223> OTHER INFORMATION: GI NO: 21536952
      NR DESCRIPTION: unknown
<220> FEATURE:
<221> NAME/KEY: misc_feature
<222> LOCATION: (132)..(132)
<223> OTHER INFORMATION: Xaa is any aa, unknown or other
<220> FEATURE:
<221> NAME/KEY: misc_feature
<222> LOCATION: (139)..(139)
<223> OTHER INFORMATION: Xaa is any aa, unknown or other

<400> SEQUENCE: 42

Ser Ser His Ser Leu Ser Leu Ser Phe Leu Ser Phe Gln Leu Ile
 1               5                  10                  15

Glu Ala Phe Ile Lys His Leu Leu Lys Met Ala Lys Val Gly Lys Leu
                20                  25                  30

Thr Lys Leu Lys Ser Ala Ile Lys Arg Trp Pro Ser Leu Thr Arg Leu
            35                  40                  45

Ser Arg Asn Ser Ser Ser Val Ser Ser Asn Lys Gly Val Ser Gly Lys
    50                  55                  60

Gly Thr Ser Leu Asn Ser Ser Lys Glu His Glu His Glu Gln Glu Gln
65                  70                  75                  80

Leu Arg Ala Val Tyr Val Gly Lys Ser Arg Arg Arg Tyr Leu Val Asn
                85                  90                  95

Ser Glu Val Ile Asp His Pro Val Phe Gln Leu Val Asp Arg Ser
                100                 105                 110

Cys Ser Ser Asn Ser Ser Ser Ser His His His Asp Asp Asp Gly Val
            115                 120                 125

Val Val Val Xaa Cys Glu Val Val Leu Phe Xaa His Leu Leu Trp Met
    130                 135                 140

Leu Glu Ser Glu
145

<210> SEQ ID NO 43
<211> LENGTH: 123
<212> TYPE: PRT
<213> ORGANISM: Glycine max
<220> FEATURE:
<221> NAME/KEY: misc_feature
<222> LOCATION: (1)..(123)
<223> OTHER INFORMATION: Ceres Seq. ID no. 3456815
<220> FEATURE:
<221> NAME/KEY: misc_feature
<222> LOCATION: (7)..(121)
<223> OTHER INFORMATION: PFAM Description: Auxin responsive protein
<220> FEATURE:
<221> NAME/KEY: misc_feature
<222> LOCATION: (1)..(122)
<223> OTHER INFORMATION: GI NO: 50946385
      NR DESCRIPTION: auxin-induced protein-related-like protein
<220> FEATURE:
<221> NAME/KEY: misc_feature
<222> LOCATION: (1)..(122)
<223> OTHER INFORMATION: GI NO: 21554070
      NR DESCRIPTION: unknown
<220> FEATURE:
<221> NAME/KEY: misc_feature
<222> LOCATION: (1)..(122)
<223> OTHER INFORMATION: GI NO: 15242071
      NR DESCRIPTION: putative protein; protein id: At5g20820.1
```

```
<220> FEATURE:
<221> NAME/KEY: misc_feature
<222> LOCATION: (20)..(121)
<223> OTHER INFORMATION: GI NO: 21536952
      NR DESCRIPTION: unknown
<220> FEATURE:
<221> NAME/KEY: misc_feature
<222> LOCATION: (107)..(107)
<223> OTHER INFORMATION: Xaa is any aa, unknown or other
<220> FEATURE:
<221> NAME/KEY: misc_feature
<222> LOCATION: (114)..(114)
<223> OTHER INFORMATION: Xaa is any aa, unknown or other

<400> SEQUENCE: 43

Met Ala Lys Val Gly Lys Leu Thr Lys Leu Lys Ser Ala Ile Lys Arg
1               5                   10                  15

Trp Pro Ser Leu Thr Arg Leu Ser Arg Asn Ser Ser Val Ser Ser
            20                  25                  30

Asn Lys Gly Val Ser Gly Lys Gly Thr Ser Leu Asn Ser Ser Lys Glu
            35                  40                  45

His Glu His Glu Gln Glu Gln Leu Arg Ala Val Tyr Val Gly Lys Ser
        50                  55                  60

Arg Arg Arg Tyr Leu Val Asn Ser Glu Val Ile Asp His Pro Val Phe
65                  70                  75                  80

Gln Glu Leu Val Asp Arg Ser Cys Ser Ser Asn Ser Ser Ser Ser His
                85                  90                  95

His His Asp Asp Asp Gly Val Val Val Val Xaa Cys Glu Val Val Leu
            100                 105                 110

Phe Xaa His Leu Leu Trp Met Leu Glu Ser Glu
            115                 120

<210> SEQ ID NO 44
<211> LENGTH: 547
<212> TYPE: DNA
<213> ORGANISM: Glycine max
<220> FEATURE:
<221> NAME/KEY: misc_feature
<222> LOCATION: (1)..(547)
<223> OTHER INFORMATION: Ceres Seq. ID no. 12448255
<220> FEATURE:
<221> NAME/KEY: misc_feature
<222> LOCATION: (527)..(527)
<223> OTHER INFORMATION: n is a, c, t, g, unknown, or other

<400> SEQUENCE: 44
aatcactaca accctaagaa gaagaaatca tcatgagttc aaaaaatagt atagatagga      60
agccgaagca ctatgttctg gtgcatgggg cttgctatgg agcttggctt tggtataagc    120
tcaagccacg cttggaatct gcagggcaca aggtcacagt gctcgacctt gcagcttctg    180
gaaccaacat gaagaaaatt gaagatgttg acactttctc acagtacact gagcctttgt    240
tgcagctaat ggccacaatt cccccaaata gaaggtagt tctagttggt cacagtcttg     300
ggggctcaa catagcactt gcaatggaaa agttcccaga aaaggttgca gttggtgttt     360
tcgtaacagc tataattcca gacattgaac acaagccatc ctatgtcttg aaaagatgc     420
tgcatagaat tacgtactaa agttcaagac tcatgcggaa ggaaaaatca accgtgggag    480
gagtcttgtc ggtgcagtga gataaagtag aataaataaa gcatgcncca ttcagaaatg    540
gcacccc                                                             547

<210> SEQ ID NO 45
<211> LENGTH: 135
<212> TYPE: PRT
```

```
<213> ORGANISM: Glycine max
<220> FEATURE:
<221> NAME/KEY: misc_feature
<222> LOCATION: (1)..(135)
<223> OTHER INFORMATION: Ceres Seq. ID no. 12448256
<220> FEATURE:
<221> NAME/KEY: misc_feature
<222> LOCATION: (39)..(128)
<223> OTHER INFORMATION: PFAM Description: alpha/beta hydrolase fold
<220> FEATURE:
<221> NAME/KEY: misc_feature
<222> LOCATION: (6)..(134)
<223> OTHER INFORMATION: GI NO: 21554666
     NR DESCRIPTION: putative acetone-cyanohydrin lyase
<220> FEATURE:
<221> NAME/KEY: misc_feature
<222> LOCATION: (6)..(130)
<223> OTHER INFORMATION: GI NO: 7488034
     NR DESCRIPTION: probable (S)-acetone-cyanohydrin lyase
<220> FEATURE:
<221> NAME/KEY: misc_feature
<222> LOCATION: (7)..(128)
<223> OTHER INFORMATION: GI NO: 14279437
     NR DESCRIPTION: ethylene-induced esterase
<220> FEATURE:
<221> NAME/KEY: misc_feature
<222> LOCATION: (6)..(128)
<223> OTHER INFORMATION: GI NO: 27754457
     NR DESCRIPTION: putative acetone-cyanohydrin lyase
<220> FEATURE:
<221> NAME/KEY: misc_feature
<222> LOCATION: (9)..(132)
<223> OTHER INFORMATION: GI NO: 40549303
     NR DESCRIPTION: salicylic acid-binding protein 2
<220> FEATURE:
<221> NAME/KEY: misc_feature
<222> LOCATION: (14)..(130)
<223> OTHER INFORMATION: GI NO: 2780225
     NR DESCRIPTION: alpha-hydroxynitrile lyase
<220> FEATURE:
<221> NAME/KEY: misc_feature
<222> LOCATION: (7)..(130)
<223> OTHER INFORMATION: GI NO: 15028131
     NR DESCRIPTION: putative alpha-hydroxynitrile lyase
<220> FEATURE:
<221> NAME/KEY: misc_feature
<222> LOCATION: (13)..(130)
<223> OTHER INFORMATION: GI NO: 631916
     NR DESCRIPTION: acetone-cyanhydrin lyase (EC 4.1.2.37)
<220> FEATURE:
<221> NAME/KEY: misc_feature
<222> LOCATION: (7)..(130)
<223> OTHER INFORMATION: GI NO: 16648679
     NR DESCRIPTION: AT5g10300/F18D22_70
<220> FEATURE:
<221> NAME/KEY: misc_feature
<222> LOCATION: (8)..(133)
<223> OTHER INFORMATION: GI NO: 28393451
     NR DESCRIPTION: putative acetone-cyanohydrin lyase

<400> SEQUENCE: 45

Met Ser Ser Lys Asn Ser Ile Asp Arg Lys Pro Lys His Tyr Val Leu
1               5                   10                  15

Val His Gly Ala Cys Tyr Gly Ala Trp Leu Trp Tyr Lys Leu Lys Pro
            20                  25                  30

Arg Leu Glu Ser Ala Gly His Lys Val Thr Val Leu Asp Leu Ala Ala
        35                  40                  45

Ser Gly Thr Asn Met Lys Lys Ile Glu Asp Val Asp Thr Phe Ser Gln
    50                  55                  60

Tyr Thr Glu Pro Leu Leu Gln Leu Met Ala Thr Ile Pro Pro Asn Lys
65                  70                  75                  80

Lys Val Val Leu Val Gly His Ser Leu Gly Gly Leu Asn Ile Ala Leu
                85                  90                  95
```

```
Ala Met Glu Lys Phe Pro Glu Lys Val Ala Val Gly Val Phe Val Thr
                100                 105                 110

Ala Ile Ile Pro Asp Ile Glu His Lys Pro Ser Tyr Val Leu Glu Lys
        115                 120                 125

Met Leu His Arg Ile Thr Tyr
        130                 135

<210> SEQ ID NO 46
<211> LENGTH: 83
<212> TYPE: PRT
<213> ORGANISM: Glycine max
<220> FEATURE:
<221> NAME/KEY: misc_feature
<222> LOCATION: (1)..(83)
<223> OTHER INFORMATION: Ceres Seq. ID no. 12448257
<220> FEATURE:
<221> NAME/KEY: misc_feature
<222> LOCATION: (1)..(76)
<223> OTHER INFORMATION: PFAM Description: alpha/beta hydrolase fold
<220> FEATURE:
<221> NAME/KEY: misc_feature
<222> LOCATION: (1)..(82)
<223> OTHER INFORMATION: GI NO: 21554666
      NR DESCRIPTION: putative acetone-cyanohydrin lyase
<220> FEATURE:
<221> NAME/KEY: misc_feature
<222> LOCATION: (1)..(78)
<223> OTHER INFORMATION: GI NO: 7488034
      NR DESCRIPTION: probable (S)-acetone-cyanohydrin lyase
<220> FEATURE:
<221> NAME/KEY: misc_feature
<222> LOCATION: (1)..(76)
<223> OTHER INFORMATION: GI NO: 14279437
      NR DESCRIPTION: ethylene-induced esterase
<220> FEATURE:
<221> NAME/KEY: misc_feature
<222> LOCATION: (1)..(76)
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (1)..(80)
<223> OTHER INFORMATION: GI NO: 40549303
      NR DESCRIPTION: salicylic acid-binding protein 2
<220> FEATURE:
<221> NAME/KEY: misc_feature
<222> LOCATION: (1)..(78)
<223> OTHER INFORMATION: GI NO: 2780225
      NR DESCRIPTION: alpha-hydroxynitrile lyase
<220> FEATURE:
<221> NAME/KEY: misc_feature
<222> LOCATION: (1)..(78)
<223> OTHER INFORMATION: GI NO: 15028131
      NR DESCRIPTION: putative alpha-hydroxynitrile lyase
<220> FEATURE:
<221> NAME/KEY: misc_feature
<222> LOCATION: (1)..(78)
<223> OTHER INFORMATION: GI NO: 631916
      NR DESCRIPTION: acetone-cyanhydrin lyase (EC 4.1.2.37)
<220> FEATURE:
<221> NAME/KEY: misc_feature
<222> LOCATION: (1)..(78)
<223> OTHER INFORMATION: GI NO: 16648679
      NR DESCRIPTION: AT5g10300/F18D22_70
<220> FEATURE:
<221> NAME/KEY: misc_feature
<222> LOCATION: (1)..(81)
<223> OTHER INFORMATION: GI NO: 28393451
      NR DESCRIPTION: putative acetone-cyanohydrin lyase

<400> SEQUENCE: 46

Met Lys Lys Ile Glu Asp Val Asp Thr Phe Ser Gln Tyr Thr Glu Pro
1               5                   10                  15

Leu Leu Gln Leu Met Ala Thr Ile Pro Pro Asn Lys Lys Val Val Leu
            20                  25                  30
```

```
Val Gly His Ser Leu Gly Gly Leu Asn Ile Ala Leu Ala Met Glu Lys
            35                  40                  45

Phe Pro Glu Lys Val Ala Val Gly Val Phe Val Thr Ala Ile Ile Pro
     50                  55                  60

Asp Ile Glu His Lys Pro Ser Tyr Val Leu Glu Lys Met Leu His Arg
 65                  70                  75                  80

Ile Thr Tyr

<210> SEQ ID NO 47
<211> LENGTH: 427
<212> TYPE: DNA
<213> ORGANISM: Glycine max
<220> FEATURE:
<221> NAME/KEY: misc_feature
<222> LOCATION: (1)..(427)
<223> OTHER INFORMATION: Ceres Seq. ID no. 13638578

<400> SEQUENCE: 47
aagaaacgaa gctgctagct gctcggcgca cacatgtcgt catcctcctc ctctgcgcca      60
gcggccgccg tggcgacgtc gacccgcctc atcctggtgc acggcacggg ccacggcggg     120
tggtgctggt acaaggtcgc caccctcctc cgcgccgcgg ggcaccgcgt cgacgcgccg     180
gacctcgcgg cctgcggcgc cgacgcgcgc cggctgagcg acgcgccaac cttcgaggac     240
tacacgcgcc ccctgctcga cgcgctccgg gccctcccgg acggcgagcg agcggtgctc     300
gtgggccaca gcttcggcgg catgagcgtc gcgctcgccg ccgaggagtt ccccgacaag     360
gtcgccgccg ccgtgttcct caccgccttc atgccggact cgccggccc gcgcacccgc     420 gtcatcg                                                               427

<210> SEQ ID NO 48
<211> LENGTH: 141
<212> TYPE: PRT
<213> ORGANISM: Glycine max
<220> FEATURE:
<221> NAME/KEY: misc_feature
<222> LOCATION: (1)..(141)
<223> OTHER INFORMATION: Ceres Seq. ID no. 13638579
<220> FEATURE:
<221> NAME/KEY: misc_feature
<222> LOCATION: (19)..(140)
<223> OTHER INFORMATION: PFAM Description: Subtilase family

<400> SEQUENCE: 48

Glu Thr Lys Leu Leu Ala Ala Arg Arg Thr His Val Val Ile Leu Leu
 1               5                  10                  15

Leu Cys Ala Ser Gly Arg Arg Gly Asp Val Asp Pro Pro His Pro Gly
             20                  25                  30

Ala Arg His Gly Pro Arg Arg Val Val Leu Val Gln Gly Arg His Pro
         35                  40                  45

Pro Pro Arg Arg Gly Ala Pro Arg Arg Ala Gly Pro Arg Gly Leu
     50                  55                  60

Arg Arg Arg Arg Ala Pro Ala Glu Arg Ala Asn Leu Arg Gly Leu
 65                  70                  75                  80

His Ala Pro Pro Ala Arg Arg Ala Pro Gly Pro Gly Arg Arg Ala
                 85                  90                  95

Ser Gly Ala Arg Gly Pro Gln Leu Arg Arg His Glu Arg Arg Ala Arg
            100                 105                 110

Arg Arg Gly Val Pro Arg Gln Gly Arg Arg Arg Val Pro His Arg
        115                 120                 125
```

-continued

```
Leu His Ala Gly Leu Arg Arg Pro Ala His Pro Arg His
        130                 135                 140

<210> SEQ ID NO 49
<211> LENGTH: 131
<212> TYPE: PRT
<213> ORGANISM: Glycine max
<220> FEATURE:
<221> NAME/KEY: misc_feature
<222> LOCATION: (1)..(131)
<223> OTHER INFORMATION: Ceres Seq. ID no. 13638580
<220> FEATURE:
<221> NAME/KEY: misc_feature
<222> LOCATION: (44)..(130)
<223> OTHER INFORMATION: PFAM Description: alpha/beta hydrolase fold
<220> FEATURE:
<221> NAME/KEY: misc_feature
<222> LOCATION: (5)..(130)
<223> OTHER INFORMATION: GI NO: 34915034
      NR DESCRIPTION: putative acetone-cyanohydrin lyase
<220> FEATURE:
<221> NAME/KEY: misc_feature
<222> LOCATION: (1)..(130)
<223> OTHER INFORMATION: GI NO: 34914020
      NR DESCRIPTION: OJ1014_G12.25
<220> FEATURE:
<221> NAME/KEY: misc_feature
<222> LOCATION: (8)..(130)
<223> OTHER INFORMATION: GI NO: 34914024
      NR DESCRIPTION: OJ1014_G12.27
<220> FEATURE:
<221> NAME/KEY: misc_feature
<222> LOCATION: (19)..(122)
<223> OTHER INFORMATION: GI NO: 34908770
      NR DESCRIPTION: P0415A04.19
<220> FEATURE:
<221> NAME/KEY: misc_feature
<222> LOCATION: (14)..(127)
<223> OTHER INFORMATION: GI NO: 34907174
      NR DESCRIPTION: putative pir7b (Pseudomonas inducible protein)
<220> FEATURE:
<221> NAME/KEY: misc_feature
<222> LOCATION: (14)..(125)
<223> OTHER INFORMATION: GI NO: 34907176
      NR DESCRIPTION: pir7b protein (Pseudomonas inducible protein)
<220> FEATURE:
<221> NAME/KEY: misc_feature
<222> LOCATION: (20)..(125)
<223> OTHER INFORMATION: GI NO: 498747
      NR DESCRIPTION: Pir7b
<220> FEATURE:
<221> NAME/KEY: misc_feature
<222> LOCATION: (20)..(122)
<223> OTHER INFORMATION: GI NO: 7488034
      NR DESCRIPTION: probable (S)-acetone-cyanohydrin lyase
<220> FEATURE:
<221> NAME/KEY: misc_feature
<222> LOCATION: (20)..(125)
<223> OTHER INFORMATION: GI NO: 34907178
      NR DESCRIPTION: pir7a protein (Pseudomonas inducible protein)
<220> FEATURE:
<221> NAME/KEY: misc_feature
<222> LOCATION: (20)..(122)
<223> OTHER INFORMATION: GI NO: 27754457
      NR DESCRIPTION: putative acetone-cyanohydrin lyase

<400> SEQUENCE: 49

Met Ser Ser Ser Ser Ser Ala Pro Ala Ala Val Ala Thr Ser
1               5                   10                  15

Thr Arg Leu Ile Leu Val His Gly Thr Gly His Gly Gly Trp Cys Trp
            20                  25                  30

Tyr Lys Val Ala Thr Leu Leu Arg Ala Ala Gly His Arg Val Asp Ala
        35                  40                  45

Pro Asp Leu Ala Ala Cys Gly Ala Asp Ala Arg Arg Leu Ser Asp Ala
    50                  55                  60
```

```
Pro Thr Phe Glu Asp Tyr Thr Arg Pro Leu Leu Asp Ala Leu Arg Ala
 65                  70                  75                  80

Leu Pro Asp Gly Glu Arg Ala Val Leu Val Gly His Ser Phe Gly Gly
                 85                  90                  95

Met Ser Val Ala Leu Ala Ala Glu Glu Phe Pro Asp Lys Val Ala Ala
            100                 105                 110

Ala Val Phe Leu Thr Ala Phe Met Pro Asp Cys Ala Gly Pro Arg Thr
        115                 120                 125

Arg Val Ile
    130

<210> SEQ ID NO 50
<211> LENGTH: 71
<212> TYPE: PRT
<213> ORGANISM: Glycine max
<220> FEATURE:
<221> NAME/KEY: misc_feature
<222> LOCATION: (1)..(71)
<223> OTHER INFORMATION: Ceres Seq. ID no. 13638581
<220> FEATURE:
<221> NAME/KEY: misc_feature
<222> LOCATION: (1)..(71)
<223> OTHER INFORMATION: PFAM Description: Cupin
<220> FEATURE:
<221> NAME/KEY: misc_feature
<222> LOCATION: (3)..(71)
<223> OTHER INFORMATION: GI NO: 50941143
      NR DESCRIPTION: CLAVATA1 receptor kinase( CLV1)-like protein
<220> FEATURE:
<221> NAME/KEY: misc_feature
<222> LOCATION: (6)..(71)
<223> OTHER INFORMATION: GI NO: 29828765
      NR DESCRIPTION: putative protoporphyrinogen oxidase

<400> SEQUENCE: 50

Arg Asn Glu Ala Ala Ser Cys Ser Ala His Thr Cys Arg His Pro Pro
  1               5                  10                  15

Pro Leu Arg Gln Arg Pro Pro Trp Arg Arg Pro Ala Ser Ser Trp
             20                  25                  30

Cys Thr Ala Arg Ala Thr Ala Gly Gly Ala Gly Thr Arg Ser Pro Pro
         35                  40                  45

Ser Ser Ala Pro Arg Gly Thr Ala Ser Thr Arg Thr Ser Arg Pro
 50                  55                  60

Ala Ala Pro Thr Arg Ala Gly
 65                  70

<210> SEQ ID NO 51
<211> LENGTH: 626
<212> TYPE: DNA
<213> ORGANISM: Glycine max
<220> FEATURE:
<221> NAME/KEY: misc_feature
<222> LOCATION: (1)..(626)
<223> OTHER INFORMATION: Ceres Seq. ID no. 12480973

<400> SEQUENCE: 51
agagagagaa caaagaatca cagaaagggg tggtgtctgc ttcgaaagct taataatttg     60
tttatttcca gaacatcata gttttcgcag cagcacacta acacattact catatcatat    120
aataagatgg cccgttctct ctcgcaagcc aaacgtattg tgtccttgt tgctcaatct     180 atctccctaa ttcccgttca tcggcgaggt tacgcagtgg catccgatgt atcggtaaga    240
gttggattgg gtaatattgg gcgaaggaat ggaatcgtgg gaggtgtaga agagaagcct    300
gatacaagag atggttcaaa agcctactca actgattggg ccccagaccc agtaacaggt    360
```

-continued

```
tactataggc ccattaacca caccccctgaa attgacccgg tggagcttcg gcataggttg      420
ctccgatcac ctccactaga gcctagagga gttgctggac acccatgaca tgcccaaatt      480
ttacttagga tttggtttgg tttggtttgg tttggtaggg taaccttgtg ttgttgttcc      540
acaaaataca aggttttgtt aaacgttac tacttcctat gtaccctaga atctactttt       600
aaggttatgg ttcttattat tagtcc                                          626
```

```
<210> SEQ ID NO 52
<211> LENGTH: 113
<212> TYPE: PRT
<213> ORGANISM: Glycine max
<220> FEATURE:
<221> NAME/KEY: misc_feature
<222> LOCATION: (1)..(113)
<223> OTHER INFORMATION: Ceres Seq. ID no. 12480974
<220> FEATURE:
<221> NAME/KEY: misc_feature
<222> LOCATION: (1)..(100)
<223> OTHER INFORMATION: PFAM Description: Late embryogenesis abundant
      protein
<220> FEATURE:
<221> NAME/KEY: misc_feature
<222> LOCATION: (1)..(113)
<223> OTHER INFORMATION: GI NO: 7488660
      NR DESCRIPTION: desiccation protective protein LEA5
<220> FEATURE:
<221> NAME/KEY: misc_feature
<222> LOCATION: (1)..(101)
<223> OTHER INFORMATION: GI NO: 1370589
      NR DESCRIPTION: protein induced upon tuberization
<220> FEATURE:
<221> NAME/KEY: misc_feature
<222> LOCATION: (1)..(100)
<223> OTHER INFORMATION: GI NO: 7489029
      NR DESCRIPTION: late-embryogenesis protein homolog
<220> FEATURE:
<221> NAME/KEY: misc_feature
<222> LOCATION: (15)..(99)
<223> OTHER INFORMATION: GI NO: 34894580
      NR DESCRIPTION: zinc-induced protein-like

<400> SEQUENCE: 52

Met Ala Arg Ser Leu Ser Gln Ala Lys Arg Ile Gly Val Leu Val Ala
1               5                   10                  15

Gln Ser Ile Ser Leu Ile Pro Val His Arg Arg Gly Tyr Ala Val Ala
                20                  25                  30

Ser Asp Val Ser Val Arg Val Gly Leu Gly Asn Ile Gly Arg Arg Asn
            35                  40                  45

Gly Ile Val Gly Gly Val Glu Glu Lys Pro Asp Thr Arg Asp Gly Ser
        50                  55                  60

Lys Ala Tyr Ser Thr Asp Trp Ala Pro Asp Pro Val Thr Gly Tyr Tyr
65                  70                  75                  80

Arg Pro Ile Asn His Thr Pro Glu Ile Asp Pro Val Glu Leu Arg His
                85                  90                  95

Arg Leu Leu Arg Ser Pro Pro Leu Glu Pro Arg Gly Val Ala Gly His
            100                 105                 110

Pro

<210> SEQ ID NO 53
<211> LENGTH: 62
<212> TYPE: PRT
<213> ORGANISM: Glycine max
<220> FEATURE:
<221> NAME/KEY: misc_feature
<222> LOCATION: (1)..(62)
<223> OTHER INFORMATION: Ceres Seq. ID no. 12480975
```

<400> SEQUENCE: 53

Glu Arg Glu Gln Arg Ile Thr Glu Arg Gly Gly Val Cys Phe Glu Ser
1               5                   10                  15

Leu Ile Ile Cys Leu Phe Pro Glu His His Ser Phe Arg Ser Ser Thr
            20                  25                  30

Leu Thr His Tyr Ser Tyr His Ile Ile Arg Trp Pro Val Leu Ser Arg
        35                  40                  45

Lys Pro Asn Val Leu Val Ser Leu Leu Leu Asn Leu Ser Pro
    50                  55                  60

<210> SEQ ID NO 54
<211> LENGTH: 971
<212> TYPE: DNA
<213> ORGANISM: Glycine max
<220> FEATURE:
<221> NAME/KEY: misc_feature
<222> LOCATION: (1)..(971)
<223> OTHER INFORMATION: Ceres Seq. ID no. 13638849

<400> SEQUENCE: 54

| | |
|---|---|
| atccaacaca aaaccaaaca ggtcttacgc aacaaatgga gagcacccag agcaacacaa | 60 |
| gcgtgatgaa ccatttcatc ctggtgcacg gcctctgcca cggggcctgg tgttggtaca | 120 |
| aggtggttgc ggcgcttcag gcagcggggc accgtgtcac ggcggtcgac ctggccgcgt | 180 |
| ccggcgctca cccggcgcgc atcgacgagg tgcactcgtt cgaggagtac tcccagcctc | 240 |
| tgcttgacgt agtggccgcg cgccagaggg tgacggcga gaggctgatt ctggtcgggc | 300 |
| acagccacgg cgggctcagc ttggcgctag ccatggagag gttccccggc aaggtcgccg | 360 |
| ccgccgtgtt cgcagccgcc gggatgccgt gcgttggcaa gcacatgggc gtcaccaccg | 420 |
| aggagttcat gcgaaggaca tcatcggaag gactcatgga ctgcaagatg ctgccaatca | 480 |
| ataacaacca cggtgcaggg gttgcaatga taatgggccc aaacttctta gcacacaaga | 540 |
| actaccagca aagttcacct gaggatttgg ccctggcaaa aatgttggtg agaccgggaa | 600 |
| acctgttcat ggaggatccg gtgatgaagg atgcaagcct gctcaccgat accaactacg | 660 |
| ggtcggtgaa gaaggtatat gtggtagcaa aggctgatgg ctccagcacc gaggagatgc | 720 |
| agcgttggat ggtgttgttg agccccggca cggaggctga ggagatcgcg ggagctgacc | 780 |
| acgccatcat gagctcaagg cctagggagc tctgtgatgc tctggtcaag atcgccgaca | 840 |
| gcttaaatac ttgctaaatt gtacgatata tatccctgga aatcaatgta ggtgtgtact | 900 |
| tgattttcat ctaaaaataa atatgttcag tgatactatt aaatcaatgg aaattaagta | 960 |
| gtattaccett c | 971 |

<210> SEQ ID NO 55
<211> LENGTH: 284
<212> TYPE: PRT
<213> ORGANISM: Glycine max
<220> FEATURE:
<221> NAME/KEY: misc_feature
<222> LOCATION: (1)..(284)
<223> OTHER INFORMATION: Ceres Seq. ID no. 13638850
<220> FEATURE:
<221> NAME/KEY: misc_feature
<222> LOCATION: (50)..(276)
<223> OTHER INFORMATION: PFAM Description: alpha/beta hydrolase fold
<220> FEATURE:
<221> NAME/KEY: misc_feature
<222> LOCATION: (18)..(279)
<223> OTHER INFORMATION: GI NO: 34907176
    NR DESCRIPTION: pir7b protein (Pseudomonas inducible protein)
<220> FEATURE:

-continued

```
<221> NAME/KEY: misc_feature
<222> LOCATION: (24)..(279)
<223> OTHER INFORMATION: GI NO: 498747
      NR DESCRIPTION: Pir7b
<220> FEATURE:
<221> NAME/KEY: misc_feature
<222> LOCATION: (24)..(278)
<223> OTHER INFORMATION: GI NO: 34907178
      NR DESCRIPTION: pir7a protein (Pseudomonas inducible protein)
<220> FEATURE:
<221> NAME/KEY: misc_feature
<222> LOCATION: (24)..(282)
<223> OTHER INFORMATION: GI NO: 40549303
      NR DESCRIPTION: salicylic acid-binding protein 2
<220> FEATURE:
<221> NAME/KEY: misc_feature
<222> LOCATION: (24)..(278)
<223> OTHER INFORMATION: GI NO: 14279437
      NR DESCRIPTION: ethylene-induced esterase
<220> FEATURE:
<221> NAME/KEY: misc_feature
<222> LOCATION: (23)..(278)
<223> OTHER INFORMATION: GI NO: 41814856
      NR DESCRIPTION: methylesterase
<220> FEATURE:
<221> NAME/KEY: misc_feature
<222> LOCATION: (24)..(279)
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (24)..(282)
<223> OTHER INFORMATION: GI NO: 21554666
      NR DESCRIPTION: putative acetone-cyanohydrin lyase
<220> FEATURE:
<221> NAME/KEY: misc_feature
<222> LOCATION: (23)..(280)
<223> OTHER INFORMATION: GI NO: 34914020
      NR DESCRIPTION: OJ1014_G12.25
<220> FEATURE:
<221> NAME/KEY: misc_feature
<222> LOCATION: (17)..(278)
<223> OTHER INFORMATION: GI NO: 21595837
      NR DESCRIPTION: polyneuridine aldehyde esterase

<400> SEQUENCE: 55

Pro Thr Gln Asn Gln Thr Gly Leu Thr Gln Gln Met Glu Ser Thr Gln
1               5                   10                  15

Ser Asn Thr Ser Val Met Asn His Phe Ile Leu Val His Gly Leu Cys
            20                  25                  30

His Gly Ala Trp Cys Trp Tyr Lys Val Val Ala Ala Leu Gln Ala Ala
        35                  40                  45

Gly His Arg Val Thr Ala Val Asp Leu Ala Ala Ser Gly Ala His Pro
    50                  55                  60

Ala Arg Ile Asp Glu Val His Ser Phe Glu Glu Tyr Ser Gln Pro Leu
65                  70                  75                  80

Leu Asp Val Val Ala Ala Pro Glu Gly Asp Gly Glu Arg Leu Ile
                85                  90                  95

Leu Val Gly His Ser His Gly Gly Leu Ser Leu Ala Leu Ala Met Glu
                100                 105                 110

Arg Phe Pro Gly Lys Val Ala Ala Val Phe Ala Ala Ala Gly Met
            115                 120                 125

Pro Cys Val Gly Lys His Met Gly Val Thr Thr Glu Glu Phe Met Arg
    130                 135                 140

Arg Thr Ser Ser Glu Gly Leu Met Asp Cys Lys Met Leu Pro Ile Asn
145                 150                 155                 160

Asn Asn His Gly Ala Gly Val Ala Met Ile Met Gly Pro Asn Phe Leu
                165                 170                 175
```

-continued

```
Ala His Lys Asn Tyr Gln Gln Ser Ser Pro Glu Asp Leu Ala Leu Ala
            180                 185                 190

Lys Met Leu Val Arg Pro Gly Asn Leu Phe Met Glu Asp Pro Val Met
        195                 200                 205

Lys Asp Ala Ser Leu Leu Thr Asp Thr Asn Tyr Gly Ser Val Lys Lys
210                 215                 220

Val Tyr Val Val Ala Lys Ala Asp Gly Ser Ser Thr Glu Glu Met Gln
225                 230                 235                 240

Arg Trp Met Val Leu Leu Ser Pro Gly Thr Glu Ala Glu Glu Ile Ala
                245                 250                 255

Gly Ala Asp His Ala Ile Met Ser Ser Arg Pro Arg Glu Leu Cys Asp
            260                 265                 270

Ala Leu Val Lys Ile Ala Asp Ser Leu Asn Thr Cys
            275                 280

<210> SEQ ID NO 56
<211> LENGTH: 273
<212> TYPE: PRT
<213> ORGANISM: Glycine max
<220> FEATURE:
<221> NAME/KEY: misc_feature
<222> LOCATION: (1)..(273)
<223> OTHER INFORMATION: Ceres Seq. ID no. 13638851
<220> FEATURE:
<221> NAME/KEY: misc_feature
<222> LOCATION: (39)..(265)
<223> OTHER INFORMATION: PFAM Description: alpha/beta hydrolase fold
<220> FEATURE:
<221> NAME/KEY: misc_feature
<222> LOCATION: (7)..(268)
<223> OTHER INFORMATION: GI NO: 34907176
      NR DESCRIPTION: pir7b protein (Pseudomonas inducible protein)
<220> FEATURE:
<221> NAME/KEY: misc_feature
<222> LOCATION: (13)..(268)
<223> OTHER INFORMATION: GI NO: 498747
      NR DESCRIPTION: Pir7b
<220> FEATURE:
<221> NAME/KEY: misc_feature
<222> LOCATION: (13)..(267)
<223> OTHER INFORMATION: GI NO: 34907178
      NR DESCRIPTION: pir7a protein (Pseudomonas inducible protein)
<220> FEATURE:
<221> NAME/KEY: misc_feature
<222> LOCATION: (13)..(271)
<223> OTHER INFORMATION: GI NO: 40549303
      NR DESCRIPTION: salicylic acid-binding protein 2
<220> FEATURE:
<221> NAME/KEY: misc_feature
<222> LOCATION: (13)..(267)
<223> OTHER INFORMATION: GI NO: 14279437
      NR DESCRIPTION: ethylene-induced esterase
<220> FEATURE:
<221> NAME/KEY: misc_feature
<222> LOCATION: (12)..(267)
<223> OTHER INFORMATION: GI NO: 41814856
      NR DESCRIPTION: methylesterase
<220> FEATURE:
<221> NAME/KEY: misc_feature
<222> LOCATION: (13)..(268)
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (13)..(271)
<223> OTHER INFORMATION: GI NO: 21554666
      NR DESCRIPTION: putative acetone-cyanohydrin lyase
<220> FEATURE:
<221> NAME/KEY: misc_feature
<222> LOCATION: (12)..(269)
<223> OTHER INFORMATION: GI NO: 34914020
      NR DESCRIPTION: OJ1014_G12.25
<220> FEATURE:
```

<221> NAME/KEY: misc_feature
<222> LOCATION: (6)..(267)
<223> OTHER INFORMATION: GI NO: 21595837
      NR DESCRIPTION: polyneuridine aldehyde esterase

<400> SEQUENCE: 56

```
Met Glu Ser Thr Gln Ser Asn Thr Ser Val Met Asn His Phe Ile Leu
1               5                   10                  15

Val His Gly Leu Cys His Gly Ala Trp Cys Trp Tyr Lys Val Val Ala
            20                  25                  30

Ala Leu Gln Ala Ala Gly His Arg Val Thr Ala Val Asp Leu Ala Ala
        35                  40                  45

Ser Gly Ala His Pro Ala Arg Ile Asp Glu Val His Ser Phe Glu Glu
    50                  55                  60

Tyr Ser Gln Pro Leu Leu Asp Val Val Ala Ala Pro Glu Gly Asp
65                  70                  75                  80

Gly Glu Arg Leu Ile Leu Val Gly His Ser His Gly Gly Leu Ser Leu
                85                  90                  95

Ala Leu Ala Met Glu Arg Phe Pro Gly Lys Val Ala Ala Val Phe
            100                 105                 110

Ala Ala Ala Gly Met Pro Cys Val Gly Lys His Met Gly Val Thr Thr
        115                 120                 125

Glu Glu Phe Met Arg Arg Thr Ser Ser Glu Gly Leu Met Asp Cys Lys
    130                 135                 140

Met Leu Pro Ile Asn Asn Asn His Gly Ala Gly Val Ala Met Ile Met
145                 150                 155                 160

Gly Pro Asn Phe Leu Ala His Lys Asn Tyr Gln Gln Ser Ser Pro Glu
                165                 170                 175

Asp Leu Ala Leu Ala Lys Met Leu Val Arg Pro Gly Asn Leu Phe Met
            180                 185                 190

Glu Asp Pro Val Met Lys Asp Ala Ser Leu Leu Thr Asp Thr Asn Tyr
        195                 200                 205

Gly Ser Val Lys Lys Val Tyr Val Val Ala Lys Ala Asp Gly Ser Ser
    210                 215                 220

Thr Glu Glu Met Gln Arg Trp Met Val Leu Leu Ser Pro Gly Thr Glu
225                 230                 235                 240

Ala Glu Glu Ile Ala Gly Ala Asp His Ala Ile Met Ser Ser Arg Pro
                245                 250                 255

Arg Glu Leu Cys Asp Ala Leu Val Lys Ile Ala Asp Ser Leu Asn Thr
            260                 265                 270

Cys
```

<210> SEQ ID NO 57
<211> LENGTH: 263
<212> TYPE: PRT
<213> ORGANISM: Glycine max
<220> FEATURE:
<221> NAME/KEY: misc_feature
<222> LOCATION: (1)..(263)
<223> OTHER INFORMATION: Ceres Seq. ID no. 13638852
<220> FEATURE:
<221> NAME/KEY: misc_feature
<222> LOCATION: (29)..(255)
<223> OTHER INFORMATION: PFAM Description: alpha/beta hydrolase fold
<220> FEATURE:
<221> NAME/KEY: misc_feature
<222> LOCATION: (1)..(258)
<223> OTHER INFORMATION: GI NO: 34907176
      NR DESCRIPTION: pir7b protein (Pseudomonas inducible protein)
<220> FEATURE:
<221> NAME/KEY: misc_feature

```
<222> LOCATION: (3)..(258)
<223> OTHER INFORMATION: GI NO: 498747
       NR DESCRIPTION: Pir7b
<220> FEATURE:
<221> NAME/KEY: misc_feature
<222> LOCATION: (3)..(257)
<223> OTHER INFORMATION: GI NO: 34907178
       NR DESCRIPTION: pir7a protein (Pseudomonas inducible protein)
<220> FEATURE:
<221> NAME/KEY: misc_feature
<222> LOCATION: (3)..(261)
<223> OTHER INFORMATION: GI NO: 40549303
       NR DESCRIPTION: salicylic acid-binding protein 2
<220> FEATURE:
<221> NAME/KEY: misc_feature
<222> LOCATION: (3)..(257)
<223> OTHER INFORMATION: GI NO: 14279437
       NR DESCRIPTION: ethylene-induced esterase
<220> FEATURE:
<221> NAME/KEY: misc_feature
<222> LOCATION: (2)..(257)
<223> OTHER INFORMATION: GI NO: 41814856
       NR DESCRIPTION: methylesterase
<220> FEATURE:
<221> NAME/KEY: misc_feature
<222> LOCATION: (3)..(258)
<223> OTHER INFORMATION: GI NO: 27754457
       NR DESCRIPTION: putative acetone-cyanohydrin lyase
<220> FEATURE:
<221> NAME/KEY: misc_feature
<222> LOCATION: (3)..(261)
<223> OTHER INFORMATION: GI NO: 21554666
       NR DESCRIPTION: putative acetone-cyanohydrin lyase
<220> FEATURE:
<221> NAME/KEY: misc_feature
<222> LOCATION: (2)..(259)
<223> OTHER INFORMATION: GI NO: 34914020
       NR DESCRIPTION: OJ1014_G12.25
<220> FEATURE:
<221> NAME/KEY: misc_feature
<222> LOCATION: (1)..(257)
<223> OTHER INFORMATION: GI NO: 21595837
       NR DESCRIPTION: polyneuridine aldehyde esterase

<400> SEQUENCE: 57

Met Asn His Phe Ile Leu Val His Gly Leu Cys His Gly Ala Trp Cys
1               5                   10                  15

Trp Tyr Lys Val Val Ala Ala Leu Gln Ala Ala Gly His Arg Val Thr
            20                  25                  30

Ala Val Asp Leu Ala Ala Ser Gly Ala His Pro Ala Arg Ile Asp Glu
        35                  40                  45

Val His Ser Phe Glu Glu Tyr Ser Gln Pro Leu Leu Asp Val Val Ala
    50                  55                  60

Ala Ala Pro Glu Gly Asp Gly Glu Arg Leu Ile Leu Val Gly His Ser
65                  70                  75                  80

His Gly Gly Leu Ser Leu Ala Leu Ala Met Glu Arg Phe Pro Gly Lys
                85                  90                  95

Val Ala Ala Val Phe Ala Ala Ala Gly Met Pro Cys Val Gly Lys
            100                 105                 110

His Met Gly Val Thr Thr Glu Glu Phe Met Arg Arg Thr Ser Ser Glu
        115                 120                 125

Gly Leu Met Asp Cys Lys Met Leu Pro Ile Asn Asn His Gly Ala
    130                 135                 140

Gly Val Ala Met Ile Met Gly Pro Asn Phe Leu Ala His Lys Asn Tyr
145                 150                 155                 160

Gln Gln Ser Ser Pro Glu Asp Leu Ala Leu Ala Lys Met Leu Val Arg
                165                 170                 175

Pro Gly Asn Leu Phe Met Glu Asp Pro Val Met Lys Asp Ala Ser Leu
```

```
                          180                 185                 190
Leu Thr Asp Thr Asn Tyr Gly Ser Val Lys Lys Val Tyr Val Val Ala
            195                 200                 205

Lys Ala Asp Gly Ser Ser Thr Glu Glu Met Gln Arg Trp Met Val Leu
        210                 215                 220

Leu Ser Pro Gly Thr Glu Ala Glu Ile Ala Gly Ala Asp His Ala
225                 230                 235                 240

Ile Met Ser Ser Arg Pro Arg Glu Leu Cys Asp Ala Leu Val Lys Ile
                245                 250                 255

Ala Asp Ser Leu Asn Thr Cys
            260

<210> SEQ ID NO 58
<211> LENGTH: 466
<212> TYPE: DNA
<213> ORGANISM: Triticum aestivum
<220> FEATURE:
<221> NAME/KEY: misc_feature
<222> LOCATION: (1)..(466)
<223> OTHER INFORMATION: Ceres Seq. ID no. 11404534
<220> FEATURE:
<221> NAME/KEY: misc_feature
<222> LOCATION: (36)..(36)
<223> OTHER INFORMATION: n is a, c, t, g, unknown, or other

<400> SEQUENCE: 58
atactccaca gctaacgaca agcacggacc gcgganaaac agtcgcaaaa ccccacgtgt      60
gcacatcgag atgaggctc cggcggacca aaccagsagc aagcacatcg ttctggtgca     120
cggcgcatgc gtcggcggct gggcctggtt caaggtggcc acgcggctca gggacgccgg    180
gccaccgcgt cagcacgcct gacctcgcgg cgtcgggcgt cgaccccagg ccgctgcgcg    240
aggtgccgac gttcttcgac tacaccaagc cgctgctgga cctcctggar tcsctcycgc    300
ccggggagaa ggtggtgctc gtcggccaca gcctcggcgg cgtgaacatc gccctcgcct    360
gcgagctgtt cccggagaag gtcgccgccg cggtgttcct ctccgccttt atgccggacc    420
acaggtcgtc gccggcgtac gtgctcgaaa agttcgtgga gggggg                  466

<210> SEQ ID NO 59
<211> LENGTH: 154
<212> TYPE: PRT
<213> ORGANISM: Triticum aestivum
<220> FEATURE:
<221> NAME/KEY: misc_feature
<222> LOCATION: (1)..(154)
<223> OTHER INFORMATION: Ceres Seq. ID no. 11404535
<220> FEATURE:
<221> NAME/KEY: misc_feature
<222> LOCATION: (61)..(153)
<223> OTHER INFORMATION: PFAM Description: alpha/beta hydrolase fold
<220> FEATURE:
<221> NAME/KEY: misc_feature
<222> LOCATION: (60)..(153)
<223> OTHER INFORMATION: GI NO: 34908770
       NR DESCRIPTION: P0415A04.19
<220> FEATURE:
<221> NAME/KEY: misc_feature
<222> LOCATION: (60)..(153)
<223> OTHER INFORMATION: GI NO: 40549303
       NR DESCRIPTION: salicylic acid-binding protein 2
<220> FEATURE:
<221> NAME/KEY: misc_feature
<222> LOCATION: (60)..(153)
<223> OTHER INFORMATION: GI NO: 7488034
       NR DESCRIPTION: probable (S)-acetone-cyanohydrin lyase
<220> FEATURE:
<221> NAME/KEY: misc_feature
<222> LOCATION: (60)..(151)
```

```
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (60)..(153)
<223> OTHER INFORMATION: GI NO: 15028131
      NR DESCRIPTION: putative alpha-hydroxynitrile lyase
<220> FEATURE:
<221> NAME/KEY: misc_feature
<222> LOCATION: (60)..(151)
<223> OTHER INFORMATION: GI NO: 21554666
      NR DESCRIPTION: putative acetone-cyanohydrin lyase
<220> FEATURE:
<221> NAME/KEY: misc_feature
<222> LOCATION: (60)..(153)
<223> OTHER INFORMATION: GI NO: 16648679
      NR DESCRIPTION: AT5g10300/F18D22_70
<220> FEATURE:
<221> NAME/KEY: misc_feature
<222> LOCATION: (60)..(153)
<223> OTHER INFORMATION: GI NO: 14279437
      NR DESCRIPTION: ethylene-induced esterase
<220> FEATURE:
<221> NAME/KEY: misc_feature
<222> LOCATION: (60)..(138)
<223> OTHER INFORMATION: GI NO: 498747
      NR DESCRIPTION: Pir7b
<220> FEATURE:
<221> NAME/KEY: misc_feature
<222> LOCATION: (60)..(152)
<223> OTHER INFORMATION: GI NO: 28393451
      NR DESCRIPTION: putative acetone-cyanohydrin lyase
<220> FEATURE:
<221> NAME/KEY: misc_feature
<222> LOCATION: (12)..(12)
<223> OTHER INFORMATION: Xaa is any aa, unknown or other
<220> FEATURE:
<221> NAME/KEY: misc_feature
<222> LOCATION: (32)..(32)
<223> OTHER INFORMATION: Xaa is any aa, unknown or other
<220> FEATURE:
<221> NAME/KEY: misc_feature
<222> LOCATION: (96)..(96)
<223> OTHER INFORMATION: Xaa is any aa, unknown or other
<220> FEATURE:
<221> NAME/KEY: misc_feature
<222> LOCATION: (97)..(97)
<223> OTHER INFORMATION: Xaa is any aa, unknown or other
<220> FEATURE:
<221> NAME/KEY: misc_feature
<222> LOCATION: (99)..(99)
<223> OTHER INFORMATION: Xaa is any aa, unknown or other

<400> SEQUENCE: 59

Thr Pro Gln Leu Thr Thr Ser Thr Asp Arg Gly Xaa Thr Val Ala Lys
1               5                   10                  15

Pro His Val Cys Thr Ser Arg Trp Arg Leu Arg Arg Thr Lys Pro Xaa
            20                  25                  30

Ala Ser Thr Ser Phe Trp Cys Thr Ala His Ala Ser Ala Ala Gly Pro
        35                  40                  45

Gly Ser Arg Trp Pro Arg Gly Ser Gly Thr Pro Gly His Arg Val Ser
    50                  55                  60

Thr Pro Asp Leu Ala Ala Ser Gly Val Asp Pro Arg Pro Leu Arg Glu
65                  70                  75                  80

Val Pro Thr Phe Phe Asp Tyr Thr Lys Pro Leu Leu Asp Leu Leu Xaa
                85                  90                  95

Xaa Leu Xaa Pro Gly Glu Lys Val Val Leu Val Gly His Ser Leu Gly
            100                 105                 110

Gly Val Asn Ile Ala Leu Ala Cys Glu Leu Phe Pro Glu Lys Val Ala
        115                 120                 125

Ala Ala Val Phe Leu Ser Ala Phe Met Pro Asp His Arg Ser Ser Pro
```

Ala Tyr Val Leu Glu Lys Phe Val Glu Gly
145                 150

<210> SEQ ID NO 60
<211> LENGTH: 1088
<212> TYPE: DNA
<213> ORGANISM: Triticum aestivum
<220> FEATURE:
<221> NAME/KEY: misc_feature
<222> LOCATION: (1)..(1088)
<223> OTHER INFORMATION: Ceres Seq. ID no. 16446802

<400> SEQUENCE: 60

| | | | | |
|---|---|---|---|---|
| atcggagcca | cagctacagc | tcaagcacag | aaaaacagcc | acaaaacccc | acccatgcac | 60 |
| atggaggctt | gtgcgggcca | agctagcagc | gcgcacatcg | tcctggtgca | cggcgcatgc | 120 |
| ctcggcggct | ggtcctggtt | caaggtggcg | acgcggctca | ggtcggccgg | gcaccgcgtc | 180 |
| agcacgcctg | acctcgcggc | gtccggcgtc | gaccccaggc | cgctgcgcga | ggtgccgacg | 240 |
| ttccgcgact | acaccaagcc | gctgctggac | ctcctggagt | ccctcccgtc | cggcgagaag | 300 |
| gtggtgctcg | tcggccacag | cctcggcggc | gtgaacgtcg | ccctcgcctg | cgagctgttt | 360 |
| ccggagaaga | tcgccgctgc | ggtgttcgtc | gccgccttca | tgccggacca | caggtcgccg | 420 |
| ccgtcgtacg | tccttgaaaa | gttcgtggag | gggagaacgc | tggactggat | ggacacggag | 480 |
| tttaagcctc | aagatcctga | ggggaagctg | cctacttcca | tgctgttcgg | gccgctggtc | 540 |
| actcgtgcaa | agttcttcca | gttgtgttcg | ccggaggacc | tcacgctggg | acgatccctg | 600 |
| atgagggtca | actccatgtt | cgtggacgac | ctgaggctgc | agccgccgca | caccgaggcc | 660 |
| cgctacgggt | cggtgcgcaa | ggcgtacgtc | gtcttcaagg | acgaccacgc | catcgtcgag | 720 |
| cagttccagc | ggtggatggt | gcacaactac | cccgtggacg | aggtgatgga | aatcgatggc | 780 |
| gcggaccaca | tggcgttgct | ctcgacgccg | accgagctgg | cgcgctgcct | cgctgacatc | 840 |
| gccgtcaagt | atgctgcttg | acttcctcgc | aaaaaataaa | agaaaagtct | gctgcttgac | 900 |
| gatggtgtgg | cgcacgttgc | ttgctgatct | atacatctgt | ctaccttatg | gtttgtcccg | 960 |
| ttcgttaggt | ttcagagact | tctactgcac | tctatttcag | accgataatg | tttcaacatc | 1020 |
| gtatcgtggt | gcatgtaact | ttgctatttt | atatttgaag | ataaatgttg | gcaaaaaaaa | 1080 |
| aaaaaaaa | | | | | | 1088 |

<210> SEQ ID NO 61
<211> LENGTH: 286
<212> TYPE: PRT
<213> ORGANISM: Triticum aestivum
<220> FEATURE:
<221> NAME/KEY: misc_feature
<222> LOCATION: (1)..(286)
<223> OTHER INFORMATION: Ceres Seq. ID no. 16605607
<220> FEATURE:
<221> NAME/KEY: misc_feature
<222> LOCATION: (58)..(279)
<223> OTHER INFORMATION: PFAM Description: alpha/beta hydrolase fold
<220> FEATURE:
<221> NAME/KEY: misc_feature
<222> LOCATION: (26)..(285)
<223> OTHER INFORMATION: GI NO: 34908770
      NR DESCRIPTION: P0415A04.19
<220> FEATURE:
<221> NAME/KEY: misc_feature
<222> LOCATION: (25)..(285)
<223> OTHER INFORMATION: GI NO: 34915034
      NR DESCRIPTION: putative acetone-cyanohydrin lyase
<220> FEATURE:
<221> NAME/KEY: misc_feature

```
<222> LOCATION: (25)..(284)
<223> OTHER INFORMATION: GI NO: 34914020
       NR DESCRIPTION: OJ1014_G12.25
<220> FEATURE:
<221> NAME/KEY: misc_feature
<222> LOCATION: (32)..(284)
<223> OTHER INFORMATION: GI NO: 40549303
       NR DESCRIPTION: salicylic acid-binding protein 2
<220> FEATURE:
<221> NAME/KEY: misc_feature
<222> LOCATION: (21)..(285)
<223> OTHER INFORMATION: GI NO: 14279437
       NR DESCRIPTION: ethylene-induced esterase
<220> FEATURE:
<221> NAME/KEY: misc_feature
<222> LOCATION: (155)..(284)
<223> OTHER INFORMATION: GI NO: 34914024
       NR DESCRIPTION: OJ1014_G12.27
<220> FEATURE:
<221> NAME/KEY: misc_feature
<222> LOCATION: (29)..(149)
<223> OTHER INFORMATION: GI NO: 34914024
       NR DESCRIPTION: OJ1014_G12.27
<220> FEATURE:
<221> NAME/KEY: misc_feature
<222> LOCATION: (32)..(284)
<223> OTHER INFORMATION: GI NO: 27754457
       NR DESCRIPTION: putative acetone-cyanohydrin lyase
<220> FEATURE:
<221> NAME/KEY: misc_feature
<222> LOCATION: (32)..(284)
<223> OTHER INFORMATION: GI NO: 41814856
       NR DESCRIPTION: methylesterase
<220> FEATURE:
<221> NAME/KEY: misc_feature
<222> LOCATION: (34)..(281)
<223> OTHER INFORMATION: GI NO: 21595837
       NR DESCRIPTION: polyneuridine aldehyde esterase

<400> SEQUENCE: 61

Ile Gly Ala Thr Ala Thr Ala Gln Ala Gln Lys Asn Ser His Lys Thr
1               5                   10                  15

Pro Pro Met His Met Glu Ala Cys Ala Gly Gln Ala Ser Ser Ala His
            20                  25                  30

Ile Val Leu Val His Gly Ala Cys Leu Gly Gly Trp Ser Trp Phe Lys
        35                  40                  45

Val Ala Thr Arg Leu Arg Ser Ala Gly His Arg Val Ser Thr Pro Asp
    50                  55                  60

Leu Ala Ala Ser Gly Val Asp Pro Arg Pro Leu Arg Glu Val Pro Thr
65                  70                  75                  80

Phe Arg Asp Tyr Thr Lys Pro Leu Leu Asp Leu Leu Glu Ser Leu Pro
                85                  90                  95

Ser Gly Glu Lys Val Val Leu Val Gly His Ser Leu Gly Gly Val Asn
            100                 105                 110

Val Ala Leu Ala Cys Glu Leu Phe Pro Glu Lys Ile Ala Ala Ala Val
        115                 120                 125

Phe Val Ala Ala Phe Met Pro Asp His Arg Ser Pro Pro Ser Tyr Val
    130                 135                 140

Leu Glu Lys Phe Val Glu Gly Arg Thr Leu Asp Trp Met Asp Thr Glu
145                 150                 155                 160

Phe Lys Pro Gln Asp Pro Glu Gly Lys Leu Pro Thr Ser Met Leu Phe
                165                 170                 175

Gly Pro Leu Val Thr Arg Ala Lys Phe Phe Gln Leu Cys Ser Pro Glu
            180                 185                 190

Asp Leu Thr Leu Gly Arg Ser Leu Met Arg Val Asn Ser Met Phe Val
        195                 200                 205
```

```
Asp Asp Leu Arg Leu Gln Pro Pro His Thr Glu Ala Arg Tyr Gly Ser
    210                 215                 220

Val Arg Lys Ala Tyr Val Val Phe Lys Asp Asp His Ala Ile Val Glu
225                 230                 235                 240

Gln Phe Gln Arg Trp Met Val His Asn Tyr Pro Val Asp Glu Val Met
                245                 250                 255

Glu Ile Asp Gly Ala Asp His Met Ala Leu Leu Ser Thr Pro Thr Glu
                260                 265                 270

Leu Ala Arg Cys Leu Ala Asp Ile Ala Val Lys Tyr Ala Ala
                275                 280                 285

<210> SEQ ID NO 62
<211> LENGTH: 268
<212> TYPE: PRT
<213> ORGANISM: Triticum aestivum
<220> FEATURE:
<221> NAME/KEY: misc_feature
<222> LOCATION: (1)..(268)
<223> OTHER INFORMATION: Ceres Seq. ID no. 16605608
<220> FEATURE:
<221> NAME/KEY: misc_feature
<222> LOCATION: (40)..(261)
<223> OTHER INFORMATION: PFAM Description: alpha/beta hydrolase fold
<220> FEATURE:
<221> NAME/KEY: misc_feature
<222> LOCATION: (8)..(267)
<223> OTHER INFORMATION: GI NO: 34908770
      NR DESCRIPTION: P0415A04.19
<220> FEATURE:
<221> NAME/KEY: misc_feature
<222> LOCATION: (7)..(267)
<223> OTHER INFORMATION: GI NO: 34915034
      NR DESCRIPTION: putative acetone-cyanohydrin lyase
<220> FEATURE:
<221> NAME/KEY: misc_feature
<222> LOCATION: (7)..(266)
<223> OTHER INFORMATION: GI NO: 34914020
      NR DESCRIPTION: OJ1014_G12.25
<220> FEATURE:
<221> NAME/KEY: misc_feature
<222> LOCATION: (14)..(266)
<223> OTHER INFORMATION: GI NO: 40549303
      NR DESCRIPTION: salicylic acid-binding protein 2
<220> FEATURE:
<221> NAME/KEY: misc_feature
<222> LOCATION: (3)..(267)
<223> OTHER INFORMATION: GI NO: 14279437
      NR DESCRIPTION: ethylene-induced esterase
<220> FEATURE:
<221> NAME/KEY: misc_feature
<222> LOCATION: (137)..(266)
<223> OTHER INFORMATION: GI NO: 34914024
      NR DESCRIPTION: OJ1014_G12.27
<220> FEATURE:
<221> NAME/KEY: misc_feature
<222> LOCATION: (11)..(131)
<223> OTHER INFORMATION: GI NO: 34914024
      NR DESCRIPTION: OJ1014_G12.27
<220> FEATURE:
<221> NAME/KEY: misc_feature
<222> LOCATION: (14)..(266)
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (14)..(266)
<223> OTHER INFORMATION: GI NO: 41814856
      NR DESCRIPTION: methylesterase
<220> FEATURE:
<221> NAME/KEY: misc_feature
<222> LOCATION: (16)..(263)
<223> OTHER INFORMATION: GI NO: 21595837
      NR DESCRIPTION: polyneuridine aldehyde esterase

<400> SEQUENCE: 62
```

```
Met His Met Glu Ala Cys Ala Gly Gln Ala Ser Ser Ala His Ile Val
1               5                   10                  15

Leu Val His Gly Ala Cys Leu Gly Gly Trp Ser Trp Phe Lys Val Ala
            20                  25                  30

Thr Arg Leu Arg Ser Ala Gly His Arg Val Ser Thr Pro Asp Leu Ala
        35                  40                  45

Ala Ser Gly Val Asp Pro Arg Pro Leu Arg Glu Val Pro Thr Phe Arg
    50                  55                  60

Asp Tyr Thr Lys Pro Leu Leu Asp Leu Leu Ser Leu Pro Ser Gly
65                  70                  75                  80

Glu Lys Val Val Leu Val Gly His Ser Leu Gly Gly Val Asn Val Ala
                85                  90                  95

Leu Ala Cys Glu Leu Phe Pro Glu Lys Ile Ala Ala Val Phe Val
                100                 105                 110

Ala Ala Phe Met Pro Asp His Arg Ser Pro Ser Tyr Val Leu Glu
            115                 120                 125

Lys Phe Val Glu Gly Arg Thr Leu Asp Trp Met Asp Thr Glu Phe Lys
130                 135                 140

Pro Gln Asp Pro Glu Gly Lys Leu Pro Thr Ser Met Leu Phe Gly Pro
145                 150                 155                 160

Leu Val Thr Arg Ala Lys Phe Phe Gln Leu Cys Ser Pro Glu Asp Leu
                165                 170                 175

Thr Leu Gly Arg Ser Leu Met Arg Val Asn Ser Met Phe Val Asp Asp
            180                 185                 190

Leu Arg Leu Gln Pro Pro His Thr Glu Ala Arg Tyr Gly Ser Val Arg
        195                 200                 205

Lys Ala Tyr Val Val Phe Lys Asp Asp His Ala Ile Val Glu Gln Phe
210                 215                 220

Gln Arg Trp Met Val His Asn Tyr Pro Val Asp Glu Val Met Glu Ile
225                 230                 235                 240

Asp Gly Ala Asp His Met Ala Leu Leu Ser Thr Pro Thr Glu Leu Ala
                245                 250                 255

Arg Cys Leu Ala Asp Ile Ala Val Lys Tyr Ala Ala
            260                 265

<210> SEQ ID NO 63
<211> LENGTH: 266
<212> TYPE: PRT
<213> ORGANISM: Triticum aestivum
<220> FEATURE:
<221> NAME/KEY: misc_feature
<222> LOCATION: (1)..(266)
<223> OTHER INFORMATION: Ceres Seq. ID no. 16613014
<220> FEATURE:
<221> NAME/KEY: misc_feature
<222> LOCATION: (38)..(259)
<223> OTHER INFORMATION: PFAM Description: alpha/beta hydrolase fold
<220> FEATURE:
<221> NAME/KEY: misc_feature
<222> LOCATION: (6)..(265)
<223> OTHER INFORMATION: GI NO: 34908770
      NR DESCRIPTION: P0415A04.19
<220> FEATURE:
<221> NAME/KEY: misc_feature
<222> LOCATION: (5)..(265)
<223> OTHER INFORMATION: GI NO: 34915034
      NR DESCRIPTION: putative acetone-cyanohydrin lyase
<220> FEATURE:
<221> NAME/KEY: misc_feature
<222> LOCATION: (5)..(264)
<223> OTHER INFORMATION: GI NO: 34914020
      NR DESCRIPTION: OJ1014_G12.25
```

```
<220> FEATURE:
<221> NAME/KEY: misc_feature
<222> LOCATION: (12)..(264)
<223> OTHER INFORMATION: GI NO: 40549303
      NR DESCRIPTION: salicylic acid-binding protein 2
<220> FEATURE:
<221> NAME/KEY: misc_feature
<222> LOCATION: (1)..(265)
<223> OTHER INFORMATION: GI NO: 14279437
      NR DESCRIPTION: ethylene-induced esterase
<220> FEATURE:
<221> NAME/KEY: misc_feature
<222> LOCATION: (135)..(264)
<223> OTHER INFORMATION: GI NO: 34914024
      NR DESCRIPTION: OJ1014_G12.27
<220> FEATURE:
<221> NAME/KEY: misc_feature
<222> LOCATION: (9)..(129)
<223> OTHER INFORMATION: GI NO: 34914024
      NR DESCRIPTION: OJ1014_G12.27
<220> FEATURE:
<221> NAME/KEY: misc_feature
<222> LOCATION: (12)..(264)
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (12)..(264)
<223> OTHER INFORMATION: GI NO: 41814856
      NR DESCRIPTION: methylesterase
<220> FEATURE:
<221> NAME/KEY: misc_feature
<222> LOCATION: (14)..(261)
<223> OTHER INFORMATION: GI NO: 21595837
      NR DESCRIPTION: polyneuridine aldehyde esterase

<400> SEQUENCE: 63

Met Glu Ala Cys Ala Gly Gln Ala Ser Ser Ala His Ile Val Leu Val
1               5                   10                  15

His Gly Ala Cys Leu Gly Gly Trp Ser Trp Phe Lys Val Ala Thr Arg
            20                  25                  30

Leu Arg Ser Ala Gly His Arg Val Ser Thr Pro Asp Leu Ala Ala Ser
        35                  40                  45

Gly Val Asp Pro Arg Pro Leu Arg Glu Val Pro Thr Phe Arg Asp Tyr
    50                  55                  60

Thr Lys Pro Leu Leu Asp Leu Leu Glu Ser Leu Pro Ser Gly Glu Lys
65                  70                  75                  80

Val Val Leu Val Gly His Ser Leu Gly Gly Val Asn Val Ala Leu Ala
                85                  90                  95

Cys Glu Leu Phe Pro Glu Lys Ile Ala Ala Ala Val Phe Val Ala Ala
            100                 105                 110

Phe Met Pro Asp His Arg Ser Pro Ser Tyr Val Leu Glu Lys Phe
        115                 120                 125

Val Glu Gly Arg Thr Leu Asp Trp Met Asp Thr Glu Phe Lys Pro Gln
    130                 135                 140

Asp Pro Glu Gly Lys Leu Pro Thr Ser Met Leu Phe Gly Pro Leu Val
145                 150                 155                 160

Thr Arg Ala Lys Phe Phe Gln Leu Cys Ser Pro Glu Asp Leu Thr Leu
                165                 170                 175

Gly Arg Ser Leu Met Arg Val Asn Ser Met Phe Val Asp Asp Leu Arg
            180                 185                 190

Leu Gln Pro Pro His Thr Glu Ala Arg Tyr Gly Ser Val Arg Lys Ala
        195                 200                 205

Tyr Val Val Phe Lys Asp Asp His Ala Ile Val Glu Gln Phe Gln Arg
    210                 215                 220
```

```
Trp Met Val His Asn Tyr Pro Val Asp Glu Val Met Glu Ile Asp Gly
225                 230                 235                 240

Ala Asp His Met Ala Leu Leu Ser Thr Pro Thr Glu Leu Ala Arg Cys
                245                 250                 255

Leu Ala Asp Ile Ala Val Lys Tyr Ala Ala
            260                 265

<210> SEQ ID NO 64
<211> LENGTH: 469
<212> TYPE: DNA
<213> ORGANISM: Triticum aestivum
<220> FEATURE:
<221> NAME/KEY: misc_feature
<222> LOCATION: (1)..(469)
<223> OTHER INFORMATION: Ceres Seq. ID no. 13545725

<400> SEQUENCE: 64
gacaaacata tctgcaagcc gctcgccgct caccggcggc ggcatagcca gtcgaactct      60
tgcctgaggt gaaatcggat ggaggggagc agcagcggcg agcacttcat gctcgtccac     120
ggcctcggcc acggcgcgtg gtgctggtac aagctggtgc cgatgctccg cgccgcgggg     180
caccgggtca ccgcgctcga catggccgcg tccggcgcgc acccggcgcg catggacgag     240
gtgccgtcct tcgaggacta ctcgcggccg ctgctcgacg ccgtggccgc ggcaccggcc     300
ggcgagaggc tggtcctggt cgggcacagc ctcggcgggc tcaacatcgc gctcgccatg     360
gagaggttcc gcgcaaggt cgccgcggcc gtgttcctgg ccgcgtgcat gccgtgcgtc     420
ggcaggcaca tgggcgtcac yacggaggag atcatgagac ggatcaagc                469

<210> SEQ ID NO 65
<211> LENGTH: 130
<212> TYPE: PRT
<213> ORGANISM: Triticum aestivum
<220> FEATURE:
<221> NAME/KEY: misc_feature
<222> LOCATION: (1)..(130)
<223> OTHER INFORMATION: Ceres Seq. ID no. 13545726
<220> FEATURE:
<221> NAME/KEY: misc_feature
<222> LOCATION: (35)..(128)
<223> OTHER INFORMATION: PFAM Description: alpha/beta hydrolase fold
<220> FEATURE:
<221> NAME/KEY: misc_feature
<222> LOCATION: (7)..(129)
<223> OTHER INFORMATION: GI NO: 34907178
     NR DESCRIPTION: pir7a protein (Pseudomonas inducible protein)
<220> FEATURE:
<221> NAME/KEY: misc_feature
<222> LOCATION: (1)..(128)
<223> OTHER INFORMATION: GI NO: 34907176
     NR DESCRIPTION: pir7b protein (Pseudomonas inducible protein)
<220> FEATURE:
<221> NAME/KEY: misc_feature
<222> LOCATION: (6)..(128)
<223> OTHER INFORMATION: GI NO: 498747
     NR DESCRIPTION: Pir7b
<220> FEATURE:
<221> NAME/KEY: misc_feature
<222> LOCATION: (1)..(118)
<223> OTHER INFORMATION: GI NO: 34907174
     NR DESCRIPTION: putative pir7b (Pseudomonas inducible protein)
<220> FEATURE:
<221> NAME/KEY: misc_feature
<222> LOCATION: (4)..(112)
<223> OTHER INFORMATION: GI NO: 34915034
     NR DESCRIPTION: putative acetone-cyanohydrin lyase
<220> FEATURE:
<221> NAME/KEY: misc_feature
<222> LOCATION: (4)..(112)
<223> OTHER INFORMATION: GI NO: 34914020
     NR DESCRIPTION: OJ1014_G12.25
```

```
<220> FEATURE:
<221> NAME/KEY: misc_feature
<222> LOCATION: (9)..(112)
<223> OTHER INFORMATION: GI NO: 41814856
      NR DESCRIPTION: methylesterase
<220> FEATURE:
<221> NAME/KEY: misc_feature
<222> LOCATION: (8)..(112)
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (8)..(112)
<223> OTHER INFORMATION: GI NO: 7488034
      NR DESCRIPTION: probable (S)-acetone-cyanohydrin lyase
<220> FEATURE:
<221> NAME/KEY: misc_feature
<222> LOCATION: (7)..(112)
<223> OTHER INFORMATION: GI NO: 40549303
      NR DESCRIPTION: salicylic acid-binding protein 2
<220> FEATURE:
<221> NAME/KEY: misc_feature
<222> LOCATION: (121)..(121)
<223> OTHER INFORMATION: Xaa is any aa, unknown or other

<400> SEQUENCE: 65

Met Glu Gly Ser Ser Ser Gly Glu His Phe Met Leu Val His Gly Leu
1               5                   10                  15

Gly His Gly Ala Trp Cys Trp Tyr Lys Leu Val Pro Met Leu Arg Ala
            20                  25                  30

Ala Gly His Arg Val Thr Ala Leu Asp Met Ala Ala Ser Gly Ala His
        35                  40                  45

Pro Ala Arg Met Asp Glu Val Pro Ser Phe Glu Asp Tyr Ser Arg Pro
    50                  55                  60

Leu Leu Asp Ala Val Ala Ala Pro Ala Gly Glu Arg Leu Val Leu
65                  70                  75                  80

Val Gly His Ser Leu Gly Gly Leu Asn Ile Ala Leu Ala Met Glu Arg
                85                  90                  95

Phe Pro Arg Lys Val Ala Ala Ala Val Phe Leu Ala Ala Cys Met Pro
            100                 105                 110

Cys Val Gly Arg His Met Gly Val Xaa Thr Glu Glu Ile Met Arg Arg
        115                 120                 125

Ile Lys
    130

<210> SEQ ID NO 66
<211> LENGTH: 120
<212> TYPE: PRT
<213> ORGANISM: Triticum aestivum
<220> FEATURE:
<221> NAME/KEY: misc_feature
<222> LOCATION: (1)..(120)
<223> OTHER INFORMATION: Ceres Seq. ID no. 13545727
<220> FEATURE:
<221> NAME/KEY: misc_feature
<222> LOCATION: (25)..(118)
<223> OTHER INFORMATION: PFAM Description: alpha/beta hydrolase fold
<220> FEATURE:
<221> NAME/KEY: misc_feature
<222> LOCATION: (1)..(119)
<223> OTHER INFORMATION: GI NO: 34907178
      NR DESCRIPTION: pir7a protein (Pseudomonas inducible protein)
<220> FEATURE:
<221> NAME/KEY: misc_feature
<222> LOCATION: (1)..(118)
<223> OTHER INFORMATION: GI NO: 34907176
      NR DESCRIPTION: pir7b protein (Pseudomonas inducible protein)
<220> FEATURE:
<221> NAME/KEY: misc_feature
<222> LOCATION: (1)..(118)
```

```
<223> OTHER INFORMATION: GI NO: 498747
      NR DESCRIPTION: Pir7b
<220> FEATURE:
<221> NAME/KEY: misc_feature
<222> LOCATION: (1)..(108)
<223> OTHER INFORMATION: GI NO: 34907174
      NR DESCRIPTION: putative pir7b (Pseudomonas inducible protein)
<220> FEATURE:
<221> NAME/KEY: misc_feature
<222> LOCATION: (1)..(102)
<223> OTHER INFORMATION: GI NO: 34915034
      NR DESCRIPTION: putative acetone-cyanohydrin lyase
<220> FEATURE:
<221> NAME/KEY: misc_feature
<222> LOCATION: (1)..(102)
<223> OTHER INFORMATION: GI NO: 34914020
      NR DESCRIPTION: OJ1014_G12.25
<220> FEATURE:
<221> NAME/KEY: misc_feature
<222> LOCATION: (1)..(102)
<223> OTHER INFORMATION: GI NO: 41814856
      NR DESCRIPTION: methylesterase
<220> FEATURE:
<221> NAME/KEY: misc_feature
<222> LOCATION: (1)..(102)
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (1)..(102)
<223> OTHER INFORMATION: GI NO: 7488034
      NR DESCRIPTION: probable (S)-acetone-cyanohydrin lyase
<220> FEATURE:
<221> NAME/KEY: misc_feature
<222> LOCATION: (1)..(102)
<223> OTHER INFORMATION: GI NO: 40549303
      NR DESCRIPTION: salicylic acid-binding protein 2
<220> FEATURE:
<221> NAME/KEY: misc_feature
<222> LOCATION: (111)..(111)
<223> OTHER INFORMATION: Xaa is any aa, unknown or other

<400> SEQUENCE: 66

Met Leu Val His Gly Leu Gly His Gly Ala Trp Cys Trp Tyr Lys Leu
1               5                   10                  15

Val Pro Met Leu Arg Ala Ala Gly His Arg Val Thr Ala Leu Asp Met
            20                  25                  30

Ala Ala Ser Gly Ala His Pro Ala Arg Met Asp Glu Val Pro Ser Phe
        35                  40                  45

Glu Asp Tyr Ser Arg Pro Leu Leu Asp Ala Val Ala Ala Pro Ala
    50                  55                  60

Gly Glu Arg Leu Val Leu Val Gly His Ser Leu Gly Gly Leu Asn Ile
65                  70                  75                  80

Ala Leu Ala Met Glu Arg Phe Pro Arg Lys Val Ala Ala Val Phe
                85                  90                  95

Leu Ala Ala Cys Met Pro Cys Val Gly Arg His Met Gly Val Xaa Thr
            100                 105                 110

Glu Glu Ile Met Arg Arg Ile Lys
        115                 120

<210> SEQ ID NO 67
<211> LENGTH: 102
<212> TYPE: PRT
<213> ORGANISM: Triticum aestivum
<220> FEATURE:
<221> NAME/KEY: misc_feature
<222> LOCATION: (1)..(102)
<223> OTHER INFORMATION: Ceres Seq. ID no. 13545728
<220> FEATURE:
<221> NAME/KEY: misc_feature
<222> LOCATION: (7)..(100)
```

-continued

```
<223> OTHER INFORMATION: PFAM Description: alpha/beta hydrolase fold
<220> FEATURE:
<221> NAME/KEY: misc_feature
<222> LOCATION: (1)..(101)
<223> OTHER INFORMATION: GI NO: 34907178
      NR DESCRIPTION: pir7a protein (Pseudomonas inducible protein)
<220> FEATURE:
<221> NAME/KEY: misc_feature
<222> LOCATION: (1)..(100)
<223> OTHER INFORMATION: GI NO: 34907176
      NR DESCRIPTION: pir7b protein (Pseudomonas inducible protein)
<220> FEATURE:
<221> NAME/KEY: misc_feature
<222> LOCATION: (1)..(100)
<223> OTHER INFORMATION: GI NO: 498747
      NR DESCRIPTION: Pir7b
<220> FEATURE:
<221> NAME/KEY: misc_feature
<222> LOCATION: (1)..(90)
<223> OTHER INFORMATION: GI NO: 34907174
      NR DESCRIPTION: putative pir7b (Pseudomonas inducible protein)
<220> FEATURE:
<221> NAME/KEY: misc_feature
<222> LOCATION: (1)..(84)
<223> OTHER INFORMATION: GI NO: 34915034
      NR DESCRIPTION: putative acetone-cyanohydrin lyase
<220> FEATURE:
<221> NAME/KEY: misc_feature
<222> LOCATION: (1)..(84)
<223> OTHER INFORMATION: GI NO: 34914020
      NR DESCRIPTION: OJ1014_G12.25
<220> FEATURE:
<221> NAME/KEY: misc_feature
<222> LOCATION: (1)..(84)
<223> OTHER INFORMATION: GI NO: 41814856
      NR DESCRIPTION: methylesterase
<220> FEATURE:
<221> NAME/KEY: misc_feature
<222> LOCATION: (1)..(84)
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (1)..(84)
<223> OTHER INFORMATION: GI NO: 7488034
      NR DESCRIPTION: probable (S)-acetone-cyanohydrin lyase
<220> FEATURE:
<221> NAME/KEY: misc_feature
<222> LOCATION: (1)..(84)
<223> OTHER INFORMATION: GI NO: 40549303
      NR DESCRIPTION: salicylic acid-binding protein 2
<220> FEATURE:
<221> NAME/KEY: misc_feature
<222> LOCATION: (93)..(93)
<223> OTHER INFORMATION: Xaa is any aa, unknown or other

<400> SEQUENCE: 67

Met Leu Arg Ala Ala Gly His Arg Val Thr Ala Leu Asp Met Ala Ala
1               5                   10                  15

Ser Gly Ala His Pro Ala Arg Met Asp Glu Val Pro Ser Phe Glu Asp
                20                  25                  30

Tyr Ser Arg Pro Leu Leu Asp Ala Val Ala Ala Pro Ala Gly Glu
        35                  40                  45

Arg Leu Val Leu Val Gly His Ser Leu Gly Gly Leu Asn Ile Ala Leu
    50                  55                  60

Ala Met Glu Arg Phe Pro Arg Lys Val Ala Ala Val Phe Leu Ala
65                  70                  75                  80

Ala Cys Met Pro Cys Val Gly Arg His Met Gly Val Xaa Thr Glu Glu
                85                  90                  95

Ile Met Arg Arg Ile Lys
            100
```

```
<210> SEQ ID NO 68
<211> LENGTH: 455
<212> TYPE: DNA
<213> ORGANISM: Triticum aestivum
<220> FEATURE:
<221> NAME/KEY: misc_feature
<222> LOCATION: (1)..(455)
<223> OTHER INFORMATION: Ceres Seq. ID no. 4288946

<400> SEQUENCE: 68
atccaacaca aaacaaaaca aattttacac aggaaatgaa gagcactcag agcaacagca      60
gcaacagcgt gaggaaccat ttcatcctgg tgcacggcct ctgccacggc gcgtggtgct     120
ggtacaaggt ggtcgcggcg cttgaggcag cggggcaccg cgtcacggca gtcgacctcg     180
ccgcttccgg cgcccacccg gcgcgcgtcg acgaggtgca ctcgttcgag gagtactcgc     240
ggccgctgct cgacgtgctg gccgcggcgc cggagggtga cggcgaragg ctgattctgg     300
tcgggcacag ccatggcggg ctcagcttgg cactagccat ggagaggttc tccggcaagg     360
tcgccgccgc cgtgttcgca gccgccggga tgccgtgtgt tggcaagcac atgggcatca     420
ccaccgagga gttcatgcga agaaaacatc cgaag                                455

<210> SEQ ID NO 69
<211> LENGTH: 151
<212> TYPE: PRT
<213> ORGANISM: Triticum aestivum
<220> FEATURE:
<221> NAME/KEY: misc_feature
<222> LOCATION: (1)..(151)
<223> OTHER INFORMATION: Ceres Seq. ID no. 4288947
<220> FEATURE:
<221> NAME/KEY: misc_feature
<222> LOCATION: (52)..(150)
<223> OTHER INFORMATION: PFAM Description: alpha/beta hydrolase fold
<220> FEATURE:
<221> NAME/KEY: misc_feature
<222> LOCATION: (20)..(150)
<223> OTHER INFORMATION: GI NO: 34907176
     NR DESCRIPTION: pir7b protein (Pseudomonas inducible protein)
<220> FEATURE:
<221> NAME/KEY: misc_feature
<222> LOCATION: (24)..(150)
<223> OTHER INFORMATION: GI NO: 498747
     NR DESCRIPTION: Pir7b
<220> FEATURE:
<221> NAME/KEY: misc_feature
<222> LOCATION: (26)..(150)
<223> OTHER INFORMATION: GI NO: 34907178
     NR DESCRIPTION: pir7a protein (Pseudomonas inducible protein)
<220> FEATURE:
<221> NAME/KEY: misc_feature
<222> LOCATION: (20)..(137)
<223> OTHER INFORMATION: GI NO: 34907174
     NR DESCRIPTION: putative pir7b (Pseudomonas inducible protein)
<220> FEATURE:
<221> NAME/KEY: misc_feature
<222> LOCATION: (26)..(147)
<223> OTHER INFORMATION: GI NO: 14279437
     NR DESCRIPTION: ethylene-induced esterase
<220> FEATURE:
<221> NAME/KEY: misc_feature
<222> LOCATION: (19)..(143)
<223> OTHER INFORMATION: GI NO: 21554666
     NR DESCRIPTION: putative acetone-cyanohydrin lyase
<220> FEATURE:
<221> NAME/KEY: misc_feature
<222> LOCATION: (19)..(131)
<223> OTHER INFORMATION: GI NO: 7488034
     NR DESCRIPTION: probable (S)-acetone-cyanohydrin lyase
<220> FEATURE:
<221> NAME/KEY: misc_feature
<222> LOCATION: (19)..(131)
<223> OTHER INFORMATION: GI NO: 27754457
     NR DESCRIPTION: putative acetone-cyanohydrin lyase
```

```
<220> FEATURE:
<221> NAME/KEY: misc_feature
<222> LOCATION: (24)..(131)
<223> OTHER INFORMATION: GI NO: 41814856
      NR DESCRIPTION: methylesterase
<220> FEATURE:
<221> NAME/KEY: misc_feature
<222> LOCATION: (12)..(131)
<223> OTHER INFORMATION: GI NO: 34915034
      NR DESCRIPTION: putative acetone-cyanohydrin lyase
<220> FEATURE:
<221> NAME/KEY: misc_feature
<222> LOCATION: (95)..(95)
<223> OTHER INFORMATION: Xaa is any aa, unknown or other

<400> SEQUENCE: 69

Pro Thr Gln Asn Lys Thr Asn Phe Thr Gln Glu Met Lys Ser Thr Gln
1               5                   10                  15

Ser Asn Ser Ser Asn Ser Val Arg Asn His Phe Ile Leu Val His Gly
            20                  25                  30

Leu Cys His Gly Ala Trp Cys Trp Tyr Lys Val Val Ala Ala Leu Glu
        35                  40                  45

Ala Ala Gly His Arg Val Thr Ala Val Asp Leu Ala Ala Ser Gly Ala
    50                  55                  60

His Pro Ala Arg Val Asp Glu Val His Ser Phe Glu Glu Tyr Ser Arg
65                  70                  75                  80

Pro Leu Leu Asp Val Leu Ala Ala Pro Glu Gly Asp Gly Xaa Arg
                85                  90                  95

Leu Ile Leu Val Gly His Ser His Gly Gly Leu Ser Leu Ala Leu Ala
            100                 105                 110

Met Glu Arg Phe Ser Gly Lys Val Ala Ala Val Phe Ala Ala Ala
        115                 120                 125

Gly Met Pro Cys Val Gly Lys His Met Gly Ile Thr Thr Glu Glu Phe
    130                 135                 140

Met Arg Arg Lys His Pro Lys
145                 150

<210> SEQ ID NO 70
<211> LENGTH: 140
<212> TYPE: PRT
<213> ORGANISM: Triticum aestivum
<220> FEATURE:
<221> NAME/KEY: misc_feature
<222> LOCATION: (1)..(140)
<223> OTHER INFORMATION: Ceres Seq. ID no. 4288948
<220> FEATURE:
<221> NAME/KEY: misc_feature
<222> LOCATION: (41)..(139)
<223> OTHER INFORMATION: PFAM Description: alpha/beta hydrolase fold
<220> FEATURE:
<221> NAME/KEY: misc_feature
<222> LOCATION: (9)..(139)
<223> OTHER INFORMATION: GI NO: 34907176
      NR DESCRIPTION: pir7b protein (Pseudomonas inducible protein)
<220> FEATURE:
<221> NAME/KEY: misc_feature
<222> LOCATION: (13)..(139)
<223> OTHER INFORMATION: GI NO: 498747
      NR DESCRIPTION: Pir7b
<220> FEATURE:
<221> NAME/KEY: misc_feature
<222> LOCATION: (15)..(139)
<223> OTHER INFORMATION: GI NO: 34907178
      NR DESCRIPTION: pir7a protein (Pseudomonas inducible protein)
<220> FEATURE:
<221> NAME/KEY: misc_feature
<222> LOCATION: (9)..(126)
<223> OTHER INFORMATION: GI NO: 34907174
      NR DESCRIPTION: putative pir7b (Pseudomonas inducible protein)
```

```
<220> FEATURE:
<221> NAME/KEY: misc_feature
<222> LOCATION: (15)..(136)
<223> OTHER INFORMATION: GI NO: 14279437
      NR DESCRIPTION: ethylene-induced esterase
<220> FEATURE:
<221> NAME/KEY: misc_feature
<222> LOCATION: (8)..(132)
<223> OTHER INFORMATION: GI NO: 21554666
      NR DESCRIPTION: putative acetone-cyanohydrin lyase
<220> FEATURE:
<221> NAME/KEY: misc_feature
<222> LOCATION: (8)..(120)
<223> OTHER INFORMATION: GI NO: 7488034
      NR DESCRIPTION: probable (S)-acetone-cyanohydrin lyase
<220> FEATURE:
<221> NAME/KEY: misc_feature
<222> LOCATION: (8)..(120)
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (13)..(120)
<223> OTHER INFORMATION: GI NO: 41814856
      NR DESCRIPTION: methylesterase
<220> FEATURE:
<221> NAME/KEY: misc_feature
<222> LOCATION: (1)..(120)
<223> OTHER INFORMATION: GI NO: 34915034
      NR DESCRIPTION: putative acetone-cyanohydrin lyase
<220> FEATURE:
<221> NAME/KEY: misc_feature
<222> LOCATION: (84)..(84)
<223> OTHER INFORMATION: Xaa is any aa, unknown or other

<400> SEQUENCE: 70

Met Lys Ser Thr Gln Ser Asn Ser Asn Ser Val Arg Asn His Phe
1               5                   10                  15

Ile Leu Val His Gly Leu Cys His Gly Ala Trp Cys Trp Tyr Lys Val
            20                  25                  30

Val Ala Ala Leu Glu Ala Ala Gly His Arg Val Thr Ala Val Asp Leu
        35                  40                  45

Ala Ala Ser Gly Ala His Pro Ala Arg Val Asp Glu Val His Ser Phe
    50                  55                  60

Glu Glu Tyr Ser Arg Pro Leu Leu Asp Val Leu Ala Ala Ala Pro Glu
65                  70                  75                  80

Gly Asp Gly Xaa Arg Leu Ile Leu Val Gly His Ser His Gly Gly Leu
                85                  90                  95

Ser Leu Ala Leu Ala Met Glu Arg Phe Ser Gly Lys Val Ala Ala Ala
            100                 105                 110

Val Phe Ala Ala Ala Gly Met Pro Cys Val Gly Lys His Met Gly Ile
        115                 120                 125

Thr Thr Glu Glu Phe Met Arg Arg Lys His Pro Lys
    130                 135                 140

<210> SEQ ID NO 71
<211> LENGTH: 1044
<212> TYPE: DNA
<213> ORGANISM: Triticum aestivum
<220> FEATURE:
<221> NAME/KEY: misc_feature
<222> LOCATION: (1)..(1044)
<223> OTHER INFORMATION: Ceres Seq. ID no. 16602710

<400> SEQUENCE: 71
ctgctttcgc tttactgaa aacttattgc catgtgcgcc catgctggcg aggtaccctc      60
ggcaaagata tctgcaagag caggagccgc tcgccgccgg tagcatagcc agtcgatctc    120
```

```
ttgccggagg tgaaatccga tggaggggag cagcagcggc aagcacttca tcctcatcca      180
cggcctctgc cacggcgcgt ggtgctggta caagctggtg ccgatgctcc gcgccgcggg      240
gcaccgcgtc accgcgctcg acatggccgc gtccggcgcg cacccggcgc gcatggacga      300
ggtgccgtcc ttcgaggact actcttggcc gctgctcgac gcggtggccg cggcaccggc      360
gggcgagagg ctagtcctgg tcgggcacag cctcgggggg ctcaacatcg cgctcgccat      420
ggagaggttc ccgcgcaagg tcgccgcggc cgtgttcctg gccgcgtgca tgccgtgcgt      480
cggcaggcac atgggcgcca ccacggagga gatcatgaga cggatcaagc cggatttctt      540
catggacatg aagaggatgg ttctgaacac gagccaggc cctcgacctg cactcgtgtt       600
tggtccaaaa atattggcag caaagctgta cgatcgaagc tcaggtgagg atcagacgct      660
ggctacgatg ctggtgagac cgggctgcca gttcttggat gaccctacca tgaaggacga      720
ggctctgctc accgaagcca agtacgggtc ggtgaagaag gtgtacgtgg tggccatggc      780
cgacgcatca aactccgagg agatgcagcg ttggatggtc gacatgagcc ccggcacgga      840
ggccgaggag atcgccggag cggatcacat ggccatgtgc tccaaaccca gggagctctg      900
tgatgtcctg ctccggatag ccgacaagta tgaatgaatt gattgtccac acagttagac      960
ttgtactccg taatatcttc ccatgaattt ctcgttcgct gagagttaag tttgttgtta     1020
cctttttcaa aaaaaaaaaa aaaa                                            1044

<210> SEQ ID NO 72
<211> LENGTH: 265
<212> TYPE: PRT
<213> ORGANISM: Triticum aestivum
<220> FEATURE:
<221> NAME/KEY: misc_feature
<222> LOCATION: (1)..(265)
<223> OTHER INFORMATION: Ceres Seq. ID no. 16606373
<220> FEATURE:
<221> NAME/KEY: misc_feature
<222> LOCATION: (35)..(259)
<223> OTHER INFORMATION: PFAM Description: alpha/beta hydrolase fold
<220> FEATURE:
<221> NAME/KEY: misc_feature
<222> LOCATION: (7)..(265)
<223> OTHER INFORMATION: GI NO: 34907178
    NR DESCRIPTION: pir7a protein (Pseudomonas inducible protein)
<220> FEATURE:
<221> NAME/KEY: misc_feature
<222> LOCATION: (1)..(265)
<223> OTHER INFORMATION: GI NO: 34907176
    NR DESCRIPTION: pir7b protein (Pseudomonas inducible protein)
<220> FEATURE:
<221> NAME/KEY: misc_feature
<222> LOCATION: (6)..(265)
<223> OTHER INFORMATION: GI NO: 498747
    NR DESCRIPTION: Pir7b
<220> FEATURE:
<221> NAME/KEY: misc_feature
<222> LOCATION: (1)..(118)
<223> OTHER INFORMATION: GI NO: 34907174
    NR DESCRIPTION: putative pir7b (Pseudomonas inducible protein)
<220> FEATURE:
<221> NAME/KEY: misc_feature
<222> LOCATION: (170)..(265)
<223> OTHER INFORMATION: GI NO: 34907174
    NR DESCRIPTION: putative pir7b (Pseudomonas inducible protein)
<220> FEATURE:
<221> NAME/KEY: misc_feature
<222> LOCATION: (7)..(264)
<223> OTHER INFORMATION: GI NO: 40549303
    NR DESCRIPTION: salicylic acid-binding protein 2
<220> FEATURE:
<221> NAME/KEY: misc_feature
<222> LOCATION: (9)..(264)
<223> OTHER INFORMATION: GI NO: 41814856
    NR DESCRIPTION: methylesterase
```

```
<220> FEATURE:
<221> NAME/KEY: misc_feature
<222> LOCATION: (8)..(264)
<223> OTHER INFORMATION: GI NO: 14279437
      NR DESCRIPTION: ethylene-induced esterase
<220> FEATURE:
<221> NAME/KEY: misc_feature
<222> LOCATION: (1)..(264)
<223> OTHER INFORMATION: GI NO: 34915034
      NR DESCRIPTION: putative acetone-cyanohydrin lyase
<220> FEATURE:
<221> NAME/KEY: misc_feature
<222> LOCATION: (136)..(264)
<223> OTHER INFORMATION: GI NO: 34914024
      NR DESCRIPTION: OJ1014_G12.27

<400> SEQUENCE: 72

Met Glu Gly Ser Ser Ser Gly Lys His Phe Ile Leu Ile His Gly Leu
1               5                   10                  15

Cys His Gly Ala Trp Cys Trp Tyr Lys Leu Val Pro Met Leu Arg Ala
            20                  25                  30

Ala Gly His Arg Val Thr Ala Leu Asp Met Ala Ala Ser Gly Ala His
        35                  40                  45

Pro Ala Arg Met Asp Glu Val Pro Ser Phe Glu Asp Tyr Ser Trp Pro
    50                  55                  60

Leu Leu Asp Ala Val Ala Ala Pro Ala Gly Glu Arg Leu Val Leu
65                  70                  75                  80

Val Gly His Ser Leu Gly Gly Leu Asn Ile Ala Leu Ala Met Glu Arg
                85                  90                  95

Phe Pro Arg Lys Val Ala Ala Val Phe Leu Ala Ala Cys Met Pro
            100                 105                 110

Cys Val Gly Arg His Met Gly Ala Thr Thr Glu Glu Ile Met Arg Arg
        115                 120                 125

Ile Lys Pro Asp Phe Phe Met Asp Met Lys Arg Met Val Leu Asn Thr
    130                 135                 140

Ser Gln Gly Pro Arg Pro Ala Leu Val Phe Gly Pro Lys Ile Leu Ala
145                 150                 155                 160

Ala Lys Leu Tyr Asp Arg Ser Ser Gly Glu Asp Gln Thr Leu Ala Thr
                165                 170                 175

Met Leu Val Arg Pro Gly Cys Gln Phe Leu Asp Asp Pro Thr Met Lys
            180                 185                 190

Asp Glu Ala Leu Leu Thr Glu Ala Lys Tyr Gly Ser Val Lys Lys Val
        195                 200                 205

Tyr Val Val Ala Met Ala Asp Ala Ser Asn Ser Glu Glu Met Gln Arg
    210                 215                 220

Trp Met Val Asp Met Ser Pro Gly Thr Glu Ala Glu Ile Ala Gly
225                 230                 235                 240

Ala Asp His Met Ala Met Cys Ser Lys Pro Arg Glu Leu Cys Asp Val
                245                 250                 255

Leu Leu Arg Ile Ala Asp Lys Tyr Glu
            260                 265

<210> SEQ ID NO 73
<211> LENGTH: 237
<212> TYPE: PRT
<213> ORGANISM: Triticum aestivum
<220> FEATURE:
<221> NAME/KEY: misc_feature
<222> LOCATION: (1)..(237)
<223> OTHER INFORMATION: Ceres Seq. ID no. 16606374
<220> FEATURE:
<221> NAME/KEY: misc_feature
```

```
-continued

<222> LOCATION: (7)..(231)
<223> OTHER INFORMATION: PFAM Description: alpha/beta hydrolase fold
<220> FEATURE:
<221> NAME/KEY: misc_feature
<222> LOCATION: (1)..(237)
<223> OTHER INFORMATION: GI NO: 34907178
      NR DESCRIPTION: pir7a protein (Pseudomonas inducible protein)
<220> FEATURE:
<221> NAME/KEY: misc_feature
<222> LOCATION: (1)..(237)
<223> OTHER INFORMATION: GI NO: 34907176
      NR DESCRIPTION: pir7b protein (Pseudomonas inducible protein)
<220> FEATURE:
<221> NAME/KEY: misc_feature
<222> LOCATION: (1)..(237)
<223> OTHER INFORMATION: GI NO: 498747
      NR DESCRIPTION: Pir7b
<220> FEATURE:
<221> NAME/KEY: misc_feature
<222> LOCATION: (1)..(90)
<223> OTHER INFORMATION: GI NO: 34907174
      NR DESCRIPTION: putative pir7b (Pseudomonas inducible protein)
<220> FEATURE:
<221> NAME/KEY: misc_feature
<222> LOCATION: (142)..(237)
<223> OTHER INFORMATION: GI NO: 34907174
      NR DESCRIPTION: putative pir7b (Pseudomonas inducible protein)
<220> FEATURE:
<221> NAME/KEY: misc_feature
<222> LOCATION: (1)..(236)
<223> OTHER INFORMATION: GI NO: 40549303
      NR DESCRIPTION: salicylic acid-binding protein 2
<220> FEATURE:
<221> NAME/KEY: misc_feature
<222> LOCATION: (1)..(236)
<223> OTHER INFORMATION: GI NO: 41814856
      NR DESCRIPTION: methylesterase
<220> FEATURE:
<221> NAME/KEY: misc_feature
<222> LOCATION: (1)..(236)
<223> OTHER INFORMATION: GI NO: 14279437
      NR DESCRIPTION: ethylene-induced esterase
<220> FEATURE:
<221> NAME/KEY: misc_feature
<222> LOCATION: (1)..(236)
<223> OTHER INFORMATION: GI NO: 34915034
      NR DESCRIPTION: putative acetone-cyanohydrin lyase
<220> FEATURE:
<221> NAME/KEY: misc_feature
<222> LOCATION: (108)..(236)
<223> OTHER INFORMATION: GI NO: 34914024
      NR DESCRIPTION: OJ1014_G12.27

<400> SEQUENCE: 73

Met Leu Arg Ala Ala Gly His Arg Val Thr Ala Leu Asp Met Ala Ala
1               5                   10                  15

Ser Gly Ala His Pro Ala Arg Met Asp Glu Val Pro Ser Phe Glu Asp
                20                  25                  30

Tyr Ser Trp Pro Leu Leu Asp Ala Val Ala Ala Pro Ala Gly Glu
            35                  40                  45

Arg Leu Val Leu Val Gly His Ser Leu Gly Gly Leu Asn Ile Ala Leu
    50                  55                  60

Ala Met Glu Arg Phe Pro Arg Lys Val Ala Ala Val Phe Leu Ala
65                  70                  75                  80

Ala Cys Met Pro Cys Val Gly Arg His Met Gly Ala Thr Thr Glu Glu
                85                  90                  95

Ile Met Arg Arg Ile Lys Pro Asp Phe Phe Met Asp Met Lys Arg Met
                100                 105                 110

Val Leu Asn Thr Ser Gln Gly Pro Arg Pro Ala Leu Val Phe Gly Pro
            115                 120                 125

Lys Ile Leu Ala Ala Lys Leu Tyr Asp Arg Ser Ser Gly Glu Asp Gln
```

```
                130                 135                 140
Thr Leu Ala Thr Met Leu Val Arg Pro Gly Cys Gln Phe Leu Asp Asp
145                 150                 155                 160

Pro Thr Met Lys Asp Glu Ala Leu Leu Thr Glu Ala Lys Tyr Gly Ser
                165                 170                 175

Val Lys Lys Val Tyr Val Val Ala Met Ala Asp Ala Ser Asn Ser Glu
                180                 185                 190

Glu Met Gln Arg Trp Met Val Asp Met Ser Pro Gly Thr Glu Ala Glu
                195                 200                 205

Glu Ile Ala Gly Ala Asp His Met Ala Met Cys Ser Lys Pro Arg Glu
            210                 215                 220

Leu Cys Asp Val Leu Leu Arg Ile Ala Asp Lys Tyr Glu
225                 230                 235
```

<210> SEQ ID NO 74
<211> LENGTH: 224
<212> TYPE: PRT
<213> ORGANISM: Triticum aestivum
<220> FEATURE:
<221> NAME/KEY: misc_feature
<222> LOCATION: (1)..(224)
<223> OTHER INFORMATION: Ceres Seq. ID no. 16606375
<220> FEATURE:
<221> NAME/KEY: misc_feature
<222> LOCATION: (1)..(218)
<223> OTHER INFORMATION: PFAM Description: alpha/beta hydrolase fold
<220> FEATURE:
<221> NAME/KEY: misc_feature
<222> LOCATION: (1)..(224)
<223> OTHER INFORMATION: GI NO: 34907178
    NR DESCRIPTION: pir7a protein (Pseudomonas inducible protein)
<220> FEATURE:
<221> NAME/KEY: misc_feature
<222> LOCATION: (1)..(224)
<223> OTHER INFORMATION: GI NO: 34907176
    NR DESCRIPTION: pir7b protein (Pseudomonas inducible protein)
<220> FEATURE:
<221> NAME/KEY: misc_feature
<222> LOCATION: (1)..(224)
<223> OTHER INFORMATION: GI NO: 498747
    NR DESCRIPTION: Pir7b
<220> FEATURE:
<221> NAME/KEY: misc_feature
<222> LOCATION: (1)..(77)
<223> OTHER INFORMATION: GI NO: 34907174
    NR DESCRIPTION: putative pir7b (Pseudomonas inducible protein)
<220> FEATURE:
<221> NAME/KEY: misc_feature
<222> LOCATION: (129)..(224)
<223> OTHER INFORMATION: GI NO: 34907174
    NR DESCRIPTION: putative pir7b (Pseudomonas inducible protein)
<220> FEATURE:
<221> NAME/KEY: misc_feature
<222> LOCATION: (1)..(223)
<223> OTHER INFORMATION: GI NO: 40549303
    NR DESCRIPTION: salicylic acid-binding protein 2
<220> FEATURE:
<221> NAME/KEY: misc_feature
<222> LOCATION: (1)..(223)
<223> OTHER INFORMATION: GI NO: 41814856
    NR DESCRIPTION: methylesterase
<220> FEATURE:
<221> NAME/KEY: misc_feature
<222> LOCATION: (1)..(223)
<223> OTHER INFORMATION: GI NO: 14279437
    NR DESCRIPTION: ethylene-induced esterase
<220> FEATURE:
<221> NAME/KEY: misc_feature
<222> LOCATION: (1)..(223)
<223> OTHER INFORMATION: GI NO: 34915034
    NR DESCRIPTION: putative acetone-cyanohydrin lyase
<220> FEATURE:
<221> NAME/KEY: misc_feature

```
<222> LOCATION: (95)..(223)
<223> OTHER INFORMATION: GI NO: 34914024
      NR DESCRIPTION: OJ1014_G12.27

<400> SEQUENCE: 74
```

| | | | | | | | | | | | | | | |
|---|---|---|---|---|---|---|---|---|---|---|---|---|---|---|
| Met | Ala | Ala | Ser | Gly | Ala | His | Pro | Ala | Arg | Met | Asp | Glu | Val | Pro | Ser |
| 1 | | | | 5 | | | | | 10 | | | | | 15 |

Met Ala Ala Ser Gly Ala His Pro Ala Arg Met Asp Glu Val Pro Ser
1               5                   10                  15

Phe Glu Asp Tyr Ser Trp Pro Leu Leu Asp Ala Val Ala Ala Pro
                20                  25                  30

Ala Gly Glu Arg Leu Val Leu Val Gly His Ser Leu Gly Gly Leu Asn
            35                  40                  45

Ile Ala Leu Ala Met Glu Arg Phe Pro Arg Lys Val Ala Ala Val
        50                  55                  60

Phe Leu Ala Ala Cys Met Pro Cys Val Gly Arg His Met Gly Ala Thr
65                  70                  75                  80

Thr Glu Glu Ile Met Arg Arg Ile Lys Pro Asp Phe Phe Met Asp Met
                85                  90                  95

Lys Arg Met Val Leu Asn Thr Ser Gln Gly Pro Arg Pro Ala Leu Val
                100                 105                 110

Phe Gly Pro Lys Ile Leu Ala Ala Lys Leu Tyr Asp Arg Ser Ser Gly
            115                 120                 125

Glu Asp Gln Thr Leu Ala Thr Met Leu Val Arg Pro Gly Cys Gln Phe
    130                 135                 140

Leu Asp Asp Pro Thr Met Lys Asp Glu Ala Leu Leu Thr Glu Ala Lys
145                 150                 155                 160

Tyr Gly Ser Val Lys Lys Val Tyr Val Ala Met Ala Asp Ala Ser
                165                 170                 175

Asn Ser Glu Glu Met Gln Arg Trp Met Val Asp Met Ser Pro Gly Thr
            180                 185                 190

Glu Ala Glu Glu Ile Ala Gly Ala Asp His Met Ala Met Cys Ser Lys
        195                 200                 205

Pro Arg Glu Leu Cys Asp Val Leu Leu Arg Ile Ala Asp Lys Tyr Glu
    210                 215                 220

```
<210> SEQ ID NO 75
<211> LENGTH: 455
<212> TYPE: DNA
<213> ORGANISM: Triticum aestivum
<220> FEATURE:
<221> NAME/KEY: misc_feature
<222> LOCATION: (1)..(455)
<223> OTHER INFORMATION: Ceres Seq. ID no. 11425729
<220> FEATURE:
<221> NAME/KEY: misc_feature
<222> LOCATION: (425)..(425)
<223> OTHER INFORMATION: n is a, c, t, g, unknown, or other

<400> SEQUENCE: 75
aagtcatccc tacgcctcct ctctctttcc gactgaactc caagaacatc ttctcatttt      60
ctctgcttcc aatggcgaag gcgggctga gcagcaagct caagtgcatg atcaggcggt      120
ggcactcgtc gagccggatc tcgcgcacgc cctcggcggc gtcgcacggc ggcggcggcg      180
gcgaggagga ggacccgtgg ggccgcggcg tcggcggcgg cgcggcgtcg ttccacggcg      240
ccgacagcgt gccccggggc ctccacccgg tctacgtcgg caagtcgcgc cgccgctacc      300
tcatcgccgc cgacctcgtc tgccacccgc tgttccagaa cctcgtggac cgctcgggcg      360
gcggcgtggg cggcgacggc gccggcggca ccatcatcgg ctgcgaggtg gtgctgttcg      420 agcancctcct gtggatgctg gagaacgcgg acccg                              455
```

```
<210> SEQ ID NO 76
<211> LENGTH: 151
<212> TYPE: PRT
<213> ORGANISM: Triticum aestivum
<220> FEATURE:
<221> NAME/KEY: misc_feature
<222> LOCATION: (1)..(151)
<223> OTHER INFORMATION: Ceres Seq. ID no. 11425730
<220> FEATURE:
<221> NAME/KEY: misc_feature
<222> LOCATION: (52)..(143)
<223> OTHER INFORMATION: PFAM Description: Subtilase family
<220> FEATURE:
<221> NAME/KEY: misc_feature
<222> LOCATION: (142)..(142)
<223> OTHER INFORMATION: Xaa is any aa, unknown or other

<400> SEQUENCE: 76

Ser His Pro Tyr Ala Ser Ser Leu Phe Pro Thr Glu Leu Gln Glu His
 1               5                  10                  15

Leu Leu Ile Phe Ser Ala Ser Asn Gly Glu Gly Arg Ala Glu Gln Gln
            20                  25                  30

Ala Gln Val His Asp Gln Ala Val Ala Leu Val Glu Pro Asp Leu Ala
        35                  40                  45

His Ala Leu Gly Gly Val Ala Arg Arg Arg Arg Arg Gly Gly Gly
    50                  55                  60

Pro Val Gly Pro Arg Arg Arg Arg Arg Arg Val Val Pro Arg Arg
65                  70                  75                  80

Arg Gln Arg Ala Pro Gly Pro Pro Gly Leu Arg Arg Gln Val Ala
                85                  90                  95

Pro Pro Leu Pro His Arg Arg Arg Pro Arg Leu Pro Pro Ala Val Pro
            100                 105                 110

Glu Pro Arg Gly Pro Leu Gly Arg Arg Arg Gly Arg Arg Arg Arg Arg
        115                 120                 125

Arg His His His Arg Leu Arg Gly Gly Ala Val Arg Ala Xaa Pro Val
    130                 135                 140

Asp Ala Gly Glu Arg Gly Pro
145                 150

<210> SEQ ID NO 77
<211> LENGTH: 151
<212> TYPE: PRT
<213> ORGANISM: Triticum aestivum
<220> FEATURE:
<221> NAME/KEY: misc_feature
<222> LOCATION: (1)..(151)
<223> OTHER INFORMATION: Ceres Seq. ID no. 11425731
<220> FEATURE:
<221> NAME/KEY: misc_feature
<222> LOCATION: (87)..(147)
<223> OTHER INFORMATION: PFAM Description: Auxin responsive protein
<220> FEATURE:
<221> NAME/KEY: misc_feature
<222> LOCATION: (24)..(150)
<223> OTHER INFORMATION: GI NO: 50946385
      NR DESCRIPTION: auxin-induced protein-related-like protein
<220> FEATURE:
<221> NAME/KEY: misc_feature
<222> LOCATION: (87)..(150)
<223> OTHER INFORMATION: GI NO: 15242071
      NR DESCRIPTION: putative protein; protein id: At5g20820.1
<220> FEATURE:
<221> NAME/KEY: misc_feature
<222> LOCATION: (87)..(150)
<223> OTHER INFORMATION: GI NO: 21554070
      NR DESCRIPTION: unknown
<220> FEATURE:
<221> NAME/KEY: misc_feature
```

```
<222> LOCATION: (83)..(150)
<223> OTHER INFORMATION: GI NO: 24943206
      NR DESCRIPTION: auxin-regulated protein
<220> FEATURE:
<221> NAME/KEY: misc_feature
<222> LOCATION: (141)..(141)
<223> OTHER INFORMATION: Xaa is any aa, unknown or other

<400> SEQUENCE: 77

Val Ile Pro Thr Pro Pro Leu Ser Phe Arg Leu Asn Ser Lys Asn Ile
1               5                   10                  15

Phe Ser Phe Ser Leu Leu Pro Met Ala Lys Gly Gly Leu Ser Ser Lys
            20                  25                  30

Leu Lys Cys Met Ile Arg Arg Trp His Ser Ser Arg Ile Ser Arg
        35                  40                  45

Thr Pro Ser Ala Ala Ser His Gly Gly Gly Gly Glu Glu Glu Asp
    50                  55                  60

Pro Trp Gly Arg Gly Val Gly Gly Ala Ala Ser Phe His Gly Ala
65              70                  75                  80

Asp Ser Val Pro Pro Gly Leu His Pro Val Tyr Val Gly Lys Ser Arg
            85                  90                  95

Arg Arg Tyr Leu Ile Ala Ala Asp Leu Val Cys His Pro Leu Phe Gln
            100                 105                 110

Asn Leu Val Asp Arg Ser Gly Gly Val Gly Gly Asp Gly Ala Gly
            115                 120                 125

Gly Thr Ile Ile Gly Cys Glu Val Val Leu Phe Glu Xaa Leu Leu Trp
    130                 135                 140

Met Leu Glu Asn Ala Asp Pro
145                 150

<210> SEQ ID NO 78
<211> LENGTH: 128
<212> TYPE: PRT
<213> ORGANISM: Triticum aestivum
<220> FEATURE:
<221> NAME/KEY: misc_feature
<222> LOCATION: (1)..(128)
<223> OTHER INFORMATION: Ceres Seq. ID no. 11425732
<220> FEATURE:
<221> NAME/KEY: misc_feature
<222> LOCATION: (64)..(124)
<223> OTHER INFORMATION: PFAM Description: Auxin responsive protein
<220> FEATURE:
<221> NAME/KEY: misc_feature
<222> LOCATION: (1)..(127)
<223> OTHER INFORMATION: GI NO: 50946385
      NR DESCRIPTION: auxin-induced protein-related-like protein
<220> FEATURE:
<221> NAME/KEY: misc_feature
<222> LOCATION: (64)..(127)
<223> OTHER INFORMATION: GI NO: 15242071
      NR DESCRIPTION: putative protein; protein id: At5g20820.1
<220> FEATURE:
<221> NAME/KEY: misc_feature
<222> LOCATION: (64)..(127)
<223> OTHER INFORMATION: GI NO: 21554070
      NR DESCRIPTION: unknown
<220> FEATURE:
<221> NAME/KEY: misc_feature
<222> LOCATION: (60)..(127)
<223> OTHER INFORMATION: GI NO: 24943206
      NR DESCRIPTION: auxin-regulated protein
<220> FEATURE:
<221> NAME/KEY: misc_feature
<222> LOCATION: (118)..(118)
<223> OTHER INFORMATION: Xaa is any aa, unknown or other

<400> SEQUENCE: 78
```

```
Met Ala Lys Gly Gly Leu Ser Ser Lys Leu Lys Cys Met Ile Arg Arg
1               5                   10                  15

Trp His Ser Ser Ser Arg Ile Ser Arg Thr Pro Ser Ala Ala Ser His
            20                  25                  30

Gly Gly Gly Gly Gly Glu Glu Glu Asp Pro Trp Gly Arg Gly Val Gly
        35                  40                  45

Gly Gly Ala Ala Ser Phe His Gly Ala Asp Ser Val Pro Pro Gly Leu
    50                  55                  60

His Pro Val Tyr Val Gly Lys Ser Arg Arg Arg Tyr Leu Ile Ala Ala
65                  70                  75                  80

Asp Leu Val Cys His Pro Leu Phe Gln Asn Leu Val Asp Arg Ser Gly
                85                  90                  95

Gly Gly Val Gly Gly Asp Gly Ala Gly Gly Thr Ile Ile Gly Cys Glu
            100                 105                 110

Val Val Leu Phe Glu Xaa Leu Leu Trp Met Leu Glu Asn Ala Asp Pro
            115                 120                 125
```

<210> SEQ ID NO 79
<211> LENGTH: 421
<212> TYPE: DNA
<213> ORGANISM: Triticum aestivum
<220> FEATURE:
<221> NAME/KEY: misc_feature
<222> LOCATION: (1)..(421)
<223> OTHER INFORMATION: Ceres Seq. ID no. 11425947

<400> SEQUENCE: 79

```
tccaaaaatc aacacaaac caaacaggtt ttacgctacg caagaaatgg agagcaccca      60
gagcaacagt gtgaggagcc atttcatcct ggtgcacggc ctctgccatg gggcttggtg     120
ctggtacaaa gtggtcgcgg cgctcgaggc cgcggggcac cgcgtcacgg cgatcgacct    180
cgccgcttcg ggtacccacc cggcgcgcgt tgacgaggtg cactcgttcg aggagtactc    240
gcggccgctg ctcgacgtgg tggccgcggc ccggcgggt gacggcgaga ggctgattct    300
ggtcgggcac agccacggcg gcctcagctt ggcgctagcc atggagaggt tccccggcaa    360
gatcgccgct gccgtgttcg cggccgctgc gatgccgagc gtcgggaagc acatgggcgt    420
c                                                                    421
```

<210> SEQ ID NO 80
<211> LENGTH: 140
<212> TYPE: PRT
<213> ORGANISM: Triticum aestivum
<220> FEATURE:
<221> NAME/KEY: misc_feature
<222> LOCATION: (1)..(140)
<223> OTHER INFORMATION: Ceres Seq. ID no. 11425948
<220> FEATURE:
<221> NAME/KEY: misc_feature
<222> LOCATION: (53)..(139)
<223> OTHER INFORMATION: PFAM Description: alpha/beta hydrolase fold
<220> FEATURE:
<221> NAME/KEY: misc_feature
<222> LOCATION: (21)..(139)
<223> OTHER INFORMATION: GI NO: 34907176
      NR DESCRIPTION: pir7b protein (Pseudomonas inducible protein)
<220> FEATURE:
<221> NAME/KEY: misc_feature
<222> LOCATION: (25)..(139)
<223> OTHER INFORMATION: GI NO: 498747
      NR DESCRIPTION: Pir7b
<220> FEATURE:
<221> NAME/KEY: misc_feature
<222> LOCATION: (16)..(138)
<223> OTHER INFORMATION: GI NO: 34907174
      NR DESCRIPTION: putative pir7b (Pseudomonas inducible protein)

```
<220> FEATURE:
<221> NAME/KEY: misc_feature
<222> LOCATION: (27)..(139)
<223> OTHER INFORMATION: GI NO: 34907178
      NR DESCRIPTION: pir7a protein (Pseudomonas inducible protein)
<220> FEATURE:
<221> NAME/KEY: misc_feature
<222> LOCATION: (27)..(132)
<223> OTHER INFORMATION: GI NO: 14279437
      NR DESCRIPTION: ethylene-induced esterase
<220> FEATURE:
<221> NAME/KEY: misc_feature
<222> LOCATION: (25)..(137)
<223> OTHER INFORMATION: GI NO: 21554666
      NR DESCRIPTION: putative acetone-cyanohydrin lyase
<220> FEATURE:
<221> NAME/KEY: misc_feature
<222> LOCATION: (25)..(132)
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (25)..(132)
<223> OTHER INFORMATION: GI NO: 41814856
      NR DESCRIPTION: methylesterase
<220> FEATURE:
<221> NAME/KEY: misc_feature
<222> LOCATION: (26)..(132)
<223> OTHER INFORMATION: GI NO: 34914020
      NR DESCRIPTION: OJ1014_G12.25
<220> FEATURE:
<221> NAME/KEY: misc_feature
<222> LOCATION: (28)..(137)
<223> OTHER INFORMATION: GI NO: 2780225
      NR DESCRIPTION: alpha-hydroxynitrile lyase

<400> SEQUENCE: 80

Pro Lys Ile Gln His Lys Pro Asn Arg Phe Tyr Ala Thr Gln Glu Met
1               5                   10                  15

Glu Ser Thr Gln Ser Asn Ser Val Arg Ser His Phe Ile Leu Val His
            20                  25                  30

Gly Leu Cys His Gly Ala Trp Cys Trp Tyr Lys Val Val Ala Ala Leu
        35                  40                  45

Glu Ala Ala Gly His Arg Val Thr Ala Ile Asp Leu Ala Ala Ser Gly
    50                  55                  60

Thr His Pro Ala Arg Val Asp Glu Val His Ser Phe Glu Glu Tyr Ser
65                  70                  75                  80

Arg Pro Leu Leu Asp Val Val Ala Ala Pro Ala Gly Asp Gly Glu
                85                  90                  95

Arg Leu Ile Leu Val Gly His Ser His Gly Gly Leu Ser Leu Ala Leu
            100                 105                 110

Ala Met Glu Arg Phe Pro Gly Lys Ile Ala Ala Val Phe Ala Ala
        115                 120                 125

Ala Ala Met Pro Ser Val Gly Lys His Met Gly Val
    130                 135                 140

<210> SEQ ID NO 81
<211> LENGTH: 125
<212> TYPE: PRT
<213> ORGANISM: Triticum aestivum
<220> FEATURE:
<221> NAME/KEY: misc_feature
<222> LOCATION: (1)..(125)
<223> OTHER INFORMATION: Ceres Seq. ID no. 11425949
<220> FEATURE:
<221> NAME/KEY: misc_feature
<222> LOCATION: (38)..(124)
<223> OTHER INFORMATION: PFAM Description: alpha/beta hydrolase fold
<220> FEATURE:
<221> NAME/KEY: misc_feature
```

```
<222> LOCATION: (6)..(124)
<223> OTHER INFORMATION: GI NO: 34907176
      NR DESCRIPTION: pir7b protein (Pseudomonas inducible protein)
<220> FEATURE:
<221> NAME/KEY: misc_feature
<222> LOCATION: (10)..(124)
<223> OTHER INFORMATION: GI NO: 498747
      NR DESCRIPTION: Pir7b
<220> FEATURE:
<221> NAME/KEY: misc_feature
<222> LOCATION: (1)..(123)
<223> OTHER INFORMATION: GI NO: 34907174
      NR DESCRIPTION: putative pir7b (Pseudomonas inducible protein)
<220> FEATURE:
<221> NAME/KEY: misc_feature
<222> LOCATION: (12)..(124)
<223> OTHER INFORMATION: GI NO: 34907178
      NR DESCRIPTION: pir7a protein (Pseudomonas inducible protein)
<220> FEATURE:
<221> NAME/KEY: misc_feature
<222> LOCATION: (12)..(117)
<223> OTHER INFORMATION: GI NO: 14279437
      NR DESCRIPTION: ethylene-induced esterase
<220> FEATURE:
<221> NAME/KEY: misc_feature
<222> LOCATION: (10)..(122)
<223> OTHER INFORMATION: GI NO: 21554666
      NR DESCRIPTION: putative acetone-cyanohydrin lyase
<220> FEATURE:
<221> NAME/KEY: misc_feature
<222> LOCATION: (10)..(117)
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (10)..(117)
<223> OTHER INFORMATION: GI NO: 41814856
      NR DESCRIPTION: methylesterase
<220> FEATURE:
<221> NAME/KEY: misc_feature
<222> LOCATION: (11)..(117)
<223> OTHER INFORMATION: GI NO: 34914020
      NR DESCRIPTION: OJ1014_G12.25
<220> FEATURE:
<221> NAME/KEY: misc_feature
<222> LOCATION: (13)..(122)
<223> OTHER INFORMATION: GI NO: 2780225
      NR DESCRIPTION: alpha-hydroxynitrile lyase

<400> SEQUENCE: 81

Met Glu Ser Thr Gln Ser Asn Ser Val Arg Ser His Phe Ile Leu Val
1               5                   10                  15

His Gly Leu Cys His Gly Ala Trp Cys Trp Tyr Lys Val Val Ala Ala
            20                  25                  30

Leu Glu Ala Gly His Arg Val Thr Ala Ile Asp Leu Ala Ala Ser
        35                  40                  45

Gly Thr His Pro Ala Arg Val Asp Glu Val His Ser Phe Glu Glu Tyr
    50                  55                  60

Ser Arg Pro Leu Leu Asp Val Val Ala Ala Pro Ala Gly Asp Gly
65                  70                  75                  80

Glu Arg Leu Ile Leu Val Gly His Ser His Gly Gly Leu Ser Leu Ala
                85                  90                  95

Leu Ala Met Glu Arg Phe Pro Gly Lys Ile Ala Ala Val Phe Ala
            100                 105                 110

Ala Ala Ala Met Pro Ser Val Gly Lys His Met Gly Val
            115                 120                 125

<210> SEQ ID NO 82
<211> LENGTH: 70
<212> TYPE: PRT
<213> ORGANISM: Triticum aestivum
```

```
<220> FEATURE:
<221> NAME/KEY: misc_feature
<222> LOCATION: (1)..(70)
<223> OTHER INFORMATION: Ceres Seq. ID no. 11425950

<400> SEQUENCE: 82

Ser Lys Asn Pro Thr Gln Thr Lys Gln Val Leu Arg Tyr Ala Arg Asn
1               5                   10                  15

Gly Glu His Pro Glu Gln Gln Cys Glu Glu Pro Phe His Pro Gly Ala
            20                  25                  30

Arg Pro Leu Pro Trp Gly Leu Val Leu Val Gln Ser Gly Arg Gly Ala
        35                  40                  45

Arg Gly Arg Gly Ala Pro Arg His Gly Asp Arg Pro Arg Arg Phe Gly
    50                  55                  60

Tyr Pro Pro Gly Ala Arg
65                  70

<210> SEQ ID NO 83
<211> LENGTH: 433
<212> TYPE: DNA
<213> ORGANISM: Triticum aestivum
<220> FEATURE:
<221> NAME/KEY: misc_feature
<222> LOCATION: (1)..(433)
<223> OTHER INFORMATION: Ceres Seq. ID no. 4603108

<400> SEQUENCE: 83
gaaaaaagtc atccctacgc ctcctttctc tttccgactg aaccccaaga acatcctctc      60
catctctctc tgcttccaat ggcgaagggc gggctgagca gcaagctcaa gtgcatgatc    120
aggcggtggc actcgtcgag ccggatctcc cgcacgccct cggcggtgtc gcacggcggc    180
ggcgaggagg aggacccgtg gggccgcggc gtcggcgggg gcggggcgg cgcggcgtcg      240 ttccacggcg ccgacggcgt gccccgggc ctccacccgg tgtacgtcgg caagtcgcgc      300
cgccgctacc tcatcgccgc cgacctcgtc tgccacccgc tgttccagaa cctcgtggac    360
cgctcgggcg gcggcgtggg cggcgacggc gccggcggca ccatcatcgg ctgcgaggtg    420
gtgctgttcg agc                                                       433

<210> SEQ ID NO 84
<211> LENGTH: 144
<212> TYPE: PRT
<213> ORGANISM: Triticum aestivum
<220> FEATURE:
<221> NAME/KEY: misc_feature
<222> LOCATION: (1)..(144)
<223> OTHER INFORMATION: Ceres Seq. ID no. 4603109
<220> FEATURE:
<221> NAME/KEY: misc_feature
<222> LOCATION: (91)..(143)
<223> OTHER INFORMATION: PFAM Description: Auxin responsive protein
<220> FEATURE:
<221> NAME/KEY: misc_feature
<222> LOCATION: (27)..(143)
<223> OTHER INFORMATION: GI NO: 50946385
    NR DESCRIPTION: auxin-induced protein-related-like protein
<220> FEATURE:
<221> NAME/KEY: misc_feature
<222> LOCATION: (91)..(143)
<223> OTHER INFORMATION: GI NO: 15242071
    NR DESCRIPTION: putative protein; protein id: At5g20820.1
<220> FEATURE:
<221> NAME/KEY: misc_feature
<222> LOCATION: (91)..(143)
<223> OTHER INFORMATION: GI NO: 21554070
    NR DESCRIPTION: unknown

<400> SEQUENCE: 84
```

```
Glu Lys Ser His Pro Tyr Ala Ser Phe Leu Phe Pro Thr Glu Pro Gln
1               5                   10                  15

Glu His Pro Leu His Leu Ser Leu Leu Pro Met Ala Lys Gly Gly Leu
            20                  25                  30

Ser Ser Lys Leu Lys Cys Met Ile Arg Arg Trp His Ser Ser Arg
        35                  40                  45

Ile Ser Arg Thr Pro Ser Ala Val Ser His Gly Gly Gly Glu Glu Glu
50                  55                  60

Asp Pro Trp Gly Arg Gly Val Gly Gly Gly Gly Gly Ala Ala Ser
65              70                  75                  80

Phe His Gly Ala Asp Gly Val Pro Pro Gly Leu His Pro Val Tyr Val
                85                  90                  95

Gly Lys Ser Arg Arg Arg Tyr Leu Ile Ala Ala Asp Leu Val Cys His
            100                 105                 110

Pro Leu Phe Gln Asn Leu Val Asp Arg Ser Gly Gly Gly Val Gly Gly
        115                 120                 125

Asp Gly Ala Gly Gly Thr Ile Ile Gly Cys Glu Val Val Leu Phe Glu
    130                 135                 140
```

<210> SEQ ID NO 85
<211> LENGTH: 118
<212> TYPE: PRT
<213> ORGANISM: Triticum aestivum
<220> FEATURE:
<221> NAME/KEY: misc_feature
<222> LOCATION: (1)..(118)
<223> OTHER INFORMATION: Ceres Seq. ID no. 4603110
<220> FEATURE:
<221> NAME/KEY: misc_feature
<222> LOCATION: (65)..(117)
<223> OTHER INFORMATION: PFAM Description: Auxin responsive protein
<220> FEATURE:
<221> NAME/KEY: misc_feature
<222> LOCATION: (1)..(117)
<223> OTHER INFORMATION: GI NO: 50946385
       NR DESCRIPTION: auxin-induced protein-related-like protein
<220> FEATURE:
<221> NAME/KEY: misc_feature
<222> LOCATION: (65)..(117)
<223> OTHER INFORMATION: GI NO: 15242071
       NR DESCRIPTION: putative protein; protein id: At5g20820.1
<220> FEATURE:
<221> NAME/KEY: misc_feature
<222> LOCATION: (65)..(117)
<223> OTHER INFORMATION: GI NO: 21554070
       NR DESCRIPTION: unknown

<400> SEQUENCE: 85

```
Met Ala Lys Gly Gly Leu Ser Ser Lys Leu Lys Cys Met Ile Arg Arg
1               5                   10                  15

Trp His Ser Ser Ser Arg Ile Ser Arg Thr Pro Ser Ala Val Ser His
            20                  25                  30

Gly Gly Gly Glu Glu Glu Asp Pro Trp Gly Arg Gly Val Gly Gly Gly
            35                  40                  45

Gly Gly Gly Ala Ala Ser Phe His Gly Ala Asp Gly Val Pro Pro Gly
50                  55                  60

Leu His Pro Val Tyr Val Gly Lys Ser Arg Arg Arg Tyr Leu Ile Ala
65                  70                  75                  80

Ala Asp Leu Val Cys His Pro Leu Phe Gln Asn Leu Val Asp Arg Ser
                85                  90                  95

Gly Gly Gly Val Gly Gly Asp Gly Ala Gly Gly Thr Ile Ile Gly Cys
            100                 105                 110
```

Glu Val Val Leu Phe Glu
        115

<210> SEQ ID NO 86
<211> LENGTH: 106
<212> TYPE: PRT
<213> ORGANISM: Triticum aestivum
<220> FEATURE:
<221> NAME/KEY: misc_feature
<222> LOCATION: (1)..(106)
<223> OTHER INFORMATION: Ceres Seq. ID no. 4603111
<220> FEATURE:
<221> NAME/KEY: misc_feature
<222> LOCATION: (53)..(105)
<223> OTHER INFORMATION: PFAM Description: Auxin responsive protein
<220> FEATURE:
<221> NAME/KEY: misc_feature
<222> LOCATION: (1)..(105)
<223> OTHER INFORMATION: GI NO: 50946385
      NR DESCRIPTION: auxin-induced protein-related-like protein
<220> FEATURE:
<221> NAME/KEY: misc_feature
<222> LOCATION: (53)..(105)
<223> OTHER INFORMATION: GI NO: 15242071
      NR DESCRIPTION: putative protein; protein id: At5g20820.1
<220> FEATURE:
<221> NAME/KEY: misc_feature
<222> LOCATION: (53)..(105)
<223> OTHER INFORMATION: GI NO: 21554070
      NR DESCRIPTION: unknown

<400> SEQUENCE: 86

Met Ile Arg Arg Trp His Ser Ser Arg Ile Ser Arg Thr Pro Ser
1               5                   10                  15

Ala Val Ser His Gly Gly Gly Glu Glu Glu Asp Pro Trp Gly Arg Gly
            20                  25                  30

Val Gly Gly Gly Gly Gly Gly Ala Ala Ser Phe His Gly Ala Asp Gly
            35                  40                  45

Val Pro Pro Gly Leu His Pro Val Tyr Val Gly Lys Ser Arg Arg Arg
        50                  55                  60

Tyr Leu Ile Ala Ala Asp Leu Val Cys His Pro Leu Phe Gln Asn Leu
65                  70                  75                  80

Val Asp Arg Ser Gly Gly Gly Val Gly Gly Asp Gly Ala Gly Gly Thr
                85                  90                  95

Ile Ile Gly Cys Glu Val Val Leu Phe Glu
            100                 105

<210> SEQ ID NO 87
<211> LENGTH: 481
<212> TYPE: DNA
<213> ORGANISM: Triticum aestivum
<220> FEATURE:
<221> NAME/KEY: misc_feature
<222> LOCATION: (1)..(481)
<223> OTHER INFORMATION: Ceres Seq. ID no. 11427493
<220> FEATURE:
<221> NAME/KEY: misc_feature
<222> LOCATION: (382)..(382)
<223> OTHER INFORMATION: n is a, c, t, g, unknown, or other

<400> SEQUENCE: 87
gccaagaaac gaagctgcta gctgctcggc gcacacatgt cgtcatcctc ctcctctgcg    60
ccagcggccg ccgtggcgac gtcgacccgc ctcatcctgg tgcacggcac gggccacggc   120
gggtggtgct ggtacaaggt cgccaccctc ctccgcgccg cggggcaccg cgtcgacgcg   180 ccggaccctcg cggcctgcgg cgccgacgcg cgccggctga cgacgcgcc aaccttcgag   240 gactacacgc gccccctgct cgacgcgctc cgggccctcc cggacggcga gcgagcggtg   300

```
ctcgtgggcc acagcttcgg cggcatgagc gtcgcgctcg ccgccgagga gttccccgac    360
aaggtcgccg ccgccgtgtt cntcagcgcc ttcatgccgg actgccgg cccgcgcacc     420 cgcgttatcg agcaggtccc cgtgtccgac tggatggaca gcgtgstcga cgaggagcac    480
g                                                                   481
```

<210> SEQ ID NO 88
<211> LENGTH: 159
<212> TYPE: PRT
<213> ORGANISM: Triticum aestivum
<220> FEATURE:
<221> NAME/KEY: misc_feature
<222> LOCATION: (1)..(159)
<223> OTHER INFORMATION: Ceres Seq. ID no. 11427494
<220> FEATURE:
<221> NAME/KEY: misc_feature
<222> LOCATION: (20)..(158)
<223> OTHER INFORMATION: PFAM Description: Subtilase family
<220> FEATURE:
<221> NAME/KEY: misc_feature
<222> LOCATION: (127)..(127)
<223> OTHER INFORMATION: Xaa is any aa, unknown or other
<220> FEATURE:
<221> NAME/KEY: misc_feature
<222> LOCATION: (155)..(155)
<223> OTHER INFORMATION: Xaa is any aa, unknown or other

<400> SEQUENCE: 88

```
Gln Glu Thr Lys Leu Leu Ala Ala Arg Arg Thr His Val Val Ile Leu
1               5                   10                  15

Leu Leu Cys Ala Ser Gly Arg Arg Gly Asp Val Asp Pro Pro His Pro
            20                  25                  30

Gly Ala Arg His Gly Pro Arg Val Val Leu Val Gln Gly Arg His
        35                  40                  45

Pro Pro Pro Arg Arg Gly Ala Pro Arg Arg Ala Gly Pro Arg Gly
    50                  55                  60

Leu Arg Arg Arg Arg Ala Pro Ala Glu Arg Arg Ala Asn Leu Arg Gly
65                  70                  75                  80

Leu His Ala Pro Pro Ala Arg Arg Ala Pro Gly Pro Pro Gly Arg Arg
                85                  90                  95

Ala Ser Gly Ala Arg Gly Pro Gln Leu Arg Arg His Glu Arg Arg Ala
            100                 105                 110

Arg Arg Arg Gly Val Pro Arg Gln Gly Arg Arg Arg Val Xaa Gln
        115                 120                 125

Arg Leu His Ala Gly Leu Arg Arg Pro Ala His Pro Arg Tyr Arg Ala
    130                 135                 140

Gly Pro Arg Val Arg Leu Asp Gly Gln Arg Xaa Arg Arg Gly Ala
145                 150                 155
```

<210> SEQ ID NO 89
<211> LENGTH: 148
<212> TYPE: PRT
<213> ORGANISM: Triticum aestivum
<220> FEATURE:
<221> NAME/KEY: misc_feature
<222> LOCATION: (1)..(148)
<223> OTHER INFORMATION: Ceres Seq. ID no. 11427495
<220> FEATURE:
<221> NAME/KEY: misc_feature
<222> LOCATION: (44)..(147)
<223> OTHER INFORMATION: PFAM Description: alpha/beta hydrolase fold
<220> FEATURE:
<221> NAME/KEY: misc_feature
<222> LOCATION: (5)..(147)
<223> OTHER INFORMATION: GI NO: 34915034

```
      NR DESCRIPTION: putative acetone-cyanohydrin lyase
<220> FEATURE:
<221> NAME/KEY: misc_feature
<222> LOCATION: (1)..(147)
<223> OTHER INFORMATION: GI NO: 34914020
      NR DESCRIPTION: OJ1014_G12.25
<220> FEATURE:
<221> NAME/KEY: misc_feature
<222> LOCATION: (8)..(141)
<223> OTHER INFORMATION: GI NO: 34914024
      NR DESCRIPTION: OJ1014_G12.27
<220> FEATURE:
<221> NAME/KEY: misc_feature
<222> LOCATION: (19)..(146)
<223> OTHER INFORMATION: GI NO: 34908770
      NR DESCRIPTION: P0415A04.19
<220> FEATURE:
<221> NAME/KEY: misc_feature
<222> LOCATION: (14)..(127)
<223> OTHER INFORMATION: GI NO: 34907174
      NR DESCRIPTION: putative pir7b (Pseudomonas inducible protein)
<220> FEATURE:
<221> NAME/KEY: misc_feature
<222> LOCATION: (14)..(146)
<223> OTHER INFORMATION: GI NO: 34907176
      NR DESCRIPTION: pir7b protein (Pseudomonas inducible protein)
<220> FEATURE:
<221> NAME/KEY: misc_feature
<222> LOCATION: (20)..(146)
<223> OTHER INFORMATION: GI NO: 498747
      NR DESCRIPTION: Pir7b
<220> FEATURE:
<221> NAME/KEY: misc_feature
<222> LOCATION: (20)..(134)
<223> OTHER INFORMATION: GI NO: 7488034
      NR DESCRIPTION: probable (S)-acetone-cyanohydrin lyase
<220> FEATURE:
<221> NAME/KEY: misc_feature
<222> LOCATION: (20)..(125)
<223> OTHER INFORMATION: GI NO: 34907178
      NR DESCRIPTION: pir7a protein (Pseudomonas inducible protein)
<220> FEATURE:
<221> NAME/KEY: misc_feature
<222> LOCATION: (20)..(140)
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (116)..(116)
<223> OTHER INFORMATION: Xaa is any aa, unknown or other
<220> FEATURE:
<221> NAME/KEY: misc_feature
<222> LOCATION: (144)..(144)
<223> OTHER INFORMATION: Xaa is any aa, unknown or other

<400> SEQUENCE: 89

Met Ser Ser Ser Ser Ser Ser Ala Pro Ala Ala Val Ala Thr Ser
1               5                  10                  15

Thr Arg Leu Ile Leu Val His Gly Thr Gly His Gly Gly Trp Cys Trp
            20                  25                  30

Tyr Lys Val Ala Thr Leu Leu Arg Ala Ala Gly His Arg Val Asp Ala
        35                  40                  45

Pro Asp Leu Ala Ala Cys Gly Ala Asp Ala Arg Arg Leu Ser Asp Ala
    50                  55                  60

Pro Thr Phe Glu Asp Tyr Thr Arg Pro Leu Leu Asp Ala Leu Arg Ala
65                  70                  75                  80

Leu Pro Asp Gly Glu Arg Ala Val Leu Val Gly His Ser Phe Gly Gly
                85                  90                  95

Met Ser Val Ala Leu Ala Ala Glu Glu Phe Pro Asp Lys Val Ala Ala
            100                 105                 110

Ala Val Phe Xaa Ser Ala Phe Met Pro Asp Cys Ala Gly Pro Arg Thr
        115                 120                 125
```

-continued

```
Arg Val Ile Glu Gln Val Pro Val Ser Asp Trp Met Asp Ser Val Xaa
    130                 135                 140

Asp Glu Glu His
145

<210> SEQ ID NO 90
<211> LENGTH: 832
<212> TYPE: DNA
<213> ORGANISM: Zea mays subsp. mays
<220> FEATURE:
<221> NAME/KEY: misc_feature
<222> LOCATION: (1)..(832)
<223> OTHER INFORMATION: Ceres Seq. ID no. 12402005

<400> SEQUENCE: 90
accacaccac acgcgccgca aagcagagca cggggggcctg agagcagagc gccatcagcc      60
atcctttgcc tgcccaagca gcaagcagca gcagcaacgg cggctggccc gatggctctg     120
tctctctccg gcacctccgc ccgcttcgcc ctcgcgtcgc tggtcccccg ggccagggcc     180
tacgcggcgt cggcggcgtc cggggccatg aggcgcgcgg cggagggcgc ggccgcgggc     240
gaggccaagg aggccgggcg cgccgccgcc gccgctgccg agggctcgtg ggtgcccgac     300
cccgtcacgg gccactaccg ccccgccaac tgggccgccg ccgtcgaccc cgccgacctc     360
cgcgccgctc acctcgcccg cacctacgcc cgggcctgag cggccccggc tcccttcacc     420
ctgctccgcc tcgtctcgta tgacatacgc gcaccgtacg taccagggtg agacgaggtg     480
aggggtcggg gttcgtgtgg cgaacggcgt gttgagccac gcgcgcgtgc gcccgcgctc     540
tgtgacgccc ggaacgttct tgggagagcg cgagcgaggt cttgtctctt ctcggtgcgg     600
gtcgctgtgc catgtgatgt gatgtgacgc tggatcgttt tgggtccgac caacgggaga     660
agagcggcct gtggtcgccg tcgccgccgt gtgtgggctg gatggcctgc tttcttgtgc     720
tcctcctata tatcagatgt actccctcca aggagcaggg tttcgctacc ttttcgtact     780
cgctacagct acagctagta cgtactatac taataaaagc tgcagttttct tc            832

<210> SEQ ID NO 91
<211> LENGTH: 132
<212> TYPE: PRT
<213> ORGANISM: Zea mays subsp. mays
<220> FEATURE:
<221> NAME/KEY: misc_feature
<222> LOCATION: (1)..(132)
<223> OTHER INFORMATION: Ceres Seq. ID no. 12402006
<220> FEATURE:
<221> NAME/KEY: misc_feature
<222> LOCATION: (38)..(125)
<223> OTHER INFORMATION: PFAM Description: Late embryogenesis abundant
      protein
<220> FEATURE:
<221> NAME/KEY: misc_feature
<222> LOCATION: (32)..(132)
<223> OTHER INFORMATION: GI NO: 7489602
      NR DESCRIPTION: zinc inducible protein homolog
<220> FEATURE:
<221> NAME/KEY: misc_feature
<222> LOCATION: (32)..(112)
<223> OTHER INFORMATION: GI NO: 7489606
      NR DESCRIPTION: zinc-induced protein
<220> FEATURE:
<221> NAME/KEY: misc_feature
<222> LOCATION: (32)..(112)
<223> OTHER INFORMATION: GI NO: 19347607
      NR DESCRIPTION: Ramy1

<400> SEQUENCE: 91

Thr Thr Pro His Ala Pro Gln Ser Arg Ala Arg Gly Pro Glu Ser Arg
```

```
                1               5                   10                  15
Ala Pro Ser Ala Ile Leu Cys Leu Pro Lys Gln Gln Ala Ala Ala
                    20                  25                  30

Thr Ala Ala Gly Pro Met Ala Leu Ser Leu Ser Gly Thr Ser Ala Arg
            35                  40                  45

Phe Ala Leu Ala Ser Leu Val Pro Arg Ala Arg Ala Tyr Ala Ala Ser
    50                  55                  60

Ala Ala Ser Gly Ala Met Arg Arg Ala Ala Glu Gly Ala Ala Ala Gly
65                  70                  75                  80

Glu Ala Lys Glu Ala Gly Arg Ala Ala Ala Ala Ala Glu Gly Ser
                85                  90                  95

Trp Val Pro Asp Pro Val Thr Gly His Tyr Arg Pro Ala Asn Trp Ala
                100                 105                 110

Ala Ala Val Asp Pro Ala Asp Leu Arg Ala Ala His Leu Ala Arg Thr
                115                 120                 125

Tyr Ala Arg Ala
    130
```

<210> SEQ ID NO 92
<211> LENGTH: 95
<212> TYPE: PRT
<213> ORGANISM: Zea mays subsp. mays
<220> FEATURE:
<221> NAME/KEY: misc_feature
<222> LOCATION: (1)..(95)
<223> OTHER INFORMATION: Ceres Seq. ID no. 12402007
<220> FEATURE:
<221> NAME/KEY: misc_feature
<222> LOCATION: (1)..(88)
<223> OTHER INFORMATION: PFAM Description: Late embryogenesis abundant
      protein
<220> FEATURE:
<221> NAME/KEY: misc_feature
<222> LOCATION: (1)..(95)
<223> OTHER INFORMATION: GI NO: 7489602
      NR DESCRIPTION: zinc inducible protein homolog
<220> FEATURE:
<221> NAME/KEY: misc_feature
<222> LOCATION: (1)..(75)
<223> OTHER INFORMATION: GI NO: 7489606
      NR DESCRIPTION: zinc-induced protein
<220> FEATURE:
<221> NAME/KEY: misc_feature
<222> LOCATION: (1)..(75)
<223> OTHER INFORMATION: GI NO: 19347607
      NR DESCRIPTION: Ramy1

<400> SEQUENCE: 92

```
Met Ala Leu Ser Leu Ser Gly Thr Ser Ala Arg Phe Ala Leu Ala Ser
1               5                   10                  15

Leu Val Pro Arg Ala Arg Ala Tyr Ala Ala Ser Ala Ala Ser Gly Ala
                20                  25                  30

Met Arg Arg Ala Ala Glu Gly Ala Ala Ala Gly Glu Ala Lys Glu Ala
            35                  40                  45

Gly Arg Ala Ala Ala Ala Ala Glu Gly Ser Trp Val Pro Asp Pro
    50                  55                  60

Val Thr Gly His Tyr Arg Pro Ala Asn Trp Ala Ala Val Asp Pro
65                  70                  75                  80

Ala Asp Leu Arg Ala Ala His Leu Ala Arg Thr Tyr Ala Arg Ala
                85                  90                  95
```

<210> SEQ ID NO 93
<211> LENGTH: 69
<212> TYPE: PRT

```
<213> ORGANISM: Zea mays subsp. mays
<220> FEATURE:
<221> NAME/KEY: misc_feature
<222> LOCATION: (1)..(69)
<223> OTHER INFORMATION: Ceres Seq. ID no. 12402008
<220> FEATURE:
<221> NAME/KEY: misc_feature
<222> LOCATION: (36)..(69)
<223> OTHER INFORMATION: GI NO: 21219450
      NR DESCRIPTION: putative secreted proline-rich protein
<220> FEATURE:
<221> NAME/KEY: misc_feature
<222> LOCATION: (42)..(69)
<223> OTHER INFORMATION: GI NO: 6523547
      NR DESCRIPTION: hydroxyproline-rich glycoprotein DZ-HRGP
<220> FEATURE:
<221> NAME/KEY: misc_feature
<222> LOCATION: (43)..(69)
<223> OTHER INFORMATION: GI NO: 50728126
      NR DESCRIPTION: PREDICTED: similar to Wiskott-Aldrich
      syndrome gene-like protein; neural Wiskott-Aldrich
      syndrome protein; Wiskott-Aldrich syndrome gene-like
<220> FEATURE:
<221> NAME/KEY: misc_feature
<222> LOCATION: (46)..(69)
<223> OTHER INFORMATION: GI NO: 6649859
      NR DESCRIPTION: kexin-like serine endoprotease
<220> FEATURE:
<221> NAME/KEY: misc_feature
<222> LOCATION: (45)..(69)
<223> OTHER INFORMATION: GI NO: 15706272
      NR DESCRIPTION: N-WASP protein
<220> FEATURE:
<221> NAME/KEY: misc_feature
<222> LOCATION: (43)..(69)
<223> OTHER INFORMATION: GI NO: 6523547
      NR DESCRIPTION: hydroxyproline-rich glycoprotein DZ-HRGP
<220> FEATURE:
<221> NAME/KEY: misc_feature
<222> LOCATION: (5)..(69)
<223> OTHER INFORMATION: GI NO: 23274133
      NR DESCRIPTION: Similar to serine/arginine repetitive matrix 1
<220> FEATURE:
<221> NAME/KEY: misc_feature
<222> LOCATION: (5)..(69)
<223> OTHER INFORMATION: GI NO: 42542379
      NR DESCRIPTION: Ser/Arg-related nuclear matrix protein
<220> FEATURE:
<221> NAME/KEY: misc_feature
<222> LOCATION: (43)..(69)
<223> OTHER INFORMATION: GI NO: 6523547
      NR DESCRIPTION: hydroxyproline-rich glycoprotein DZ-HRGP
<220> FEATURE:
<221> NAME/KEY: misc_feature
<222> LOCATION: (43)..(69)
<223> OTHER INFORMATION: GI NO: 6523547
      NR DESCRIPTION: hydroxyproline-rich glycoprotein DZ-HRGP

<400> SEQUENCE: 93

Pro His His Thr Arg Arg Lys Ala Glu His Gly Gly Leu Arg Ala Glu
1               5                   10                  15

Arg His Gln Pro Ser Phe Ala Cys Pro Ser Ser Lys Gln Gln Gln Gln
            20                  25                  30

Arg Arg Leu Ala Arg Trp Leu Cys Leu Ser Pro Ala Pro Pro Pro Ala
        35                  40                  45

Ser Pro Ser Arg Arg Trp Ser Pro Gly Pro Gly Pro Thr Arg Arg Arg
    50                  55                  60

Arg Arg Pro Gly Pro
65

<210> SEQ ID NO 94
<211> LENGTH: 992
<212> TYPE: DNA
<213> ORGANISM: Zea mays subsp. mays
```

```
<220> FEATURE:
<221> NAME/KEY: misc_feature
<222> LOCATION: (1)..(992)
<223> OTHER INFORMATION: Ceres Seq. ID no. 12391473

<400> SEQUENCE: 94
gcacgagacc attacctaga acatcctaat cgaaaagatc gaagtgtgct tgcgtcctga     60
tcccaccaac cgcagaggac agaggaccat ggagagcggc acggagcggc ggcggcacca    120
cttcgtgctg gtgcacggca cctgccacgg cgcgtggtgc tggtacaagg tggccaccct    180
cctgtcatcc gcgggccacc gcgtgacggc gctggacatg gccgcgtgcg cgcgccagcc    240
cgggcgcgcc gaggaggtgc cgtcctttga ggagtacagc cgcccgctcc tggccacggt    300
ggccggcctg gcgcccgagg agaaggtggt cctcgtcggc cacagcttcg gcggggtcag    360
cctcgcgctg gccatggagc agtacccgga cagggtcgcc gtcgccgtct tcgtcgcgac    420
cggcatgccc tccgctggga agccgatggc gttcgtcttc gagcagtttt tgcaagaaga    480
gtacccagcg gaccgctaca tggactgcga attcgaaacc agcggcgacc cccagcgtcc    540
cgtggagaca tttcggttcg ggccacagta cctgaagcag agactgtacc agctcagccc    600
cccagaggat ttgaccctgg caatggcgat gttgaggccg tcacagcggt tccgagacga    660
cgcgacgatg aagggggcg tcctgacggc ggagcggtac ggcggcgtga ggcgggtgtg    720
cgtcgtcgcc gaggacgacg cgtcagtgcc ggcaggcttc ctgcggcgga tggcgtcgtg    780
gaaccccggc acggaggtga gggggttgca gggagccgat catatgtcca tgctctcgaa    840
accaggggag ctgtcagaac ttctcatgga ggttgccaac aagtacagct gaaacttgta    900
tcatgtaaat ggctatcagc aaaatggttg ttcaggtacg cttgtttcag atgaacaaat    960
ggagacggaa gtttgaagta acacgatgaa at                                   992

<210> SEQ ID NO 95
<211> LENGTH: 267
<212> TYPE: PRT
<213> ORGANISM: Zea mays subsp. mays
<220> FEATURE:
<221> NAME/KEY: misc_feature
<222> LOCATION: (1)..(267)
<223> OTHER INFORMATION: Ceres Seq. ID no. 12391474
<220> FEATURE:
<221> NAME/KEY: misc_feature
<222> LOCATION: (37)..(261)
<223> OTHER INFORMATION: PFAM Description: alpha/beta hydrolase fold
<220> FEATURE:
<221> NAME/KEY: misc_feature
<222> LOCATION: (1)..(266)
<223> OTHER INFORMATION: GI NO: 34907176
      NR DESCRIPTION: pir7b protein (Pseudomonas inducible protein)
<220> FEATURE:
<221> NAME/KEY: misc_feature
<222> LOCATION: (9)..(266)
<223> OTHER INFORMATION: GI NO: 498747
      NR DESCRIPTION: Pir7b
<220> FEATURE:
<221> NAME/KEY: misc_feature
<222> LOCATION: (11)..(266)
<223> OTHER INFORMATION: GI NO: 34907178
      NR DESCRIPTION: pir7a protein (Pseudomonas inducible protein)
<220> FEATURE:
<221> NAME/KEY: misc_feature
<222> LOCATION: (11)..(267)
<223> OTHER INFORMATION: GI NO: 40549303
      NR DESCRIPTION: salicylic acid-binding protein 2
<220> FEATURE:
<221> NAME/KEY: misc_feature
<222> LOCATION: (1)..(118)
<223> OTHER INFORMATION: GI NO: 34907174
      NR DESCRIPTION: putative pir7b (Pseudomonas inducible protein)
<220> FEATURE:
```

```
<221> NAME/KEY: misc_feature
<222> LOCATION: (172)..(266)
<223> OTHER INFORMATION: GI NO: 34907174
      NR DESCRIPTION: putative pir7b (Pseudomonas inducible protein)
<220> FEATURE:
<221> NAME/KEY: misc_feature
<222> LOCATION: (6)..(266)
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (1)..(267)
<223> OTHER INFORMATION: GI NO: 14279437
      NR DESCRIPTION: ethylene-induced esterase
<220> FEATURE:
<221> NAME/KEY: misc_feature
<222> LOCATION: (11)..(267)
<223> OTHER INFORMATION: GI NO: 34908770
      NR DESCRIPTION: P0415A04.19
<220> FEATURE:
<221> NAME/KEY: misc_feature
<222> LOCATION: (12)..(263)
<223> OTHER INFORMATION: GI NO: 21595837
      NR DESCRIPTION: polyneuridine aldehyde esterase

<400> SEQUENCE: 95
```

Met Glu Ser Gly Thr Glu Arg Arg His His Phe Val Leu Val His
1               5                   10                  15

Gly Thr Cys His Gly Ala Trp Cys Trp Tyr Lys Val Ala Thr Leu Leu
            20                  25                  30

Ser Ser Ala Gly His Arg Val Thr Ala Leu Asp Met Ala Ala Cys Gly
        35                  40                  45

Ala Ser Pro Gly Arg Ala Glu Glu Val Pro Ser Phe Glu Glu Tyr Ser
50                  55                  60

Arg Pro Leu Leu Ala Thr Val Ala Gly Leu Ala Pro Glu Glu Lys Val
65                  70                  75                  80

Val Leu Val Gly His Ser Phe Gly Gly Val Ser Leu Ala Leu Ala Met
                85                  90                  95

Glu Gln Tyr Pro Asp Arg Val Ala Val Ala Val Phe Val Ala Thr Gly
            100                 105                 110

Met Pro Ser Ala Gly Lys Pro Met Ala Phe Val Phe Glu Gln Phe Leu
        115                 120                 125

Gln Glu Glu Tyr Pro Ala Asp Arg Tyr Met Asp Cys Glu Phe Glu Thr
130                 135                 140

Ser Gly Asp Pro Gln Arg Pro Val Glu Thr Phe Arg Phe Gly Pro Gln
145                 150                 155                 160

Tyr Leu Lys Gln Arg Leu Tyr Gln Leu Ser Pro Pro Glu Asp Leu Thr
                165                 170                 175

Leu Ala Met Ala Met Leu Arg Pro Ser Gln Arg Phe Arg Asp Asp Ala
            180                 185                 190

Thr Met Lys Gly Gly Val Leu Thr Ala Glu Arg Tyr Gly Gly Val Arg
        195                 200                 205

Arg Val Cys Val Val Ala Glu Asp Asp Ala Ser Val Pro Ala Gly Phe
210                 215                 220

Leu Arg Arg Met Ala Ser Trp Asn Pro Gly Thr Glu Val Arg Gly Leu
225                 230                 235                 240

Gln Gly Ala Asp His Met Ser Met Leu Ser Lys Pro Gly Glu Leu Ser
                245                 250                 255

Glu Leu Leu Met Glu Val Ala Asn Lys Tyr Ser
            260                 265

```
<210> SEQ ID NO 96
```

```
<211> LENGTH: 224
<212> TYPE: PRT
<213> ORGANISM: Zea mays subsp. mays
<220> FEATURE:
<221> NAME/KEY: misc_feature
<222> LOCATION: (1)..(224)
<223> OTHER INFORMATION: Ceres Seq. ID no. 12391475
<220> FEATURE:
<221> NAME/KEY: misc_feature
<222> LOCATION: (1)..(218)
<223> OTHER INFORMATION: PFAM Description: alpha/beta hydrolase fold
<220> FEATURE:
<221> NAME/KEY: misc_feature
<222> LOCATION: (1)..(223)
<223> OTHER INFORMATION: GI NO: 34907176
      NR DESCRIPTION: pir7b protein (Pseudomonas inducible protein)
<220> FEATURE:
<221> NAME/KEY: misc_feature
<222> LOCATION: (1)..(223)
<223> OTHER INFORMATION: GI NO: 498747
      NR DESCRIPTION: Pir7b
<220> FEATURE:
<221> NAME/KEY: misc_feature
<222> LOCATION: (1)..(223)
<223> OTHER INFORMATION: GI NO: 34907178
      NR DESCRIPTION: pir7a protein (Pseudomonas inducible protein)
<220> FEATURE:
<221> NAME/KEY: misc_feature
<222> LOCATION: (1)..(224)
<223> OTHER INFORMATION: GI NO: 40549303
      NR DESCRIPTION: salicylic acid-binding protein 2
<220> FEATURE:
<221> NAME/KEY: misc_feature
<222> LOCATION: (1)..(75)
<223> OTHER INFORMATION: GI NO: 34907174
      NR DESCRIPTION: putative pir7b (Pseudomonas inducible protein)
<220> FEATURE:
<221> NAME/KEY: misc_feature
<222> LOCATION: (129)..(223)
<223> OTHER INFORMATION: GI NO: 34907174
      NR DESCRIPTION: putative pir7b (Pseudomonas inducible protein)
<220> FEATURE:
<221> NAME/KEY: misc_feature
<222> LOCATION: (1)..(223)
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (1)..(224)
<223> OTHER INFORMATION: GI NO: 14279437
      NR DESCRIPTION: ethylene-induced esterase
<220> FEATURE:
<221> NAME/KEY: misc_feature
<222> LOCATION: (1)..(224)
<223> OTHER INFORMATION: GI NO: 34908770
      NR DESCRIPTION: P0415A04.19
<220> FEATURE:
<221> NAME/KEY: misc_feature
<222> LOCATION: (1)..(220)
<223> OTHER INFORMATION: GI NO: 21595837
      NR DESCRIPTION: polyneuridine aldehyde esterase

<400> SEQUENCE: 96

Met Ala Ala Cys Gly Ala Ser Pro Gly Arg Ala Glu Glu Val Pro Ser
1               5                   10                  15

Phe Glu Glu Tyr Ser Arg Pro Leu Leu Ala Thr Val Ala Gly Leu Ala
                20                  25                  30

Pro Glu Glu Lys Val Val Leu Val Gly His Ser Phe Gly Gly Val Ser
            35                  40                  45

Leu Ala Leu Ala Met Glu Gln Tyr Pro Asp Arg Val Ala Val Ala Val
        50                  55                  60

Phe Val Ala Thr Gly Met Pro Ser Ala Gly Lys Pro Met Ala Phe Val
65                  70                  75                  80

Phe Glu Gln Phe Leu Gln Glu Glu Tyr Pro Ala Asp Arg Tyr Met Asp
```

```
                85                  90                  95
Cys Glu Phe Glu Thr Ser Gly Asp Pro Gln Arg Pro Val Glu Thr Phe
            100                 105                 110
Arg Phe Gly Pro Gln Tyr Leu Lys Gln Arg Leu Tyr Gln Leu Ser Pro
            115                 120                 125
Pro Glu Asp Leu Thr Leu Ala Met Ala Met Leu Arg Pro Ser Gln Arg
        130                 135                 140
Phe Arg Asp Asp Ala Thr Met Lys Gly Val Leu Thr Ala Glu Arg
145                 150                 155                 160
Tyr Gly Gly Val Arg Arg Val Cys Val Val Ala Glu Asp Asp Ala Ser
                165                 170                 175
Val Pro Ala Gly Phe Leu Arg Arg Met Ala Ser Trp Asn Pro Gly Thr
            180                 185                 190
Glu Val Arg Gly Leu Gln Gly Ala Asp His Met Ser Met Leu Ser Lys
            195                 200                 205
Pro Gly Glu Leu Ser Glu Leu Leu Met Glu Val Ala Asn Lys Tyr Ser
        210                 215                 220

<210> SEQ ID NO 97
<211> LENGTH: 172
<212> TYPE: PRT
<213> ORGANISM: Zea mays subsp. mays
<220> FEATURE:
<221> NAME/KEY: misc_feature
<222> LOCATION: (1)..(172)
<223> OTHER INFORMATION: Ceres Seq. ID no. 12391476
<220> FEATURE:
<221> NAME/KEY: misc_feature
<222> LOCATION: (1)..(166)
<223> OTHER INFORMATION: PFAM Description: alpha/beta hydrolase fold
<220> FEATURE:
<221> NAME/KEY: misc_feature
<222> LOCATION: (1)..(171)
<223> OTHER INFORMATION: GI NO: 34907176
      NR DESCRIPTION: pir7b protein (Pseudomonas inducible protein)
<220> FEATURE:
<221> NAME/KEY: misc_feature
<222> LOCATION: (1)..(171)
<223> OTHER INFORMATION: GI NO: 498747
      NR DESCRIPTION: Pir7b
<220> FEATURE:
<221> NAME/KEY: misc_feature
<222> LOCATION: (1)..(171)
<223> OTHER INFORMATION: GI NO: 34907178
      NR DESCRIPTION: pir7a protein (Pseudomonas inducible protein)
<220> FEATURE:
<221> NAME/KEY: misc_feature
<222> LOCATION: (1)..(172)
<223> OTHER INFORMATION: GI NO: 40549303
      NR DESCRIPTION: salicylic acid-binding protein 2
<220> FEATURE:
<221> NAME/KEY: misc_feature
<222> LOCATION: (1)..(23)
<223> OTHER INFORMATION: GI NO: 34907174
      NR DESCRIPTION: putative pir7b (Pseudomonas inducible protein)
<220> FEATURE:
<221> NAME/KEY: misc_feature
<222> LOCATION: (77)..(171)
<223> OTHER INFORMATION: GI NO: 34907174
      NR DESCRIPTION: putative pir7b (Pseudomonas inducible protein)
<220> FEATURE:
<221> NAME/KEY: misc_feature
<222> LOCATION: (1)..(171)
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (1)..(172)
<223> OTHER INFORMATION: GI NO: 14279437
      NR DESCRIPTION: ethylene-induced esterase
<220> FEATURE:
```

```
<221> NAME/KEY: misc_feature
<222> LOCATION: (1)..(172)
<223> OTHER INFORMATION: GI NO: 34908770
      NR DESCRIPTION: P0415A04.19
<220> FEATURE:
<221> NAME/KEY: misc_feature
<222> LOCATION: (1)..(168)
<223> OTHER INFORMATION: GI NO: 21595837
      NR DESCRIPTION: polyneuridine aldehyde esterase

<400> SEQUENCE: 97
```

Met Glu Gln Tyr Pro Asp Arg Val Ala Val Ala Phe Val Ala Thr
1               5                   10                  15

Gly Met Pro Ser Ala Gly Lys Pro Met Ala Phe Val Phe Glu Gln Phe
            20                  25                  30

Leu Gln Glu Glu Tyr Pro Ala Asp Arg Tyr Met Asp Cys Glu Phe Glu
        35                  40                  45

Thr Ser Gly Asp Pro Gln Arg Pro Val Glu Thr Phe Arg Phe Gly Pro
    50                  55                  60

Gln Tyr Leu Lys Gln Arg Leu Tyr Gln Leu Ser Pro Pro Glu Asp Leu
65              70                  75                  80

Thr Leu Ala Met Ala Met Leu Arg Pro Ser Gln Arg Phe Arg Asp Asp
                85                  90                  95

Ala Thr Met Lys Gly Gly Val Leu Thr Ala Glu Arg Tyr Gly Gly Val
            100                 105                 110

Arg Arg Val Cys Val Val Ala Glu Asp Asp Ala Ser Val Pro Ala Gly
        115                 120                 125

Phe Leu Arg Arg Met Ala Ser Trp Asn Pro Gly Thr Glu Val Arg Gly
    130                 135                 140

Leu Gln Gly Ala Asp His Met Ser Met Leu Ser Lys Pro Gly Glu Leu
145             150                 155                 160

Ser Glu Leu Leu Met Glu Val Ala Asn Lys Tyr Ser
                165                 170

```
<210> SEQ ID NO 98
<211> LENGTH: 953
<212> TYPE: DNA
<213> ORGANISM: Zea mays subsp. mays
<220> FEATURE:
<221> NAME/KEY: misc_feature
<222> LOCATION: (1)..(953)
<223> OTHER INFORMATION: Ceres Seq. ID no. 13599613

<400> SEQUENCE: 98
aggaaataat atacaaaatc aaaggttaag aaaaaaaatg ggtgaggaga agaatcagca      60
gcacttcgtg ctagtacatg gtgcatgcca cggcgcgtgg tgctggaaca aggttaagcc    120
gcttctcgag gcctccggcc accgcgtaac cgccttagac ctagctgctt cgggtataga    180
cacaaccagg tctatcactg agatctccac atgcgaacaa tactctgagc cattgataca    240
gctaatcgcc tcattaccaa gtgatgagaa ggttgtgctc gttggtcata gctttggagg    300
gttcagctta gccatggcca tggataagtt tccagacaaa atctctgtct cagtcttcgt    360
gactgctttc atgcccgata ccaaacactc accatcgttc gtcgtggata gtttaaacg     420 ggatacgcca ccagaagcat ggttgggctc ggagttcaaa tcatatggct cagacaattc    480
cggtgtgtca atgtctttca gcactgagtt catgaagcac gctctctatc aactttctcc    540
tgttgaggat attgagcttg gattgctttt aaagaggccc ggatcattgt tcatcaacga    600
tttatccaag gtggagaact tttcggacaa agggtatgga tctgttcctc gagcttacat    660
tgtgtgcaaa gaggacaaaa caattacaaa agaaattcag tggtggatga tcgataatta    720
```

```
tccgacgaaa gtagtgaagg agatggagga cacagatcat atgccaatgt tctgcaagcc    780
tcagttacta agtgactatc tcttggaaat cgcggaaaaa ttagcttaaa ttatcttgtt    840
atgaaaatgt atttggatac aaataagtgt tgtcctgcaa atgggtcttt ctaaagatca    900 agactttat cgcgttcaaa tgtttgacat aatttaaaat aaacttaaca gtc            953
```

```
<210> SEQ ID NO 99
<211> LENGTH: 275
<212> TYPE: PRT
<213> ORGANISM: Zea mays subsp. mays
<220> FEATURE:
<221> NAME/KEY: misc_feature
<222> LOCATION: (1)..(275)
<223> OTHER INFORMATION: Ceres Seq. ID no. 15218860
<220> FEATURE:
<221> NAME/KEY: misc_feature
<222> LOCATION: (47)..(268)
<223> OTHER INFORMATION: PFAM Description: alpha/beta hydrolase fold
<220> FEATURE:
<221> NAME/KEY: misc_feature
<222> LOCATION: (13)..(275)
<223> OTHER INFORMATION: GI NO: 21554666
      NR DESCRIPTION: putative acetone-cyanohydrin lyase
<220> FEATURE:
<221> NAME/KEY: misc_feature
<222> LOCATION: (13)..(273)
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (19)..(275)
<223> OTHER INFORMATION: GI NO: 14279437
      NR DESCRIPTION: ethylene-induced esterase
<220> FEATURE:
<221> NAME/KEY: misc_feature
<222> LOCATION: (17)..(273)
<223> OTHER INFORMATION: GI NO: 40549303
      NR DESCRIPTION: salicylic acid-binding protein 2
<220> FEATURE:
<221> NAME/KEY: misc_feature
<222> LOCATION: (20)..(275)
<223> OTHER INFORMATION: GI NO: 34908770
      NR DESCRIPTION: P0415A04.19
<220> FEATURE:
<221> NAME/KEY: misc_feature
<222> LOCATION: (23)..(275)
<223> OTHER INFORMATION: GI NO: 34915034
      NR DESCRIPTION: putative acetone-cyanohydrin lyase
<220> FEATURE:
<221> NAME/KEY: misc_feature
<222> LOCATION: (22)..(272)
<223> OTHER INFORMATION: GI NO: 21595837
      NR DESCRIPTION: polyneuridine aldehyde esterase
<220> FEATURE:
<221> NAME/KEY: misc_feature
<222> LOCATION: (15)..(272)
<223> OTHER INFORMATION: GI NO: 25404802
      NR DESCRIPTION: probable alpha/beta hydrolase F23O10.18
<220> FEATURE:
<221> NAME/KEY: misc_feature
<222> LOCATION: (55)..(255)
<223> OTHER INFORMATION: GI NO: 25518436
      NR DESCRIPTION: hypothetical protein T1K7.26
<220> FEATURE:
<221> NAME/KEY: misc_feature
<222> LOCATION: (22)..(130)
<223> OTHER INFORMATION: GI NO: 21222782
      NR DESCRIPTION: putative esterase

<400> SEQUENCE: 99

Gly Asn Asn Ile Gln Asn Gln Arg Leu Arg Lys Lys Met Gly Glu Glu
1               5                   10                  15

Lys Asn Gln Gln His Phe Val Leu Val His Gly Ala Cys His Gly Ala
            20                  25                  30
```

Trp Cys Trp Asn Lys Val Lys Pro Leu Leu Glu Ala Ser Gly His Arg
         35                  40                  45

Val Thr Ala Leu Asp Leu Ala Ala Ser Gly Ile Asp Thr Thr Arg Ser
 50                  55                  60

Ile Thr Glu Ile Ser Thr Cys Glu Gln Tyr Ser Glu Pro Leu Ile Gln
 65                  70                  75                  80

Leu Ile Ala Ser Leu Pro Ser Asp Glu Lys Val Val Leu Val Gly His
                 85                  90                  95

Ser Phe Gly Gly Phe Ser Leu Ala Met Ala Met Asp Lys Phe Pro Asp
                100                 105                 110

Lys Ile Ser Val Ser Val Phe Val Thr Ala Phe Met Pro Asp Thr Lys
                115                 120                 125

His Ser Pro Ser Phe Val Val Asp Lys Phe Lys Arg Asp Thr Pro Pro
        130                 135                 140

Glu Ala Trp Leu Gly Ser Glu Phe Lys Ser Tyr Gly Ser Asp Asn Ser
145                 150                 155                 160

Gly Val Ser Met Ser Phe Ser Thr Glu Phe Met Lys His Ala Leu Tyr
                165                 170                 175

Gln Leu Ser Pro Val Glu Asp Ile Glu Leu Gly Leu Leu Leu Lys Arg
                180                 185                 190

Pro Gly Ser Leu Phe Ile Asn Asp Leu Ser Lys Val Glu Asn Phe Ser
        195                 200                 205

Asp Lys Gly Tyr Gly Ser Val Pro Arg Ala Tyr Ile Val Cys Lys Glu
210                 215                 220

Asp Lys Thr Ile Thr Lys Glu Ile Gln Trp Trp Met Ile Asp Asn Tyr
225                 230                 235                 240

Pro Thr Lys Val Val Lys Glu Met Glu Asp Thr Asp His Met Pro Met
                245                 250                 255

Phe Cys Lys Pro Gln Leu Leu Ser Asp Tyr Leu Leu Glu Ile Ala Glu
        260                 265                 270

Lys Leu Ala
        275

<210> SEQ ID NO 100
<211> LENGTH: 263
<212> TYPE: PRT
<213> ORGANISM: Zea mays subsp. mays
<220> FEATURE:
<221> NAME/KEY: misc_feature
<222> LOCATION: (1)..(263)
<223> OTHER INFORMATION: Ceres Seq. ID no. 15218861
<220> FEATURE:
<221> NAME/KEY: misc_feature
<222> LOCATION: (35)..(256)
<223> OTHER INFORMATION: PFAM Description: alpha/beta hydrolase fold
<220> FEATURE:
<221> NAME/KEY: misc_feature
<222> LOCATION: (1)..(263)
<223> OTHER INFORMATION: GI NO: 21554666
    NR DESCRIPTION: putative acetone-cyanohydrin lyase
<220> FEATURE:
<221> NAME/KEY: misc_feature
<222> LOCATION: (1)..(261)
<223> OTHER INFORMATION: GI NO: 27754457
    NR DESCRIPTION: putative acetone-cyanohydrin lyase
<220> FEATURE:
<221> NAME/KEY: misc_feature
<222> LOCATION: (7)..(263)
<223> OTHER INFORMATION: GI NO: 14279437
    NR DESCRIPTION: ethylene-induced esterase
<220> FEATURE:
<221> NAME/KEY: misc_feature
<222> LOCATION: (5)..(261)

-continued

```
<223> OTHER INFORMATION: GI NO: 40549303
      NR DESCRIPTION: salicylic acid-binding protein 2
<220> FEATURE:
<221> NAME/KEY: misc_feature
<222> LOCATION: (8)..(263)
<223> OTHER INFORMATION: GI NO: 34908770
      NR DESCRIPTION: P0415A04.19
<220> FEATURE:
<221> NAME/KEY: misc_feature
<222> LOCATION: (11)..(263)
<223> OTHER INFORMATION: GI NO: 34915034
      NR DESCRIPTION: putative acetone-cyanohydrin lyase
<220> FEATURE:
<221> NAME/KEY: misc_feature
<222> LOCATION: (10)..(260)
<223> OTHER INFORMATION: GI NO: 21595837
      NR DESCRIPTION: polyneuridine aldehyde esterase
<220> FEATURE:
<221> NAME/KEY: misc_feature
<222> LOCATION: (3)..(260)
<223> OTHER INFORMATION: GI NO: 25404802
      NR DESCRIPTION: probable alpha/beta hydrolase F23O10.18
<220> FEATURE:
<221> NAME/KEY: misc_feature
<222> LOCATION: (43)..(243)
<223> OTHER INFORMATION: GI NO: 25518436
      NR DESCRIPTION: hypothetical protein T1K7.26
<220> FEATURE:
<221> NAME/KEY: misc_feature
<222> LOCATION: (10)..(118)
<223> OTHER INFORMATION: GI NO: 21222782
      NR DESCRIPTION: putative esterase

<400> SEQUENCE: 100

Met Gly Glu Glu Lys Asn Gln Gln His Phe Val Leu Val His Gly Ala
 1               5                  10                  15

Cys His Gly Ala Trp Cys Trp Asn Lys Val Lys Pro Leu Leu Glu Ala
                20                  25                  30

Ser Gly His Arg Val Thr Ala Leu Asp Leu Ala Ala Ser Gly Ile Asp
            35                  40                  45

Thr Thr Arg Ser Ile Thr Glu Ile Ser Thr Cys Glu Gln Tyr Ser Glu
        50                  55                  60

Pro Leu Ile Gln Leu Ile Ala Ser Leu Pro Ser Asp Glu Lys Val Val
65                  70                  75                  80

Leu Val Gly His Ser Phe Gly Gly Phe Ser Leu Ala Met Ala Met Asp
                85                  90                  95

Lys Phe Pro Asp Lys Ile Ser Val Ser Val Phe Val Thr Ala Phe Met
            100                 105                 110

Pro Asp Thr Lys His Ser Pro Ser Phe Val Val Asp Lys Phe Lys Arg
        115                 120                 125

Asp Thr Pro Pro Glu Ala Trp Leu Gly Ser Glu Phe Lys Ser Tyr Gly
    130                 135                 140

Ser Asp Asn Ser Gly Val Ser Met Ser Phe Ser Thr Glu Phe Met Lys
145                 150                 155                 160

His Ala Leu Tyr Gln Leu Ser Pro Val Glu Asp Ile Glu Leu Gly Leu
                165                 170                 175

Leu Leu Lys Arg Pro Gly Ser Leu Phe Ile Asn Asp Leu Ser Lys Val
            180                 185                 190

Glu Asn Phe Ser Asp Lys Gly Tyr Gly Ser Val Pro Arg Ala Tyr Ile
        195                 200                 205

Val Cys Lys Glu Asp Lys Thr Ile Thr Lys Glu Ile Gln Trp Trp Met
    210                 215                 220

Ile Asp Asn Tyr Pro Thr Lys Val Val Lys Glu Met Glu Asp Thr Asp
225                 230                 235                 240
```

-continued

```
His Met Pro Met Phe Cys Lys Pro Gln Leu Leu Ser Asp Tyr Leu Leu
            245                 250                 255

Glu Ile Ala Glu Lys Leu Ala
            260

<210> SEQ ID NO 101
<211> LENGTH: 171
<212> TYPE: PRT
<213> ORGANISM: Zea mays subsp. mays
<220> FEATURE:
<221> NAME/KEY: misc_feature
<222> LOCATION: (1)..(171)
<223> OTHER INFORMATION: Ceres Seq. ID no. 15218862
<220> FEATURE:
<221> NAME/KEY: misc_feature
<222> LOCATION: (1)..(164)
<223> OTHER INFORMATION: PFAM Description: alpha/beta hydrolase fold
<220> FEATURE:
<221> NAME/KEY: misc_feature
<222> LOCATION: (1)..(171)
<223> OTHER INFORMATION: GI NO: 21554666
      NR DESCRIPTION: putative acetone-cyanohydrin lyase
<220> FEATURE:
<221> NAME/KEY: misc_feature
<222> LOCATION: (1)..(169)
<223> OTHER INFORMATION: GI NO: 27754457
      NR DESCRIPTION: putative acetone-cyanohydrin lyase
<220> FEATURE:
<221> NAME/KEY: misc_feature
<222> LOCATION: (1)..(171)
<223> OTHER INFORMATION: GI NO: 14279437
      NR DESCRIPTION: ethylene-induced esterase
<220> FEATURE:
<221> NAME/KEY: misc_feature
<222> LOCATION: (1)..(169)
<223> OTHER INFORMATION: GI NO: 40549303
      NR DESCRIPTION: salicylic acid-binding protein 2
<220> FEATURE:
<221> NAME/KEY: misc_feature
<222> LOCATION: (1)..(171)
<223> OTHER INFORMATION: GI NO: 34908770
      NR DESCRIPTION: P0415A04.19
<220> FEATURE:
<221> NAME/KEY: misc_feature
<222> LOCATION: (1)..(171)
<223> OTHER INFORMATION: GI NO: 34915034
      NR DESCRIPTION: putative acetone-cyanohydrin lyase
<220> FEATURE:
<221> NAME/KEY: misc_feature
<222> LOCATION: (1)..(168)
<223> OTHER INFORMATION: GI NO: 21595837
      NR DESCRIPTION: polyneuridine aldehyde esterase
<220> FEATURE:
<221> NAME/KEY: misc_feature
<222> LOCATION: (1)..(168)
<223> OTHER INFORMATION: GI NO: 25404802
      NR DESCRIPTION: probable alpha/beta hydrolase F23O10.18
<220> FEATURE:
<221> NAME/KEY: misc_feature
<222> LOCATION: (1)..(151)
<223> OTHER INFORMATION: GI NO: 25518436
      NR DESCRIPTION: hypothetical protein T1K7.26
<220> FEATURE:
<221> NAME/KEY: misc_feature
<222> LOCATION: (1)..(26)
<223> OTHER INFORMATION: GI NO: 21222782
      NR DESCRIPTION: putative esterase

<400> SEQUENCE: 101

Met Ala Met Asp Lys Phe Pro Asp Lys Ile Ser Val Ser Val Phe Val
1               5                   10                  15

Thr Ala Phe Met Pro Asp Thr Lys His Ser Pro Ser Phe Val Val Asp
            20                  25                  30

Lys Phe Lys Arg Asp Thr Pro Pro Glu Ala Trp Leu Gly Ser Glu Phe
        35                  40                  45
```

```
Lys Ser Tyr Gly Ser Asp Asn Ser Gly Val Ser Met Ser Phe Ser Thr
        50                  55                  60
Glu Phe Met Lys His Ala Leu Tyr Gln Leu Ser Pro Val Glu Asp Ile
 65                  70                  75                  80
Glu Leu Gly Leu Leu Lys Arg Pro Gly Ser Leu Phe Ile Asn Asp
                85                  90                  95
Leu Ser Lys Val Glu Asn Phe Ser Asp Lys Gly Tyr Gly Ser Val Pro
            100                 105                 110
Arg Ala Tyr Ile Val Cys Lys Glu Asp Lys Thr Ile Thr Lys Glu Ile
            115                 120                 125
Gln Trp Trp Met Ile Asp Asn Tyr Pro Thr Lys Val Val Lys Glu Met
130                 135                 140
Glu Asp Thr Asp His Met Pro Met Phe Cys Lys Pro Gln Leu Leu Ser
145                 150                 155                 160
Asp Tyr Leu Leu Glu Ile Ala Glu Lys Leu Ala
            165                 170

<210> SEQ ID NO 102
<211> LENGTH: 279
<212> TYPE: DNA
<213> ORGANISM: Brassica napus
<220> FEATURE:
<221> NAME/KEY: misc_feature
<222> LOCATION: (1)..(279)
<223> OTHER INFORMATION: Ceres Seq. ID no. 4779038
<220> FEATURE:
<221> NAME/KEY: misc_feature
<222> LOCATION: (198)..(198)
<223> OTHER INFORMATION: n is a, c, t, g, unknown, or other

<400> SEQUENCE: 102
aagaacatct caaacatttt tattcttcat tcaatatttt gagacccccc cacacacaca      60
ctcatataat catttatcct cataaaccct aaacccctacc tagtttcagc aactatattg    120
ttccaaatcc aagagaaagg gttagattct ttttcaatgg ccaaagttgg gaagctgaca    180
aagctcaagt cggcgatnaa gaaatggcct tcattcgcca agaaccacca ccactcatcc    240
tcctcagccg ccgtctccga tgagctctca gaggacaac                           279

<210> SEQ ID NO 103
<211> LENGTH: 41
<212> TYPE: PRT
<213> ORGANISM: Brassica napus
<220> FEATURE:
<221> NAME/KEY: misc_feature
<222> LOCATION: (1)..(41)
<223> OTHER INFORMATION: Ceres Seq. ID no. 4779039
<220> FEATURE:
<221> NAME/KEY: misc_feature
<222> LOCATION: (14)..(14)
<223> OTHER INFORMATION: Xaa is any aa, unknown or other

<400> SEQUENCE: 103

Met Ala Lys Val Gly Lys Leu Thr Lys Leu Lys Ser Ala Xaa Lys Lys
1               5                   10                  15
Trp Pro Ser Phe Ala Lys Asn His His Ser Ser Ser Ser Ala Ala
            20                  25                  30
Val Ser Asp Glu Leu Ser Glu Asp Asn
            35                  40

<210> SEQ ID NO 104
<211> LENGTH: 263
<212> TYPE: PRT
```

```
<213> ORGANISM: Arabidopsis thaliana
<220> FEATURE:
<221> NAME/KEY: misc_feature
<222> LOCATION: (1)..(263)
<223> OTHER INFORMATION: Public GI no. 48310671
<220> FEATURE:
<221> NAME/KEY: misc_feature
<222> LOCATION: (1)..(263)
<223> OTHER INFORMATION: Ortholog of Ceres CDNA ID no. 12333678
      at SEQ ID NO. 12
      with e-value of 1.59E-115 and percent identity of 80.61

<400> SEQUENCE: 104
```

Met Ser Glu Glu Lys Arg Lys Gln His Phe Val Leu Val His Gly Ser
1               5                   10                  15

Cys His Gly Ala Trp Cys Trp Tyr Lys Val Lys Pro Leu Leu Glu Ala
            20                  25                  30

Val Gly His Arg Val Thr Ala Val Asp Leu Ala Ala Ser Gly Ile Asp
        35                  40                  45

Thr Thr Arg Ser Ile Thr Asp Ile Pro Thr Cys Glu Gln Tyr Ser Glu
50                  55                  60

Pro Leu Thr Lys Leu Leu Thr Ser Leu Pro Asn Asp Glu Lys Val Val
65                  70                  75                  80

Leu Val Gly His Ser Phe Gly Gly Leu Asn Leu Ala Ile Ala Met Glu
                85                  90                  95

Lys Phe Pro Glu Lys Ile Ser Val Ala Val Phe Leu Thr Ala Phe Met
            100                 105                 110

Pro Asp Thr Glu His Ser Pro Ser Phe Val Leu Asp Lys Phe Gly Ser
        115                 120                 125

Asn Met Pro Gln Glu Ala Trp Met Gly Thr Glu Phe Glu Pro Tyr Gly
130                 135                 140

Ser Asp Asn Ser Gly Leu Ser Met Phe Phe Ser Pro Asp Phe Met Lys
145                 150                 155                 160

Leu Gly Leu Tyr Gln Leu Ser Pro Val Glu Asp Leu Glu Leu Gly Leu
                165                 170                 175

Leu Leu Met Arg Pro Gly Ser Leu Phe Ile Asn Asp Leu Ser Lys Met
            180                 185                 190

Lys Asn Phe Ser Asp Glu Gly Tyr Gly Ser Val Pro Arg Val Phe Ile
        195                 200                 205

Val Cys Lys Glu Asp Lys Ala Ile Pro Glu Glu Arg Gln Arg Trp Met
210                 215                 220

Ile Asp Asn Phe Pro Val Asn Leu Val Met Glu Met Glu Glu Thr Asp
225                 230                 235                 240

His Met Pro Met Phe Cys Lys Pro Gln Gln Leu Ser Asp Tyr Phe Leu
                245                 250                 255

Lys Ile Ala Asp Lys Phe Val
            260

```
<210> SEQ ID NO 105
<211> LENGTH: 263
<212> TYPE: PRT
<213> ORGANISM: Arabidopsis thaliana
<220> FEATURE:
<221> NAME/KEY: misc_feature
<222> LOCATION: (1)..(263)
<223> OTHER INFORMATION: Ceres CLONE ID no. 1010900
<220> FEATURE:
<221> NAME/KEY: misc_feature
<222> LOCATION: (1)..(263)
<223> OTHER INFORMATION: Ortholog of Ceres CDNA ID no. 12333678
      at SEQ ID NO. 12
      with e-value of 1.40E-115 and percent identity of 80.61
```

<400> SEQUENCE: 105

```
Met Ser Glu Glu Lys Arg Lys Gln His Phe Val Leu Val His Gly Ser
1               5                   10                  15

Cys His Gly Ala Trp Cys Trp Tyr Lys Val Lys Pro Leu Leu Glu Ala
                20                  25                  30

Val Gly His Arg Val Thr Ala Val Asp Leu Ala Ala Ser Gly Ile Asp
            35                  40                  45

Thr Thr Arg Ser Ile Thr Asp Ile Pro Thr Cys Glu Gln Tyr Ser Glu
50                  55                  60

Pro Leu Thr Lys Leu Leu Thr Ser Leu Pro Asn Asp Glu Lys Val Val
65                  70                  75                  80

Leu Val Gly His Ser Phe Gly Gly Leu Asn Leu Ala Ile Ala Met Glu
                85                  90                  95

Lys Phe Pro Glu Lys Ile Ser Val Ala Val Phe Leu Thr Ala Phe Met
                100                 105                 110

Pro Asp Thr Glu His Ser Pro Ser Phe Val Leu Asp Lys Phe Gly Ser
            115                 120                 125

Asn Met Pro Gln Glu Ala Trp Met Gly Thr Glu Phe Glu Pro Tyr Gly
130                 135                 140

Ser Asp Asn Ser Gly Leu Ser Met Phe Phe Ser Pro Asp Phe Met Lys
145                 150                 155                 160

Leu Gly Leu Tyr Gln Leu Ser Pro Val Glu Asp Glu Leu Gly Leu
                165                 170                 175

Leu Leu Met Arg Pro Gly Ser Leu Phe Ile Asn Asp Leu Ser Lys Met
            180                 185                 190

Lys Asn Phe Ser Asp Glu Gly Tyr Gly Ser Val Pro Arg Val Phe Ile
                195                 200                 205

Val Cys Lys Glu Asp Lys Ala Ile Pro Glu Glu Arg Gln Arg Trp Met
210                 215                 220

Ile Asp Asn Phe Pro Val Asn Leu Val Met Glu Met Glu Glu Thr Asp
225                 230                 235                 240

His Met Pro Met Phe Cys Lys Pro Gln Gln Leu Ser Asp Tyr Phe Leu
                245                 250                 255

Lys Ile Ala Asp Lys Phe Val
            260
```

<210> SEQ ID NO 106
<211> LENGTH: 263
<212> TYPE: PRT
<213> ORGANISM: Arabidopsis thaliana
<220> FEATURE:
<221> NAME/KEY: misc_feature
<222> LOCATION: (1)..(263)
<223> OTHER INFORMATION: Public GI no. 27754457
<220> FEATURE:
<221> NAME/KEY: misc_feature
<222> LOCATION: (1)..(263)
<223> OTHER INFORMATION: Ortholog of Ceres CDNA ID no. 12333678
    at SEQ ID NO. 12
    with e-value of 2.89E-115 and percent identity of 80.61

<400> SEQUENCE: 106

```
Met Ser Glu Glu Lys Arg Lys Gln His Phe Val Leu Val His Gly Ser
1               5                   10                  15

Cys His Gly Ala Trp Cys Trp Tyr Lys Val Lys Pro Leu Leu Glu Ala
                20                  25                  30

Val Gly His Arg Val Thr Ala Val Asp Leu Ala Ala Ser Gly Ile Asp
            35                  40                  45
```

Thr Thr Arg Ser Ile Thr Asp Ile Pro Thr Cys Glu Gln Tyr Ser Glu
                50                  55                  60

Pro Leu Thr Lys Leu Leu Thr Ser Leu Pro Asn Asp Glu Lys Val Val
 65                  70                  75                  80

Leu Val Gly His Ser Phe Gly Gly Leu Asn Leu Ala Ile Ala Met Glu
                 85                  90                  95

Lys Phe Pro Lys Lys Ile Ser Val Ala Val Phe Leu Thr Ala Phe Met
                100                 105                 110

Pro Asp Thr Glu His Ser Pro Ser Phe Val Leu Asp Lys Phe Gly Ser
                115                 120                 125

Asn Met Pro Gln Glu Ala Trp Met Gly Thr Glu Phe Glu Pro Tyr Gly
            130                 135                 140

Ser Asp Asn Ser Gly Leu Ser Met Phe Phe Ser Pro Asp Phe Met Lys
145                 150                 155                 160

Leu Gly Leu Tyr Gln Leu Ser Pro Val Glu Asp Leu Glu Leu Gly Leu
                165                 170                 175

Leu Leu Met Arg Pro Gly Ser Leu Phe Ile Asn Asp Leu Ser Lys Met
            180                 185                 190

Lys Asn Phe Ser Asp Glu Gly Tyr Gly Ser Val Pro Arg Val Phe Ile
                195                 200                 205

Val Cys Lys Glu Asp Lys Ala Ile Pro Glu Gly Arg Gln Arg Trp Met
210                 215                 220

Ile Asp Asn Phe Pro Val Asn Leu Val Met Glu Met Glu Glu Thr Asp
225                 230                 235                 240

His Met Pro Met Phe Cys Lys Pro Gln Gln Leu Ser Asp Tyr Phe Leu
                245                 250                 255

Lys Ile Ala Asp Lys Phe Val
            260

<210> SEQ ID NO 107
<211> LENGTH: 263
<212> TYPE: PRT
<213> ORGANISM: Zea mays
<220> FEATURE:
<221> NAME/KEY: misc_feature
<222> LOCATION: (1)..(263)
<223> OTHER INFORMATION: Ceres CLONE ID no. 1065042
<220> FEATURE:
<221> NAME/KEY: misc_feature
<222> LOCATION: (1)..(263)
<223> OTHER INFORMATION: Ortholog of  Ceres CDNA ID no. 12333678
      at SEQ ID NO. 12
      with e-value of 8.69E-114 and percent identity of 79.85

<400> SEQUENCE: 107

Met Gly Glu Glu Lys Asn Gln Gln His Phe Val Leu Val His Gly Ala
 1               5                  10                  15

Cys His Gly Ala Trp Cys Trp Asn Lys Val Lys Pro Leu Leu Glu Ala
                20                  25                  30

Ser Gly His Arg Val Thr Ala Leu Asp Leu Ala Ala Ser Gly Ile Asp
            35                  40                  45

Thr Thr Arg Ser Ile Thr Glu Ile Ser Thr Cys Glu Gln Tyr Ser Glu
 50                  55                  60

Pro Leu Ile Gln Leu Ile Ala Ser Leu Pro Ser Asp Glu Lys Val Val
 65                  70                  75                  80

Leu Val Gly His Ser Phe Gly Gly Phe Ser Leu Ala Met Ala Met Asp
                 85                  90                  95

Lys Phe Pro Asp Lys Ile Ser Val Ser Val Phe Val Thr Ala Phe Met

```
            100                 105                 110
Pro Asp Thr Lys His Ser Pro Ser Phe Val Val Asp Lys Phe Lys Arg
            115                 120                 125

Asp Thr Pro Pro Glu Ala Trp Leu Gly Ser Glu Phe Lys Ser Tyr Gly
            130                 135                 140

Ser Asp Asn Ser Gly Val Ser Met Ser Phe Ser Thr Glu Phe Met Lys
145                 150                 155                 160

His Ala Leu Tyr Gln Leu Ser Pro Val Glu Asp Ile Glu Leu Gly Leu
                165                 170                 175

Leu Leu Lys Arg Pro Gly Ser Leu Phe Ile Asn Asp Leu Ser Lys Val
            180                 185                 190

Glu Asn Phe Ser Asp Lys Gly Tyr Gly Ser Val Pro Arg Ala Tyr Ile
            195                 200                 205

Val Cys Lys Glu Asp Lys Thr Ile Thr Lys Glu Ile Gln Trp Trp Met
            210                 215                 220

Ile Asp Asn Tyr Pro Thr Lys Val Val Lys Glu Met Glu Asp Thr Asp
225                 230                 235                 240

His Met Pro Met Phe Cys Lys Pro Gln Leu Leu Ser Asp Tyr Leu Leu
                245                 250                 255

Glu Ile Ala Glu Lys Leu Ala
            260

<210> SEQ ID NO 108
<211> LENGTH: 272
<212> TYPE: PRT
<213> ORGANISM: Arabidopsis thaliana
<220> FEATURE:
<221> NAME/KEY: misc_feature
<222> LOCATION: (1)..(272)
<223> OTHER INFORMATION: Public GI no. 3242720
<220> FEATURE:
<221> NAME/KEY: misc_feature
<222> LOCATION: (1)..(272)
<223> OTHER INFORMATION: Ortholog of Ceres CDNA ID no. 12333678
      at SEQ ID NO. 12
      with e-value of 6.40E-110 and percent identity of 83.07

<400> SEQUENCE: 108

Met Tyr Glu Asn Gly Ile Ser Phe Ile Ile Ser Leu Leu Ile Cys Gly
1               5                   10                  15

Cys Val Lys Ser Glu Glu Met Met Lys Gln His Phe Val Leu Val His
            20                  25                  30

Gly Ser Cys Leu Gly Ala Trp Cys Trp Tyr Lys Val Lys Pro Leu Leu
        35                  40                  45

Glu Ala Ser Gly His Arg Val Thr Ala Leu Asp Leu Ala Ala Cys Gly
    50                  55                  60

Ile Asp Thr Arg Ser Ile Thr Asp Ile Ser Thr Cys Glu Gln Tyr Ser
65                  70                  75                  80

Glu Pro Leu Ile Gln Leu Met Thr Ser Leu Pro Asn Asp Glu Lys Val
                85                  90                  95

Val Leu Val Gly His Ser Tyr Gly Gly Leu Thr Leu Ala Ile Ala Met
            100                 105                 110

Asp Lys Phe Pro Asp Lys Ile Ser Val Ser Val Phe Val Thr Ser Phe
            115                 120                 125

Met Pro Asp Thr Lys Asn Ser Pro Ser Phe Val Leu Glu Lys Phe Ala
            130                 135                 140

Ser Thr Met Thr Pro Glu Asp Trp Met Gly Ser Glu Leu Glu Pro Tyr
145                 150                 155                 160
```

```
Val Val Phe Ser Ala Glu Phe Thr Lys His Arg Ile Leu Gln Leu Ser
                165                 170                 175

Pro Ile Glu Asp Leu Glu Leu Arg Leu Leu Lys Arg Pro Gly Ser
        180                 185                 190

Leu Phe Leu Asn Asp Leu Ser Arg Met Lys Asn Phe Ser Glu Lys Gly
            195                 200                 205

Tyr Gly Ser Val Pro Arg Ala Tyr Ile Val Ser Lys Asp Asp His Thr
        210                 215                 220

Ile Ser Glu Glu Tyr Gln Arg Trp Met Ile Asp Asn Tyr Pro Pro Asn
225                 230                 235                 240

Leu Val Ile Glu Met Glu Gly Thr Asp His Leu Pro Leu Phe Cys Lys
                245                 250                 255

Pro Gln Leu Leu Ser Asp His Leu Leu Ala Ile Ala Asp Lys Phe Ser
            260                 265                 270

<210> SEQ ID NO 109
<211> LENGTH: 267
<212> TYPE: PRT
<213> ORGANISM: Citrus sinensis
<220> FEATURE:
<221> NAME/KEY: misc_feature
<222> LOCATION: (1)..(267)
<223> OTHER INFORMATION: Public GI no. 14279437
<220> FEATURE:
<221> NAME/KEY: misc_feature
<222> LOCATION: (1)..(267)
<223> OTHER INFORMATION: Ortholog of  Ceres CDNA ID no. 12333678
      at SEQ ID NO. 12
      with e-value of 1.09E-69 and percent identity of 54.58

<400> SEQUENCE: 109

Met Glu Glu Val Val Gly Met Glu Glu Lys His Phe Val Leu Val His
1               5                   10                  15

Gly Val Asn His Gly Ala Trp Cys Trp Tyr Lys Leu Lys Ala Arg Leu
            20                  25                  30

Val Ala Gly Gly His Arg Val Thr Ala Val Asp Leu Ala Ala Ser Gly
        35                  40                  45

Ile Asn Met Lys Arg Ile Glu Asp Val His Thr Phe His Ala Tyr Ser
    50                  55                  60

Glu Pro Leu Met Glu Val Leu Ala Ser Leu Pro Ala Glu Glu Lys Val
65                  70                  75                  80

Ile Leu Val Gly His Ser Leu Gly Gly Val Thr Leu Ala Leu Ala Gly
                85                  90                  95

Asp Lys Phe Pro His Lys Ile Ser Val Ala Val Phe Val Thr Ala Phe
            100                 105                 110

Met Pro Asp Thr Thr His Arg Pro Ser Phe Val Leu Glu Gln Tyr Ser
        115                 120                 125

Glu Lys Met Gly Lys Glu Asp Asp Ser Trp Leu Asp Thr Gln Phe Ser
    130                 135                 140

Gln Cys Asp Ala Ser Asn Pro Ser His Ile Ser Met Leu Phe Gly Arg
145                 150                 155                 160

Glu Phe Leu Thr Ile Lys Ile Tyr Gln Leu Cys Pro Pro Glu Asp Leu
                165                 170                 175

Glu Leu Ala Lys Met Leu Val Arg Pro Gly Ser Met Phe Ile Asp Asn
            180                 185                 190

Leu Ser Lys Glu Ser Lys Phe Ser Asp Glu Gly Tyr Gly Ser Val Lys
        195                 200                 205

Arg Val Tyr Leu Val Cys Glu Glu Asp Ile Gly Leu Pro Lys Gln Phe
    210                 215                 220
```

```
Gln His Trp Met Ile Gln Asn Tyr Pro Val Asn Glu Val Met Glu Ile
225                 230                 235                 240

Lys Gly Gly Asp His Met Ala Met Leu Ser Asp Pro Gln Lys Leu Cys
            245                 250                 255

Asp Cys Leu Ser Gln Ile Ser Leu Lys Tyr Ala
            260                 265

<210> SEQ ID NO 110
<211> LENGTH: 260
<212> TYPE: PRT
<213> ORGANISM: Nicotiana tabacum
<220> FEATURE:
<221> NAME/KEY: misc_feature
<222> LOCATION: (1)..(260)
<223> OTHER INFORMATION: Public GI no. 40549303
<220> FEATURE:
<221> NAME/KEY: misc_feature
<222> LOCATION: (1)..(260)
<223> OTHER INFORMATION: Ortholog of  Ceres CDNA ID no. 12333678
      at SEQ ID NO. 12
      with e-value of 4.09E-68 and percent identity of 53.67

<400> SEQUENCE: 110

Met Lys Glu Gly Lys His Phe Val Leu Val His Gly Ala Cys His Gly
1               5                   10                  15

Gly Trp Ser Trp Tyr Lys Leu Lys Pro Leu Leu Glu Ala Ala Gly His
            20                  25                  30

Lys Val Thr Ala Leu Asp Leu Ala Ala Ser Gly Thr Asp Leu Arg Lys
        35                  40                  45

Ile Glu Glu Leu Arg Thr Leu Tyr Asp Tyr Thr Leu Pro Leu Met Glu
    50                  55                  60

Leu Met Glu Ser Leu Ser Ala Asp Glu Lys Val Ile Leu Val Gly His
65                  70                  75                  80

Ser Leu Gly Gly Met Asn Leu Gly Leu Ala Met Glu Lys Tyr Pro Gln
                85                  90                  95

Lys Ile Tyr Ala Ala Val Phe Leu Ala Ala Phe Met Pro Asp Ser Val
            100                 105                 110

His Asn Ser Ser Phe Val Leu Glu Gln Tyr Asn Glu Arg Thr Pro Ala
        115                 120                 125

Glu Asn Trp Leu Asp Thr Gln Phe Leu Pro Tyr Gly Ser Pro Glu Glu
    130                 135                 140

Pro Leu Thr Ser Met Phe Phe Gly Pro Lys Phe Leu Ala His Lys Leu
145                 150                 155                 160

Tyr Gln Leu Cys Ser Pro Glu Asp Leu Ala Leu Ala Ser Ser Leu Val
                165                 170                 175

Arg Pro Ser Ser Leu Phe Met Glu Asp Leu Ser Lys Ala Lys Tyr Phe
            180                 185                 190

Thr Asp Glu Arg Phe Gly Ser Val Lys Arg Val Tyr Ile Val Cys Thr
        195                 200                 205

Glu Asp Lys Gly Ile Pro Glu Glu Phe Gln Arg Trp Gln Ile Asp Asn
    210                 215                 220

Ile Gly Val Thr Glu Ala Ile Glu Ile Lys Gly Ala Asp His Met Ala
225                 230                 235                 240

Met Leu Cys Glu Pro Gln Lys Leu Cys Ala Ser Leu Leu Glu Ile Ala
                245                 250                 255

His Lys Tyr Asn
            260
```

-continued

<210> SEQ ID NO 111
<211> LENGTH: 264
<212> TYPE: PRT
<213> ORGANISM: Rauvolfia serpentina
<220> FEATURE:
<221> NAME/KEY: misc_feature
<222> LOCATION: (1)..(264)
<223> OTHER INFORMATION: Public GI no. 50401192
<220> FEATURE:
<221> NAME/KEY: misc_feature
<222> LOCATION: (1)..(264)
<223> OTHER INFORMATION: Ortholog of Ceres CDNA ID no. 12333678
      at SEQ ID NO. 12
      with e-value of 8.00E-64 and percent identity of 48.46

<400> SEQUENCE: 111

Met His Ser Ala Ala Asn Ala Lys Gln Gln Lys His Phe Val Leu Val
1               5                   10                  15

His Gly Gly Cys Leu Gly Ala Trp Ile Trp Tyr Lys Leu Lys Pro Leu
            20                  25                  30

Leu Glu Ser Ala Gly His Lys Val Thr Ala Val Asp Leu Ser Ala Ala
        35                  40                  45

Gly Ile Asn Pro Arg Arg Leu Asp Glu Ile His Thr Phe Arg Asp Tyr
    50                  55                  60

Ser Glu Pro Leu Met Glu Val Met Ala Ser Ile Pro Pro Asp Glu Lys
65                  70                  75                  80

Val Val Leu Leu Gly His Ser Phe Gly Gly Met Ser Leu Gly Leu Ala
                85                  90                  95

Met Glu Thr Tyr Pro Glu Lys Ile Ser Val Ala Val Phe Met Ser Ala
            100                 105                 110

Met Met Pro Asp Pro Asn His Ser Leu Thr Tyr Pro Phe Glu Lys Tyr
        115                 120                 125

Asn Glu Lys Cys Pro Ala Asp Met Met Leu Asp Ser Gln Phe Ser Thr
    130                 135                 140

Tyr Gly Asn Pro Glu Asn Pro Gly Met Ser Met Ile Leu Gly Pro Gln
145                 150                 155                 160

Phe Met Ala Leu Lys Met Phe Gln Asn Cys Ser Val Glu Asp Leu Glu
                165                 170                 175

Leu Ala Lys Met Leu Thr Arg Pro Gly Ser Leu Phe Phe Gln Asp Leu
            180                 185                 190

Ala Lys Ala Lys Lys Phe Ser Thr Glu Arg Tyr Gly Ser Val Lys Arg
        195                 200                 205

Ala Tyr Ile Phe Cys Asn Glu Asp Lys Ser Phe Pro Val Glu Phe Gln
    210                 215                 220

Lys Trp Phe Val Glu Ser Val Gly Ala Asp Lys Val Lys Glu Ile Lys
225                 230                 235                 240

Glu Ala Asp His Met Gly Met Leu Ser Gln Pro Arg Glu Val Cys Lys
                245                 250                 255

Cys Leu Leu Asp Ile Ser Asp Ser
            260

<210> SEQ ID NO 112
<211> LENGTH: 130
<212> TYPE: PRT
<213> ORGANISM: Arabidopsis thaliana
<220> FEATURE:
<221> NAME/KEY: misc_feature
<222> LOCATION: (1)..(130)
<223> OTHER INFORMATION: Ceres CLONE ID no. 25463
<220> FEATURE:
<221> NAME/KEY: misc_feature
<222> LOCATION: (1)..(130)

```
<223> OTHER INFORMATION: Ortholog of Ceres CDNA ID no. 12333678
      at SEQ ID NO. 12
      with e-value of 1.49E-63 and percent identity of 96.92

<400> SEQUENCE: 112

Met Ser Glu Glu Lys Arg Lys Gln His Phe Val Leu Val His Gly Ala
1               5                   10                  15

Cys His Gly Ala Trp Cys Trp Tyr Lys Val Lys Pro Leu Leu Glu Ala
            20                  25                  30

Leu Gly His Arg Val Thr Ala Leu Asp Leu Ala Ala Ser Gly Ile Asp
        35                  40                  45

Thr Thr Arg Ser Ile Thr Asp Ile Ser Thr Cys Glu Gln Tyr Ser Glu
50                  55                  60

Pro Leu Met Gln Leu Met Thr Ser Leu Pro Asn Asp Glu Lys Val Val
65                  70                  75                  80

Leu Val Gly His Ser Phe Gly Gly Leu Ser Leu Ala Leu Ala Met Asp
                85                  90                  95

Lys Phe Pro Asp Lys Ile Ser Val Ser Val Phe Val Thr Ala Phe Met
            100                 105                 110

Pro Asp Thr Lys His Ser Pro Ser Phe Val Glu Glu Lys Val Tyr Ile
        115                 120                 125

Ser Phe
    130

<210> SEQ ID NO 113
<211> LENGTH: 141
<212> TYPE: PRT
<213> ORGANISM: Arabidopsis thaliana
<220> FEATURE:
<221> NAME/KEY: misc_feature
<222> LOCATION: (1)..(141)
<223> OTHER INFORMATION: Public GI no. 7488034
<220> FEATURE:
<221> NAME/KEY: misc_feature
<222> LOCATION: (1)..(141)
<223> OTHER INFORMATION: Ortholog of Ceres CDNA ID no. 12333678
      at SEQ ID NO. 12
      with e-value of 4.79E-58 and percent identity of 81.56

<400> SEQUENCE: 113

Met Ser Glu Glu Lys Arg Lys Gln His Phe Val Leu Val His Gly Ser
1               5                   10                  15

Cys His Gly Ala Trp Cys Trp Tyr Lys Val Lys Pro Leu Leu Glu Ala
            20                  25                  30

Val Gly His Arg Val Thr Ala Val Asp Leu Ala Ala Ser Gly Ile Asp
        35                  40                  45

Thr Thr Arg Ser Ile Thr Asp Ile Pro Thr Cys Glu Gln Tyr Ser Glu
50                  55                  60

Pro Leu Thr Lys Leu Leu Thr Ser Leu Pro Asn Asp Glu Lys Val Val
65                  70                  75                  80

Leu Val Gly His Ser Phe Gly Gly Leu Asn Leu Ala Ile Ala Met Glu
                85                  90                  95

Lys Phe Pro Glu Lys Ile Ser Val Ala Val Phe Leu Thr Ala Phe Met
            100                 105                 110

Pro Asp Thr Glu His Ser Pro Ser Phe Val Leu Asp Lys Val Leu Glu
        115                 120                 125

Ala Thr Cys Leu Lys Lys His Gly Trp Ala Pro Asn Ser
130                 135                 140

<210> SEQ ID NO 114
```

```
<211> LENGTH: 268
<212> TYPE: PRT
<213> ORGANISM: Triticum aestivum
<220> FEATURE:
<221> NAME/KEY: misc_feature
<222> LOCATION: (1)..(268)
<223> OTHER INFORMATION: Ceres CLONE ID no. 644331
<220> FEATURE:
<221> NAME/KEY: misc_feature
<222> LOCATION: (1)..(268)
<223> OTHER INFORMATION: Ortholog of  Ceres CDNA ID no. 12333678
      at SEQ ID NO. 12
      with e-value of 7.09E-32 and percent identity of 33.08

<400> SEQUENCE: 114

Met His Met Glu Ala Cys Ala Gly Gln Ala Ser Ser Ala His Ile Val
1               5                   10                  15

Leu Val His Gly Ala Cys Leu Gly Gly Trp Ser Trp Phe Lys Val Ala
            20                  25                  30

Thr Arg Leu Arg Ser Ala Gly His Arg Val Ser Thr Pro Asp Leu Ala
        35                  40                  45

Ala Ser Gly Val Asp Pro Arg Pro Leu Arg Glu Val Pro Thr Phe Arg
    50                  55                  60

Asp Tyr Thr Lys Pro Leu Asp Leu Leu Glu Ser Leu Pro Ser Gly
65                  70                  75                  80

Glu Lys Val Val Leu Val Gly His Ser Leu Gly Gly Val Asn Val Ala
                85                  90                  95

Leu Ala Cys Glu Leu Phe Pro Glu Lys Ile Ala Ala Ala Val Phe Val
            100                 105                 110

Ala Ala Phe Met Pro Asp His Arg Ser Pro Ser Tyr Val Leu Glu
        115                 120                 125

Lys Phe Val Glu Gly Arg Thr Leu Asp Trp Met Asp Thr Glu Phe Lys
    130                 135                 140

Pro Gln Asp Pro Glu Gly Lys Leu Pro Thr Ser Met Leu Phe Gly Pro
145                 150                 155                 160

Leu Val Thr Arg Ala Lys Phe Phe Gln Leu Cys Ser Pro Glu Asp Leu
                165                 170                 175

Thr Leu Gly Arg Ser Leu Met Arg Val Asn Ser Met Phe Val Asp Asp
            180                 185                 190

Leu Arg Leu Gln Pro Pro His Thr Glu Ala Arg Tyr Gly Ser Val Arg
        195                 200                 205

Lys Ala Tyr Val Val Phe Lys Asp Asp His Ala Ile Val Glu Gln Phe
    210                 215                 220

Gln Arg Trp Met Val His Asn Tyr Pro Val Asp Glu Val Met Glu Ile
225                 230                 235                 240

Asp Gly Ala Asp His Met Ala Leu Leu Ser Thr Pro Thr Glu Leu Ala
                245                 250                 255

Arg Cys Leu Ala Asp Ile Ala Val Lys Tyr Ala Ala
            260                 265

<210> SEQ ID NO 115
<211> LENGTH: 267
<212> TYPE: PRT
<213> ORGANISM: Zea mays
<220> FEATURE:
<221> NAME/KEY: misc_feature
<222> LOCATION: (1)..(267)
<223> OTHER INFORMATION: Ceres CLONE ID no. 381168
<220> FEATURE:
<221> NAME/KEY: misc_feature
<222> LOCATION: (1)..(267)
<223> OTHER INFORMATION: Ortholog of  Ceres CDNA ID no. 12333678
``` at SEQ ID NO. 12
with e-value of 1.10E-51 and percent identity of 43.51

<400> SEQUENCE: 115

Met Glu Ser Gly Thr Glu Arg Arg His His Phe Val Leu Val His
1               5                   10                  15

Gly Thr Cys His Gly Ala Trp Cys Trp Tyr Lys Val Ala Thr Leu Leu
            20                  25                  30

Ser Ser Ala Gly His Arg Val Thr Ala Leu Asp Met Ala Ala Cys Gly
        35                  40                  45

Ala Ser Pro Gly Arg Ala Glu Glu Val Pro Ser Phe Glu Tyr Ser
    50                  55                  60

Arg Pro Leu Leu Ala Thr Val Ala Gly Leu Ala Pro Glu Glu Lys Val
65                  70                  75                  80

Val Leu Val Gly His Ser Phe Gly Gly Val Ser Leu Ala Leu Ala Met
                85                  90                  95

Glu Gln Tyr Pro Asp Arg Val Ala Val Ala Val Phe Val Ala Thr Gly
                100                 105                 110

Met Pro Ser Ala Gly Lys Pro Met Ala Phe Val Phe Glu Gln Phe Leu
            115                 120                 125

Gln Glu Glu Tyr Pro Ala Asp Arg Tyr Met Asp Cys Glu Phe Glu Thr
        130                 135                 140

Ser Gly Asp Pro Gln Arg Pro Val Glu Thr Phe Arg Phe Gly Pro Gln
145                 150                 155                 160

Tyr Leu Lys Gln Arg Leu Tyr Gln Leu Ser Pro Pro Glu Asp Leu Thr
                165                 170                 175

Leu Ala Met Ala Met Leu Arg Pro Ser Gln Arg Phe Arg Asp Asp Ala
            180                 185                 190

Thr Met Lys Gly Gly Val Leu Thr Ala Glu Arg Tyr Gly Gly Val Arg
        195                 200                 205

Arg Val Cys Val Val Ala Glu Asp Asp Ala Ser Val Pro Ala Gly Phe
    210                 215                 220

Leu Arg Arg Met Ala Ser Trp Asn Pro Gly Thr Glu Val Arg Gly Leu
225                 230                 235                 240

Gln Gly Ala Asp His Met Ser Met Leu Ser Lys Pro Gly Glu Leu Ser
                245                 250                 255

Glu Leu Leu Met Glu Val Ala Asn Lys Tyr Ser
            260                 265

<210> SEQ ID NO 116
<211> LENGTH: 268
<212> TYPE: PRT
<213> ORGANISM: Oryza sativa subsp. indica
<220> FEATURE:
<221> NAME/KEY: misc_feature
<222> LOCATION: (1)..(268)
<223> OTHER INFORMATION: Public GI no. 34907176
<220> FEATURE:
<221> NAME/KEY: misc_feature
<222> LOCATION: (1)..(268)
<223> OTHER INFORMATION: Ortholog of Ceres CDNA ID no. 12333678
    at SEQ ID NO. 12
    with e-value of 1.29E-50 and percent identity of 43.13

<400> SEQUENCE: 116

Met Glu Ile Ser Ser Ser Ser Lys Lys His Phe Ile Leu Val His Gly
1               5                   10                  15

Leu Cys His Gly Ala Trp Cys Trp Tyr Arg Val Val Ala Ala Leu Arg
            20                  25                  30

```
Ala Ala Gly His Arg Ala Thr Ala Leu Asp Met Ala Ala Ser Gly Ala
        35                  40                  45

His Pro Ala Arg Val Asp Glu Val Gly Thr Phe Glu Glu Tyr Ser Arg
    50                  55                  60

Pro Leu Leu Asp Ala Val Ala Ala Ala Ala Pro Gly Glu Arg Leu
65                  70                  75                  80

Val Leu Val Gly His Ser His Gly Gly Leu Ser Val Ala Leu Ala Met
                85                  90                  95

Glu Arg Phe Pro Asp Lys Val Ala Ala Val Phe Val Ala Ala Ala
            100                 105                 110

Met Pro Cys Val Gly Lys His Met Gly Val Pro Thr Glu Glu Phe Met
            115                 120                 125

Arg Arg Thr Ala Pro Glu Gly Leu Leu Met Asp Cys Glu Met Val Ala
        130                 135                 140

Ile Asn Asn Ser Gln Gly Ser Gly Val Ala Ile Asn Leu Gly Pro Thr
145                 150                 155                 160

Phe Leu Ala Gln Lys Tyr Tyr Gln Gln Ser Pro Ala Glu Asp Leu Ala
                165                 170                 175

Leu Ala Lys Met Leu Val Arg Pro Gly Asn Gln Phe Met Asp Asp Pro
            180                 185                 190

Val Met Lys Asp Glu Ser Leu Leu Thr Asn Gly Asn Tyr Gly Ser Val
            195                 200                 205

Lys Lys Val Tyr Val Ile Ala Lys Ala Asp Ser Ser Thr Glu Glu
        210                 215                 220

Met Gln Arg Trp Met Val Ala Met Ser Pro Gly Thr Asp Val Glu Glu
225                 230                 235                 240

Ile Ala Gly Ala Asp His Ala Val Met Asn Ser Lys Pro Arg Glu Leu
                245                 250                 255

Cys Asp Ile Leu Ile Lys Ile Ala Asn Lys Tyr Glu
            260                 265

<210> SEQ ID NO 117
<211> LENGTH: 262
<212> TYPE: PRT
<213> ORGANISM: Oryza sativa subsp. japonica
<220> FEATURE:
<221> NAME/KEY: misc_feature
<222> LOCATION: (1)..(262)
<223> OTHER INFORMATION: Public GI no. 498747
<220> FEATURE:
<221> NAME/KEY: misc_feature
<222> LOCATION: (1)..(262)
<223> OTHER INFORMATION: Ortholog of  Ceres CDNA ID no. 12333678
      at SEQ ID NO. 12
      with e-value of 1.29E-50 and percent identity of 43.58

<400> SEQUENCE: 117

Ser Lys Lys His Phe Ile Leu Val His Gly Leu Cys His Gly Ala Trp
1               5                   10                  15

Cys Trp Tyr Arg Val Val Ala Ala Leu Arg Ala Ala Gly His Arg Ala
            20                  25                  30

Thr Ala Leu Asp Met Ala Ala Ser Gly Ala His Pro Ala Arg Val Asp
        35                  40                  45

Glu Val Gly Thr Phe Glu Glu Tyr Ser Arg Pro Leu Leu Asp Ala Val
    50                  55                  60

Ala Ala Ala Ala Ala Pro Gly Glu Arg Leu Val Leu Val Gly His Ser
65                  70                  75                  80

His Gly Gly Leu Ser Val Ala Leu Ala Met Glu Arg Phe Pro Asp Lys
                85                  90                  95
```

Val Ala Ala Ala Val Phe Val Ala Ala Met Pro Cys Val Gly Lys
            100                 105                 110

His Met Gly Val Pro Thr Glu Glu Phe Met Arg Arg Thr Ala Pro Glu
            115                 120                 125

Gly Leu Leu Met Asp Cys Glu Met Val Ala Ile Asn Asn Ser Gln Gly
            130                 135                 140

Ser Gly Val Ala Ile Asn Leu Gly Pro Thr Phe Leu Ala Gln Lys Tyr
145                 150                 155                 160

Tyr Gln Gln Ser Pro Ala Glu Asp Leu Ala Leu Ala Lys Met Leu Val
                165                 170                 175

Arg Pro Gly Asn Gln Phe Met Asp Asp Pro Val Met Lys Asp Glu Ser
                180                 185                 190

Leu Leu Thr Asn Gly Asn Tyr Gly Ser Val Lys Val Tyr Val Ile
            195                 200                 205

Ala Lys Ala Asp Ser Ser Thr Glu Glu Met Gln Arg Trp Met Val
    210                 215                 220

Ala Met Ser Pro Gly Thr Asp Val Glu Glu Ile Ala Gly Ala Asp His
225                 230                 235                 240

Ala Val Met Asn Ser Lys Pro Arg Glu Leu Cys Asp Ile Leu Ile Lys
                245                 250                 255

Ile Ala Asn Lys Tyr Glu
            260

<210> SEQ ID NO 118
<211> LENGTH: 273
<212> TYPE: PRT
<213> ORGANISM: Glycine max
<220> FEATURE:
<221> NAME/KEY: misc_feature
<222> LOCATION: (1)..(273)
<223> OTHER INFORMATION: Ceres CLONE ID no. 1059805
<220> FEATURE:
<221> NAME/KEY: misc_feature
<222> LOCATION: (1)..(273)
<223> OTHER INFORMATION: Ortholog of Ceres CDNA ID no. 12333678
      at SEQ ID NO. 12
      with e-value of 1.09E-49 and percent identity of 41.6

<400> SEQUENCE: 118

Met Glu Ser Thr Gln Ser Asn Thr Ser Val Met Asn His Phe Ile Leu
1               5                   10                  15

Val His Gly Leu Cys His Gly Ala Trp Cys Trp Tyr Lys Val Val Ala
            20                  25                  30

Ala Leu Gln Ala Ala Gly His Arg Val Thr Ala Val Asp Leu Ala Ala
        35                  40                  45

Ser Gly Ala His Pro Ala Arg Ile Asp Glu Val His Ser Phe Glu Glu
    50                  55                  60

Tyr Ser Gln Pro Leu Leu Asp Val Val Ala Ala Pro Glu Gly Asp
65                  70                  75                  80

Gly Glu Arg Leu Ile Leu Val Gly His Ser His Gly Gly Leu Ser Leu
                85                  90                  95

Ala Leu Ala Met Glu Arg Phe Pro Gly Lys Val Ala Ala Val Phe
            100                 105                 110

Ala Ala Ala Gly Met Pro Cys Val Gly Lys His Met Gly Val Thr Thr
        115                 120                 125

Glu Glu Phe Met Arg Arg Thr Ser Ser Glu Gly Leu Met Asp Cys Lys
    130                 135                 140

Met Leu Pro Ile Asn Asn Asn His Gly Ala Gly Val Ala Met Ile Met

```
              145                 150                 155                 160

Gly Pro Asn Phe Leu Ala His Lys Asn Tyr Gln Gln Ser Ser Pro Glu
                165                 170                 175

Asp Leu Ala Leu Ala Lys Met Leu Val Arg Pro Gly Asn Leu Phe Met
                180                 185                 190

Glu Asp Pro Val Met Lys Asp Ala Ser Leu Leu Thr Asp Thr Asn Tyr
                195                 200                 205

Gly Ser Val Lys Lys Val Tyr Val Ala Lys Ala Asp Gly Ser Ser
            210                 215                 220

Thr Glu Glu Met Gln Arg Trp Met Val Leu Leu Ser Pro Gly Thr Glu
225                 230                 235                 240

Ala Glu Glu Ile Ala Gly Ala Asp His Ala Ile Met Ser Ser Arg Pro
                245                 250                 255

Arg Glu Leu Cys Asp Ala Leu Val Lys Ile Ala Asp Ser Leu Asn Thr
                260                 265                 270

Cys

<210> SEQ ID NO 119
<211> LENGTH: 265
<212> TYPE: PRT
<213> ORGANISM: Triticum aestivum
<220> FEATURE:
<221> NAME/KEY: misc_feature
<222> LOCATION: (1)..(265)
<223> OTHER INFORMATION: Ceres CLONE ID no. 936068
<220> FEATURE:
<221> NAME/KEY: misc_feature
<222> LOCATION: (1)..(265)
<223> OTHER INFORMATION: Ortholog of  Ceres CDNA ID no. 12333678
      at SEQ ID NO. 12
      with e-value of 2.09E-23 and percent identity of 53.26

<400> SEQUENCE: 119

Met Glu Gly Ser Ser Ser Gly Lys His Phe Ile Leu Ile His Gly Leu
1               5                   10                  15

Cys His Gly Ala Trp Cys Trp Tyr Lys Leu Val Pro Met Leu Arg Ala
                20                  25                  30

Ala Gly His Arg Val Thr Ala Leu Asp Met Ala Ala Ser Gly Ala His
            35                  40                  45

Pro Ala Arg Met Asp Glu Val Pro Ser Phe Glu Asp Tyr Ser Trp Pro
        50                  55                  60

Leu Leu Asp Ala Val Ala Ala Pro Ala Gly Glu Arg Leu Val Leu
65                  70                  75                  80

Val Gly His Ser Leu Gly Gly Leu Asn Ile Ala Leu Ala Met Glu Arg
                85                  90                  95

Phe Pro Arg Lys Val Ala Ala Val Phe Leu Ala Ala Cys Met Pro
                100                 105                 110

Cys Val Gly Arg His Met Gly Ala Thr Thr Glu Glu Ile Met Arg Arg
            115                 120                 125

Ile Lys Pro Asp Phe Phe Met Asp Met Lys Arg Met Val Leu Asn Thr
        130                 135                 140

Ser Gln Gly Pro Arg Pro Ala Leu Val Phe Gly Pro Lys Ile Leu Ala
145                 150                 155                 160

Ala Lys Leu Tyr Asp Arg Ser Ser Gly Glu Asp Gln Thr Leu Ala Thr
                165                 170                 175

Met Leu Val Arg Pro Gly Cys Gln Phe Leu Asp Asp Pro Thr Met Lys
            180                 185                 190

Asp Glu Ala Leu Leu Thr Glu Ala Lys Tyr Gly Ser Val Lys Lys Val
```

```
            195                 200                 205
Tyr Val Val Ala Met Ala Asp Ala Ser Asn Ser Glu Glu Met Gln Arg
    210                 215                 220

Trp Met Val Asp Met Ser Pro Gly Thr Glu Ala Glu Ile Ala Gly
225                 230                 235                 240

Ala Asp His Met Ala Met Cys Ser Lys Pro Arg Glu Leu Cys Asp Val
                245                 250                 255

Leu Leu Arg Ile Ala Asp Lys Tyr Glu
                260                 265

<210> SEQ ID NO 120
<211> LENGTH: 93
<212> TYPE: PRT
<213> ORGANISM: Brassica napus
<220> FEATURE:
<221> NAME/KEY: misc_feature
<222> LOCATION: (1)..(93)
<223> OTHER INFORMATION: Ceres CLONE ID no. 1034942
<220> FEATURE:
<221> NAME/KEY: misc_feature
<222> LOCATION: (1)..(93)
<223> OTHER INFORMATION: Ortholog of Ceres CDNA ID no. 12333678
      at SEQ ID NO. 12
      with e-value of 3.90E-40 and percent identity of 87.1

<400> SEQUENCE: 120

Met Gly Glu Glu Lys Asn Gln Gln His Phe Val Leu Val His Gly Ala
1               5                   10                  15

Cys His Gly Ala Trp Cys Trp Asn Lys Val Lys Pro Leu Leu Glu Ala
                20                  25                  30

Ser Gly His Arg Val Thr Ala Leu Asp Leu Ala Ala Ser Gly Ile Asp
            35                  40                  45

Thr Thr Arg Ser Ile Thr Glu Ile Ser Thr Cys Glu Gln Tyr Ser Glu
    50                  55                  60

Pro Leu Ile Gln Leu Ile Ala Ser Leu Pro Ser Asp Gly Lys Val Val
65                  70                  75                  80

Leu Val Gly His Ser Phe Gly Gly Phe Ser Leu Ala Met
                85                  90

<210> SEQ ID NO 121
<211> LENGTH: 135
<212> TYPE: PRT
<213> ORGANISM: Glycine max
<220> FEATURE:
<221> NAME/KEY: misc_feature
<222> LOCATION: (1)..(135)
<223> OTHER INFORMATION: Ceres CLONE ID no. 723429
<220> FEATURE:
<221> NAME/KEY: misc_feature
<222> LOCATION: (1)..(135)
<223> OTHER INFORMATION: Ortholog of Ceres CDNA ID no. 12333678
      at SEQ ID NO. 12
      with e-value of 4.39E-39 and percent identity of 58.78

<400> SEQUENCE: 121

Met Ser Ser Lys Asn Ser Ile Asp Arg Lys Pro Lys His Tyr Val Leu
1               5                   10                  15

Val His Gly Ala Cys Tyr Gly Ala Trp Leu Trp Tyr Lys Leu Lys Pro
                20                  25                  30

Arg Leu Glu Ser Ala Gly His Lys Val Thr Val Leu Asp Leu Ala Ala
            35                  40                  45

Ser Gly Thr Asn Met Lys Lys Ile Glu Asp Val Asp Thr Phe Ser Gln
    50                  55                  60
```

Tyr Thr Glu Pro Leu Leu Gln Leu Met Ala Thr Ile Pro Pro Asn Lys
65                  70                  75                  80

Lys Val Val Leu Val Gly His Ser Leu Gly Gly Leu Asn Ile Ala Leu
                85                  90                  95

Ala Met Glu Lys Phe Pro Glu Lys Val Ala Val Gly Val Phe Val Thr
            100                 105                 110

Ala Ile Ile Pro Asp Ile Glu His Lys Pro Ser Tyr Val Leu Glu Lys
        115                 120                 125

Met Leu His Arg Ile Thr Tyr
    130                 135

<210> SEQ ID NO 122
<211> LENGTH: 215
<212> TYPE: PRT
<213> ORGANISM: Oryza sativa subsp. japonica
<220> FEATURE:
<221> NAME/KEY: misc_feature
<222> LOCATION: (1)..(215)
<223> OTHER INFORMATION: Public GI no. 34907174
<220> FEATURE:
<221> NAME/KEY: misc_feature
<222> LOCATION: (1)..(215)
<223> OTHER INFORMATION: Ortholog of Ceres CDNA ID no. 12333678
      at SEQ ID NO. 12
      with e-value of 8.79E-34 and percent identity of 45.28

<400> SEQUENCE: 122

Met Glu Gly Ser Ser Ser Ser Lys His Phe Ile Leu Val His Gly
1               5                   10                  15

Leu Cys His Gly Ala Trp Cys Trp Tyr Lys Val Val Thr Met Leu Arg
                20                  25                  30

Ser Glu Gly His Arg Val Thr Ala Leu Asp Leu Ala Ala Ser Gly Val
            35                  40                  45

His Pro Ala Arg Val Asp Glu Val His Ser Phe Glu Glu Tyr Ser Gln
        50                  55                  60

Pro Leu Leu Asp Ala Val Ala Glu Ala Pro Ala Gly Glu Arg Leu Ile
65                  70                  75                  80

Leu Val Gly His Ser Phe Gly Gly Leu Ser Ile Ala Leu Ala Met Glu
                85                  90                  95

Arg Phe Pro Glu Lys Ile Ala Val Ala Val Phe Val Ala Ala Ala Val
            100                 105                 110

Pro Cys Val Gly Lys Arg Ile Ile Pro Glu Asp Leu Thr Leu Ala Lys
        115                 120                 125

Leu Leu Val Arg Pro Thr Ser Gln Phe Val Asp Asp Pro Thr Met Lys
130                 135                 140

Asp Asp Arg Leu Leu Thr Ser Ala Asn Tyr Gly Ser Val Lys Arg Val
145                 150                 155                 160

Cys Leu Met Ala Met Glu Asp Asp Leu Lys Glu Val His Arg Tyr Met
                165                 170                 175

Ile Thr Leu Ser Pro Gly Val Glu Val Glu Ile Ala Gly Ala Asp
            180                 185                 190

His Ala Val Met Cys Ser Arg Pro Arg Glu Leu Ser Asp Leu Leu Ala
        195                 200                 205

Lys Ile Gly Ser Lys Tyr Asp
    210                 215

<210> SEQ ID NO 123
<211> LENGTH: 125
<212> TYPE: PRT
<213> ORGANISM: Triticum aestivum

```
<220> FEATURE:
<221> NAME/KEY: misc_feature
<222> LOCATION: (1)..(125)
<223> OTHER INFORMATION: Ceres CLONE ID no. 1005331
<220> FEATURE:
<221> NAME/KEY: misc_feature
<222> LOCATION: (1)..(125)
<223> OTHER INFORMATION: Ortholog of  Ceres CDNA ID no. 12333678
      at SEQ ID NO. 12
      with e-value of 1.70E-30 and percent identity of 56.3

<400> SEQUENCE: 123

Met Glu Ser Thr Gln Ser Asn Ser Val Arg Ser His Phe Ile Leu Val
1               5                   10                  15

His Gly Leu Cys His Gly Ala Trp Cys Trp Tyr Lys Val Val Ala Ala
            20                  25                  30

Leu Glu Ala Ala Gly His Arg Val Thr Ala Ile Asp Leu Ala Ala Ser
        35                  40                  45

Gly Thr His Pro Ala Arg Val Asp Glu Val His Ser Phe Glu Glu Tyr
    50                  55                  60

Ser Arg Pro Leu Leu Asp Val Val Ala Ala Pro Ala Gly Asp Gly
65                  70                  75                  80

Glu Arg Leu Ile Leu Val Gly His Ser His Gly Gly Leu Ser Leu Ala
                85                  90                  95

Leu Ala Met Glu Arg Phe Pro Gly Lys Ile Ala Ala Val Phe Ala
            100                 105                 110

Ala Ala Ala Met Pro Ser Val Gly Lys His Met Gly Val
        115                 120                 125

<210> SEQ ID NO 124
<211> LENGTH: 131
<212> TYPE: PRT
<213> ORGANISM: Glycine max
<220> FEATURE:
<221> NAME/KEY: misc_feature
<222> LOCATION: (1)..(131)
<223> OTHER INFORMATION: Ceres CLONE ID no. 1016894
<220> FEATURE:
<221> NAME/KEY: misc_feature
<222> LOCATION: (1)..(131)
<223> OTHER INFORMATION: Ortholog of  Ceres CDNA ID no. 12333678
      at SEQ ID NO. 12
      with e-value of 1.19E-29 and percent identity of 53.28

<400> SEQUENCE: 124

Met Ser Ser Ser Ser Ser Ala Pro Ala Ala Val Ala Thr Ser
1               5                   10                  15

Thr Arg Leu Ile Leu Val His Gly Thr Gly His Gly Gly Trp Cys Trp
            20                  25                  30

Tyr Lys Val Ala Thr Leu Leu Arg Ala Ala Gly His Arg Val Asp Ala
        35                  40                  45

Pro Asp Leu Ala Ala Cys Gly Ala Asp Ala Arg Arg Leu Ser Asp Ala
    50                  55                  60

Pro Thr Phe Glu Asp Tyr Thr Arg Pro Leu Leu Asp Ala Leu Arg Ala
65                  70                  75                  80

Leu Pro Asp Gly Glu Arg Ala Val Leu Val Gly His Ser Phe Gly Gly
                85                  90                  95

Met Ser Val Ala Leu Ala Ala Glu Glu Phe Pro Asp Lys Val Ala Ala
            100                 105                 110

Ala Val Phe Leu Thr Ala Phe Met Pro Asp Cys Ala Gly Pro Arg Thr
        115                 120                 125

Arg Val Ile
```

-continued

130

<210> SEQ ID NO 125
<211> LENGTH: 140
<212> TYPE: PRT
<213> ORGANISM: Triticum aestivum
<220> FEATURE:
<221> NAME/KEY: misc_feature
<222> LOCATION: (1)..(140)
<223> OTHER INFORMATION: Ceres CLONE ID no. 757560
<220> FEATURE:
<221> NAME/KEY: misc_feature
<222> LOCATION: (1)..(140)
<223> OTHER INFORMATION: Ortholog of Ceres CDNA ID no. 12333678
    at SEQ ID NO. 12
    with e-value of 4.09E-29 and percent identity of 47.73
<220> FEATURE:
<221> NAME/KEY: misc_feature
<222> LOCATION: (84)..(84)
<223> OTHER INFORMATION: Xaa is any aa, unknown, or other

<400> SEQUENCE: 125

Met Lys Ser Thr Gln Ser Asn Ser Ser Asn Ser Val Arg Asn His Phe
1               5                   10                  15

Ile Leu Val His Gly Leu Cys His Gly Ala Trp Cys Trp Tyr Lys Val
            20                  25                  30

Val Ala Ala Leu Glu Ala Ala Gly His Arg Val Thr Ala Val Asp Leu
        35                  40                  45

Ala Ala Ser Gly Ala His Pro Ala Arg Val Asp Glu Val His Ser Phe
    50                  55                  60

Glu Glu Tyr Ser Arg Pro Leu Leu Asp Val Leu Ala Ala Pro Glu
65                  70                  75                  80

Gly Asp Gly Xaa Arg Leu Ile Leu Val Gly His Ser His Gly Leu
            85                  90                  95

Ser Leu Ala Leu Ala Met Glu Arg Phe Ser Gly Lys Val Ala Ala Ala
            100                 105                 110

Val Phe Ala Ala Ala Gly Met Pro Cys Val Gly Lys His Met Gly Ile
        115                 120                 125

Thr Thr Glu Glu Phe Met Arg Arg Lys His Pro Lys
    130                 135                 140

<210> SEQ ID NO 126
<211> LENGTH: 148
<212> TYPE: PRT
<213> ORGANISM: Triticum aestivum
<220> FEATURE:
<221> NAME/KEY: misc_feature
<222> LOCATION: (1)..(148)
<223> OTHER INFORMATION: Ceres CLONE ID no. 1018595
<220> FEATURE:
<221> NAME/KEY: misc_feature
<222> LOCATION: (1)..(148)
<223> OTHER INFORMATION: Ortholog of Ceres CDNA ID no. 12333678
    at SEQ ID NO. 12
    with e-value of 4.09E-29 and percent identity of 50.36
<220> FEATURE:
<221> NAME/KEY: misc_feature
<222> LOCATION: (116)..(116)
<223> OTHER INFORMATION: Xaa is any aa, unknown, or other
<220> FEATURE:
<221> NAME/KEY: misc_feature
<222> LOCATION: (144)..(144)
<223> OTHER INFORMATION: Xaa is any aa, unknown, or other

<400> SEQUENCE: 126

Met Ser Ser Ser Ser Ser Ala Pro Ala Ala Val Ala Thr Ser
1               5                   10                  15

```
Thr Arg Leu Ile Leu Val His Gly Thr Gly His Gly Gly Trp Cys Trp
         20                  25                  30

Tyr Lys Val Ala Thr Leu Leu Arg Ala Ala Gly His Arg Val Asp Ala
     35                  40                  45

Pro Asp Leu Ala Ala Cys Gly Ala Asp Ala Arg Arg Leu Ser Asp Ala
 50                  55                  60

Pro Thr Phe Glu Asp Tyr Thr Arg Pro Leu Leu Asp Ala Leu Arg Ala
 65                  70                  75                  80

Leu Pro Asp Gly Glu Arg Ala Val Leu Val Gly His Ser Phe Gly Gly
             85                  90                  95

Met Ser Val Ala Leu Ala Ala Glu Glu Phe Pro Asp Lys Val Ala Ala
            100                 105                 110

Ala Val Phe Xaa Ser Ala Phe Met Pro Asp Cys Ala Gly Pro Arg Thr
            115                 120                 125

Arg Val Ile Glu Gln Val Pro Val Ser Asp Trp Met Asp Ser Val Xaa
        130                 135                 140

Asp Glu Glu His
145

<210> SEQ ID NO 127
<211> LENGTH: 130
<212> TYPE: PRT
<213> ORGANISM: Triticum aestivum
<220> FEATURE:
<221> NAME/KEY: misc_feature
<222> LOCATION: (1)..(130)
<223> OTHER INFORMATION: Ceres CLONE ID no. 735301
<220> FEATURE:
<221> NAME/KEY: misc_feature
<222> LOCATION: (1)..(130)
<223> OTHER INFORMATION: Ortholog of  Ceres CDNA ID no. 12333678
      at SEQ ID NO. 12
      with e-value of 6.60E-29 and percent identity of 47.69

<400> SEQUENCE: 127

Met Glu Gly Ser Ser Ser Gly Glu His Phe Met Leu Val His Gly Leu
 1               5                  10                  15

Gly His Gly Ala Trp Cys Trp Tyr Lys Leu Val Pro Met Leu Arg Ala
             20                  25                  30

Ala Gly His Arg Val Thr Ala Leu Asp Met Ala Ala Ser Gly Ala His
         35                  40                  45

Pro Ala Arg Met Asp Glu Val Pro Ser Phe Glu Asp Tyr Ser Arg Pro
 50                  55                  60

Leu Leu Asp Ala Val Ala Ala Pro Ala Gly Glu Arg Leu Val Leu
 65                  70                  75                  80

Val Gly His Ser Leu Gly Gly Leu Asn Ile Ala Leu Ala Met Glu Arg
             85                  90                  95

Phe Pro Arg Lys Val Ala Ala Val Phe Leu Ala Ala Cys Met Pro
            100                 105                 110

Cys Val Gly Arg His Met Gly Val Xaa Thr Glu Glu Ile Met Arg Arg
            115                 120                 125

Ile Lys
130

<210> SEQ ID NO 128
<211> LENGTH: 154
<212> TYPE: PRT
<213> ORGANISM: Triticum aestivum
<220> FEATURE:
<221> NAME/KEY: misc_feature
<222> LOCATION: (1)..(154)
```

<223> OTHER INFORMATION: Ceres CLONE ID no. 616073
<220> FEATURE:
<221> NAME/KEY: misc_feature
<222> LOCATION: (1)..(154)
<223> OTHER INFORMATION: Ortholog of Ceres CDNA ID no. 12333678
      at SEQ ID NO. 12
      with e-value of 9.59E-21 and percent identity of 41.41

<400> SEQUENCE: 128

Thr Pro Gln Leu Thr Thr Ser Thr Asp Arg Gly Xaa Thr Val Ala Lys
1               5                   10                  15

Pro His Val Cys Thr Ser Arg Trp Arg Leu Arg Thr Lys Pro Xaa
            20                  25                  30

Ala Ser Thr Ser Phe Trp Cys Thr Ala His Ala Ser Ala Ala Gly Pro
        35                  40                  45

Gly Ser Arg Trp Pro Arg Gly Ser Gly Thr Pro Gly His Arg Val Ser
    50                  55                  60

Thr Pro Asp Leu Ala Ala Ser Gly Val Asp Pro Arg Pro Leu Arg Glu
65                  70                  75                  80

Val Pro Thr Phe Phe Asp Tyr Thr Lys Pro Leu Leu Asp Leu Leu Xaa
                85                  90                  95

Xaa Leu Xaa Pro Gly Glu Lys Val Val Leu Val Gly His Ser Leu Gly
            100                 105                 110

Gly Val Asn Ile Ala Leu Ala Cys Glu Leu Phe Pro Glu Lys Val Ala
        115                 120                 125

Ala Ala Val Phe Leu Ser Ala Phe Met Pro Asp His Arg Ser Ser Pro
    130                 135                 140

Ala Tyr Val Leu Glu Lys Phe Val Glu Gly
145                 150

<210> SEQ ID NO 129
<211> LENGTH: 392
<212> TYPE: PRT
<213> ORGANISM: Artificial Sequence
<220> FEATURE:
<221> NAME/KEY: misc_feature
<222> LOCATION: (1)..(392)
<223> OTHER INFORMATION: Consensus Sequence of Ceres CDNA ID no.
      12333678 at SEQ ID NO. 12 and orthologs
<220> FEATURE:
<221> NAME/KEY: misc_feature
<222> LOCATION: (1)..(1)
<223> OTHER INFORMATION: Xaa is any aa
<220> FEATURE:
<221> NAME/KEY: misc_feature
<222> LOCATION: (8)..(8)
<223> OTHER INFORMATION: Xaa is Gly or Gln
<220> FEATURE:
<221> NAME/KEY: misc_feature
<222> LOCATION: (10)..(10)
<223> OTHER INFORMATION: Xaa is any aa or nothing
<220> FEATURE:
<221> NAME/KEY: misc_feature
<222> LOCATION: (12)..(12)
<223> OTHER INFORMATION: Xaa is Ser or Arg
<220> FEATURE:
<221> NAME/KEY: misc_feature
<222> LOCATION: (13)..(13)
<223> OTHER INFORMATION: Xaa is Ile, Val, Leu, or Met
<220> FEATURE:
<221> NAME/KEY: misc_feature
<222> LOCATION: (14)..(14)
<223> OTHER INFORMATION: Xaa is Cys or Gly
<220> FEATURE:
<221> NAME/KEY: misc_feature
<222> LOCATION: (15)..(15)
<223> OTHER INFORMATION: Xaa is Ser or Val
<220> FEATURE:
<221> NAME/KEY: misc_feature

```
-continued

<222> LOCATION: (16)..(16)
<223> OTHER INFORMATION: Xaa is any aa
<220> FEATURE:
<221> NAME/KEY: misc_feature
<222> LOCATION: (17)..(17)
<223> OTHER INFORMATION: Xaa is Ala  or Val
<220> FEATURE:
<221> NAME/KEY: misc_feature
<222> LOCATION: (18)..(18)
<223> OTHER INFORMATION: Xaa is any aa
<220> FEATURE:
<221> NAME/KEY: misc_feature
<222> LOCATION: (19)..(19)
<223> OTHER INFORMATION: Xaa is any aa
<220> FEATURE:
<221> NAME/KEY: misc_feature
<222> LOCATION: (20)..(20)
<223> OTHER INFORMATION: Xaa is any aa
<220> FEATURE:
<221> NAME/KEY: misc_feature
<222> LOCATION: (21)..(21)
<223> OTHER INFORMATION: Xaa is Ile, Val, Leu, or Met
<220> FEATURE:
<221> NAME/KEY: misc_feature
<222> LOCATION: (22)..(22)
<223> OTHER INFORMATION: Xaa is Thr, Gly, or Ser
<220> FEATURE:
<221> NAME/KEY: misc_feature
<222> LOCATION: (23)..(23)
<223> OTHER INFORMATION: Xaa is any aa
<220> FEATURE:
<221> NAME/KEY: misc_feature
<222> LOCATION: (24)..(24)
<223> OTHER INFORMATION: Xaa is Ser  or Ile
<220> FEATURE:
<221> NAME/KEY: misc_feature
<222> LOCATION: (25)..(25)
<223> OTHER INFORMATION: Xaa is any aa
<220> FEATURE:
<221> NAME/KEY: misc_feature
<222> LOCATION: (26)..(26)
<223> OTHER INFORMATION: Xaa is Val  or His
<220> FEATURE:
<221> NAME/KEY: misc_feature
<222> LOCATION: (27)..(27)
<223> OTHER INFORMATION: Xaa is any aa
<220> FEATURE:
<221> NAME/KEY: misc_feature
<222> LOCATION: (29)..(29)
<223> OTHER INFORMATION: Xaa is Arg  or Gly
<220> FEATURE:
<221> NAME/KEY: misc_feature
<222> LOCATION: (30)..(30)
<223> OTHER INFORMATION: Xaa is any aa
<220> FEATURE:
<221> NAME/KEY: misc_feature
<222> LOCATION: (31)..(31)
<223> OTHER INFORMATION: Xaa is Tyr  or Ala
<220> FEATURE:
<221> NAME/KEY: misc_feature
<222> LOCATION: (32)..(32)
<223> OTHER INFORMATION: Xaa is Val  or Ala
<220> FEATURE:
<221> NAME/KEY: misc_feature
<222> LOCATION: (33)..(33)
<223> OTHER INFORMATION: Xaa is Ala  or Val
<220> FEATURE:
<221> NAME/KEY: misc_feature
<222> LOCATION: (34)..(34)
<223> OTHER INFORMATION: Xaa is Thr, Gly, or Ser
<220> FEATURE:
<221> NAME/KEY: misc_feature
<222> LOCATION: (35)..(35)
<223> OTHER INFORMATION: Xaa is any aa
<220> FEATURE:
<221> NAME/KEY: misc_feature
<222> LOCATION: (36)..(36)
<223> OTHER INFORMATION: Xaa is any aa
<220> FEATURE:
<221> NAME/KEY: misc_feature
```

```
<222> LOCATION: (37)..(37)
<223> OTHER INFORMATION: Xaa is any aa or nothing
<220> FEATURE:
<221> NAME/KEY: misc_feature
<222> LOCATION: (38)..(38)
<223> OTHER INFORMATION: Xaa is any aa or nothing
<220> FEATURE:
<221> NAME/KEY: misc_feature
<222> LOCATION: (39)..(39)
<223> OTHER INFORMATION: Xaa is any aa or nothing
<220> FEATURE:
<221> NAME/KEY: misc_feature
<222> LOCATION: (40)..(40)
<223> OTHER INFORMATION: Xaa is any aa or nothing
<220> FEATURE:
<221> NAME/KEY: misc_feature
<222> LOCATION: (41)..(41)
<223> OTHER INFORMATION: Xaa is any aa or nothing
<220> FEATURE:
<221> NAME/KEY: misc_feature
<222> LOCATION: (43)..(43)
<223> OTHER INFORMATION: Xaa is any aa
<220> FEATURE:
<221> NAME/KEY: misc_feature
<222> LOCATION: (44)..(44)
<223> OTHER INFORMATION: Xaa is any aa or nothing
<220> FEATURE:
<221> NAME/KEY: misc_feature
<222> LOCATION: (45)..(45)
<223> OTHER INFORMATION: Xaa is any aa or nothing
<220> FEATURE:
<221> NAME/KEY: misc_feature
<222> LOCATION: (46)..(46)
<223> OTHER INFORMATION: Xaa is Thr, Gly, or Ser
<220> FEATURE:
<221> NAME/KEY: misc_feature
<222> LOCATION: (47)..(47)
<223> OTHER INFORMATION: Xaa is any aa
<220> FEATURE:
<221> NAME/KEY: misc_feature
<222> LOCATION: (48)..(48)
<223> OTHER INFORMATION: Xaa is Gly  or Ile
<220> FEATURE:
<221> NAME/KEY: misc_feature
<222> LOCATION: (49)..(49)
<223> OTHER INFORMATION: Xaa is Thr, Gly, or Ser
<220> FEATURE:
<221> NAME/KEY: misc_feature
<222> LOCATION: (50)..(50)
<223> OTHER INFORMATION: Xaa is Ser  or Arg
<220> FEATURE:
<221> NAME/KEY: misc_feature
<222> LOCATION: (51)..(51)
<223> OTHER INFORMATION: Xaa is any aa
<220> FEATURE:
<221> NAME/KEY: misc_feature
<222> LOCATION: (52)..(52)
<223> OTHER INFORMATION: Xaa is any aa
<220> FEATURE:
<221> NAME/KEY: misc_feature
<222> LOCATION: (53)..(53)
<223> OTHER INFORMATION: Xaa is any aa
<220> FEATURE:
<221> NAME/KEY: misc_feature
<222> LOCATION: (54)..(54)
<223> OTHER INFORMATION: Xaa is any aa
<220> FEATURE:
<221> NAME/KEY: misc_feature
<222> LOCATION: (55)..(55)
<223> OTHER INFORMATION: Xaa is Val  or Lys
<220> FEATURE:
<221> NAME/KEY: misc_feature
<222> LOCATION: (57)..(57)
<223> OTHER INFORMATION: Xaa is any aa
<220> FEATURE:
<221> NAME/KEY: misc_feature
<222> LOCATION: (58)..(58)
<223> OTHER INFORMATION: Xaa is any aa
<220> FEATURE:
<221> NAME/KEY: misc_feature
```

```
<222> LOCATION: (59)..(59)
<223> OTHER INFORMATION: Xaa is Glu or Lys
<220> FEATURE:
<221> NAME/KEY: misc_feature
<222> LOCATION: (60)..(60)
<223> OTHER INFORMATION: Xaa is any aa
<220> FEATURE:
<221> NAME/KEY: misc_feature
<222> LOCATION: (61)..(61)
<223> OTHER INFORMATION: Xaa is any aa
<220> FEATURE:
<221> NAME/KEY: misc_feature
<222> LOCATION: (62)..(62)
<223> OTHER INFORMATION: Xaa is any aa
<220> FEATURE:
<221> NAME/KEY: misc_feature
<222> LOCATION: (63)..(63)
<223> OTHER INFORMATION: Xaa is any aa
<220> FEATURE:
<221> NAME/KEY: misc_feature
<222> LOCATION: (64)..(64)
<223> OTHER INFORMATION: Xaa is any aa
<220> FEATURE:
<221> NAME/KEY: misc_feature
<222> LOCATION: (65)..(65)
<223> OTHER INFORMATION: Xaa is any aa
<220> FEATURE:
<221> NAME/KEY: misc_feature
<222> LOCATION: (66)..(66)
<223> OTHER INFORMATION: Xaa is any aa or nothing
<220> FEATURE:
<221> NAME/KEY: misc_feature
<222> LOCATION: (67)..(67)
<223> OTHER INFORMATION: Xaa is Thr, Gly, or Ser
<220> FEATURE:
<221> NAME/KEY: misc_feature
<222> LOCATION: (68)..(68)
<223> OTHER INFORMATION: Xaa is Glu or Ser
<220> FEATURE:
<221> NAME/KEY: misc_feature
<222> LOCATION: (69)..(69)
<223> OTHER INFORMATION: Xaa is Ser or Lys
<220> FEATURE:
<221> NAME/KEY: misc_feature
<222> LOCATION: (70)..(70)
<223> OTHER INFORMATION: Xaa is Thr, Gly, or Ser
<220> FEATURE:
<221> NAME/KEY: misc_feature
<222> LOCATION: (71)..(71)
<223> OTHER INFORMATION: Xaa is any aa or nothing
<220> FEATURE:
<221> NAME/KEY: misc_feature
<222> LOCATION: (72)..(72)
<223> OTHER INFORMATION: Xaa is any aa or nothing
<220> FEATURE:
<221> NAME/KEY: misc_feature
<222> LOCATION: (73)..(73)
<223> OTHER INFORMATION: Xaa is any aa or nothing
<220> FEATURE:
<221> NAME/KEY: misc_feature
<222> LOCATION: (74)..(74)
<223> OTHER INFORMATION: Xaa is any aa or nothing
<220> FEATURE:
<221> NAME/KEY: misc_feature
<222> LOCATION: (76)..(76)
<223> OTHER INFORMATION: Xaa is any aa
<220> FEATURE:
<221> NAME/KEY: misc_feature
<222> LOCATION: (83)..(83)
<223> OTHER INFORMATION: Xaa is Tyr or His
<220> FEATURE:
<221> NAME/KEY: misc_feature
<222> LOCATION: (87)..(87)
<223> OTHER INFORMATION: Xaa is any aa
<220> FEATURE:
<221> NAME/KEY: misc_feature
<222> LOCATION: (89)..(89)
<223> OTHER INFORMATION: Xaa is any aa
<220> FEATURE:
<221> NAME/KEY: misc_feature
```

```
<222> LOCATION: (90)..(90)
<223> OTHER INFORMATION: Xaa is Thr, Gly, or Ser
<220> FEATURE:
<221> NAME/KEY: misc_feature
<222> LOCATION: (91)..(91)
<223> OTHER INFORMATION: Xaa is any aa
<220> FEATURE:
<221> NAME/KEY: misc_feature
<222> LOCATION: (92)..(92)
<223> OTHER INFORMATION: Xaa is Glu  or Ala
<220> FEATURE:
<221> NAME/KEY: misc_feature
<222> LOCATION: (93)..(93)
<223> OTHER INFORMATION: Xaa is Ile, Val, Leu, or Met
<220> FEATURE:
<221> NAME/KEY: misc_feature
<222> LOCATION: (96)..(96)
<223> OTHER INFORMATION: Xaa is Ala  or Val
<220> FEATURE:
<221> NAME/KEY: misc_feature
<222> LOCATION: (97)..(97)
<223> OTHER INFORMATION: Xaa is Asp or Glu
<220> FEATURE:
<221> NAME/KEY: misc_feature
<222> LOCATION: (100)..(100)
<223> OTHER INFORMATION: Xaa is any aa
<220> FEATURE:
<221> NAME/KEY: misc_feature
<222> LOCATION: (101)..(101)
<223> OTHER INFORMATION: Xaa is any aa
<220> FEATURE:
<221> NAME/KEY: misc_feature
<222> LOCATION: (104)..(104)
<223> OTHER INFORMATION: Xaa is Lys, Arg, or His
<220> FEATURE:
<221> NAME/KEY: misc_feature
<222> LOCATION: (105)..(105)
<223> OTHER INFORMATION: Xaa is any aa
<220> FEATURE:
<221> NAME/KEY: misc_feature
<222> LOCATION: (107)..(107)
<223> OTHER INFORMATION: Xaa is Ala  or Val
<220> FEATURE:
<221> NAME/KEY: misc_feature
<222> LOCATION: (108)..(108)
<223> OTHER INFORMATION: Xaa is Lys, Arg, or His
<220> FEATURE:
<221> NAME/KEY: misc_feature
<222> LOCATION: (111)..(111)
<223> OTHER INFORMATION: Xaa is any aa
<220> FEATURE:
<221> NAME/KEY: misc_feature
<222> LOCATION: (112)..(112)
<223> OTHER INFORMATION: Xaa is any aa
<220> FEATURE:
<221> NAME/KEY: misc_feature
<222> LOCATION: (113)..(113)
<223> OTHER INFORMATION: Xaa is any aa
<220> FEATURE:
<221> NAME/KEY: misc_feature
<222> LOCATION: (114)..(114)
<223> OTHER INFORMATION: Xaa is any aa
<220> FEATURE:
<221> NAME/KEY: misc_feature
<222> LOCATION: (115)..(115)
<223> OTHER INFORMATION: Xaa is any aa
<220> FEATURE:
<221> NAME/KEY: misc_feature
<222> LOCATION: (116)..(116)
<223> OTHER INFORMATION: Xaa is any aa
<220> FEATURE:
<221> NAME/KEY: misc_feature
<222> LOCATION: (117)..(117)
<223> OTHER INFORMATION: Xaa is any aa
<220> FEATURE:
<221> NAME/KEY: misc_feature
<222> LOCATION: (119)..(119)
<223> OTHER INFORMATION: Xaa is any aa
<220> FEATURE:
<221> NAME/KEY: misc_feature
```

```
<222> LOCATION: (120)..(120)
<223> OTHER INFORMATION: Xaa is Ile, Val, Leu, or Met
<220> FEATURE:
<221> NAME/KEY: misc_feature
<222> LOCATION: (122)..(122)
<223> OTHER INFORMATION: Xaa is Ile, Val, Leu, or Met
<220> FEATURE:
<221> NAME/KEY: misc_feature
<222> LOCATION: (125)..(125)
<223> OTHER INFORMATION: Xaa is any aa
<220> FEATURE:
<221> NAME/KEY: misc_feature
<222> LOCATION: (126)..(126)
<223> OTHER INFORMATION: Xaa is Cys  or Gly
<220> FEATURE:
<221> NAME/KEY: misc_feature
<222> LOCATION: (127)..(127)
<223> OTHER INFORMATION: Xaa is any aa
<220> FEATURE:
<221> NAME/KEY: misc_feature
<222> LOCATION: (129)..(129)
<223> OTHER INFORMATION: Xaa is Thr, Gly, or Ser
<220> FEATURE:
<221> NAME/KEY: misc_feature
<222> LOCATION: (131)..(131)
<223> OTHER INFORMATION: Xaa is any aa
<220> FEATURE:
<221> NAME/KEY: misc_feature
<222> LOCATION: (133)..(133)
<223> OTHER INFORMATION: Xaa is any aa
<220> FEATURE:
<221> NAME/KEY: misc_feature
<222> LOCATION: (135)..(135)
<223> OTHER INFORMATION: Xaa is Ile, Val, Leu, or Met
<220> FEATURE:
<221> NAME/KEY: misc_feature
<222> LOCATION: (136)..(136)
<223> OTHER INFORMATION: Xaa is any aa
<220> FEATURE:
<221> NAME/KEY: misc_feature
<222> LOCATION: (137)..(137)
<223> OTHER INFORMATION: Xaa is any aa
<220> FEATURE:
<221> NAME/KEY: misc_feature
<222> LOCATION: (138)..(138)
<223> OTHER INFORMATION: Xaa is any aa
<220> FEATURE:
<221> NAME/KEY: misc_feature
<222> LOCATION: (140)..(140)
<223> OTHER INFORMATION: Xaa is any aa
<220> FEATURE:
<221> NAME/KEY: misc_feature
<222> LOCATION: (141)..(141)
<223> OTHER INFORMATION: Xaa is Thr, Gly, or Ser
<220> FEATURE:
<221> NAME/KEY: misc_feature
<222> LOCATION: (142)..(142)
<223> OTHER INFORMATION: Xaa is any aa
<220> FEATURE:
<221> NAME/KEY: misc_feature
<222> LOCATION: (145)..(145)
<223> OTHER INFORMATION: Xaa is Lys, Arg, or His
<220> FEATURE:
<221> NAME/KEY: misc_feature
<222> LOCATION: (147)..(147)
<223> OTHER INFORMATION: Xaa is any aa
<220> FEATURE:
<221> NAME/KEY: misc_feature
<222> LOCATION: (148)..(148)
<223> OTHER INFORMATION: Xaa is any aa
<220> FEATURE:
<221> NAME/KEY: misc_feature
<222> LOCATION: (149)..(149)
<223> OTHER INFORMATION: Xaa is any aa
<220> FEATURE:
<221> NAME/KEY: misc_feature
<222> LOCATION: (151)..(151)
<223> OTHER INFORMATION: Xaa is Ile, Val, Leu, or Met
<220> FEATURE:
<221> NAME/KEY: misc_feature
```

```
<222> LOCATION: (154)..(154)
<223> OTHER INFORMATION: Xaa is Ser or Cys
<220> FEATURE:
<221> NAME/KEY: misc_feature
<222> LOCATION: (156)..(156)
<223> OTHER INFORMATION: Xaa is any aa
<220> FEATURE:
<221> NAME/KEY: misc_feature
<222> LOCATION: (157)..(157)
<223> OTHER INFORMATION: Xaa is any aa
<220> FEATURE:
<221> NAME/KEY: misc_feature
<222> LOCATION: (158)..(158)
<223> OTHER INFORMATION: Xaa is any aa
<220> FEATURE:
<221> NAME/KEY: misc_feature
<222> LOCATION: (159)..(159)
<223> OTHER INFORMATION: Xaa is any aa or nothing
<220> FEATURE:
<221> NAME/KEY: misc_feature
<222> LOCATION: (160)..(160)
<223> OTHER INFORMATION: Xaa is Lys, Arg, or His
<220> FEATURE:
<221> NAME/KEY: misc_feature
<222> LOCATION: (161)..(161)
<223> OTHER INFORMATION: Xaa is any aa
<220> FEATURE:
<221> NAME/KEY: misc_feature
<222> LOCATION: (162)..(162)
<223> OTHER INFORMATION: Xaa is any aa or nothing
<220> FEATURE:
<221> NAME/KEY: misc_feature
<222> LOCATION: (163)..(163)
<223> OTHER INFORMATION: Xaa is any aa or nothing
<220> FEATURE:
<221> NAME/KEY: misc_feature
<222> LOCATION: (164)..(164)
<223> OTHER INFORMATION: Xaa is Asp or Glu
<220> FEATURE:
<221> NAME/KEY: misc_feature
<222> LOCATION: (165)..(165)
<223> OTHER INFORMATION: Xaa is any aa
<220> FEATURE:
<221> NAME/KEY: misc_feature
<222> LOCATION: (166)..(166)
<223> OTHER INFORMATION: Xaa is any aa
<220> FEATURE:
<221> NAME/KEY: misc_feature
<222> LOCATION: (167)..(167)
<223> OTHER INFORMATION: Xaa is Thr, Gly, or Ser
<220> FEATURE:
<221> NAME/KEY: misc_feature
<222> LOCATION: (168)..(168)
<223> OTHER INFORMATION: Xaa is Cys or Phe
<220> FEATURE:
<221> NAME/KEY: misc_feature
<222> LOCATION: (169)..(169)
<223> OTHER INFORMATION: Xaa is any aa
<220> FEATURE:
<221> NAME/KEY: misc_feature
<222> LOCATION: (170)..(170)
<223> OTHER INFORMATION: Xaa is any aa
<220> FEATURE:
<221> NAME/KEY: misc_feature
<222> LOCATION: (172)..(172)
<223> OTHER INFORMATION: Xaa is Thr, Gly, or Ser
<220> FEATURE:
<221> NAME/KEY: misc_feature
<222> LOCATION: (173)..(173)
<223> OTHER INFORMATION: Xaa is any aa
<220> FEATURE:
<221> NAME/KEY: misc_feature
<222> LOCATION: (176)..(176)
<223> OTHER INFORMATION: Xaa is any aa
<220> FEATURE:
<221> NAME/KEY: misc_feature
<222> LOCATION: (177)..(177)
<223> OTHER INFORMATION: Xaa is any aa
<220> FEATURE:
<221> NAME/KEY: misc_feature
```

```
<222> LOCATION: (178)..(178)
<223> OTHER INFORMATION: Xaa is any aa
<220> FEATURE:
<221> NAME/KEY: misc_feature
<222> LOCATION: (179)..(179)
<223> OTHER INFORMATION: Xaa is Ile, Val, Leu, or Met
<220> FEATURE:
<221> NAME/KEY: misc_feature
<222> LOCATION: (180)..(180)
<223> OTHER INFORMATION: Xaa is any aa
<220> FEATURE:
<221> NAME/KEY: misc_feature
<222> LOCATION: (181)..(181)
<223> OTHER INFORMATION: Xaa is Thr, Gly, or Ser
<220> FEATURE:
<221> NAME/KEY: misc_feature
<222> LOCATION: (182)..(182)
<223> OTHER INFORMATION: Xaa is any aa
<220> FEATURE:
<221> NAME/KEY: misc_feature
<222> LOCATION: (183)..(183)
<223> OTHER INFORMATION: Xaa is Pro  or Ala
<220> FEATURE:
<221> NAME/KEY: misc_feature
<222> LOCATION: (184)..(184)
<223> OTHER INFORMATION: Xaa is any aa
<220> FEATURE:
<221> NAME/KEY: misc_feature
<222> LOCATION: (185)..(185)
<223> OTHER INFORMATION: Xaa is any aa
<220> FEATURE:
<221> NAME/KEY: misc_feature
<222> LOCATION: (186)..(186)
<223> OTHER INFORMATION: Xaa is any aa
<220> FEATURE:
<221> NAME/KEY: misc_feature
<222> LOCATION: (187)..(187)
<223> OTHER INFORMATION: Xaa is any aa or nothing
<220> FEATURE:
<221> NAME/KEY: misc_feature
<222> LOCATION: (188)..(188)
<223> OTHER INFORMATION: Xaa is any aa or nothing
<220> FEATURE:
<221> NAME/KEY: misc_feature
<222> LOCATION: (189)..(189)
<223> OTHER INFORMATION: Xaa is any aa or nothing
<220> FEATURE:
<221> NAME/KEY: misc_feature
<222> LOCATION: (190)..(190)
<223> OTHER INFORMATION: Xaa is any aa or nothing
<220> FEATURE:
<221> NAME/KEY: misc_feature
<222> LOCATION: (191)..(191)
<223> OTHER INFORMATION: Xaa is any aa or nothing
<220> FEATURE:
<221> NAME/KEY: misc_feature
<222> LOCATION: (192)..(192)
<223> OTHER INFORMATION: Xaa is Lys, Arg, or His
<220> FEATURE:
<221> NAME/KEY: misc_feature
<222> LOCATION: (193)..(193)
<223> OTHER INFORMATION: Xaa is any aa
<220> FEATURE:
<221> NAME/KEY: misc_feature
<222> LOCATION: (194)..(194)
<223> OTHER INFORMATION: Xaa is Ile, Val, Leu, or Met
<220> FEATURE:
<221> NAME/KEY: misc_feature
<222> LOCATION: (200)..(200)
<223> OTHER INFORMATION: Xaa is any aa
<220> FEATURE:
<221> NAME/KEY: misc_feature
<222> LOCATION: (203)..(203)
<223> OTHER INFORMATION: Xaa is any aa
<220> FEATURE:
<221> NAME/KEY: misc_feature
<222> LOCATION: (204)..(204)
<223> OTHER INFORMATION: Xaa is Ser  or Asn
<220> FEATURE:
<221> NAME/KEY: misc_feature
```

```
<222> LOCATION: (205)..(205)
<223> OTHER INFORMATION: Xaa is Ile, Val, Leu, or Met
<220> FEATURE:
<221> NAME/KEY: misc_feature
<222> LOCATION: (207)..(207)
<223> OTHER INFORMATION: Xaa is Ile, Val, Leu, or Met
<220> FEATURE:
<221> NAME/KEY: misc_feature
<222> LOCATION: (209)..(209)
<223> OTHER INFORMATION: Xaa is any aa
<220> FEATURE:
<221> NAME/KEY: misc_feature
<222> LOCATION: (210)..(210)
<223> OTHER INFORMATION: Xaa is Asp or Glu
<220> FEATURE:
<221> NAME/KEY: misc_feature
<222> LOCATION: (211)..(211)
<223> OTHER INFORMATION: Xaa is any aa
<220> FEATURE:
<221> NAME/KEY: misc_feature
<222> LOCATION: (212)..(212)
<223> OTHER INFORMATION: Xaa is Phe, Tyr, or Trp
<220> FEATURE:
<221> NAME/KEY: misc_feature
<222> LOCATION: (213)..(213)
<223> OTHER INFORMATION: Xaa is Pro  or Ser
<220> FEATURE:
<221> NAME/KEY: misc_feature
<222> LOCATION: (214)..(214)
<223> OTHER INFORMATION: Xaa is any aa
<220> FEATURE:
<221> NAME/KEY: misc_feature
<222> LOCATION: (215)..(215)
<223> OTHER INFORMATION: Xaa is Lys, Arg, or His
<220> FEATURE:
<221> NAME/KEY: misc_feature
<222> LOCATION: (216)..(216)
<223> OTHER INFORMATION: Xaa is Ile, Val, Leu, or Met
<220> FEATURE:
<221> NAME/KEY: misc_feature
<222> LOCATION: (217)..(217)
<223> OTHER INFORMATION: Xaa is Thr, Gly, or Ser
<220> FEATURE:
<221> NAME/KEY: misc_feature
<222> LOCATION: (218)..(218)
<223> OTHER INFORMATION: Xaa is Val  or Ala
<220> FEATURE:
<221> NAME/KEY: misc_feature
<222> LOCATION: (219)..(219)
<223> OTHER INFORMATION: Xaa is Thr, Gly, or Ser
<220> FEATURE:
<221> NAME/KEY: misc_feature
<222> LOCATION: (222)..(222)
<223> OTHER INFORMATION: Xaa is any aa
<220> FEATURE:
<221> NAME/KEY: misc_feature
<222> LOCATION: (223)..(223)
<223> OTHER INFORMATION: Xaa is Thr, Gly, or Ser
<220> FEATURE:
<221> NAME/KEY: misc_feature
<222> LOCATION: (224)..(224)
<223> OTHER INFORMATION: Xaa is Thr, Gly, or Ser
<220> FEATURE:
<221> NAME/KEY: misc_feature
<222> LOCATION: (225)..(225)
<223> OTHER INFORMATION: Xaa is any aa
<220> FEATURE:
<221> NAME/KEY: misc_feature
<222> LOCATION: (226)..(226)
<223> OTHER INFORMATION: Xaa is Ile, Val, Leu, or Met
<220> FEATURE:
<221> NAME/KEY: misc_feature
<222> LOCATION: (228)..(228)
<223> OTHER INFORMATION: Xaa is any aa
<220> FEATURE:
<221> NAME/KEY: misc_feature
<222> LOCATION: (229)..(229)
<223> OTHER INFORMATION: Xaa is any aa
<220> FEATURE:
<221> NAME/KEY: misc_feature
```

-continued

```
<222> LOCATION: (230)..(230)
<223> OTHER INFORMATION: Xaa is any aa
<220> FEATURE:
<221> NAME/KEY: misc_feature
<222> LOCATION: (231)..(231)
<223> OTHER INFORMATION: Xaa is any aa
<220> FEATURE:
<221> NAME/KEY: misc_feature
<222> LOCATION: (232)..(232)
<223> OTHER INFORMATION: Xaa is any aa
<220> FEATURE:
<221> NAME/KEY: misc_feature
<222> LOCATION: (233)..(233)
<223> OTHER INFORMATION: Xaa is any aa
<220> FEATURE:
<221> NAME/KEY: misc_feature
<222> LOCATION: (234)..(234)
<223> OTHER INFORMATION: Xaa is any aa or nothing
<220> FEATURE:
<221> NAME/KEY: misc_feature
<222> LOCATION: (235)..(235)
<223> OTHER INFORMATION: Xaa is Thr, Gly, or Ser
<220> FEATURE:
<221> NAME/KEY: misc_feature
<222> LOCATION: (236)..(236)
<223> OTHER INFORMATION: Xaa is any aa
<220> FEATURE:
<221> NAME/KEY: misc_feature
<222> LOCATION: (237)..(237)
<223> OTHER INFORMATION: Xaa is Val  or Thr
<220> FEATURE:
<221> NAME/KEY: misc_feature
<222> LOCATION: (238)..(238)
<223> OTHER INFORMATION: Xaa is any aa
<220> FEATURE:
<221> NAME/KEY: misc_feature
<222> LOCATION: (239)..(239)
<223> OTHER INFORMATION: Xaa is Asp or Glu
<220> FEATURE:
<221> NAME/KEY: misc_feature
<222> LOCATION: (240)..(240)
<223> OTHER INFORMATION: Xaa is any aa
<220> FEATURE:
<221> NAME/KEY: misc_feature
<222> LOCATION: (241)..(241)
<223> OTHER INFORMATION: Xaa is any aa
<220> FEATURE:
<221> NAME/KEY: misc_feature
<222> LOCATION: (242)..(242)
<223> OTHER INFORMATION: Xaa is any aa
<220> FEATURE:
<221> NAME/KEY: misc_feature
<222> LOCATION: (243)..(243)
<223> OTHER INFORMATION: Xaa is any aa
<220> FEATURE:
<221> NAME/KEY: misc_feature
<222> LOCATION: (244)..(244)
<223> OTHER INFORMATION: Xaa is any aa
<220> FEATURE:
<221> NAME/KEY: misc_feature
<222> LOCATION: (245)..(245)
<223> OTHER INFORMATION: Xaa is any aa
<220> FEATURE:
<221> NAME/KEY: misc_feature
<222> LOCATION: (246)..(246)
<223> OTHER INFORMATION: Xaa is any aa or nothing
<220> FEATURE:
<221> NAME/KEY: misc_feature
<222> LOCATION: (247)..(247)
<223> OTHER INFORMATION: Xaa is any aa or nothing
<220> FEATURE:
<221> NAME/KEY: misc_feature
<222> LOCATION: (248)..(248)
<223> OTHER INFORMATION: Xaa is any aa or nothing
<220> FEATURE:
<221> NAME/KEY: misc_feature
<222> LOCATION: (249)..(249)
<223> OTHER INFORMATION: Xaa is any aa or nothing
<220> FEATURE:
<221> NAME/KEY: misc_feature
```

```
<222> LOCATION: (250)..(250)
<223> OTHER INFORMATION: Xaa is any aa or nothing
<220> FEATURE:
<221> NAME/KEY: misc_feature
<222> LOCATION: (251)..(251)
<223> OTHER INFORMATION: Xaa is any aa or nothing
<220> FEATURE:
<221> NAME/KEY: misc_feature
<222> LOCATION: (252)..(252)
<223> OTHER INFORMATION: Xaa is any aa or nothing
<220> FEATURE:
<221> NAME/KEY: misc_feature
<222> LOCATION: (253)..(253)
<223> OTHER INFORMATION: Xaa is any aa or nothing
<220> FEATURE:
<221> NAME/KEY: misc_feature
<222> LOCATION: (254)..(254)
<223> OTHER INFORMATION: Xaa is any aa or nothing
<220> FEATURE:
<221> NAME/KEY: misc_feature
<222> LOCATION: (255)..(255)
<223> OTHER INFORMATION: Xaa is any aa or nothing
<220> FEATURE:
<221> NAME/KEY: misc_feature
<222> LOCATION: (256)..(256)
<223> OTHER INFORMATION: Xaa is any aa or nothing
<220> FEATURE:
<221> NAME/KEY: misc_feature
<222> LOCATION: (257)..(257)
<223> OTHER INFORMATION: Xaa is Ile, Val, Leu, or Met
<220> FEATURE:
<221> NAME/KEY: misc_feature
<222> LOCATION: (258)..(258)
<223> OTHER INFORMATION: Xaa is Gly  or Asp
<220> FEATURE:
<221> NAME/KEY: misc_feature
<222> LOCATION: (259)..(259)
<223> OTHER INFORMATION: Xaa is any aa
<220> FEATURE:
<221> NAME/KEY: misc_feature
<222> LOCATION: (260)..(260)
<223> OTHER INFORMATION: Xaa is any aa
<220> FEATURE:
<221> NAME/KEY: misc_feature
<222> LOCATION: (261)..(261)
<223> OTHER INFORMATION: Xaa is any aa
<220> FEATURE:
<221> NAME/KEY: misc_feature
<222> LOCATION: (262)..(262)
<223> OTHER INFORMATION: Xaa is any aa
<220> FEATURE:
<221> NAME/KEY: misc_feature
<222> LOCATION: (263)..(263)
<223> OTHER INFORMATION: Xaa is any aa
<220> FEATURE:
<221> NAME/KEY: misc_feature
<222> LOCATION: (264)..(264)
<223> OTHER INFORMATION: Xaa is any aa
<220> FEATURE:
<221> NAME/KEY: misc_feature
<222> LOCATION: (265)..(265)
<223> OTHER INFORMATION: Xaa is any aa
<220> FEATURE:
<221> NAME/KEY: misc_feature
<222> LOCATION: (266)..(266)
<223> OTHER INFORMATION: Xaa is any aa
<220> FEATURE:
<221> NAME/KEY: misc_feature
<222> LOCATION: (267)..(267)
<223> OTHER INFORMATION: Xaa is any aa
<220> FEATURE:
<221> NAME/KEY: misc_feature
<222> LOCATION: (268)..(268)
<223> OTHER INFORMATION: Xaa is any aa
<220> FEATURE:
<221> NAME/KEY: misc_feature
<222> LOCATION: (269)..(269)
<223> OTHER INFORMATION: Xaa is any aa
<220> FEATURE:
<221> NAME/KEY: misc_feature
```

```
<222> LOCATION: (270)..(270)
<223> OTHER INFORMATION: Xaa is any aa
<220> FEATURE:
<221> NAME/KEY: misc_feature
<222> LOCATION: (271)..(271)
<223> OTHER INFORMATION: Xaa is any aa
<220> FEATURE:
<221> NAME/KEY: misc_feature
<222> LOCATION: (272)..(272)
<223> OTHER INFORMATION: Xaa is any aa
<220> FEATURE:
<221> NAME/KEY: misc_feature
<222> LOCATION: (273)..(273)
<223> OTHER INFORMATION: Xaa is any aa
<220> FEATURE:
<221> NAME/KEY: misc_feature
<222> LOCATION: (274)..(274)
<223> OTHER INFORMATION: Xaa is any aa
<220> FEATURE:
<221> NAME/KEY: misc_feature
<222> LOCATION: (275)..(275)
<223> OTHER INFORMATION: Xaa is any aa or nothing
<220> FEATURE:
<221> NAME/KEY: misc_feature
<222> LOCATION: (276)..(276)
<223> OTHER INFORMATION: Xaa is any aa or nothing
<220> FEATURE:
<221> NAME/KEY: misc_feature
<222> LOCATION: (277)..(277)
<223> OTHER INFORMATION: Xaa is any aa or nothing
<220> FEATURE:
<221> NAME/KEY: misc_feature
<222> LOCATION: (278)..(278)
<223> OTHER INFORMATION: Xaa is any aa or nothing
<220> FEATURE:
<221> NAME/KEY: misc_feature
<222> LOCATION: (279)..(279)
<223> OTHER INFORMATION: Xaa is any aa or nothing
<220> FEATURE:
<221> NAME/KEY: misc_feature
<222> LOCATION: (280)..(280)
<223> OTHER INFORMATION: Xaa is any aa or nothing
<220> FEATURE:
<221> NAME/KEY: misc_feature
<222> LOCATION: (281)..(281)
<223> OTHER INFORMATION: Xaa is any aa or nothing
<220> FEATURE:
<221> NAME/KEY: misc_feature
<222> LOCATION: (282)..(282)
<223> OTHER INFORMATION: Xaa is Phe  or Met
<220> FEATURE:
<221> NAME/KEY: misc_feature
<222> LOCATION: (283)..(283)
<223> OTHER INFORMATION: Xaa is Thr, Gly, or Ser
<220> FEATURE:
<221> NAME/KEY: misc_feature
<222> LOCATION: (284)..(284)
<223> OTHER INFORMATION: Xaa is Thr  or Pro
<220> FEATURE:
<221> NAME/KEY: misc_feature
<222> LOCATION: (285)..(285)
<223> OTHER INFORMATION: Xaa is any aa
<220> FEATURE:
<221> NAME/KEY: misc_feature
<222> LOCATION: (286)..(286)
<223> OTHER INFORMATION: Xaa is any aa
<220> FEATURE:
<221> NAME/KEY: misc_feature
<222> LOCATION: (287)..(287)
<223> OTHER INFORMATION: Xaa is any aa
<220> FEATURE:
<221> NAME/KEY: misc_feature
<222> LOCATION: (288)..(288)
<223> OTHER INFORMATION: Xaa is any aa
<220> FEATURE:
<221> NAME/KEY: misc_feature
<222> LOCATION: (289)..(289)
<223> OTHER INFORMATION: Xaa is any aa
<220> FEATURE:
<221> NAME/KEY: misc_feature
```

```
-continued

<222> LOCATION: (290)..(290)
<223> OTHER INFORMATION: Xaa is any aa
<220> FEATURE:
<221> NAME/KEY: misc_feature
<222> LOCATION: (291)..(291)
<223> OTHER INFORMATION: Xaa is any aa
<220> FEATURE:
<221> NAME/KEY: misc_feature
<222> LOCATION: (292)..(292)
<223> OTHER INFORMATION: Xaa is Phe, Tyr, or Trp
<220> FEATURE:
<221> NAME/KEY: misc_feature
<222> LOCATION: (293)..(293)
<223> OTHER INFORMATION: Xaa is Gln  or Asp
<220> FEATURE:
<221> NAME/KEY: misc_feature
<222> LOCATION: (294)..(294)
<223> OTHER INFORMATION: Xaa is any aa
<220> FEATURE:
<221> NAME/KEY: misc_feature
<222> LOCATION: (295)..(295)
<223> OTHER INFORMATION: Xaa is Ser  or Cys
<220> FEATURE:
<221> NAME/KEY: misc_feature
<222> LOCATION: (296)..(296)
<223> OTHER INFORMATION: Xaa is Pro  or Ser
<220> FEATURE:
<221> NAME/KEY: misc_feature
<222> LOCATION: (297)..(297)
<223> OTHER INFORMATION: Xaa is any aa
<220> FEATURE:
<221> NAME/KEY: misc_feature
<222> LOCATION: (300)..(300)
<223> OTHER INFORMATION: Xaa is any aa
<220> FEATURE:
<221> NAME/KEY: misc_feature
<222> LOCATION: (301)..(301)
<223> OTHER INFORMATION: Xaa is any aa
<220> FEATURE:
<221> NAME/KEY: misc_feature
<222> LOCATION: (303)..(303)
<223> OTHER INFORMATION: Xaa is Thr, Gly, or Ser
<220> FEATURE:
<221> NAME/KEY: misc_feature
<222> LOCATION: (304)..(304)
<223> OTHER INFORMATION: Xaa is any aa
<220> FEATURE:
<221> NAME/KEY: misc_feature
<222> LOCATION: (305)..(305)
<223> OTHER INFORMATION: Xaa is any aa
<220> FEATURE:
<221> NAME/KEY: misc_feature
<222> LOCATION: (306)..(306)
<223> OTHER INFORMATION: Xaa is Ile, Val, Leu, or Met
<220> FEATURE:
<221> NAME/KEY: misc_feature
<222> LOCATION: (307)..(307)
<223> OTHER INFORMATION: Xaa is any aa
<220> FEATURE:
<221> NAME/KEY: misc_feature
<222> LOCATION: (309)..(309)
<223> OTHER INFORMATION: Xaa is Pro  or Val
<220> FEATURE:
<221> NAME/KEY: misc_feature
<222> LOCATION: (310)..(310)
<223> OTHER INFORMATION: Xaa is any aa
<220> FEATURE:
<221> NAME/KEY: misc_feature
<222> LOCATION: (311)..(311)
<223> OTHER INFORMATION: Xaa is any aa
<220> FEATURE:
<221> NAME/KEY: misc_feature
<222> LOCATION: (312)..(312)
<223> OTHER INFORMATION: Xaa is any aa
<220> FEATURE:
<221> NAME/KEY: misc_feature
<222> LOCATION: (314)..(314)
<223> OTHER INFORMATION: Xaa is any aa
<220> FEATURE:
<221> NAME/KEY: misc_feature
```

```
<222> LOCATION: (315)..(315)
<223> OTHER INFORMATION: Xaa is any aa
<220> FEATURE:
<221> NAME/KEY: misc_feature
<222> LOCATION: (316)..(316)
<223> OTHER INFORMATION: Xaa is Asp or Glu
<220> FEATURE:
<221> NAME/KEY: misc_feature
<222> LOCATION: (317)..(317)
<223> OTHER INFORMATION: Xaa is any aa
<220> FEATURE:
<221> NAME/KEY: misc_feature
<222> LOCATION: (318)..(318)
<223> OTHER INFORMATION: Xaa is any aa
<220> FEATURE:
<221> NAME/KEY: misc_feature
<222> LOCATION: (319)..(319)
<223> OTHER INFORMATION: Xaa is any aa
<220> FEATURE:
<221> NAME/KEY: misc_feature
<222> LOCATION: (320)..(320)
<223> OTHER INFORMATION: Xaa is any aa
<220> FEATURE:
<221> NAME/KEY: misc_feature
<222> LOCATION: (321)..(321)
<223> OTHER INFORMATION: Xaa is any aa
<220> FEATURE:
<221> NAME/KEY: misc_feature
<222> LOCATION: (322)..(322)
<223> OTHER INFORMATION: Xaa is any aa
<220> FEATURE:
<221> NAME/KEY: misc_feature
<222> LOCATION: (323)..(323)
<223> OTHER INFORMATION: Xaa is any aa
<220> FEATURE:
<221> NAME/KEY: misc_feature
<222> LOCATION: (324)..(324)
<223> OTHER INFORMATION: Xaa is any aa or nothing
<220> FEATURE:
<221> NAME/KEY: misc_feature
<222> LOCATION: (325)..(325)
<223> OTHER INFORMATION: Xaa is any aa or nothing
<220> FEATURE:
<221> NAME/KEY: misc_feature
<222> LOCATION: (326)..(326)
<223> OTHER INFORMATION: Xaa is any aa or nothing
<220> FEATURE:
<221> NAME/KEY: misc_feature
<222> LOCATION: (327)..(327)
<223> OTHER INFORMATION: Xaa is any aa or nothing
<220> FEATURE:
<221> NAME/KEY: misc_feature
<222> LOCATION: (328)..(328)
<223> OTHER INFORMATION: Xaa is Thr, Gly, or Ser
<220> FEATURE:
<221> NAME/KEY: misc_feature
<222> LOCATION: (329)..(329)
<223> OTHER INFORMATION: Xaa is any aa
<220> FEATURE:
<221> NAME/KEY: misc_feature
<222> LOCATION: (330)..(330)
<223> OTHER INFORMATION: Xaa is any aa
<220> FEATURE:
<221> NAME/KEY: misc_feature
<222> LOCATION: (331)..(331)
<223> OTHER INFORMATION: Xaa is any aa
<220> FEATURE:
<221> NAME/KEY: misc_feature
<222> LOCATION: (332)..(332)
<223> OTHER INFORMATION: Xaa is any aa or nothing
<220> FEATURE:
<221> NAME/KEY: misc_feature
<222> LOCATION: (335)..(335)
<223> OTHER INFORMATION: Xaa is Thr, Gly, or Ser
<220> FEATURE:
<221> NAME/KEY: misc_feature
<222> LOCATION: (337)..(337)
<223> OTHER INFORMATION: Xaa is any aa
<220> FEATURE:
<221> NAME/KEY: misc_feature
```

```
<222> LOCATION: (338)..(338)
<223> OTHER INFORMATION: Xaa is Lys, Arg, or His
<220> FEATURE:
<221> NAME/KEY: misc_feature
<222> LOCATION: (339)..(339)
<223> OTHER INFORMATION: Xaa is Ala or Val
<220> FEATURE:
<221> NAME/KEY: misc_feature
<222> LOCATION: (340)..(340)
<223> OTHER INFORMATION: Xaa is any aa
<220> FEATURE:
<221> NAME/KEY: misc_feature
<222> LOCATION: (341)..(341)
<223> OTHER INFORMATION: Xaa is Ile, Val, Leu, or Met
<220> FEATURE:
<221> NAME/KEY: misc_feature
<222> LOCATION: (343)..(343)
<223> OTHER INFORMATION: Xaa is any aa
<220> FEATURE:
<221> NAME/KEY: misc_feature
<222> LOCATION: (344)..(344)
<223> OTHER INFORMATION: Xaa is any aa
<220> FEATURE:
<221> NAME/KEY: misc_feature
<222> LOCATION: (345)..(345)
<223> OTHER INFORMATION: Xaa is any aa
<220> FEATURE:
<221> NAME/KEY: misc_feature
<222> LOCATION: (347)..(347)
<223> OTHER INFORMATION: Xaa is any aa
<220> FEATURE:
<221> NAME/KEY: misc_feature
<222> LOCATION: (348)..(348)
<223> OTHER INFORMATION: Xaa is any aa
<220> FEATURE:
<221> NAME/KEY: misc_feature
<222> LOCATION: (349)..(349)
<223> OTHER INFORMATION: Xaa is any aa
<220> FEATURE:
<221> NAME/KEY: misc_feature
<222> LOCATION: (350)..(350)
<223> OTHER INFORMATION: Xaa is any aa
<220> FEATURE:
<221> NAME/KEY: misc_feature
<222> LOCATION: (351)..(351)
<223> OTHER INFORMATION: Xaa is any aa
<220> FEATURE:
<221> NAME/KEY: misc_feature
<222> LOCATION: (352)..(352)
<223> OTHER INFORMATION: Xaa is any aa
<220> FEATURE:
<221> NAME/KEY: misc_feature
<222> LOCATION: (353)..(353)
<223> OTHER INFORMATION: Xaa is any aa
<220> FEATURE:
<221> NAME/KEY: misc_feature
<222> LOCATION: (354)..(354)
<223> OTHER INFORMATION: Xaa is Gln or Leu
<220> FEATURE:
<221> NAME/KEY: misc_feature
<222> LOCATION: (355)..(355)
<223> OTHER INFORMATION: Xaa is Arg or Trp
<220> FEATURE:
<221> NAME/KEY: misc_feature
<222> LOCATION: (356)..(356)
<223> OTHER INFORMATION: Xaa is Trp or Arg
<220> FEATURE:
<221> NAME/KEY: misc_feature
<222> LOCATION: (358)..(358)
<223> OTHER INFORMATION: Xaa is any aa
<220> FEATURE:
<221> NAME/KEY: misc_feature
<222> LOCATION: (359)..(359)
<223> OTHER INFORMATION: Xaa is any aa
<220> FEATURE:
<221> NAME/KEY: misc_feature
<222> LOCATION: (360)..(360)
<223> OTHER INFORMATION: Xaa is any aa
<220> FEATURE:
<221> NAME/KEY: misc_feature
```

```
<222> LOCATION: (361)..(361)
<223> OTHER INFORMATION: Xaa is any aa
<220> FEATURE:
<221> NAME/KEY: misc_feature
<222> LOCATION: (363)..(363)
<223> OTHER INFORMATION: Xaa is any aa
<220> FEATURE:
<221> NAME/KEY: misc_feature
<222> LOCATION: (364)..(364)
<223> OTHER INFORMATION: Xaa is any aa
<220> FEATURE:
<221> NAME/KEY: misc_feature
<222> LOCATION: (365)..(365)
<223> OTHER INFORMATION: Xaa is any aa
<220> FEATURE:
<221> NAME/KEY: misc_feature
<222> LOCATION: (366)..(366)
<223> OTHER INFORMATION: Xaa is Val or Ala
<220> FEATURE:
<221> NAME/KEY: misc_feature
<222> LOCATION: (367)..(367)
<223> OTHER INFORMATION: Xaa is any aa
<220> FEATURE:
<221> NAME/KEY: misc_feature
<222> LOCATION: (368)..(368)
<223> OTHER INFORMATION: Xaa is Glu or Gly
<220> FEATURE:
<221> NAME/KEY: misc_feature
<222> LOCATION: (369)..(369)
<223> OTHER INFORMATION: Xaa is Ile, Val, Leu, or Met
<220> FEATURE:
<221> NAME/KEY: misc_feature
<222> LOCATION: (370)..(370)
<223> OTHER INFORMATION: Xaa is any aa
<220> FEATURE:
<221> NAME/KEY: misc_feature
<222> LOCATION: (371)..(371)
<223> OTHER INFORMATION: Xaa is any aa
<220> FEATURE:
<221> NAME/KEY: misc_feature
<222> LOCATION: (372)..(372)
<223> OTHER INFORMATION: Xaa is Thr, Gly, or Ser
<220> FEATURE:
<221> NAME/KEY: misc_feature
<222> LOCATION: (375)..(375)
<223> OTHER INFORMATION: Xaa is Met or Ala
<220> FEATURE:
<221> NAME/KEY: misc_feature
<222> LOCATION: (376)..(376)
<223> OTHER INFORMATION: Xaa is any aa
<220> FEATURE:
<221> NAME/KEY: misc_feature
<222> LOCATION: (377)..(377)
<223> OTHER INFORMATION: Xaa is Ile, Val, Leu, or Met
<220> FEATURE:
<221> NAME/KEY: misc_feature
<222> LOCATION: (378)..(378)
<223> OTHER INFORMATION: Xaa is any aa
<220> FEATURE:
<221> NAME/KEY: misc_feature
<222> LOCATION: (379)..(379)
<223> OTHER INFORMATION: Xaa is Cys or Ser
<220> FEATURE:
<221> NAME/KEY: misc_feature
<222> LOCATION: (380)..(380)
<223> OTHER INFORMATION: Xaa is any aa
<220> FEATURE:
<221> NAME/KEY: misc_feature
<222> LOCATION: (382)..(382)
<223> OTHER INFORMATION: Xaa is any aa
<220> FEATURE:
<221> NAME/KEY: misc_feature
<222> LOCATION: (383)..(383)
<223> OTHER INFORMATION: Xaa is any aa
<220> FEATURE:
<221> NAME/KEY: misc_feature
<222> LOCATION: (385)..(385)
<223> OTHER INFORMATION: Xaa is any aa
<220> FEATURE:
<221> NAME/KEY: misc_feature
```

```
<222> LOCATION: (386)..(386)
<223> OTHER INFORMATION: Xaa is any aa
<220> FEATURE:
<221> NAME/KEY: misc_feature
<222> LOCATION: (387)..(387)
<223> OTHER INFORMATION: Xaa is any aa
<220> FEATURE:
<221> NAME/KEY: misc_feature
<222> LOCATION: (388)..(388)
<223> OTHER INFORMATION: Xaa is Leu  or Phe
<220> FEATURE:
<221> NAME/KEY: misc_feature
<222> LOCATION: (389)..(389)
<223> OTHER INFORMATION: Xaa is any aa
<220> FEATURE:
<221> NAME/KEY: misc_feature
<222> LOCATION: (390)..(390)
<223> OTHER INFORMATION: Xaa is any aa
<220> FEATURE:
<221> NAME/KEY: misc_feature
<222> LOCATION: (391)..(391)
<223> OTHER INFORMATION: Xaa is Ile, Val, Leu, or Met

<400> SEQUENCE: 129

Xaa Ala Ala Arg Ser Leu Ser Xaa Ala Xaa Lys Xaa Xaa Xaa Xaa
1               5                  10                  15

Xaa Xaa Xaa Xaa Xaa Xaa Xaa Xaa Xaa Arg Xaa Xaa Xaa Xaa Xaa
            20                  25                  30

Xaa Xaa Xaa Xaa Xaa Xaa Xaa Gly Xaa Xaa Xaa Xaa Xaa Xaa Xaa
        35                  40                  45

Xaa Xaa Xaa Xaa Xaa Xaa Xaa Gly Xaa Xaa Xaa Xaa Xaa Xaa Xaa
    50                  55                  60

Xaa Xaa Xaa Xaa Xaa Xaa Xaa Xaa Xaa Trp Xaa Pro Asp Pro Val
65                  70                  75                  80

Thr Gly Xaa Tyr Arg Pro Xaa Asn Xaa Xaa Xaa Xaa Asp Pro Xaa
                85                  90                  95

Xaa Leu Arg Xaa Xaa Leu Leu Xaa Xaa Lys Xaa Xaa Ser Met Xaa Xaa
            100                 105                 110

Xaa Xaa Xaa Xaa Xaa His Xaa Xaa Leu Xaa His Gly Xaa Xaa Xaa Gly
        115                 120                 125

Xaa Trp Xaa Trp Xaa Lys Xaa Xaa Xaa Xaa Leu Xaa Xaa Xaa Gly His
130                 135                 140

Xaa Val Xaa Xaa Xaa Asp Xaa Ala Ala Xaa Gly Xaa Xaa Xaa Xaa
145                 150                 155                 160

Xaa Xaa Xaa Xaa Xaa Xaa Xaa Xaa Xaa Tyr Xaa Xaa Pro Leu Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Leu Val Gly His Ser Xaa Gly Gly Xaa Xaa Ala Xaa Ala
        195                 200                 205

Xaa Xaa Xaa Xaa Xaa Xaa Xaa Xaa Xaa Val Phe Xaa Xaa Xaa
    210                 215                 220

Xaa Xaa Pro Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Glu Asp Xaa Xaa Leu Xaa Xaa
```

-continued

```
                290                 295                 300
Xaa Xaa Xaa Arg Xaa Xaa Xaa Phe Xaa Xaa Xaa Xaa Xaa Xaa Xaa
305                 310                 315                 320

Xaa Xaa Xaa Xaa Xaa Xaa Xaa Xaa Xaa Xaa Xaa Tyr Gly Xaa Val
                325                 330                 335

Xaa Xaa Xaa Xaa Xaa Val Xaa Xaa Xaa Asp Xaa Xaa Xaa Xaa Xaa
                340                 345                 350

Xaa Xaa Xaa Xaa Met Xaa Xaa Xaa Pro Xaa Xaa Xaa Xaa Xaa Xaa
                355                 360                 365

Xaa Xaa Xaa Xaa Asp His Xaa Xaa Xaa Xaa Xaa Pro Xaa Xaa Leu
                370                 375                 380

Xaa Xaa Xaa Xaa Xaa Xaa Xaa Ala
385                 390

<210> SEQ ID NO 130
<211> LENGTH: 116
<212> TYPE: PRT
<213> ORGANISM: Brassica napus
<220> FEATURE:
<221> NAME/KEY: misc_feature
<222> LOCATION: (1)..(116)
<223> OTHER INFORMATION: Ceres CLONE ID no. 1128552
<220> FEATURE:
<221> NAME/KEY: misc_feature
<222> LOCATION: (1)..(116)
<223> OTHER INFORMATION: Ortholog of  Ceres CDNA ID no. 12393104
      at SEQ ID NO. 16
      with e-value of 5.89E-52 and percent identity of 91.38

<400> SEQUENCE: 130

Met Ala Lys Val Gly Lys Leu Thr Lys Leu Lys Ser Ala Ile Lys Lys
1               5                   10                  15

Trp Pro Ser Phe Ala Lys Asn His His Ser Ser Ser Ser Ala Ala
                20                  25                  30

Val Ser Asp Glu Leu Ser Glu Asp Asn Asn Leu His Val Val Tyr Val
            35                  40                  45

Gly Gln Thr Arg Arg Pro Tyr Met Leu Arg Pro Asp Ile Ile Ser His
    50                  55                  60

Pro Leu Phe Gln Glu Leu Val Lys Lys Glu Asp Pro Leu Glu His Asp
65                  70                  75                  80

Arg Glu Ile Val Val Ala Cys Glu Val Val Leu Phe Glu His Leu Leu
                85                  90                  95

Trp Met Leu Lys Thr Gly Gln Gly Gly Ser Val Gly Glu Leu Ala
                100                 105                 110

Glu Phe Tyr Thr
        115

<210> SEQ ID NO 131
<211> LENGTH: 100
<212> TYPE: PRT
<213> ORGANISM: Brassica napus
<220> FEATURE:
<221> NAME/KEY: misc_feature
<222> LOCATION: (1)..(100)
<223> OTHER INFORMATION: Ceres CLONE ID no. 1114752
<220> FEATURE:
<221> NAME/KEY: misc_feature
<222> LOCATION: (1)..(100)
<223> OTHER INFORMATION: Ortholog of  Ceres CDNA ID no. 12393104
      at SEQ ID NO. 16
      with e-value of 4.00E-46 and percent identity of 95.0

<400> SEQUENCE: 131
```

```
Met Ala Lys Val Gly Lys Leu Thr Lys Leu Lys Ser Ala Ile Lys Lys
1               5                   10                  15

Trp Pro Ser Phe Ala Lys Asn His His Ser Ser Ser Ala Ala
                20                  25                  30

Val Ser Asp Glu Leu Ser Glu Asp Asn Asn Leu His Val Val Tyr Val
            35                  40                  45

Gly Gln Thr Arg Arg Pro Tyr Met Leu Arg Pro Asp Ile Ile Ser His
        50                  55                  60

Pro Leu Phe Gln Glu Leu Val Asp Arg Ser Ser Arg Ser Val Glu His
65                  70                  75                  80

Asp Arg Glu Ile Val Val Ser Cys Glu Val Val Leu Phe Glu His Leu
                85                  90                  95

Leu Trp Met Leu
            100
```

<210> SEQ ID NO 132
<211> LENGTH: 131
<212> TYPE: PRT
<213> ORGANISM: Arabidopsis thaliana
<220> FEATURE:
<221> NAME/KEY: misc_feature
<222> LOCATION: (1)..(131)
<223> OTHER INFORMATION: Public GI no. 26452787
<220> FEATURE:
<221> NAME/KEY: misc_feature
<222> LOCATION: (1)..(131)
<223> OTHER INFORMATION: Ortholog of Ceres CDNA ID no. 12393104
      at SEQ ID NO. 16
      with e-value of 1.10E-34 and percent identity of 73.5

<400> SEQUENCE: 132

```
Met Ala Ile Phe Gly Lys Leu Thr Lys Leu Lys Ser Ala Ile Lys Lys
1               5                   10                  15

Trp Pro Ser Leu Thr Lys Asn His His Ser Thr Met Cys Thr Ala Ser
                20                  25                  30

Thr Ala Val Ser Glu Val Ser Lys Cys Glu Asp Leu His Val Val Tyr
            35                  40                  45

Val Gly Lys Ser Arg Arg Pro Tyr Met Leu Ser Ser His Val Ile Ala
        50                  55                  60

His Pro Leu Phe Gln Glu Leu Leu Asp Arg Ser Ser Arg Phe Ile Glu
65                  70                  75                  80

Glu Arg His Asp Gln Glu Thr Val Leu Val Ala Cys Glu Val Val Leu
                85                  90                  95

Phe Glu His Leu Leu Trp Met Leu Lys Asn Ser Ser Asp His Gly
            100                 105                 110

Asp Glu Asp Asp Arg Glu Arg Gly Ser Val Glu Glu Leu Ala Glu Phe
        115                 120                 125

Tyr Thr Tyr
    130
```

<210> SEQ ID NO 133
<211> LENGTH: 127
<212> TYPE: PRT
<213> ORGANISM: Glycine max
<220> FEATURE:
<221> NAME/KEY: misc_feature
<222> LOCATION: (1)..(127)
<223> OTHER INFORMATION: Ceres CLONE ID no. 602106
<220> FEATURE:
<221> NAME/KEY: misc_feature
<222> LOCATION: (1)..(127)
<223> OTHER INFORMATION: Ortholog of Ceres CDNA ID no. 12393104
      at SEQ ID NO. 16 with e-value of 2.40E-25 and percent identity of 52.1

<400> SEQUENCE: 133

```
Met Ala Arg Gly Gly Lys Leu Met Lys Leu Lys Ser Val Leu Lys Lys
1               5                   10                  15

Trp Asn Ser Phe Gly Asn Gly Ser Lys His Ser Arg His Ser Ser
            20                  25                  30

Ser Ala Val Ala Asp Asp Glu Ser Ser Arg Ser Asp Leu His Ala
            35                  40                  45

Val Tyr Val Gly Lys Ser Arg Arg Leu Tyr Arg Val Ser Ser Asp Val
    50                  55                  60

Val Asp His Pro Val Phe Arg Glu Leu Val Glu Arg Ser Arg Asp Ser
65                  70                  75                  80

Asp Gln Gln Gln Asn Glu Asp Thr Thr Thr Ile Asn Val Val Ala Cys
                85                  90                  95

Glu Val Val Leu Phe Glu His Leu Leu Trp Met Leu Asp Asn Ala Asp
            100                 105                 110

Pro Gln Pro Glu Ser Leu Asn Glu Leu Val Asp Phe Tyr Gly Cys
            115                 120                 125
```

<210> SEQ ID NO 134
<211> LENGTH: 147
<212> TYPE: PRT
<213> ORGANISM: Glycine max
<220> FEATURE:
<221> NAME/KEY: misc_feature
<222> LOCATION: (1)..(147)
<223> OTHER INFORMATION: Ceres CLONE ID no. 613622
<220> FEATURE:
<221> NAME/KEY: misc_feature
<222> LOCATION: (1)..(147)
<223> OTHER INFORMATION: Ortholog of Ceres CDNA ID no. 12393104
      at SEQ ID NO. 16
      with e-value of 1.19E-23 and percent identity of 47.9
<220> FEATURE:
<221> NAME/KEY: misc_feature
<222> LOCATION: (32)..(32)
<223> OTHER INFORMATION: Xaa is any aa, unknown, or other

<400> SEQUENCE: 134

```
Val Leu Thr Ser His Asn Ile Thr Lys Thr Thr Thr Lys Ser Ser Leu
1               5                   10                  15

Leu His Gln Ile Leu Lys Pro Tyr Pro Thr Cys Pro Lys Gln Glu Xaa
            20                  25                  30

Leu Thr Lys Leu Lys Ser Val Leu Arg Lys Trp Asn Ser Phe Ser Asn
            35                  40                  45

Lys His Ser Gln Val Ser Val Ile Ser Ala Val Ala Asn Asp Gly Gly
    50                  55                  60

Asp Thr Ser Ser Leu Leu Pro Val Tyr Val Gly Arg Thr Arg Arg Arg
65                  70                  75                  80

Tyr Leu Val Ser Ala Asp Val Val Gly His Pro Leu Phe Arg Glu Leu
                85                  90                  95

Val Gly Arg Ser Arg Asp Gly Ser Lys Asp Glu Asp Glu Asp Thr Ile
            100                 105                 110

Asn Val Ala Cys Glu Val Val Leu Phe Glu His Leu Leu Trp Met Leu
            115                 120                 125

His Asn Ala Asp Pro Gln Pro Glu Ser Leu Asp Glu Leu Ala Asp Phe
    130                 135                 140

Tyr Ala Cys
145
```

```
<210> SEQ ID NO 135
<211> LENGTH: 124
<212> TYPE: PRT
<213> ORGANISM: Glycine max
<220> FEATURE:
<221> NAME/KEY: misc_feature
<222> LOCATION: (1)..(124)
<223> OTHER INFORMATION: Ceres CLONE ID no. 667669
<220> FEATURE:
<221> NAME/KEY: misc_feature
<222> LOCATION: (1)..(124)
<223> OTHER INFORMATION: Ortholog of Ceres CDNA ID no. 12393104
      at SEQ ID NO. 16
      with e-value of 1.39E-20 and percent identity of 56.19
<220> FEATURE:
<221> NAME/KEY: misc_feature
<222> LOCATION: (107)..(107)
<223> OTHER INFORMATION: Xaa is any aa, unknown, or other
<220> FEATURE:
<221> NAME/KEY: misc_feature
<222> LOCATION: (114)..(114)
<223> OTHER INFORMATION: Xaa is any aa, unknown, or other
<220> FEATURE:
<221> NAME/KEY: misc_feature
<222> LOCATION: (124)..(124)
<223> OTHER INFORMATION: Xaa is any aa, unknown, or other

<400> SEQUENCE: 135

Met Ala Lys Val Gly Lys Leu Thr Lys Leu Lys Ser Ala Ile Lys Arg
1               5                   10                  15

Trp Pro Ser Leu Thr Arg Leu Ser Arg Asn Ser Ser Val Ser Ser
            20                  25                  30

Asn Lys Gly Val Ser Gly Lys Gly Thr Ser Leu Asn Ser Ser Lys Glu
            35                  40                  45

His Glu His Glu Gln Glu Gln Leu Arg Ala Val Tyr Val Gly Lys Ser
        50                  55                  60

Arg Arg Arg Tyr Leu Val Asn Ser Glu Val Ile Asp His Pro Val Phe
65                  70                  75                  80

Gln Glu Leu Val Asp Arg Ser Cys Ser Ser Asn Ser Ser Ser Ser His
                85                  90                  95

His His Asp Asp Asp Gly Val Val Val Xaa Cys Glu Val Val Leu
            100                 105                 110

Phe Xaa His Leu Leu Trp Met Leu Glu Ser Glu Xaa
        115                 120

<210> SEQ ID NO 136
<211> LENGTH: 165
<212> TYPE: PRT
<213> ORGANISM: Oryza sativa subsp. japonica
<220> FEATURE:
<221> NAME/KEY: misc_feature
<222> LOCATION: (1)..(165)
<223> OTHER INFORMATION: Public GI no. 51090654
<220> FEATURE:
<221> NAME/KEY: misc_feature
<222> LOCATION: (1)..(165)
<223> OTHER INFORMATION: Ortholog of Ceres CDNA ID no. 12393104
      at SEQ ID NO. 16
      with e-value of 2.30E-18 and percent identity of 44.92

<400> SEQUENCE: 136

Met Ala Lys Gly Gly Leu Ser Lys Leu Lys Cys Met Ile Lys Arg Trp
1               5                   10                  15

His Ser Ser Ser Arg Ile Ser Arg Thr Pro Ser Gly Cys Ser Ala Ser
            20                  25                  30

Ala Gly Ser Thr Ser Ala Arg Ser Ser His Gly Gly Arg Val Gly
        35                  40                  45
```

```
Gly Glu Glu Trp Gly Arg Ser Val Val Ala Ser Gly Gly Gly Gly
    50                  55                  60

Gly Gly Gly Gly Gly Arg Gly Gly Ser Val Ser Phe His Gly Ala Asp
65                  70                  75                  80

Gly Val Pro Pro Gly Leu His Pro Val Tyr Val Gly Lys Ser Arg Arg
                85                  90                  95

Arg Tyr Leu Ile Ala Ala Asp Leu Val Gly His Pro Met Phe Gln Asn
            100                 105                 110

Leu Val Asp Arg Ser Gly Gly Gly Val Gly Gly Gly Gly Gly
            115                 120                 125

Gly Thr Val Val Gly Cys Glu Val Val Leu Phe Glu His Leu Leu Trp
    130                 135                 140

Met Leu Glu Asn Ala Asp Pro Gln Pro Glu Ser Leu Asp Glu Leu Val
145                 150                 155                 160

Glu Tyr Tyr Ala Cys
                165
```

<210> SEQ ID NO 137
<211> LENGTH: 41
<212> TYPE: PRT
<213> ORGANISM: Brassica napus
<220> FEATURE:
<221> NAME/KEY: misc_feature
<222> LOCATION: (1)..(41)
<223> OTHER INFORMATION: Ceres CLONE ID no. 1082845
<220> FEATURE:
<221> NAME/KEY: misc_feature
<222> LOCATION: (1)..(41)
<223> OTHER INFORMATION: Ortholog of Ceres CDNA ID no. 12393104
      at SEQ ID NO. 16
      with e-value of 2.10E-15 and percent identity of 95.12

<400> SEQUENCE: 137

```
Met Ala Lys Val Gly Lys Leu Thr Lys Leu Lys Ser Ala Xaa Lys Lys
1               5                   10                  15

Trp Pro Ser Phe Ala Lys Asn His His His Ser Ser Ser Ser Ala Ala
                20                  25                  30

Val Ser Asp Glu Leu Ser Glu Asp Asn
            35                  40
```

<210> SEQ ID NO 138
<211> LENGTH: 128
<212> TYPE: PRT
<213> ORGANISM: Triticum aestivum
<220> FEATURE:
<221> NAME/KEY: misc_feature
<222> LOCATION: (1)..(128)
<223> OTHER INFORMATION: Ceres CLONE ID no. 939408
<220> FEATURE:
<221> NAME/KEY: misc_feature
<222> LOCATION: (1)..(128)
<223> OTHER INFORMATION: Ortholog of Ceres CDNA ID no. 12393104
      at SEQ ID NO. 16
      with e-value of 3.80E-15 and percent identity of 40.95

<400> SEQUENCE: 138

```
Met Ala Lys Gly Gly Leu Ser Ser Lys Leu Lys Cys Met Ile Arg Arg
1               5                   10                  15

Trp His Ser Ser Ser Arg Ile Ser Arg Thr Pro Ser Ala Ala Ser His
                20                  25                  30

Gly Gly Gly Gly Gly Glu Glu Glu Asp Pro Trp Gly Arg Gly Val Gly
            35                  40                  45

Gly Gly Ala Ala Ser Phe His Gly Ala Asp Ser Val Pro Pro Gly Leu
```

```
                50                  55                  60
His Pro Val Tyr Val Gly Lys Ser Arg Arg Tyr Leu Ile Ala Ala
 65                  70                  75                  80

Asp Leu Val Cys His Pro Leu Phe Gln Asn Leu Val Asp Arg Ser Gly
                 85                  90                  95

Gly Gly Val Gly Gly Asp Gly Ala Gly Gly Thr Ile Ile Gly Cys Glu
            100                 105                 110

Val Val Leu Phe Glu Xaa Leu Leu Trp Met Leu Glu Asn Ala Asp Pro
        115                 120                 125

<210> SEQ ID NO 139
<211> LENGTH: 118
<212> TYPE: PRT
<213> ORGANISM: Triticum aestivum
<220> FEATURE:
<221> NAME/KEY: misc_feature
<222> LOCATION: (1)..(118)
<223> OTHER INFORMATION: Ceres CLONE ID no. 1017750
<220> FEATURE:
<221> NAME/KEY: misc_feature
<222> LOCATION: (1)..(118)
<223> OTHER INFORMATION: Ortholog of Ceres CDNA ID no. 12393104
      at SEQ ID NO. 16
      with e-value of 3.90E-12 and percent identity of 38.95

<400> SEQUENCE: 139

Met Ala Lys Gly Gly Leu Ser Ser Lys Leu Lys Cys Met Ile Arg Arg
 1               5                  10                  15

Trp His Ser Ser Ser Arg Ile Ser Arg Thr Pro Ser Ala Val Ser His
                20                  25                  30

Gly Gly Gly Glu Glu Glu Asp Pro Trp Gly Arg Gly Val Gly Gly Gly
             35                  40                  45

Gly Gly Gly Ala Ala Ser Phe His Gly Ala Asp Gly Val Pro Pro Gly
         50                  55                  60

Leu His Pro Val Tyr Val Gly Lys Ser Arg Arg Arg Tyr Leu Ile Ala
 65                  70                  75                  80

Ala Asp Leu Val Cys His Pro Leu Phe Gln Asn Leu Val Asp Arg Ser
                 85                  90                  95

Gly Gly Gly Val Gly Gly Asp Gly Ala Gly Gly Thr Ile Ile Gly Cys
            100                 105                 110

Glu Val Val Leu Phe Glu
        115

<210> SEQ ID NO 140
<211> LENGTH: 599
<212> TYPE: PRT
<213> ORGANISM: Artificial Sequence
<220> FEATURE:
<221> NAME/KEY: misc_feature
<222> LOCATION: (1)..(599)
<223> OTHER INFORMATION: Consensus Sequence of Ceres CDNA ID no.
      12393104 at SEQ ID NO. 16 and orthologs
<220> FEATURE:
<221> NAME/KEY: misc_feature
<222> LOCATION: (1)..(1)
<223> OTHER INFORMATION: Xaa is any aa
<220> FEATURE:
<221> NAME/KEY: misc_feature
<222> LOCATION: (8)..(8)
<223> OTHER INFORMATION: Xaa is Gly or Gln
<220> FEATURE:
<221> NAME/KEY: misc_feature
<222> LOCATION: (10)..(10)
<223> OTHER INFORMATION: Xaa is any aa or nothing
<220> FEATURE:
<221> NAME/KEY: misc_feature
```

-continued

```
<222> LOCATION: (12)..(12)
<223> OTHER INFORMATION: Xaa is Ser  or Arg
<220> FEATURE:
<221> NAME/KEY: misc_feature
<222> LOCATION: (13)..(13)
<223> OTHER INFORMATION: Xaa is Ile, Val, Leu, or Met
<220> FEATURE:
<221> NAME/KEY: misc_feature
<222> LOCATION: (14)..(14)
<223> OTHER INFORMATION: Xaa is Cys  or Gly
<220> FEATURE:
<221> NAME/KEY: misc_feature
<222> LOCATION: (15)..(15)
<223> OTHER INFORMATION: Xaa is Ser  or Val
<220> FEATURE:
<221> NAME/KEY: misc_feature
<222> LOCATION: (16)..(16)
<223> OTHER INFORMATION: Xaa is any aa
<220> FEATURE:
<221> NAME/KEY: misc_feature
<222> LOCATION: (17)..(17)
<223> OTHER INFORMATION: Xaa is Ala  or Val
<220> FEATURE:
<221> NAME/KEY: misc_feature
<222> LOCATION: (18)..(18)
<223> OTHER INFORMATION: Xaa is any aa
<220> FEATURE:
<221> NAME/KEY: misc_feature
<222> LOCATION: (19)..(19)
<223> OTHER INFORMATION: Xaa is any aa
<220> FEATURE:
<221> NAME/KEY: misc_feature
<222> LOCATION: (20)..(20)
<223> OTHER INFORMATION: Xaa is any aa
<220> FEATURE:
<221> NAME/KEY: misc_feature
<222> LOCATION: (21)..(21)
<223> OTHER INFORMATION: Xaa is Ile, Val, Leu, or Met
<220> FEATURE:
<221> NAME/KEY: misc_feature
<222> LOCATION: (22)..(22)
<223> OTHER INFORMATION: Xaa is Thr, Gly, or Ser
<220> FEATURE:
<221> NAME/KEY: misc_feature
<222> LOCATION: (23)..(23)
<223> OTHER INFORMATION: Xaa is any aa
<220> FEATURE:
<221> NAME/KEY: misc_feature
<222> LOCATION: (24)..(24)
<223> OTHER INFORMATION: Xaa is Ser  or Ile
<220> FEATURE:
<221> NAME/KEY: misc_feature
<222> LOCATION: (25)..(25)
<223> OTHER INFORMATION: Xaa is any aa
<220> FEATURE:
<221> NAME/KEY: misc_feature
<222> LOCATION: (26)..(26)
<223> OTHER INFORMATION: Xaa is Val  or His
<220> FEATURE:
<221> NAME/KEY: misc_feature
<222> LOCATION: (27)..(27)
<223> OTHER INFORMATION: Xaa is any aa
<220> FEATURE:
<221> NAME/KEY: misc_feature
<222> LOCATION: (29)..(29)
<223> OTHER INFORMATION: Xaa is Arg  or Gly
<220> FEATURE:
<221> NAME/KEY: misc_feature
<222> LOCATION: (30)..(30)
<223> OTHER INFORMATION: Xaa is any aa
<220> FEATURE:
<221> NAME/KEY: misc_feature
<222> LOCATION: (31)..(31)
<223> OTHER INFORMATION: Xaa is Tyr  or Ala
<220> FEATURE:
<221> NAME/KEY: misc_feature
<222> LOCATION: (32)..(32)
<223> OTHER INFORMATION: Xaa is Val  or Ala
<220> FEATURE:
<221> NAME/KEY: misc_feature
```

-continued

```
<222> LOCATION: (33)..(33)
<223> OTHER INFORMATION: Xaa is Ala or Val
<220> FEATURE:
<221> NAME/KEY: misc_feature
<222> LOCATION: (34)..(34)
<223> OTHER INFORMATION: Xaa is Thr, Gly, or Ser
<220> FEATURE:
<221> NAME/KEY: misc_feature
<222> LOCATION: (35)..(35)
<223> OTHER INFORMATION: Xaa is any aa
<220> FEATURE:
<221> NAME/KEY: misc_feature
<222> LOCATION: (36)..(36)
<223> OTHER INFORMATION: Xaa is any aa
<220> FEATURE:
<221> NAME/KEY: misc_feature
<222> LOCATION: (37)..(37)
<223> OTHER INFORMATION: Xaa is any aa or nothing
<220> FEATURE:
<221> NAME/KEY: misc_feature
<222> LOCATION: (38)..(38)
<223> OTHER INFORMATION: Xaa is any aa or nothing
<220> FEATURE:
<221> NAME/KEY: misc_feature
<222> LOCATION: (39)..(39)
<223> OTHER INFORMATION: Xaa is any aa or nothing
<220> FEATURE:
<221> NAME/KEY: misc_feature
<222> LOCATION: (40)..(40)
<223> OTHER INFORMATION: Xaa is any aa or nothing
<220> FEATURE:
<221> NAME/KEY: misc_feature
<222> LOCATION: (41)..(41)
<223> OTHER INFORMATION: Xaa is any aa or nothing
<220> FEATURE:
<221> NAME/KEY: misc_feature
<222> LOCATION: (43)..(43)
<223> OTHER INFORMATION: Xaa is any aa
<220> FEATURE:
<221> NAME/KEY: misc_feature
<222> LOCATION: (44)..(44)
<223> OTHER INFORMATION: Xaa is any aa or nothing
<220> FEATURE:
<221> NAME/KEY: misc_feature
<222> LOCATION: (45)..(45)
<223> OTHER INFORMATION: Xaa is any aa or nothing
<220> FEATURE:
<221> NAME/KEY: misc_feature
<222> LOCATION: (46)..(46)
<223> OTHER INFORMATION: Xaa is Thr, Gly, or Ser
<220> FEATURE:
<221> NAME/KEY: misc_feature
<222> LOCATION: (47)..(47)
<223> OTHER INFORMATION: Xaa is any aa
<220> FEATURE:
<221> NAME/KEY: misc_feature
<222> LOCATION: (48)..(48)
<223> OTHER INFORMATION: Xaa is Gly or Ile
<220> FEATURE:
<221> NAME/KEY: misc_feature
<222> LOCATION: (49)..(49)
<223> OTHER INFORMATION: Xaa is Thr, Gly, or Ser
<220> FEATURE:
<221> NAME/KEY: misc_feature
<222> LOCATION: (50)..(50)
<223> OTHER INFORMATION: Xaa is Ser or Arg
<220> FEATURE:
<221> NAME/KEY: misc_feature
<222> LOCATION: (51)..(51)
<223> OTHER INFORMATION: Xaa is any aa
<220> FEATURE:
<221> NAME/KEY: misc_feature
<222> LOCATION: (52)..(52)
<223> OTHER INFORMATION: Xaa is any aa
<220> FEATURE:
<221> NAME/KEY: misc_feature
<222> LOCATION: (53)..(53)
<223> OTHER INFORMATION: Xaa is any aa
<220> FEATURE:
<221> NAME/KEY: misc_feature
```

```
<222> LOCATION: (54)..(54)
<223> OTHER INFORMATION: Xaa is any aa
<220> FEATURE:
<221> NAME/KEY: misc_feature
<222> LOCATION: (55)..(55)
<223> OTHER INFORMATION: Xaa is Val  or Lys
<220> FEATURE:
<221> NAME/KEY: misc_feature
<222> LOCATION: (57)..(57)
<223> OTHER INFORMATION: Xaa is any aa
<220> FEATURE:
<221> NAME/KEY: misc_feature
<222> LOCATION: (58)..(58)
<223> OTHER INFORMATION: Xaa is any aa
<220> FEATURE:
<221> NAME/KEY: misc_feature
<222> LOCATION: (59)..(59)
<223> OTHER INFORMATION: Xaa is Glu  or Lys
<220> FEATURE:
<221> NAME/KEY: misc_feature
<222> LOCATION: (60)..(60)
<223> OTHER INFORMATION: Xaa is any aa
<220> FEATURE:
<221> NAME/KEY: misc_feature
<222> LOCATION: (61)..(61)
<223> OTHER INFORMATION: Xaa is any aa
<220> FEATURE:
<221> NAME/KEY: misc_feature
<222> LOCATION: (62)..(62)
<223> OTHER INFORMATION: Xaa is any aa
<220> FEATURE:
<221> NAME/KEY: misc_feature
<222> LOCATION: (63)..(63)
<223> OTHER INFORMATION: Xaa is any aa
<220> FEATURE:
<221> NAME/KEY: misc_feature
<222> LOCATION: (64)..(64)
<223> OTHER INFORMATION: Xaa is any aa
<220> FEATURE:
<221> NAME/KEY: misc_feature
<222> LOCATION: (65)..(65)
<223> OTHER INFORMATION: Xaa is any aa
<220> FEATURE:
<221> NAME/KEY: misc_feature
<222> LOCATION: (66)..(66)
<223> OTHER INFORMATION: Xaa is any aa or nothing
<220> FEATURE:
<221> NAME/KEY: misc_feature
<222> LOCATION: (67)..(67)
<223> OTHER INFORMATION: Xaa is Thr, Gly, or Ser
<220> FEATURE:
<221> NAME/KEY: misc_feature
<222> LOCATION: (68)..(68)
<223> OTHER INFORMATION: Xaa is Glu  or Ser
<220> FEATURE:
<221> NAME/KEY: misc_feature
<222> LOCATION: (69)..(69)
<223> OTHER INFORMATION: Xaa is Ser  or Lys
<220> FEATURE:
<221> NAME/KEY: misc_feature
<222> LOCATION: (70)..(70)
<223> OTHER INFORMATION: Xaa is Thr, Gly, or Ser
<220> FEATURE:
<221> NAME/KEY: misc_feature
<222> LOCATION: (71)..(71)
<223> OTHER INFORMATION: Xaa is any aa or nothing
<220> FEATURE:
<221> NAME/KEY: misc_feature
<222> LOCATION: (72)..(72)
<223> OTHER INFORMATION: Xaa is any aa or nothing
<220> FEATURE:
<221> NAME/KEY: misc_feature
<222> LOCATION: (73)..(73)
<223> OTHER INFORMATION: Xaa is any aa or nothing
<220> FEATURE:
<221> NAME/KEY: misc_feature
<222> LOCATION: (74)..(74)
<223> OTHER INFORMATION: Xaa is any aa or nothing
<220> FEATURE:
<221> NAME/KEY: misc_feature
```

```
<222> LOCATION: (76)..(76)
<223> OTHER INFORMATION: Xaa is any aa
<220> FEATURE:
<221> NAME/KEY: misc_feature
<222> LOCATION: (83)..(83)
<223> OTHER INFORMATION: Xaa is Tyr or His
<220> FEATURE:
<221> NAME/KEY: misc_feature
<222> LOCATION: (87)..(87)
<223> OTHER INFORMATION: Xaa is any aa
<220> FEATURE:
<221> NAME/KEY: misc_feature
<222> LOCATION: (89)..(89)
<223> OTHER INFORMATION: Xaa is any aa
<220> FEATURE:
<221> NAME/KEY: misc_feature
<222> LOCATION: (90)..(90)
<223> OTHER INFORMATION: Xaa is Thr, Gly, or Ser
<220> FEATURE:
<221> NAME/KEY: misc_feature
<222> LOCATION: (91)..(91)
<223> OTHER INFORMATION: Xaa is any aa
<220> FEATURE:
<221> NAME/KEY: misc_feature
<222> LOCATION: (92)..(92)
<223> OTHER INFORMATION: Xaa is Glu or Ala
<220> FEATURE:
<221> NAME/KEY: misc_feature
<222> LOCATION: (93)..(93)
<223> OTHER INFORMATION: Xaa is Ile, Val, Leu, or Met
<220> FEATURE:
<221> NAME/KEY: misc_feature
<222> LOCATION: (96)..(96)
<223> OTHER INFORMATION: Xaa is Ala or Val
<220> FEATURE:
<221> NAME/KEY: misc_feature
<222> LOCATION: (97)..(97)
<223> OTHER INFORMATION: Xaa is Asp or Glu
<220> FEATURE:
<221> NAME/KEY: misc_feature
<222> LOCATION: (100)..(100)
<223> OTHER INFORMATION: Xaa is any aa
<220> FEATURE:
<221> NAME/KEY: misc_feature
<222> LOCATION: (101)..(101)
<223> OTHER INFORMATION: Xaa is any aa
<220> FEATURE:
<221> NAME/KEY: misc_feature
<222> LOCATION: (104)..(104)
<223> OTHER INFORMATION: Xaa is Lys, Arg, or His
<220> FEATURE:
<221> NAME/KEY: misc_feature
<222> LOCATION: (105)..(105)
<223> OTHER INFORMATION: Xaa is any aa
<220> FEATURE:
<221> NAME/KEY: misc_feature
<222> LOCATION: (107)..(107)
<223> OTHER INFORMATION: Xaa is Ala or Val
<220> FEATURE:
<221> NAME/KEY: misc_feature
<222> LOCATION: (108)..(108)
<223> OTHER INFORMATION: Xaa is Lys, Arg, or His
<220> FEATURE:
<221> NAME/KEY: misc_feature
<222> LOCATION: (111)..(111)
<223> OTHER INFORMATION: Xaa is any aa
<220> FEATURE:
<221> NAME/KEY: misc_feature
<222> LOCATION: (112)..(112)
<223> OTHER INFORMATION: Xaa is any aa
<220> FEATURE:
<221> NAME/KEY: misc_feature
<222> LOCATION: (113)..(113)
<223> OTHER INFORMATION: Xaa is any aa
<220> FEATURE:
<221> NAME/KEY: misc_feature
<222> LOCATION: (114)..(114)
<223> OTHER INFORMATION: Xaa is any aa
<220> FEATURE:
<221> NAME/KEY: misc_feature
```

```
<222> LOCATION: (115)..(115)
<223> OTHER INFORMATION: Xaa is any aa
<220> FEATURE:
<221> NAME/KEY: misc_feature
<222> LOCATION: (116)..(116)
<223> OTHER INFORMATION: Xaa is any aa
<220> FEATURE:
<221> NAME/KEY: misc_feature
<222> LOCATION: (117)..(117)
<223> OTHER INFORMATION: Xaa is any aa
<220> FEATURE:
<221> NAME/KEY: misc_feature
<222> LOCATION: (119)..(119)
<223> OTHER INFORMATION: Xaa is any aa
<220> FEATURE:
<221> NAME/KEY: misc_feature
<222> LOCATION: (120)..(120)
<223> OTHER INFORMATION: Xaa is Ile, Val, Leu, or Met
<220> FEATURE:
<221> NAME/KEY: misc_feature
<222> LOCATION: (122)..(122)
<223> OTHER INFORMATION: Xaa is Ile, Val, Leu, or Met
<220> FEATURE:
<221> NAME/KEY: misc_feature
<222> LOCATION: (125)..(125)
<223> OTHER INFORMATION: Xaa is any aa
<220> FEATURE:
<221> NAME/KEY: misc_feature
<222> LOCATION: (126)..(126)
<223> OTHER INFORMATION: Xaa is Cys or Gly
<220> FEATURE:
<221> NAME/KEY: misc_feature
<222> LOCATION: (127)..(127)
<223> OTHER INFORMATION: Xaa is any aa
<220> FEATURE:
<221> NAME/KEY: misc_feature
<222> LOCATION: (129)..(129)
<223> OTHER INFORMATION: Xaa is Thr, Gly, or Ser
<220> FEATURE:
<221> NAME/KEY: misc_feature
<222> LOCATION: (131)..(131)
<223> OTHER INFORMATION: Xaa is any aa
<220> FEATURE:
<221> NAME/KEY: misc_feature
<222> LOCATION: (133)..(133)
<223> OTHER INFORMATION: Xaa is any aa
<220> FEATURE:
<221> NAME/KEY: misc_feature
<222> LOCATION: (135)..(135)
<223> OTHER INFORMATION: Xaa is Ile, Val, Leu, or Met
<220> FEATURE:
<221> NAME/KEY: misc_feature
<222> LOCATION: (136)..(136)
<223> OTHER INFORMATION: Xaa is any aa
<220> FEATURE:
<221> NAME/KEY: misc_feature
<222> LOCATION: (137)..(137)
<223> OTHER INFORMATION: Xaa is any aa
<220> FEATURE:
<221> NAME/KEY: misc_feature
<222> LOCATION: (138)..(138)
<223> OTHER INFORMATION: Xaa is any aa
<220> FEATURE:
<221> NAME/KEY: misc_feature
<222> LOCATION: (140)..(140)
<223> OTHER INFORMATION: Xaa is any aa
<220> FEATURE:
<221> NAME/KEY: misc_feature
<222> LOCATION: (141)..(141)
<223> OTHER INFORMATION: Xaa is Thr, Gly, or Ser
<220> FEATURE:
<221> NAME/KEY: misc_feature
<222> LOCATION: (142)..(142)
<223> OTHER INFORMATION: Xaa is any aa
<220> FEATURE:
<221> NAME/KEY: misc_feature
<222> LOCATION: (145)..(145)
<223> OTHER INFORMATION: Xaa is Lys, Arg, or His
<220> FEATURE:
<221> NAME/KEY: misc_feature
```

```
<222> LOCATION: (147)..(147)
<223> OTHER INFORMATION: Xaa is any aa
<220> FEATURE:
<221> NAME/KEY: misc_feature
<222> LOCATION: (148)..(148)
<223> OTHER INFORMATION: Xaa is any aa
<220> FEATURE:
<221> NAME/KEY: misc_feature
<222> LOCATION: (149)..(149)
<223> OTHER INFORMATION: Xaa is any aa
<220> FEATURE:
<221> NAME/KEY: misc_feature
<222> LOCATION: (151)..(151)
<223> OTHER INFORMATION: Xaa is Ile, Val, Leu, or Met
<220> FEATURE:
<221> NAME/KEY: misc_feature
<222> LOCATION: (154)..(154)
<223> OTHER INFORMATION: Xaa is Ser  or Cys
<220> FEATURE:
<221> NAME/KEY: misc_feature
<222> LOCATION: (156)..(156)
<223> OTHER INFORMATION: Xaa is any aa
<220> FEATURE:
<221> NAME/KEY: misc_feature
<222> LOCATION: (157)..(157)
<223> OTHER INFORMATION: Xaa is any aa
<220> FEATURE:
<221> NAME/KEY: misc_feature
<222> LOCATION: (158)..(158)
<223> OTHER INFORMATION: Xaa is any aa
<220> FEATURE:
<221> NAME/KEY: misc_feature
<222> LOCATION: (159)..(159)
<223> OTHER INFORMATION: Xaa is any aa or nothing
<220> FEATURE:
<221> NAME/KEY: misc_feature
<222> LOCATION: (160)..(160)
<223> OTHER INFORMATION: Xaa is Lys, Arg, or His
<220> FEATURE:
<221> NAME/KEY: misc_feature
<222> LOCATION: (161)..(161)
<223> OTHER INFORMATION: Xaa is any aa
<220> FEATURE:
<221> NAME/KEY: misc_feature
<222> LOCATION: (162)..(162)
<223> OTHER INFORMATION: Xaa is any aa or nothing
<220> FEATURE:
<221> NAME/KEY: misc_feature
<222> LOCATION: (163)..(163)
<223> OTHER INFORMATION: Xaa is any aa or nothing
<220> FEATURE:
<221> NAME/KEY: misc_feature
<222> LOCATION: (164)..(164)
<223> OTHER INFORMATION: Xaa is Asp or Glu
<220> FEATURE:
<221> NAME/KEY: misc_feature
<222> LOCATION: (165)..(165)
<223> OTHER INFORMATION: Xaa is any aa
<220> FEATURE:
<221> NAME/KEY: misc_feature
<222> LOCATION: (166)..(166)
<223> OTHER INFORMATION: Xaa is any aa
<220> FEATURE:
<221> NAME/KEY: misc_feature
<222> LOCATION: (167)..(167)
<223> OTHER INFORMATION: Xaa is Thr, Gly, or Ser
<220> FEATURE:
<221> NAME/KEY: misc_feature
<222> LOCATION: (168)..(168)
<223> OTHER INFORMATION: Xaa is Cys  or Phe
<220> FEATURE:
<221> NAME/KEY: misc_feature
<222> LOCATION: (169)..(169)
<223> OTHER INFORMATION: Xaa is any aa
<220> FEATURE:
<221> NAME/KEY: misc_feature
<222> LOCATION: (170)..(170)
<223> OTHER INFORMATION: Xaa is any aa
<220> FEATURE:
<221> NAME/KEY: misc_feature
```

```
<222> LOCATION: (172)..(172)
<223> OTHER INFORMATION: Xaa is Thr, Gly, or Ser
<220> FEATURE:
<221> NAME/KEY: misc_feature
<222> LOCATION: (173)..(173)
<223> OTHER INFORMATION: Xaa is any aa
<220> FEATURE:
<221> NAME/KEY: misc_feature
<222> LOCATION: (176)..(176)
<223> OTHER INFORMATION: Xaa is any aa
<220> FEATURE:
<221> NAME/KEY: misc_feature
<222> LOCATION: (177)..(177)
<223> OTHER INFORMATION: Xaa is any aa
<220> FEATURE:
<221> NAME/KEY: misc_feature
<222> LOCATION: (178)..(178)
<223> OTHER INFORMATION: Xaa is any aa
<220> FEATURE:
<221> NAME/KEY: misc_feature
<222> LOCATION: (179)..(179)
<223> OTHER INFORMATION: Xaa is Ile, Val, Leu, or Met
<220> FEATURE:
<221> NAME/KEY: misc_feature
<222> LOCATION: (180)..(180)
<223> OTHER INFORMATION: Xaa is any aa
<220> FEATURE:
<221> NAME/KEY: misc_feature
<222> LOCATION: (181)..(181)
<223> OTHER INFORMATION: Xaa is Thr, Gly, or Ser
<220> FEATURE:
<221> NAME/KEY: misc_feature
<222> LOCATION: (182)..(182)
<223> OTHER INFORMATION: Xaa is any aa
<220> FEATURE:
<221> NAME/KEY: misc_feature
<222> LOCATION: (183)..(183)
<223> OTHER INFORMATION: Xaa is Pro  or Ala
<220> FEATURE:
<221> NAME/KEY: misc_feature
<222> LOCATION: (184)..(184)
<223> OTHER INFORMATION: Xaa is any aa
<220> FEATURE:
<221> NAME/KEY: misc_feature
<222> LOCATION: (185)..(185)
<223> OTHER INFORMATION: Xaa is any aa
<220> FEATURE:
<221> NAME/KEY: misc_feature
<222> LOCATION: (186)..(186)
<223> OTHER INFORMATION: Xaa is any aa
<220> FEATURE:
<221> NAME/KEY: misc_feature
<222> LOCATION: (187)..(187)
<223> OTHER INFORMATION: Xaa is any aa or nothing
<220> FEATURE:
<221> NAME/KEY: misc_feature
<222> LOCATION: (188)..(188)
<223> OTHER INFORMATION: Xaa is any aa or nothing
<220> FEATURE:
<221> NAME/KEY: misc_feature
<222> LOCATION: (189)..(189)
<223> OTHER INFORMATION: Xaa is any aa or nothing
<220> FEATURE:
<221> NAME/KEY: misc_feature
<222> LOCATION: (190)..(190)
<223> OTHER INFORMATION: Xaa is any aa or nothing
<220> FEATURE:
<221> NAME/KEY: misc_feature
<222> LOCATION: (191)..(191)
<223> OTHER INFORMATION: Xaa is any aa or nothing
<220> FEATURE:
<221> NAME/KEY: misc_feature
<222> LOCATION: (192)..(192)
<223> OTHER INFORMATION: Xaa is Lys, Arg, or His
<220> FEATURE:
<221> NAME/KEY: misc_feature
<222> LOCATION: (193)..(193)
<223> OTHER INFORMATION: Xaa is any aa
<220> FEATURE:
<221> NAME/KEY: misc_feature
```

```
<222> LOCATION: (194)..(194)
<223> OTHER INFORMATION: Xaa is Ile, Val, Leu, or Met
<220> FEATURE:
<221> NAME/KEY: misc_feature
<222> LOCATION: (200)..(200)
<223> OTHER INFORMATION: Xaa is any aa
<220> FEATURE:
<221> NAME/KEY: misc_feature
<222> LOCATION: (203)..(203)
<223> OTHER INFORMATION: Xaa is any aa
<220> FEATURE:
<221> NAME/KEY: misc_feature
<222> LOCATION: (204)..(204)
<223> OTHER INFORMATION: Xaa is Ser or Asn
<220> FEATURE:
<221> NAME/KEY: misc_feature
<222> LOCATION: (205)..(205)
<223> OTHER INFORMATION: Xaa is Ile, Val, Leu, or Met
<220> FEATURE:
<221> NAME/KEY: misc_feature
<222> LOCATION: (207)..(207)
<223> OTHER INFORMATION: Xaa is Ile, Val, Leu, or Met
<220> FEATURE:
<221> NAME/KEY: misc_feature
<222> LOCATION: (209)..(209)
<223> OTHER INFORMATION: Xaa is any aa
<220> FEATURE:
<221> NAME/KEY: misc_feature
<222> LOCATION: (210)..(210)
<223> OTHER INFORMATION: Xaa is Asp or Glu
<220> FEATURE:
<221> NAME/KEY: misc_feature
<222> LOCATION: (211)..(211)
<223> OTHER INFORMATION: Xaa is any aa
<220> FEATURE:
<221> NAME/KEY: misc_feature
<222> LOCATION: (212)..(212)
<223> OTHER INFORMATION: Xaa is Phe, Tyr, or Trp
<220> FEATURE:
<221> NAME/KEY: misc_feature
<222> LOCATION: (213)..(213)
<223> OTHER INFORMATION: Xaa is Pro or Ser
<220> FEATURE:
<221> NAME/KEY: misc_feature
<222> LOCATION: (214)..(214)
<223> OTHER INFORMATION: Xaa is any aa
<220> FEATURE:
<221> NAME/KEY: misc_feature
<222> LOCATION: (215)..(215)
<223> OTHER INFORMATION: Xaa is Lys, Arg, or His
<220> FEATURE:
<221> NAME/KEY: misc_feature
<222> LOCATION: (216)..(216)
<223> OTHER INFORMATION: Xaa is Ile, Val, Leu, or Met
<220> FEATURE:
<221> NAME/KEY: misc_feature
<222> LOCATION: (217)..(217)
<223> OTHER INFORMATION: Xaa is Thr, Gly, or Ser
<220> FEATURE:
<221> NAME/KEY: misc_feature
<222> LOCATION: (218)..(218)
<223> OTHER INFORMATION: Xaa is Val or Ala
<220> FEATURE:
<221> NAME/KEY: misc_feature
<222> LOCATION: (219)..(219)
<223> OTHER INFORMATION: Xaa is Thr, Gly, or Ser
<220> FEATURE:
<221> NAME/KEY: misc_feature
<222> LOCATION: (222)..(222)
<223> OTHER INFORMATION: Xaa is any aa
<220> FEATURE:
<221> NAME/KEY: misc_feature
<222> LOCATION: (223)..(223)
<223> OTHER INFORMATION: Xaa is Thr, Gly, or Ser
<220> FEATURE:
<221> NAME/KEY: misc_feature
<222> LOCATION: (224)..(224)
<223> OTHER INFORMATION: Xaa is Thr, Gly, or Ser
<220> FEATURE:
<221> NAME/KEY: misc_feature
```

```
<222> LOCATION: (225)..(225)
<223> OTHER INFORMATION: Xaa is any aa
<220> FEATURE:
<221> NAME/KEY: misc_feature
<222> LOCATION: (226)..(226)
<223> OTHER INFORMATION: Xaa is Ile, Val, Leu, or Met
<220> FEATURE:
<221> NAME/KEY: misc_feature
<222> LOCATION: (228)..(228)
<223> OTHER INFORMATION: Xaa is any aa
<220> FEATURE:
<221> NAME/KEY: misc_feature
<222> LOCATION: (229)..(229)
<223> OTHER INFORMATION: Xaa is any aa
<220> FEATURE:
<221> NAME/KEY: misc_feature
<222> LOCATION: (230)..(230)
<223> OTHER INFORMATION: Xaa is any aa
<220> FEATURE:
<221> NAME/KEY: misc_feature
<222> LOCATION: (231)..(231)
<223> OTHER INFORMATION: Xaa is any aa
<220> FEATURE:
<221> NAME/KEY: misc_feature
<222> LOCATION: (232)..(232)
<223> OTHER INFORMATION: Xaa is any aa
<220> FEATURE:
<221> NAME/KEY: misc_feature
<222> LOCATION: (233)..(233)
<223> OTHER INFORMATION: Xaa is any aa
<220> FEATURE:
<221> NAME/KEY: misc_feature
<222> LOCATION: (234)..(234)
<223> OTHER INFORMATION: Xaa is any aa or nothing
<220> FEATURE:
<221> NAME/KEY: misc_feature
<222> LOCATION: (235)..(235)
<223> OTHER INFORMATION: Xaa is Thr, Gly, or Ser
<220> FEATURE:
<221> NAME/KEY: misc_feature
<222> LOCATION: (236)..(236)
<223> OTHER INFORMATION: Xaa is any aa
<220> FEATURE:
<221> NAME/KEY: misc_feature
<222> LOCATION: (237)..(237)
<223> OTHER INFORMATION: Xaa is Val or Thr
<220> FEATURE:
<221> NAME/KEY: misc_feature
<222> LOCATION: (238)..(238)
<223> OTHER INFORMATION: Xaa is any aa
<220> FEATURE:
<221> NAME/KEY: misc_feature
<222> LOCATION: (239)..(239)
<223> OTHER INFORMATION: Xaa is Asp or Glu
<220> FEATURE:
<221> NAME/KEY: misc_feature
<222> LOCATION: (240)..(240)
<223> OTHER INFORMATION: Xaa is any aa
<220> FEATURE:
<221> NAME/KEY: misc_feature
<222> LOCATION: (241)..(241)
<223> OTHER INFORMATION: Xaa is any aa
<220> FEATURE:
<221> NAME/KEY: misc_feature
<222> LOCATION: (242)..(242)
<223> OTHER INFORMATION: Xaa is any aa
<220> FEATURE:
<221> NAME/KEY: misc_feature
<222> LOCATION: (243)..(243)
<223> OTHER INFORMATION: Xaa is any aa
<220> FEATURE:
<221> NAME/KEY: misc_feature
<222> LOCATION: (244)..(244)
<223> OTHER INFORMATION: Xaa is any aa
<220> FEATURE:
<221> NAME/KEY: misc_feature
<222> LOCATION: (245)..(245)
<223> OTHER INFORMATION: Xaa is any aa
<220> FEATURE:
<221> NAME/KEY: misc_feature
```

```
<222> LOCATION: (246)..(246)
<223> OTHER INFORMATION: Xaa is any aa or nothing
<220> FEATURE:
<221> NAME/KEY: misc_feature
<222> LOCATION: (247)..(247)
<223> OTHER INFORMATION: Xaa is any aa or nothing
<220> FEATURE:
<221> NAME/KEY: misc_feature
<222> LOCATION: (248)..(248)
<223> OTHER INFORMATION: Xaa is any aa or nothing
<220> FEATURE:
<221> NAME/KEY: misc_feature
<222> LOCATION: (249)..(249)
<223> OTHER INFORMATION: Xaa is any aa or nothing
<220> FEATURE:
<221> NAME/KEY: misc_feature
<222> LOCATION: (250)..(250)
<223> OTHER INFORMATION: Xaa is any aa or nothing
<220> FEATURE:
<221> NAME/KEY: misc_feature
<222> LOCATION: (251)..(251)
<223> OTHER INFORMATION: Xaa is any aa or nothing
<220> FEATURE:
<221> NAME/KEY: misc_feature
<222> LOCATION: (252)..(252)
<223> OTHER INFORMATION: Xaa is any aa or nothing
<220> FEATURE:
<221> NAME/KEY: misc_feature
<222> LOCATION: (253)..(253)
<223> OTHER INFORMATION: Xaa is any aa or nothing
<220> FEATURE:
<221> NAME/KEY: misc_feature
<222> LOCATION: (254)..(254)
<223> OTHER INFORMATION: Xaa is any aa or nothing
<220> FEATURE:
<221> NAME/KEY: misc_feature
<222> LOCATION: (255)..(255)
<223> OTHER INFORMATION: Xaa is any aa or nothing
<220> FEATURE:
<221> NAME/KEY: misc_feature
<222> LOCATION: (256)..(256)
<223> OTHER INFORMATION: Xaa is any aa or nothing
<220> FEATURE:
<221> NAME/KEY: misc_feature
<222> LOCATION: (257)..(257)
<223> OTHER INFORMATION: Xaa is Ile, Val, Leu, or Met
<220> FEATURE:
<221> NAME/KEY: misc_feature
<222> LOCATION: (258)..(258)
<223> OTHER INFORMATION: Xaa is Gly  or Asp
<220> FEATURE:
<221> NAME/KEY: misc_feature
<222> LOCATION: (259)..(259)
<223> OTHER INFORMATION: Xaa is any aa
<220> FEATURE:
<221> NAME/KEY: misc_feature
<222> LOCATION: (260)..(260)
<223> OTHER INFORMATION: Xaa is any aa
<220> FEATURE:
<221> NAME/KEY: misc_feature
<222> LOCATION: (261)..(261)
<223> OTHER INFORMATION: Xaa is any aa
<220> FEATURE:
<221> NAME/KEY: misc_feature
<222> LOCATION: (262)..(262)
<223> OTHER INFORMATION: Xaa is any aa
<220> FEATURE:
<221> NAME/KEY: misc_feature
<222> LOCATION: (263)..(263)
<223> OTHER INFORMATION: Xaa is any aa
<220> FEATURE:
<221> NAME/KEY: misc_feature
<222> LOCATION: (264)..(264)
<223> OTHER INFORMATION: Xaa is any aa
<220> FEATURE:
<221> NAME/KEY: misc_feature
<222> LOCATION: (265)..(265)
<223> OTHER INFORMATION: Xaa is any aa
<220> FEATURE:
<221> NAME/KEY: misc_feature
```

```
<222> LOCATION: (266)..(266)
<223> OTHER INFORMATION: Xaa is any aa
<220> FEATURE:
<221> NAME/KEY: misc_feature
<222> LOCATION: (267)..(267)
<223> OTHER INFORMATION: Xaa is any aa
<220> FEATURE:
<221> NAME/KEY: misc_feature
<222> LOCATION: (268)..(268)
<223> OTHER INFORMATION: Xaa is any aa
<220> FEATURE:
<221> NAME/KEY: misc_feature
<222> LOCATION: (269)..(269)
<223> OTHER INFORMATION: Xaa is any aa
<220> FEATURE:
<221> NAME/KEY: misc_feature
<222> LOCATION: (270)..(270)
<223> OTHER INFORMATION: Xaa is any aa
<220> FEATURE:
<221> NAME/KEY: misc_feature
<222> LOCATION: (271)..(271)
<223> OTHER INFORMATION: Xaa is any aa
<220> FEATURE:
<221> NAME/KEY: misc_feature
<222> LOCATION: (272)..(272)
<223> OTHER INFORMATION: Xaa is any aa
<220> FEATURE:
<221> NAME/KEY: misc_feature
<222> LOCATION: (273)..(273)
<223> OTHER INFORMATION: Xaa is any aa
<220> FEATURE:
<221> NAME/KEY: misc_feature
<222> LOCATION: (274)..(274)
<223> OTHER INFORMATION: Xaa is any aa
<220> FEATURE:
<221> NAME/KEY: misc_feature
<222> LOCATION: (275)..(275)
<223> OTHER INFORMATION: Xaa is any aa or nothing
<220> FEATURE:
<221> NAME/KEY: misc_feature
<222> LOCATION: (276)..(276)
<223> OTHER INFORMATION: Xaa is any aa or nothing
<220> FEATURE:
<221> NAME/KEY: misc_feature
<222> LOCATION: (277)..(277)
<223> OTHER INFORMATION: Xaa is any aa or nothing
<220> FEATURE:
<221> NAME/KEY: misc_feature
<222> LOCATION: (278)..(278)
<223> OTHER INFORMATION: Xaa is any aa or nothing
<220> FEATURE:
<221> NAME/KEY: misc_feature
<222> LOCATION: (279)..(279)
<223> OTHER INFORMATION: Xaa is any aa or nothing
<220> FEATURE:
<221> NAME/KEY: misc_feature
<222> LOCATION: (280)..(280)
<223> OTHER INFORMATION: Xaa is any aa or nothing
<220> FEATURE:
<221> NAME/KEY: misc_feature
<222> LOCATION: (281)..(281)
<223> OTHER INFORMATION: Xaa is any aa or nothing
<220> FEATURE:
<221> NAME/KEY: misc_feature
<222> LOCATION: (282)..(282)
<223> OTHER INFORMATION: Xaa is Phe  or Met
<220> FEATURE:
<221> NAME/KEY: misc_feature
<222> LOCATION: (283)..(283)
<223> OTHER INFORMATION: Xaa is Thr, Gly, or Ser
<220> FEATURE:
<221> NAME/KEY: misc_feature
<222> LOCATION: (284)..(284)
<223> OTHER INFORMATION: Xaa is Thr  or Pro
<220> FEATURE:
<221> NAME/KEY: misc_feature
<222> LOCATION: (285)..(285)
<223> OTHER INFORMATION: Xaa is any aa
<220> FEATURE:
<221> NAME/KEY: misc_feature
```

-continued

```
<222> LOCATION: (286)..(286)
<223> OTHER INFORMATION: Xaa is any aa
<220> FEATURE:
<221> NAME/KEY: misc_feature
<222> LOCATION: (287)..(287)
<223> OTHER INFORMATION: Xaa is any aa
<220> FEATURE:
<221> NAME/KEY: misc_feature
<222> LOCATION: (288)..(288)
<223> OTHER INFORMATION: Xaa is any aa
<220> FEATURE:
<221> NAME/KEY: misc_feature
<222> LOCATION: (289)..(289)
<223> OTHER INFORMATION: Xaa is any aa
<220> FEATURE:
<221> NAME/KEY: misc_feature
<222> LOCATION: (290)..(290)
<223> OTHER INFORMATION: Xaa is any aa
<220> FEATURE:
<221> NAME/KEY: misc_feature
<222> LOCATION: (291)..(291)
<223> OTHER INFORMATION: Xaa is any aa
<220> FEATURE:
<221> NAME/KEY: misc_feature
<222> LOCATION: (292)..(292)
<223> OTHER INFORMATION: Xaa is Phe, Tyr, or Trp
<220> FEATURE:
<221> NAME/KEY: misc_feature
<222> LOCATION: (293)..(293)
<223> OTHER INFORMATION: Xaa is Gln or Asp
<220> FEATURE:
<221> NAME/KEY: misc_feature
<222> LOCATION: (294)..(294)
<223> OTHER INFORMATION: Xaa is any aa
<220> FEATURE:
<221> NAME/KEY: misc_feature
<222> LOCATION: (295)..(295)
<223> OTHER INFORMATION: Xaa is Ser or Cys
<220> FEATURE:
<221> NAME/KEY: misc_feature
<222> LOCATION: (296)..(296)
<223> OTHER INFORMATION: Xaa is Pro or Ser
<220> FEATURE:
<221> NAME/KEY: misc_feature
<222> LOCATION: (297)..(297)
<223> OTHER INFORMATION: Xaa is any aa
<220> FEATURE:
<221> NAME/KEY: misc_feature
<222> LOCATION: (300)..(300)
<223> OTHER INFORMATION: Xaa is any aa
<220> FEATURE:
<221> NAME/KEY: misc_feature
<222> LOCATION: (301)..(301)
<223> OTHER INFORMATION: Xaa is any aa
<220> FEATURE:
<221> NAME/KEY: misc_feature
<222> LOCATION: (303)..(303)
<223> OTHER INFORMATION: Xaa is Thr, Gly, or Ser
<220> FEATURE:
<221> NAME/KEY: misc_feature
<222> LOCATION: (304)..(304)
<223> OTHER INFORMATION: Xaa is any aa
<220> FEATURE:
<221> NAME/KEY: misc_feature
<222> LOCATION: (305)..(305)
<223> OTHER INFORMATION: Xaa is any aa
<220> FEATURE:
<221> NAME/KEY: misc_feature
<222> LOCATION: (306)..(306)
<223> OTHER INFORMATION: Xaa is Ile, Val, Leu, or Met
<220> FEATURE:
<221> NAME/KEY: misc_feature
<222> LOCATION: (307)..(307)
<223> OTHER INFORMATION: Xaa is any aa
<220> FEATURE:
<221> NAME/KEY: misc_feature
<222> LOCATION: (309)..(309)
<223> OTHER INFORMATION: Xaa is Pro or Val
<220> FEATURE:
<221> NAME/KEY: misc_feature
```

```
<222> LOCATION: (310)..(310)
<223> OTHER INFORMATION: Xaa is any aa
<220> FEATURE:
<221> NAME/KEY: misc_feature
<222> LOCATION: (311)..(311)
<223> OTHER INFORMATION: Xaa is any aa
<220> FEATURE:
<221> NAME/KEY: misc_feature
<222> LOCATION: (312)..(312)
<223> OTHER INFORMATION: Xaa is any aa
<220> FEATURE:
<221> NAME/KEY: misc_feature
<222> LOCATION: (314)..(314)
<223> OTHER INFORMATION: Xaa is any aa
<220> FEATURE:
<221> NAME/KEY: misc_feature
<222> LOCATION: (315)..(315)
<223> OTHER INFORMATION: Xaa is any aa
<220> FEATURE:
<221> NAME/KEY: misc_feature
<222> LOCATION: (316)..(316)
<223> OTHER INFORMATION: Xaa is Asp or Glu
<220> FEATURE:
<221> NAME/KEY: misc_feature
<222> LOCATION: (317)..(317)
<223> OTHER INFORMATION: Xaa is any aa
<220> FEATURE:
<221> NAME/KEY: misc_feature
<222> LOCATION: (318)..(318)
<223> OTHER INFORMATION: Xaa is any aa
<220> FEATURE:
<221> NAME/KEY: misc_feature
<222> LOCATION: (319)..(319)
<223> OTHER INFORMATION: Xaa is any aa
<220> FEATURE:
<221> NAME/KEY: misc_feature
<222> LOCATION: (320)..(320)
<223> OTHER INFORMATION: Xaa is any aa
<220> FEATURE:
<221> NAME/KEY: misc_feature
<222> LOCATION: (321)..(321)
<223> OTHER INFORMATION: Xaa is any aa
<220> FEATURE:
<221> NAME/KEY: misc_feature
<222> LOCATION: (322)..(322)
<223> OTHER INFORMATION: Xaa is any aa
<220> FEATURE:
<221> NAME/KEY: misc_feature
<222> LOCATION: (323)..(323)
<223> OTHER INFORMATION: Xaa is any aa
<220> FEATURE:
<221> NAME/KEY: misc_feature
<222> LOCATION: (324)..(324)
<223> OTHER INFORMATION: Xaa is any aa or nothing
<220> FEATURE:
<221> NAME/KEY: misc_feature
<222> LOCATION: (325)..(325)
<223> OTHER INFORMATION: Xaa is any aa or nothing
<220> FEATURE:
<221> NAME/KEY: misc_feature
<222> LOCATION: (326)..(326)
<223> OTHER INFORMATION: Xaa is any aa or nothing
<220> FEATURE:
<221> NAME/KEY: misc_feature
<222> LOCATION: (327)..(327)
<223> OTHER INFORMATION: Xaa is any aa or nothing
<220> FEATURE:
<221> NAME/KEY: misc_feature
<222> LOCATION: (328)..(328)
<223> OTHER INFORMATION: Xaa is Thr, Gly, or Ser
<220> FEATURE:
<221> NAME/KEY: misc_feature
<222> LOCATION: (329)..(329)
<223> OTHER INFORMATION: Xaa is any aa
<220> FEATURE:
<221> NAME/KEY: misc_feature
<222> LOCATION: (330)..(330)
<223> OTHER INFORMATION: Xaa is any aa
<220> FEATURE:
<221> NAME/KEY: misc_feature
```

```
<222> LOCATION: (331)..(331)
<223> OTHER INFORMATION: Xaa is any aa
<220> FEATURE:
<221> NAME/KEY: misc_feature
<222> LOCATION: (332)..(332)
<223> OTHER INFORMATION: Xaa is any aa or nothing
<220> FEATURE:
<221> NAME/KEY: misc_feature
<222> LOCATION: (335)..(335)
<223> OTHER INFORMATION: Xaa is Thr, Gly, or Ser
<220> FEATURE:
<221> NAME/KEY: misc_feature
<222> LOCATION: (337)..(337)
<223> OTHER INFORMATION: Xaa is any aa
<220> FEATURE:
<221> NAME/KEY: misc_feature
<222> LOCATION: (338)..(338)
<223> OTHER INFORMATION: Xaa is Lys, Arg, or His
<220> FEATURE:
<221> NAME/KEY: misc_feature
<222> LOCATION: (339)..(339)
<223> OTHER INFORMATION: Xaa is Ala or Val
<220> FEATURE:
<221> NAME/KEY: misc_feature
<222> LOCATION: (340)..(340)
<223> OTHER INFORMATION: Xaa is any aa
<220> FEATURE:
<221> NAME/KEY: misc_feature
<222> LOCATION: (341)..(341)
<223> OTHER INFORMATION: Xaa is Ile, Val, Leu, or Met
<220> FEATURE:
<221> NAME/KEY: misc_feature
<222> LOCATION: (343)..(343)
<223> OTHER INFORMATION: Xaa is any aa
<220> FEATURE:
<221> NAME/KEY: misc_feature
<222> LOCATION: (344)..(344)
<223> OTHER INFORMATION: Xaa is any aa
<220> FEATURE:
<221> NAME/KEY: misc_feature
<222> LOCATION: (345)..(345)
<223> OTHER INFORMATION: Xaa is any aa
<220> FEATURE:
<221> NAME/KEY: misc_feature
<222> LOCATION: (347)..(347)
<223> OTHER INFORMATION: Xaa is any aa
<220> FEATURE:
<221> NAME/KEY: misc_feature
<222> LOCATION: (348)..(348)
<223> OTHER INFORMATION: Xaa is any aa
<220> FEATURE:
<221> NAME/KEY: misc_feature
<222> LOCATION: (349)..(349)
<223> OTHER INFORMATION: Xaa is any aa
<220> FEATURE:
<221> NAME/KEY: misc_feature
<222> LOCATION: (350)..(350)
<223> OTHER INFORMATION: Xaa is any aa
<220> FEATURE:
<221> NAME/KEY: misc_feature
<222> LOCATION: (351)..(351)
<223> OTHER INFORMATION: Xaa is any aa
<220> FEATURE:
<221> NAME/KEY: misc_feature
<222> LOCATION: (352)..(352)
<223> OTHER INFORMATION: Xaa is any aa
<220> FEATURE:
<221> NAME/KEY: misc_feature
<222> LOCATION: (353)..(353)
<223> OTHER INFORMATION: Xaa is any aa
<220> FEATURE:
<221> NAME/KEY: misc_feature
<222> LOCATION: (354)..(354)
<223> OTHER INFORMATION: Xaa is Gln or Leu
<220> FEATURE:
<221> NAME/KEY: misc_feature
<222> LOCATION: (355)..(355)
<223> OTHER INFORMATION: Xaa is Arg or Trp
<220> FEATURE:
<221> NAME/KEY: misc_feature
```

-continued

```
<222> LOCATION: (356)..(356)
<223> OTHER INFORMATION: Xaa is Trp or Arg
<220> FEATURE:
<221> NAME/KEY: misc_feature
<222> LOCATION: (358)..(358)
<223> OTHER INFORMATION: Xaa is any aa
<220> FEATURE:
<221> NAME/KEY: misc_feature
<222> LOCATION: (359)..(359)
<223> OTHER INFORMATION: Xaa is any aa
<220> FEATURE:
<221> NAME/KEY: misc_feature
<222> LOCATION: (360)..(360)
<223> OTHER INFORMATION: Xaa is any aa
<220> FEATURE:
<221> NAME/KEY: misc_feature
<222> LOCATION: (361)..(361)
<223> OTHER INFORMATION: Xaa is any aa
<220> FEATURE:
<221> NAME/KEY: misc_feature
<222> LOCATION: (363)..(363)
<223> OTHER INFORMATION: Xaa is any aa
<220> FEATURE:
<221> NAME/KEY: misc_feature
<222> LOCATION: (364)..(364)
<223> OTHER INFORMATION: Xaa is any aa
<220> FEATURE:
<221> NAME/KEY: misc_feature
<222> LOCATION: (365)..(365)
<223> OTHER INFORMATION: Xaa is any aa
<220> FEATURE:
<221> NAME/KEY: misc_feature
<222> LOCATION: (366)..(366)
<223> OTHER INFORMATION: Xaa is Val or Ala
<220> FEATURE:
<221> NAME/KEY: misc_feature
<222> LOCATION: (367)..(367)
<223> OTHER INFORMATION: Xaa is any aa
<220> FEATURE:
<221> NAME/KEY: misc_feature
<222> LOCATION: (368)..(368)
<223> OTHER INFORMATION: Xaa is Glu or Gly
<220> FEATURE:
<221> NAME/KEY: misc_feature
<222> LOCATION: (369)..(369)
<223> OTHER INFORMATION: Xaa is Ile, Val, Leu, or Met
<220> FEATURE:
<221> NAME/KEY: misc_feature
<222> LOCATION: (370)..(370)
<223> OTHER INFORMATION: Xaa is any aa
<220> FEATURE:
<221> NAME/KEY: misc_feature
<222> LOCATION: (371)..(371)
<223> OTHER INFORMATION: Xaa is any aa
<220> FEATURE:
<221> NAME/KEY: misc_feature
<222> LOCATION: (372)..(372)
<223> OTHER INFORMATION: Xaa is Thr, Gly, or Ser
<220> FEATURE:
<221> NAME/KEY: misc_feature
<222> LOCATION: (375)..(375)
<223> OTHER INFORMATION: Xaa is Met or Ala
<220> FEATURE:
<221> NAME/KEY: misc_feature
<222> LOCATION: (376)..(376)
<223> OTHER INFORMATION: Xaa is any aa
<220> FEATURE:
<221> NAME/KEY: misc_feature
<222> LOCATION: (377)..(377)
<223> OTHER INFORMATION: Xaa is Ile, Val, Leu, or Met
<220> FEATURE:
<221> NAME/KEY: misc_feature
<222> LOCATION: (378)..(378)
<223> OTHER INFORMATION: Xaa is any aa
<220> FEATURE:
<221> NAME/KEY: misc_feature
<222> LOCATION: (379)..(379)
<223> OTHER INFORMATION: Xaa is Cys or Ser
<220> FEATURE:
<221> NAME/KEY: misc_feature
```

```
<222> LOCATION: (380)..(380)
<223> OTHER INFORMATION: Xaa is any aa
<220> FEATURE:
<221> NAME/KEY: misc_feature
<222> LOCATION: (382)..(382)
<223> OTHER INFORMATION: Xaa is any aa
<220> FEATURE:
<221> NAME/KEY: misc_feature
<222> LOCATION: (383)..(383)
<223> OTHER INFORMATION: Xaa is any aa
<220> FEATURE:
<221> NAME/KEY: misc_feature
<222> LOCATION: (385)..(385)
<223> OTHER INFORMATION: Xaa is any aa
<220> FEATURE:
<221> NAME/KEY: misc_feature
<222> LOCATION: (386)..(386)
<223> OTHER INFORMATION: Xaa is any aa
<220> FEATURE:
<221> NAME/KEY: misc_feature
<222> LOCATION: (387)..(387)
<223> OTHER INFORMATION: Xaa is any aa
<220> FEATURE:
<221> NAME/KEY: misc_feature
<222> LOCATION: (388)..(388)
<223> OTHER INFORMATION: Xaa is Leu or Phe
<220> FEATURE:
<221> NAME/KEY: misc_feature
<222> LOCATION: (389)..(389)
<223> OTHER INFORMATION: Xaa is any aa
<220> FEATURE:
<221> NAME/KEY: misc_feature
<222> LOCATION: (390)..(390)
<223> OTHER INFORMATION: Xaa is any aa
<220> FEATURE:
<221> NAME/KEY: misc_feature
<222> LOCATION: (391)..(391)
<223> OTHER INFORMATION: Xaa is Ile, Val, Leu, or Met
<220> FEATURE:
<221> NAME/KEY: misc_feature
<222> LOCATION: (395)..(395)
<223> OTHER INFORMATION: Xaa is Lys, Arg, or His
<220> FEATURE:
<221> NAME/KEY: misc_feature
<222> LOCATION: (396)..(396)
<223> OTHER INFORMATION: Xaa is Val or Gly
<220> FEATURE:
<221> NAME/KEY: misc_feature
<222> LOCATION: (398)..(398)
<223> OTHER INFORMATION: Xaa is Lys or Leu
<220> FEATURE:
<221> NAME/KEY: misc_feature
<222> LOCATION: (399)..(399)
<223> OTHER INFORMATION: Xaa is Leu or Ser
<220> FEATURE:
<221> NAME/KEY: misc_feature
<222> LOCATION: (400)..(400)
<223> OTHER INFORMATION: Xaa is any aa
<220> FEATURE:
<221> NAME/KEY: misc_feature
<222> LOCATION: (404)..(404)
<223> OTHER INFORMATION: Xaa is Ser or Cys
<220> FEATURE:
<221> NAME/KEY: misc_feature
<222> LOCATION: (405)..(405)
<223> OTHER INFORMATION: Xaa is any aa
<220> FEATURE:
<221> NAME/KEY: misc_feature
<222> LOCATION: (406)..(406)
<223> OTHER INFORMATION: Xaa is Ile, Val, Leu, or Met
<220> FEATURE:
<221> NAME/KEY: misc_feature
<222> LOCATION: (407)..(407)
<223> OTHER INFORMATION: Xaa is Lys, Arg, or His
<220> FEATURE:
<221> NAME/KEY: misc_feature
<222> LOCATION: (408)..(408)
<223> OTHER INFORMATION: Xaa is Lys, Arg, or His
<220> FEATURE:
<221> NAME/KEY: misc_feature
```

-continued

```
<222> LOCATION: (410)..(410)
<223> OTHER INFORMATION: Xaa is any aa
<220> FEATURE:
<221> NAME/KEY: misc_feature
<222> LOCATION: (411)..(411)
<223> OTHER INFORMATION: Xaa is any aa or nothing
<220> FEATURE:
<221> NAME/KEY: misc_feature
<222> LOCATION: (412)..(412)
<223> OTHER INFORMATION: Xaa is any aa or nothing
<220> FEATURE:
<221> NAME/KEY: misc_feature
<222> LOCATION: (413)..(413)
<223> OTHER INFORMATION: Xaa is any aa or nothing
<220> FEATURE:
<221> NAME/KEY: misc_feature
<222> LOCATION: (414)..(414)
<223> OTHER INFORMATION: Xaa is any aa or nothing
<220> FEATURE:
<221> NAME/KEY: misc_feature
<222> LOCATION: (415)..(415)
<223> OTHER INFORMATION: Xaa is any aa or nothing
<220> FEATURE:
<221> NAME/KEY: misc_feature
<222> LOCATION: (416)..(416)
<223> OTHER INFORMATION: Xaa is any aa or nothing
<220> FEATURE:
<221> NAME/KEY: misc_feature
<222> LOCATION: (417)..(417)
<223> OTHER INFORMATION: Xaa is any aa or nothing
<220> FEATURE:
<221> NAME/KEY: misc_feature
<222> LOCATION: (418)..(418)
<223> OTHER INFORMATION: Xaa is any aa or nothing
<220> FEATURE:
<221> NAME/KEY: misc_feature
<222> LOCATION: (419)..(419)
<223> OTHER INFORMATION: Xaa is any aa or nothing
<220> FEATURE:
<221> NAME/KEY: misc_feature
<222> LOCATION: (421)..(421)
<223> OTHER INFORMATION: Xaa is any aa
<220> FEATURE:
<221> NAME/KEY: misc_feature
<222> LOCATION: (422)..(422)
<223> OTHER INFORMATION: Xaa is Thr, Gly, or Ser
<220> FEATURE:
<221> NAME/KEY: misc_feature
<222> LOCATION: (423)..(423)
<223> OTHER INFORMATION: Xaa is any aa
<220> FEATURE:
<221> NAME/KEY: misc_feature
<222> LOCATION: (424)..(424)
<223> OTHER INFORMATION: Xaa is any aa
<220> FEATURE:
<221> NAME/KEY: misc_feature
<222> LOCATION: (425)..(425)
<223> OTHER INFORMATION: Xaa is any aa
<220> FEATURE:
<221> NAME/KEY: misc_feature
<222> LOCATION: (426)..(426)
<223> OTHER INFORMATION: Xaa is any aa
<220> FEATURE:
<221> NAME/KEY: misc_feature
<222> LOCATION: (427)..(427)
<223> OTHER INFORMATION: Xaa is any aa
<220> FEATURE:
<221> NAME/KEY: misc_feature
<222> LOCATION: (428)..(428)
<223> OTHER INFORMATION: Xaa is any aa
<220> FEATURE:
<221> NAME/KEY: misc_feature
<222> LOCATION: (429)..(429)
<223> OTHER INFORMATION: Xaa is any aa
<220> FEATURE:
<221> NAME/KEY: misc_feature
<222> LOCATION: (430)..(430)
<223> OTHER INFORMATION: Xaa is any aa
<220> FEATURE:
<221> NAME/KEY: misc_feature
```

-continued

```
<222> LOCATION: (431)..(431)
<223> OTHER INFORMATION: Xaa is any aa
<220> FEATURE:
<221> NAME/KEY: misc_feature
<222> LOCATION: (432)..(432)
<223> OTHER INFORMATION: Xaa is any aa
<220> FEATURE:
<221> NAME/KEY: misc_feature
<222> LOCATION: (433)..(433)
<223> OTHER INFORMATION: Xaa is any aa
<220> FEATURE:
<221> NAME/KEY: misc_feature
<222> LOCATION: (434)..(434)
<223> OTHER INFORMATION: Xaa is any aa
<220> FEATURE:
<221> NAME/KEY: misc_feature
<222> LOCATION: (435)..(435)
<223> OTHER INFORMATION: Xaa is any aa
<220> FEATURE:
<221> NAME/KEY: misc_feature
<222> LOCATION: (436)..(436)
<223> OTHER INFORMATION: Xaa is any aa
<220> FEATURE:
<221> NAME/KEY: misc_feature
<222> LOCATION: (437)..(437)
<223> OTHER INFORMATION: Xaa is any aa
<220> FEATURE:
<221> NAME/KEY: misc_feature
<222> LOCATION: (438)..(438)
<223> OTHER INFORMATION: Xaa is any aa
<220> FEATURE:
<221> NAME/KEY: misc_feature
<222> LOCATION: (439)..(439)
<223> OTHER INFORMATION: Xaa is any aa
<220> FEATURE:
<221> NAME/KEY: misc_feature
<222> LOCATION: (440)..(440)
<223> OTHER INFORMATION: Xaa is any aa
<220> FEATURE:
<221> NAME/KEY: misc_feature
<222> LOCATION: (441)..(441)
<223> OTHER INFORMATION: Xaa is any aa or nothing
<220> FEATURE:
<221> NAME/KEY: misc_feature
<222> LOCATION: (442)..(442)
<223> OTHER INFORMATION: Xaa is any aa or nothing
<220> FEATURE:
<221> NAME/KEY: misc_feature
<222> LOCATION: (443)..(443)
<223> OTHER INFORMATION: Xaa is any aa or nothing
<220> FEATURE:
<221> NAME/KEY: misc_feature
<222> LOCATION: (444)..(444)
<223> OTHER INFORMATION: Xaa is any aa or nothing
<220> FEATURE:
<221> NAME/KEY: misc_feature
<222> LOCATION: (445)..(445)
<223> OTHER INFORMATION: Xaa is any aa or nothing
<220> FEATURE:
<221> NAME/KEY: misc_feature
<222> LOCATION: (446)..(446)
<223> OTHER INFORMATION: Xaa is any aa or nothing
<220> FEATURE:
<221> NAME/KEY: misc_feature
<222> LOCATION: (447)..(447)
<223> OTHER INFORMATION: Xaa is any aa or nothing
<220> FEATURE:
<221> NAME/KEY: misc_feature
<222> LOCATION: (448)..(448)
<223> OTHER INFORMATION: Xaa is any aa or nothing
<220> FEATURE:
<221> NAME/KEY: misc_feature
<222> LOCATION: (449)..(449)
<223> OTHER INFORMATION: Xaa is any aa or nothing
<220> FEATURE:
<221> NAME/KEY: misc_feature
<222> LOCATION: (450)..(450)
<223> OTHER INFORMATION: Xaa is any aa or nothing
<220> FEATURE:
<221> NAME/KEY: misc_feature
```

-continued

```
<222> LOCATION: (451)..(451)
<223> OTHER INFORMATION: Xaa is any aa or nothing
<220> FEATURE:
<221> NAME/KEY: misc_feature
<222> LOCATION: (452)..(452)
<223> OTHER INFORMATION: Xaa is any aa or nothing
<220> FEATURE:
<221> NAME/KEY: misc_feature
<222> LOCATION: (453)..(453)
<223> OTHER INFORMATION: Xaa is any aa or nothing
<220> FEATURE:
<221> NAME/KEY: misc_feature
<222> LOCATION: (454)..(454)
<223> OTHER INFORMATION: Xaa is any aa or nothing
<220> FEATURE:
<221> NAME/KEY: misc_feature
<222> LOCATION: (455)..(455)
<223> OTHER INFORMATION: Xaa is any aa or nothing
<220> FEATURE:
<221> NAME/KEY: misc_feature
<222> LOCATION: (456)..(456)
<223> OTHER INFORMATION: Xaa is any aa or nothing
<220> FEATURE:
<221> NAME/KEY: misc_feature
<222> LOCATION: (457)..(457)
<223> OTHER INFORMATION: Xaa is any aa or nothing
<220> FEATURE:
<221> NAME/KEY: misc_feature
<222> LOCATION: (458)..(458)
<223> OTHER INFORMATION: Xaa is any aa or nothing
<220> FEATURE:
<221> NAME/KEY: misc_feature
<222> LOCATION: (459)..(459)
<223> OTHER INFORMATION: Xaa is any aa or nothing
<220> FEATURE:
<221> NAME/KEY: misc_feature
<222> LOCATION: (460)..(460)
<223> OTHER INFORMATION: Xaa is any aa or nothing
<220> FEATURE:
<221> NAME/KEY: misc_feature
<222> LOCATION: (461)..(461)
<223> OTHER INFORMATION: Xaa is any aa or nothing
<220> FEATURE:
<221> NAME/KEY: misc_feature
<222> LOCATION: (462)..(462)
<223> OTHER INFORMATION: Xaa is any aa or nothing
<220> FEATURE:
<221> NAME/KEY: misc_feature
<222> LOCATION: (463)..(463)
<223> OTHER INFORMATION: Xaa is any aa or nothing
<220> FEATURE:
<221> NAME/KEY: misc_feature
<222> LOCATION: (464)..(464)
<223> OTHER INFORMATION: Xaa is any aa or nothing
<220> FEATURE:
<221> NAME/KEY: misc_feature
<222> LOCATION: (465)..(465)
<223> OTHER INFORMATION: Xaa is any aa or nothing
<220> FEATURE:
<221> NAME/KEY: misc_feature
<222> LOCATION: (466)..(466)
<223> OTHER INFORMATION: Xaa is any aa or nothing
<220> FEATURE:
<221> NAME/KEY: misc_feature
<222> LOCATION: (467)..(467)
<223> OTHER INFORMATION: Xaa is any aa or nothing
<220> FEATURE:
<221> NAME/KEY: misc_feature
<222> LOCATION: (468)..(468)
<223> OTHER INFORMATION: Xaa is any aa or nothing
<220> FEATURE:
<221> NAME/KEY: misc_feature
<222> LOCATION: (469)..(469)
<223> OTHER INFORMATION: Xaa is any aa or nothing
<220> FEATURE:
<221> NAME/KEY: misc_feature
<222> LOCATION: (470)..(470)
<223> OTHER INFORMATION: Xaa is any aa or nothing
<220> FEATURE:
<221> NAME/KEY: misc_feature
```

```
<222> LOCATION: (471)..(471)
<223> OTHER INFORMATION: Xaa is any aa or nothing
<220> FEATURE:
<221> NAME/KEY: misc_feature
<222> LOCATION: (472)..(472)
<223> OTHER INFORMATION: Xaa is any aa or nothing
<220> FEATURE:
<221> NAME/KEY: misc_feature
<222> LOCATION: (473)..(473)
<223> OTHER INFORMATION: Xaa is any aa or nothing
<220> FEATURE:
<221> NAME/KEY: misc_feature
<222> LOCATION: (474)..(474)
<223> OTHER INFORMATION: Xaa is any aa or nothing
<220> FEATURE:
<221> NAME/KEY: misc_feature
<222> LOCATION: (475)..(475)
<223> OTHER INFORMATION: Xaa is any aa or nothing
<220> FEATURE:
<221> NAME/KEY: misc_feature
<222> LOCATION: (476)..(476)
<223> OTHER INFORMATION: Xaa is any aa or nothing
<220> FEATURE:
<221> NAME/KEY: misc_feature
<222> LOCATION: (477)..(477)
<223> OTHER INFORMATION: Xaa is any aa or nothing
<220> FEATURE:
<221> NAME/KEY: misc_feature
<222> LOCATION: (478)..(478)
<223> OTHER INFORMATION: Xaa is any aa or nothing
<220> FEATURE:
<221> NAME/KEY: misc_feature
<222> LOCATION: (479)..(479)
<223> OTHER INFORMATION: Xaa is any aa or nothing
<220> FEATURE:
<221> NAME/KEY: misc_feature
<222> LOCATION: (480)..(480)
<223> OTHER INFORMATION: Xaa is any aa or nothing
<220> FEATURE:
<221> NAME/KEY: misc_feature
<222> LOCATION: (481)..(481)
<223> OTHER INFORMATION: Xaa is any aa or nothing
<220> FEATURE:
<221> NAME/KEY: misc_feature
<222> LOCATION: (482)..(482)
<223> OTHER INFORMATION: Xaa is any aa or nothing
<220> FEATURE:
<221> NAME/KEY: misc_feature
<222> LOCATION: (483)..(483)
<223> OTHER INFORMATION: Xaa is any aa or nothing
<220> FEATURE:
<221> NAME/KEY: misc_feature
<222> LOCATION: (484)..(484)
<223> OTHER INFORMATION: Xaa is any aa or nothing
<220> FEATURE:
<221> NAME/KEY: misc_feature
<222> LOCATION: (485)..(485)
<223> OTHER INFORMATION: Xaa is any aa or nothing
<220> FEATURE:
<221> NAME/KEY: misc_feature
<222> LOCATION: (486)..(486)
<223> OTHER INFORMATION: Xaa is any aa or nothing
<220> FEATURE:
<221> NAME/KEY: misc_feature
<222> LOCATION: (487)..(487)
<223> OTHER INFORMATION: Xaa is any aa or nothing
<220> FEATURE:
<221> NAME/KEY: misc_feature
<222> LOCATION: (488)..(488)
<223> OTHER INFORMATION: Xaa is any aa or nothing
<220> FEATURE:
<221> NAME/KEY: misc_feature
<222> LOCATION: (489)..(489)
<223> OTHER INFORMATION: Xaa is any aa or nothing
<220> FEATURE:
<221> NAME/KEY: misc_feature
<222> LOCATION: (490)..(490)
<223> OTHER INFORMATION: Xaa is any aa or nothing
<220> FEATURE:
<221> NAME/KEY: misc_feature
```

-continued

```
<222> LOCATION: (491)..(491)
<223> OTHER INFORMATION: Xaa is any aa or nothing
<220> FEATURE:
<221> NAME/KEY: misc_feature
<222> LOCATION: (492)..(492)
<223> OTHER INFORMATION: Xaa is any aa or nothing
<220> FEATURE:
<221> NAME/KEY: misc_feature
<222> LOCATION: (493)..(493)
<223> OTHER INFORMATION: Xaa is any aa or nothing
<220> FEATURE:
<221> NAME/KEY: misc_feature
<222> LOCATION: (494)..(494)
<223> OTHER INFORMATION: Xaa is any aa or nothing
<220> FEATURE:
<221> NAME/KEY: misc_feature
<222> LOCATION: (495)..(495)
<223> OTHER INFORMATION: Xaa is any aa or nothing
<220> FEATURE:
<221> NAME/KEY: misc_feature
<222> LOCATION: (496)..(496)
<223> OTHER INFORMATION: Xaa is any aa or nothing
<220> FEATURE:
<221> NAME/KEY: misc_feature
<222> LOCATION: (497)..(497)
<223> OTHER INFORMATION: Xaa is any aa or nothing
<220> FEATURE:
<221> NAME/KEY: misc_feature
<222> LOCATION: (498)..(498)
<223> OTHER INFORMATION: Xaa is any aa or nothing
<220> FEATURE:
<221> NAME/KEY: misc_feature
<222> LOCATION: (500)..(500)
<223> OTHER INFORMATION: Xaa is any aa
<220> FEATURE:
<221> NAME/KEY: misc_feature
<222> LOCATION: (501)..(501)
<223> OTHER INFORMATION: Xaa is any aa
<220> FEATURE:
<221> NAME/KEY: misc_feature
<222> LOCATION: (506)..(506)
<223> OTHER INFORMATION: Xaa is any aa
<220> FEATURE:
<221> NAME/KEY: misc_feature
<222> LOCATION: (507)..(507)
<223> OTHER INFORMATION: Xaa is Thr, Gly, or Ser
<220> FEATURE:
<221> NAME/KEY: misc_feature
<222> LOCATION: (510)..(510)
<223> OTHER INFORMATION: Xaa is any aa
<220> FEATURE:
<221> NAME/KEY: misc_feature
<222> LOCATION: (512)..(512)
<223> OTHER INFORMATION: Xaa is any aa
<220> FEATURE:
<221> NAME/KEY: misc_feature
<222> LOCATION: (513)..(513)
<223> OTHER INFORMATION: Xaa is Ile, Val, Leu, or Met
<220> FEATURE:
<221> NAME/KEY: misc_feature
<222> LOCATION: (514)..(514)
<223> OTHER INFORMATION: Xaa is any aa
<220> FEATURE:
<221> NAME/KEY: misc_feature
<222> LOCATION: (515)..(515)
<223> OTHER INFORMATION: Xaa is any aa
<220> FEATURE:
<221> NAME/KEY: misc_feature
<222> LOCATION: (516)..(516)
<223> OTHER INFORMATION: Xaa is Asp or Glu
<220> FEATURE:
<221> NAME/KEY: misc_feature
<222> LOCATION: (517)..(517)
<223> OTHER INFORMATION: Xaa is Ile, Val, Leu, or Met
<220> FEATURE:
<221> NAME/KEY: misc_feature
<222> LOCATION: (518)..(518)
<223> OTHER INFORMATION: Xaa is Ile, Val, Leu, or Met
<220> FEATURE:
<221> NAME/KEY: misc_feature
```

-continued

```
<222> LOCATION: (519)..(519)
<223> OTHER INFORMATION: Xaa is any aa
<220> FEATURE:
<221> NAME/KEY: misc_feature
<222> LOCATION: (522)..(522)
<223> OTHER INFORMATION: Xaa is Ile, Val, Leu, or Met
<220> FEATURE:
<221> NAME/KEY: misc_feature
<222> LOCATION: (524)..(524)
<223> OTHER INFORMATION: Xaa is Gln  or Arg
<220> FEATURE:
<221> NAME/KEY: misc_feature
<222> LOCATION: (525)..(525)
<223> OTHER INFORMATION: Xaa is Glu  or Asn
<220> FEATURE:
<221> NAME/KEY: misc_feature
<222> LOCATION: (528)..(528)
<223> OTHER INFORMATION: Xaa is any aa
<220> FEATURE:
<221> NAME/KEY: misc_feature
<222> LOCATION: (529)..(529)
<223> OTHER INFORMATION: Xaa is Lys, Arg, or His
<220> FEATURE:
<221> NAME/KEY: misc_feature
<222> LOCATION: (530)..(530)
<223> OTHER INFORMATION: Xaa is any aa
<220> FEATURE:
<221> NAME/KEY: misc_feature
<222> LOCATION: (531)..(531)
<223> OTHER INFORMATION: Xaa is any aa
<220> FEATURE:
<221> NAME/KEY: misc_feature
<222> LOCATION: (532)..(532)
<223> OTHER INFORMATION: Xaa is any aa
<220> FEATURE:
<221> NAME/KEY: misc_feature
<222> LOCATION: (533)..(533)
<223> OTHER INFORMATION: Xaa is any aa
<220> FEATURE:
<221> NAME/KEY: misc_feature
<222> LOCATION: (534)..(534)
<223> OTHER INFORMATION: Xaa is any aa
<220> FEATURE:
<221> NAME/KEY: misc_feature
<222> LOCATION: (535)..(535)
<223> OTHER INFORMATION: Xaa is any aa
<220> FEATURE:
<221> NAME/KEY: misc_feature
<222> LOCATION: (536)..(536)
<223> OTHER INFORMATION: Xaa is any aa
<220> FEATURE:
<221> NAME/KEY: misc_feature
<222> LOCATION: (537)..(537)
<223> OTHER INFORMATION: Xaa is any aa
<220> FEATURE:
<221> NAME/KEY: misc_feature
<222> LOCATION: (538)..(538)
<223> OTHER INFORMATION: Xaa is any aa
<220> FEATURE:
<221> NAME/KEY: misc_feature
<222> LOCATION: (539)..(539)
<223> OTHER INFORMATION: Xaa is any aa or nothing
<220> FEATURE:
<221> NAME/KEY: misc_feature
<222> LOCATION: (540)..(540)
<223> OTHER INFORMATION: Xaa is any aa or nothing
<220> FEATURE:
<221> NAME/KEY: misc_feature
<222> LOCATION: (541)..(541)
<223> OTHER INFORMATION: Xaa is any aa or nothing
<220> FEATURE:
<221> NAME/KEY: misc_feature
<222> LOCATION: (542)..(542)
<223> OTHER INFORMATION: Xaa is any aa or nothing
<220> FEATURE:
<221> NAME/KEY: misc_feature
<222> LOCATION: (543)..(543)
<223> OTHER INFORMATION: Xaa is any aa or nothing
<220> FEATURE:
<221> NAME/KEY: misc_feature
```

```
<222> LOCATION: (544)..(544)
<223> OTHER INFORMATION: Xaa is any aa or nothing
<220> FEATURE:
<221> NAME/KEY: misc_feature
<222> LOCATION: (545)..(545)
<223> OTHER INFORMATION: Xaa is any aa or nothing
<220> FEATURE:
<221> NAME/KEY: misc_feature
<222> LOCATION: (546)..(546)
<223> OTHER INFORMATION: Xaa is any aa or nothing
<220> FEATURE:
<221> NAME/KEY: misc_feature
<222> LOCATION: (547)..(547)
<223> OTHER INFORMATION: Xaa is any aa or nothing
<220> FEATURE:
<221> NAME/KEY: misc_feature
<222> LOCATION: (548)..(548)
<223> OTHER INFORMATION: Xaa is any aa or nothing
<220> FEATURE:
<221> NAME/KEY: misc_feature
<222> LOCATION: (549)..(549)
<223> OTHER INFORMATION: Xaa is any aa or nothing
<220> FEATURE:
<221> NAME/KEY: misc_feature
<222> LOCATION: (550)..(550)
<223> OTHER INFORMATION: Xaa is any aa or nothing
<220> FEATURE:
<221> NAME/KEY: misc_feature
<222> LOCATION: (551)..(551)
<223> OTHER INFORMATION: Xaa is any aa or nothing
<220> FEATURE:
<221> NAME/KEY: misc_feature
<222> LOCATION: (552)..(552)
<223> OTHER INFORMATION: Xaa is any aa or nothing
<220> FEATURE:
<221> NAME/KEY: misc_feature
<222> LOCATION: (553)..(553)
<223> OTHER INFORMATION: Xaa is any aa or nothing
<220> FEATURE:
<221> NAME/KEY: misc_feature
<222> LOCATION: (554)..(554)
<223> OTHER INFORMATION: Xaa is any aa or nothing
<220> FEATURE:
<221> NAME/KEY: misc_feature
<222> LOCATION: (555)..(555)
<223> OTHER INFORMATION: Xaa is any aa or nothing
<220> FEATURE:
<221> NAME/KEY: misc_feature
<222> LOCATION: (556)..(556)
<223> OTHER INFORMATION: Xaa is Ile, Val, Leu, or Met
<220> FEATURE:
<221> NAME/KEY: misc_feature
<222> LOCATION: (557)..(557)
<223> OTHER INFORMATION: Xaa is any aa or nothing
<220> FEATURE:
<221> NAME/KEY: misc_feature
<222> LOCATION: (558)..(558)
<223> OTHER INFORMATION: Xaa is Ile, Val, Leu, or Met
<220> FEATURE:
<221> NAME/KEY: misc_feature
<222> LOCATION: (559)..(559)
<223> OTHER INFORMATION: Xaa is Thr, Gly, or Ser
<220> FEATURE:
<221> NAME/KEY: misc_feature
<222> LOCATION: (573)..(573)
<223> OTHER INFORMATION: Xaa is any aa
<220> FEATURE:
<221> NAME/KEY: misc_feature
<222> LOCATION: (574)..(574)
<223> OTHER INFORMATION: Xaa is any aa
<220> FEATURE:
<221> NAME/KEY: misc_feature
<222> LOCATION: (575)..(575)
<223> OTHER INFORMATION: Xaa is Thr, Gly, or Ser
<220> FEATURE:
<221> NAME/KEY: misc_feature
<222> LOCATION: (576)..(576)
<223> OTHER INFORMATION: Xaa is any aa or nothing
<220> FEATURE:
<221> NAME/KEY: misc_feature
```

-continued

```
<222> LOCATION: (577)..(577)
<223> OTHER INFORMATION: Xaa is any aa or nothing
<220> FEATURE:
<221> NAME/KEY: misc_feature
<222> LOCATION: (578)..(578)
<223> OTHER INFORMATION: Xaa is any aa or nothing
<220> FEATURE:
<221> NAME/KEY: misc_feature
<222> LOCATION: (579)..(579)
<223> OTHER INFORMATION: Xaa is any aa or nothing
<220> FEATURE:
<221> NAME/KEY: misc_feature
<222> LOCATION: (580)..(580)
<223> OTHER INFORMATION: Xaa is any aa or nothing
<220> FEATURE:
<221> NAME/KEY: misc_feature
<222> LOCATION: (581)..(581)
<223> OTHER INFORMATION: Xaa is any aa or nothing
<220> FEATURE:
<221> NAME/KEY: misc_feature
<222> LOCATION: (582)..(582)
<223> OTHER INFORMATION: Xaa is any aa or nothing
<220> FEATURE:
<221> NAME/KEY: misc_feature
<222> LOCATION: (583)..(583)
<223> OTHER INFORMATION: Xaa is any aa or nothing
<220> FEATURE:
<221> NAME/KEY: misc_feature
<222> LOCATION: (584)..(584)
<223> OTHER INFORMATION: Xaa is any aa or nothing
<220> FEATURE:
<221> NAME/KEY: misc_feature
<222> LOCATION: (585)..(585)
<223> OTHER INFORMATION: Xaa is Gln or Asp
<220> FEATURE:
<221> NAME/KEY: misc_feature
<222> LOCATION: (586)..(586)
<223> OTHER INFORMATION: Xaa is any aa or nothing
<220> FEATURE:
<221> NAME/KEY: misc_feature
<222> LOCATION: (587)..(587)
<223> OTHER INFORMATION: Xaa is Glu or Gln
<220> FEATURE:
<221> NAME/KEY: misc_feature
<222> LOCATION: (588)..(588)
<223> OTHER INFORMATION: Xaa is Gly or Pro
<220> FEATURE:
<221> NAME/KEY: misc_feature
<222> LOCATION: (589)..(589)
<223> OTHER INFORMATION: Xaa is Gly or Glu
<220> FEATURE:
<221> NAME/KEY: misc_feature
<222> LOCATION: (591)..(591)
<223> OTHER INFORMATION: Xaa is Ile, Val, Leu, or Met
<220> FEATURE:
<221> NAME/KEY: misc_feature
<222> LOCATION: (592)..(592)
<223> OTHER INFORMATION: Xaa is any aa
<220> FEATURE:
<221> NAME/KEY: misc_feature
<222> LOCATION: (595)..(595)
<223> OTHER INFORMATION: Xaa is Ala or Val
<220> FEATURE:
<221> NAME/KEY: misc_feature
<222> LOCATION: (596)..(596)
<223> OTHER INFORMATION: Xaa is Asp or Glu

<400> SEQUENCE: 140

Xaa Ala Ala Arg Ser Leu Ser Xaa Ala Xaa Lys Xaa Xaa Xaa Xaa Xaa
 1               5                   10                  15

Xaa Xaa Xaa Xaa Xaa Xaa Xaa Xaa Xaa Xaa Arg Xaa Xaa Xaa Xaa
            20                  25                  30

Xaa Xaa Xaa Xaa Xaa Xaa Xaa Xaa Gly Xaa Xaa Xaa Xaa Xaa Xaa
        35                  40                  45

Xaa Xaa Xaa Xaa Xaa Xaa Xaa Gly Xaa Xaa Xaa Xaa Xaa Xaa Xaa
    50                  55                  60
```

```
Xaa Xaa Xaa Xaa Xaa Xaa Xaa Xaa Xaa Trp Xaa Pro Asp Pro Val
 65                  70                  75                  80

Thr Gly Xaa Tyr Arg Pro Xaa Asn Xaa Xaa Xaa Asp Pro Xaa
                 85                  90                  95

Xaa Leu Arg Xaa Xaa Leu Leu Xaa Xaa Lys Xaa Xaa Ser Met Xaa Xaa
            100                 105                 110

Xaa Xaa Xaa Xaa Xaa His Xaa Xaa Leu Xaa His Gly Xaa Xaa Xaa Gly
            115                 120                 125

Xaa Trp Xaa Trp Xaa Lys Xaa Xaa Xaa Xaa Leu Xaa Xaa Xaa Gly His
130                 135                 140

Xaa Val Xaa Xaa Xaa Asp Xaa Ala Ala Xaa Gly Xaa Xaa Xaa Xaa Xaa
145                 150                 155                 160

Xaa Xaa Xaa Xaa Xaa Xaa Xaa Xaa Xaa Tyr Xaa Xaa Pro Leu Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Leu Val Gly His Ser Xaa Gly Gly Xaa Xaa Xaa Ala Xaa Ala
            195                 200                 205

Xaa Xaa Xaa Xaa Xaa Xaa Xaa Xaa Xaa Xaa Xaa Val Phe Xaa Xaa Xaa
            210                 215                 220

Xaa Xaa Pro Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa
                260                 265                 270

Xaa Xaa Xaa Xaa Xaa Xaa Xaa Xaa Xaa Xaa Xaa Xaa Xaa Xaa Xaa
                275                 280                 285

Xaa Xaa Xaa Xaa Xaa Xaa Xaa Xaa Glu Asp Xaa Xaa Leu Xaa Xaa
                290                 295                 300

Xaa Xaa Xaa Arg Xaa Xaa Xaa Xaa Phe Xaa Xaa Xaa Xaa Xaa Xaa
305                 310                 315                 320

Xaa Xaa Xaa Xaa Xaa Xaa Val Xaa Xaa Xaa Xaa Tyr Gly Xaa Val
                325                 330                 335

Xaa Xaa Xaa Xaa Xaa Val Xaa Xaa Xaa Asp Xaa Xaa Xaa Xaa Xaa
            340                 345                 350

Xaa Xaa Xaa Xaa Met Xaa Xaa Xaa Xaa Pro Xaa Xaa Xaa Xaa Xaa
            355                 360                 365

Xaa Xaa Xaa Xaa Asp His Xaa Xaa Xaa Xaa Xaa Pro Xaa Xaa Leu
            370                 375                 380

Xaa Xaa Xaa Xaa Xaa Xaa Xaa Ala Met Ala Xaa Xaa Gly Xaa Xaa Xaa
385                 390                 395                 400

Lys Leu Lys Xaa Xaa Xaa Xaa Xaa Trp Xaa Xaa Xaa Xaa Xaa Xaa
                405                 410                 415

Xaa Xaa Xaa Ser Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa
            435                 440                 445

Xaa Xaa Xaa Xaa Xaa Xaa Xaa Xaa Xaa Xaa Xaa Xaa Xaa Xaa Xaa
            450                 455                 460

Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
```

```
                    485                 490                 495
Xaa Xaa Leu Xaa Xaa Val Tyr Val Gly Xaa Xaa Arg Arg Xaa Tyr Xaa
            500                 505                 510

Xaa Xaa Xaa Xaa Xaa Xaa Xaa His Pro Xaa Phe Xaa Xaa Leu Val Xaa
            515                 520                 525

Xaa Xaa Xaa Xaa Xaa Xaa Xaa Xaa Xaa Xaa Xaa Xaa Xaa Xaa Xaa Xaa
            530                 535                 540

Xaa Xaa Xaa Xaa Xaa Xaa Xaa Xaa Xaa Xaa Xaa Xaa Xaa Xaa Xaa Cys
545                 550                 555                 560

Glu Val Val Leu Phe Glu His Leu Leu Trp Met Leu Xaa Xaa Xaa Xaa
            565                 570                 575

Xaa Xaa Xaa Xaa Xaa Xaa Xaa Xaa Xaa Xaa Xaa Xaa Ser Xaa Xaa
            580                 585                 590

Glu Leu Xaa Xaa Phe Tyr Thr
            595

<210> SEQ ID NO 141
<211> LENGTH: 99
<212> TYPE: PRT
<213> ORGANISM: Brassica napus
<220> FEATURE:
<221> NAME/KEY: misc_feature
<222> LOCATION: (1)..(99)
<223> OTHER INFORMATION: Ceres CLONE ID no. 976586
<220> FEATURE:
<221> NAME/KEY: misc_feature
<222> LOCATION: (1)..(99)
<223> OTHER INFORMATION: Ortholog of  Ceres CDNA ID no. 12420738
      at SEQ ID NO. 20
      with e-value of 1.19E-33 and percent identity of 82.65
<220> FEATURE:
<221> NAME/KEY: misc_feature
<222> LOCATION: (99)..(99)
<223> OTHER INFORMATION: Xaa is any aa, unknown, or other

<400> SEQUENCE: 141

Met Ala Ala Ala Arg Ser Leu Ser Gly Ala Val Lys Ser Leu Cys Ser
1               5                   10                  15

Ala Ala Ser His Asn Ile Ser Gly Ser Ile Val Leu Arg Arg Ser Tyr
            20                  25                  30

Val Ala Thr Val Pro Gly Phe Gly Lys Gly Gly Ser Thr Arg Val Thr
        35                  40                  45

Val Gly Lys Met Glu Gln Arg Ala Asn Gln Glu Ala Glu Ser Ala Trp
    50                  55                  60

Ala Pro Asp Pro Val Thr Gly Tyr Tyr Arg Pro Ser Asn Arg Ala Asp
65                  70                  75                  80

Glu Ile Asp Pro Ala Glu Leu Arg Glu Met Leu Leu Lys Asn Lys Ala
                85                  90                  95

Lys Pro Xaa

<210> SEQ ID NO 142
<211> LENGTH: 87
<212> TYPE: PRT
<213> ORGANISM: Arabidopsis thaliana
<220> FEATURE:
<221> NAME/KEY: misc_feature
<222> LOCATION: (1)..(87)
<223> OTHER INFORMATION: Public GI no. 7268339
<220> FEATURE:
<221> NAME/KEY: misc_feature
<222> LOCATION: (1)..(87)
<223> OTHER INFORMATION: Ortholog of  Ceres CDNA ID no. 12420738
      at SEQ ID NO. 20
      with e-value of 3.10E-33 and percent identity of 94.25
```

-continued

```
<400> SEQUENCE: 142

Met Ala Ala Arg Ser Leu Ser Gly Ala Val Lys Ser Leu Cys Pro Pro
1               5                   10                  15

His Pro Glu Asn Val Thr Ala Ala Gly Leu Ser Lys Gly Gly Ser Thr
            20                  25                  30

Arg Val Met Val Gly Lys Met Glu Gln Arg Gly Leu Asp Gln Glu Ala
        35                  40                  45

Glu Ser Ala Trp Gly Pro Asp Pro Val Thr Gly Tyr Tyr Arg Pro Ser
    50                  55                  60

Asn Arg Ala Ala Glu Ile Asp Pro Ala Glu Leu Arg Glu Leu Leu Leu
65                  70                  75                  80

Lys Asn Lys Ala Lys Ser Phe
                85

<210> SEQ ID NO 143
<211> LENGTH: 113
<212> TYPE: PRT
<213> ORGANISM: Glycine max
<220> FEATURE:
<221> NAME/KEY: misc_feature
<222> LOCATION: (1)..(113)
<223> OTHER INFORMATION: Public GI no. 75098170
<220> FEATURE:
<221> NAME/KEY: misc_feature
<222> LOCATION: (1)..(113)
<223> OTHER INFORMATION: Ortholog of  Ceres CDNA ID no. 12420738
      at SEQ ID NO. 20
      with e-value of 2.10E-11 and percent identity of 40.2

<400> SEQUENCE: 143

Met Ala Arg Ser Leu Ser Gln Ala Lys Arg Ile Gly Val Leu Val Ala
1               5                   10                  15

Gln Ser Ile Ser Leu Ile Pro Val His Arg Arg Gly Tyr Ala Val Ala
            20                  25                  30

Ser Asp Val Ser Val Arg Val Gly Leu Gly Asn Ile Gly Arg Arg Asn
        35                  40                  45

Gly Ile Val Gly Gly Val Glu Glu Lys Pro Asp Thr Arg Asp Gly Ser
    50                  55                  60

Lys Ala Tyr Ser Thr Asp Trp Ala Pro Asp Pro Val Thr Gly Tyr Tyr
65                  70                  75                  80

Arg Pro Ile Asn His Thr Pro Glu Ile Asp Pro Val Glu Leu Arg His
                85                  90                  95

Arg Leu Leu Arg Ser Pro Pro Leu Glu Pro Arg Gly Val Ala Gly His
            100                 105                 110

Pro

<210> SEQ ID NO 144
<211> LENGTH: 113
<212> TYPE: PRT
<213> ORGANISM: Glycine max
<220> FEATURE:
<221> NAME/KEY: misc_feature
<222> LOCATION: (1)..(113)
<223> OTHER INFORMATION: Ceres CLONE ID no. 1042120
<220> FEATURE:
<221> NAME/KEY: misc_feature
<222> LOCATION: (1)..(113)
<223> OTHER INFORMATION: Ortholog of  Ceres CDNA ID no. 12420738
      at SEQ ID NO. 20
      with e-value of 2.10E-11 and percent identity of 40.2

<400> SEQUENCE: 144
```

Met Ala Arg Ser Leu Ser Gln Ala Lys Arg Ile Gly Val Leu Val Ala
1               5                   10                  15

Gln Ser Ile Ser Leu Ile Pro Val His Arg Arg Gly Tyr Ala Val Ala
            20                  25                  30

Ser Asp Val Ser Val Arg Val Gly Leu Gly Asn Ile Gly Arg Arg Asn
            35                  40                  45

Gly Ile Val Gly Gly Val Glu Glu Lys Pro Asp Thr Arg Asp Gly Ser
        50                  55                  60

Lys Ala Tyr Ser Thr Asp Trp Ala Pro Asp Pro Val Thr Gly Tyr Tyr
65                  70                  75                  80

Arg Pro Ile Asn His Thr Pro Glu Ile Asp Pro Val Glu Leu Arg His
                85                  90                  95

Arg Leu Leu Arg Ser Pro Pro Leu Glu Pro Arg Gly Val Ala Gly His
            100                 105                 110

Pro

<210> SEQ ID NO 145
<211> LENGTH: 100
<212> TYPE: PRT
<213> ORGANISM: Glycine max
<220> FEATURE:
<221> NAME/KEY: misc_feature
<222> LOCATION: (1)..(100)
<223> OTHER INFORMATION: Ceres CLONE ID no. 561776
<220> FEATURE:
<221> NAME/KEY: misc_feature
<222> LOCATION: (1)..(100)
<223> OTHER INFORMATION: Ortholog of  Ceres CDNA ID no. 12420738
      at SEQ ID NO. 20
      with e-value of 3.39E-11 and percent identity of 42.11

<400> SEQUENCE: 145

Met Ala Gln Ser Phe Ser Pro Ala Lys Arg Ala Leu Ala Phe Ser Leu
1               5                   10                  15

His Arg Arg Gly Tyr Ala Val Ala Ser Asp Ala Ser Pro Ser Val Arg
            20                  25                  30

Gly Gly Leu Asp Ser Ile Gly Ser Arg Ser Ala Ile Glu Lys Gly Val
        35                  40                  45

Thr Lys Asn Asn Ser Gly Pro Ser Gly Ala Ser Ala Trp Ala Pro
50                  55                  60

Asp Pro Val Thr Gly Tyr Tyr Arg Pro Ile Asn His Thr Asn Glu Ile
65                  70                  75                  80

Asp Pro Val Glu Leu Arg Arg Met Leu Leu Lys His Lys Val Arg Ser
                85                  90                  95

Ser Ser Ser Ser
            100

<210> SEQ ID NO 146
<211> LENGTH: 95
<212> TYPE: PRT
<213> ORGANISM: Zea mays
<220> FEATURE:
<221> NAME/KEY: misc_feature
<222> LOCATION: (1)..(95)
<223> OTHER INFORMATION: Ceres CLONE ID no. 296494
<220> FEATURE:
<221> NAME/KEY: misc_feature
<222> LOCATION: (1)..(95)
<223> OTHER INFORMATION: Ortholog of  Ceres CDNA ID no. 12420738
      at SEQ ID NO. 20
      with e-value of 1.09E-7 and percent identity of 37.63

<400> SEQUENCE: 146

Met Ala Leu Ser Leu Ser Gly Thr Ser Ala Arg Phe Ala Leu Ala Ser
1               5                   10                  15

Leu Val Pro Arg Ala Arg Ala Tyr Ala Ser Ala Ala Ser Gly Ala
            20                  25                  30

Met Arg Arg Ala Ala Glu Gly Ala Ala Gly Glu Ala Lys Glu Ala
            35                  40                  45

Gly Arg Ala Ala Ala Ala Ala Ala Glu Gly Ser Trp Val Pro Asp Pro
    50                  55                  60

Val Thr Gly His Tyr Arg Pro Ala Asn Trp Ala Ala Val Asp Pro
65          70                  75                  80

Ala Asp Leu Arg Ala Ala His Leu Ala Arg Thr Tyr Ala Arg Ala
            85                  90                  95

<210> SEQ ID NO 147
<211> LENGTH: 109
<212> TYPE: PRT
<213> ORGANISM: Artificial Sequence
<220> FEATURE:
<221> NAME/KEY: misc_feature
<222> LOCATION: (1)..(109)
<223> OTHER INFORMATION: Consensus Sequence of Ceres CDNA ID no.
      12420738 at SEQ ID NO. 20 and orthologs
<220> FEATURE:
<221> NAME/KEY: misc_feature
<222> LOCATION: (1)..(1)
<223> OTHER INFORMATION: Xaa is any aa
<220> FEATURE:
<221> NAME/KEY: misc_feature
<222> LOCATION: (8)..(8)
<223> OTHER INFORMATION: Xaa is Gly or Gln
<220> FEATURE:
<221> NAME/KEY: misc_feature
<222> LOCATION: (10)..(10)
<223> OTHER INFORMATION: Xaa is any aa or nothing
<220> FEATURE:
<221> NAME/KEY: misc_feature
<222> LOCATION: (12)..(12)
<223> OTHER INFORMATION: Xaa is Ser or Arg
<220> FEATURE:
<221> NAME/KEY: misc_feature
<222> LOCATION: (13)..(13)
<223> OTHER INFORMATION: Xaa is Ile, Val, Leu, or Met
<220> FEATURE:
<221> NAME/KEY: misc_feature
<222> LOCATION: (14)..(14)
<223> OTHER INFORMATION: Xaa is Cys or Gly
<220> FEATURE:
<221> NAME/KEY: misc_feature
<222> LOCATION: (15)..(15)
<223> OTHER INFORMATION: Xaa is Ser or Val
<220> FEATURE:
<221> NAME/KEY: misc_feature
<222> LOCATION: (16)..(16)
<223> OTHER INFORMATION: Xaa is any aa
<220> FEATURE:
<221> NAME/KEY: misc_feature
<222> LOCATION: (17)..(17)
<223> OTHER INFORMATION: Xaa is Ala or Val
<220> FEATURE:
<221> NAME/KEY: misc_feature
<222> LOCATION: (18)..(18)
<223> OTHER INFORMATION: Xaa is any aa
<220> FEATURE:
<221> NAME/KEY: misc_feature
<222> LOCATION: (19)..(19)
<223> OTHER INFORMATION: Xaa is any aa
<220> FEATURE:
<221> NAME/KEY: misc_feature
<222> LOCATION: (20)..(20)
<223> OTHER INFORMATION: Xaa is any aa
<220> FEATURE:
<221> NAME/KEY: misc_feature
<222> LOCATION: (21)..(21)
<223> OTHER INFORMATION: Xaa is Ile, Val, Leu, or Met -continued

```
<220> FEATURE:
<221> NAME/KEY: misc_feature
<222> LOCATION: (22)..(22)
<223> OTHER INFORMATION: Xaa is Thr, Gly, or Ser
<220> FEATURE:
<221> NAME/KEY: misc_feature
<222> LOCATION: (23)..(23)
<223> OTHER INFORMATION: Xaa is any aa
<220> FEATURE:
<221> NAME/KEY: misc_feature
<222> LOCATION: (24)..(24)
<223> OTHER INFORMATION: Xaa is Ser or Ile
<220> FEATURE:
<221> NAME/KEY: misc_feature
<222> LOCATION: (25)..(25)
<223> OTHER INFORMATION: Xaa is any aa
<220> FEATURE:
<221> NAME/KEY: misc_feature
<222> LOCATION: (26)..(26)
<223> OTHER INFORMATION: Xaa is Val or His
<220> FEATURE:
<221> NAME/KEY: misc_feature
<222> LOCATION: (27)..(27)
<223> OTHER INFORMATION: Xaa is any aa
<220> FEATURE:
<221> NAME/KEY: misc_feature
<222> LOCATION: (29)..(29)
<223> OTHER INFORMATION: Xaa is Arg or Gly
<220> FEATURE:
<221> NAME/KEY: misc_feature
<222> LOCATION: (30)..(30)
<223> OTHER INFORMATION: Xaa is any aa
<220> FEATURE:
<221> NAME/KEY: misc_feature
<222> LOCATION: (31)..(31)
<223> OTHER INFORMATION: Xaa is Tyr or Ala
<220> FEATURE:
<221> NAME/KEY: misc_feature
<222> LOCATION: (32)..(32)
<223> OTHER INFORMATION: Xaa is Val or Ala
<220> FEATURE:
<221> NAME/KEY: misc_feature
<222> LOCATION: (33)..(33)
<223> OTHER INFORMATION: Xaa is Ala or Val
<220> FEATURE:
<221> NAME/KEY: misc_feature
<222> LOCATION: (34)..(34)
<223> OTHER INFORMATION: Xaa is Thr, Gly, or Ser
<220> FEATURE:
<221> NAME/KEY: misc_feature
<222> LOCATION: (35)..(35)
<223> OTHER INFORMATION: Xaa is any aa
<220> FEATURE:
<221> NAME/KEY: misc_feature
<222> LOCATION: (36)..(36)
<223> OTHER INFORMATION: Xaa is any aa
<220> FEATURE:
<221> NAME/KEY: misc_feature
<222> LOCATION: (37)..(37)
<223> OTHER INFORMATION: Xaa is any aa or nothing
<220> FEATURE:
<221> NAME/KEY: misc_feature
<222> LOCATION: (38)..(38)
<223> OTHER INFORMATION: Xaa is any aa or nothing
<220> FEATURE:
<221> NAME/KEY: misc_feature
<222> LOCATION: (39)..(39)
<223> OTHER INFORMATION: Xaa is any aa or nothing
<220> FEATURE:
<221> NAME/KEY: misc_feature
<222> LOCATION: (40)..(40)
<223> OTHER INFORMATION: Xaa is any aa or nothing
<220> FEATURE:
<221> NAME/KEY: misc_feature
<222> LOCATION: (41)..(41)
<223> OTHER INFORMATION: Xaa is any aa or nothing
<220> FEATURE:
<221> NAME/KEY: misc_feature
<222> LOCATION: (43)..(43)
<223> OTHER INFORMATION: Xaa is any aa
```

```
<220> FEATURE:
<221> NAME/KEY: misc_feature
<222> LOCATION: (44)..(44)
<223> OTHER INFORMATION: Xaa is any aa or nothing
<220> FEATURE:
<221> NAME/KEY: misc_feature
<222> LOCATION: (45)..(45)
<223> OTHER INFORMATION: Xaa is any aa or nothing
<220> FEATURE:
<221> NAME/KEY: misc_feature
<222> LOCATION: (46)..(46)
<223> OTHER INFORMATION: Xaa is Thr, Gly, or Ser
<220> FEATURE:
<221> NAME/KEY: misc_feature
<222> LOCATION: (47)..(47)
<223> OTHER INFORMATION: Xaa is any aa
<220> FEATURE:
<221> NAME/KEY: misc_feature
<222> LOCATION: (48)..(48)
<223> OTHER INFORMATION: Xaa is Gly or Ile
<220> FEATURE:
<221> NAME/KEY: misc_feature
<222> LOCATION: (49)..(49)
<223> OTHER INFORMATION: Xaa is Thr, Gly, or Ser
<220> FEATURE:
<221> NAME/KEY: misc_feature
<222> LOCATION: (50)..(50)
<223> OTHER INFORMATION: Xaa is Ser or Arg
<220> FEATURE:
<221> NAME/KEY: misc_feature
<222> LOCATION: (51)..(51)
<223> OTHER INFORMATION: Xaa is any aa
<220> FEATURE:
<221> NAME/KEY: misc_feature
<222> LOCATION: (52)..(52)
<223> OTHER INFORMATION: Xaa is any aa
<220> FEATURE:
<221> NAME/KEY: misc_feature
<222> LOCATION: (53)..(53)
<223> OTHER INFORMATION: Xaa is any aa
<220> FEATURE:
<221> NAME/KEY: misc_feature
<222> LOCATION: (54)..(54)
<223> OTHER INFORMATION: Xaa is any aa
<220> FEATURE:
<221> NAME/KEY: misc_feature
<222> LOCATION: (55)..(55)
<223> OTHER INFORMATION: Xaa is Val or Lys
<220> FEATURE:
<221> NAME/KEY: misc_feature
<222> LOCATION: (57)..(57)
<223> OTHER INFORMATION: Xaa is any aa
<220> FEATURE:
<221> NAME/KEY: misc_feature
<222> LOCATION: (58)..(58)
<223> OTHER INFORMATION: Xaa is any aa
<220> FEATURE:
<221> NAME/KEY: misc_feature
<222> LOCATION: (59)..(59)
<223> OTHER INFORMATION: Xaa is Glu or Lys
<220> FEATURE:
<221> NAME/KEY: misc_feature
<222> LOCATION: (60)..(60)
<223> OTHER INFORMATION: Xaa is any aa
<220> FEATURE:
<221> NAME/KEY: misc_feature
<222> LOCATION: (61)..(61)
<223> OTHER INFORMATION: Xaa is any aa
<220> FEATURE:
<221> NAME/KEY: misc_feature
<222> LOCATION: (62)..(62)
<223> OTHER INFORMATION: Xaa is any aa
<220> FEATURE:
<221> NAME/KEY: misc_feature
<222> LOCATION: (63)..(63)
<223> OTHER INFORMATION: Xaa is any aa
<220> FEATURE:
<221> NAME/KEY: misc_feature
<222> LOCATION: (64)..(64)
<223> OTHER INFORMATION: Xaa is any aa
```

-continued

```
<220> FEATURE:
<221> NAME/KEY: misc_feature
<222> LOCATION: (65)..(65)
<223> OTHER INFORMATION: Xaa is any aa
<220> FEATURE:
<221> NAME/KEY: misc_feature
<222> LOCATION: (66)..(66)
<223> OTHER INFORMATION: Xaa is any aa or nothing
<220> FEATURE:
<221> NAME/KEY: misc_feature
<222> LOCATION: (67)..(67)
<223> OTHER INFORMATION: Xaa is Thr, Gly, or Ser
<220> FEATURE:
<221> NAME/KEY: misc_feature
<222> LOCATION: (68)..(68)
<223> OTHER INFORMATION: Xaa is Glu or Ser
<220> FEATURE:
<221> NAME/KEY: misc_feature
<222> LOCATION: (69)..(69)
<223> OTHER INFORMATION: Xaa is Ser or Lys
<220> FEATURE:
<221> NAME/KEY: misc_feature
<222> LOCATION: (70)..(70)
<223> OTHER INFORMATION: Xaa is Thr, Gly, or Ser
<220> FEATURE:
<221> NAME/KEY: misc_feature
<222> LOCATION: (71)..(71)
<223> OTHER INFORMATION: Xaa is any aa or nothing
<220> FEATURE:
<221> NAME/KEY: misc_feature
<222> LOCATION: (72)..(72)
<223> OTHER INFORMATION: Xaa is any aa or nothing
<220> FEATURE:
<221> NAME/KEY: misc_feature
<222> LOCATION: (73)..(73)
<223> OTHER INFORMATION: Xaa is any aa or nothing
<220> FEATURE:
<221> NAME/KEY: misc_feature
<222> LOCATION: (74)..(74)
<223> OTHER INFORMATION: Xaa is any aa or nothing
<220> FEATURE:
<221> NAME/KEY: misc_feature
<222> LOCATION: (76)..(76)
<223> OTHER INFORMATION: Xaa is any aa
<220> FEATURE:
<221> NAME/KEY: misc_feature
<222> LOCATION: (83)..(83)
<223> OTHER INFORMATION: Xaa is Tyr or His
<220> FEATURE:
<221> NAME/KEY: misc_feature
<222> LOCATION: (87)..(87)
<223> OTHER INFORMATION: Xaa is any aa
<220> FEATURE:
<221> NAME/KEY: misc_feature
<222> LOCATION: (89)..(89)
<223> OTHER INFORMATION: Xaa is any aa
<220> FEATURE:
<221> NAME/KEY: misc_feature
<222> LOCATION: (90)..(90)
<223> OTHER INFORMATION: Xaa is Thr, Gly, or Ser
<220> FEATURE:
<221> NAME/KEY: misc_feature
<222> LOCATION: (91)..(91)
<223> OTHER INFORMATION: Xaa is any aa
<220> FEATURE:
<221> NAME/KEY: misc_feature
<222> LOCATION: (92)..(92)
<223> OTHER INFORMATION: Xaa is Glu or Ala
<220> FEATURE:
<221> NAME/KEY: misc_feature
<222> LOCATION: (93)..(93)
<223> OTHER INFORMATION: Xaa is Ile, Val, Leu, or Met
<220> FEATURE:
<221> NAME/KEY: misc_feature
<222> LOCATION: (96)..(96)
<223> OTHER INFORMATION: Xaa is Ala or Val
<220> FEATURE:
<221> NAME/KEY: misc_feature
<222> LOCATION: (97)..(97)
<223> OTHER INFORMATION: Xaa is Asp or Glu
```

```
<220> FEATURE:
<221> NAME/KEY: misc_feature
<222> LOCATION: (100)..(100)
<223> OTHER INFORMATION: Xaa is any aa
<220> FEATURE:
<221> NAME/KEY: misc_feature
<222> LOCATION: (101)..(101)
<223> OTHER INFORMATION: Xaa is any aa
<220> FEATURE:
<221> NAME/KEY: misc_feature
<222> LOCATION: (104)..(104)
<223> OTHER INFORMATION: Xaa is Lys, Arg, or His
<220> FEATURE:
<221> NAME/KEY: misc_feature
<222> LOCATION: (105)..(105)
<223> OTHER INFORMATION: Xaa is any aa
<220> FEATURE:
<221> NAME/KEY: misc_feature
<222> LOCATION: (107)..(107)
<223> OTHER INFORMATION: Xaa is Ala or Val
<220> FEATURE:
<221> NAME/KEY: misc_feature
<222> LOCATION: (108)..(108)
<223> OTHER INFORMATION: Xaa is Lys, Arg, or His

<400> SEQUENCE: 147

Xaa Ala Ala Arg Ser Leu Ser Xaa Ala Xaa Lys Xaa Xaa Xaa Xaa Xaa
1               5                   10                  15

Xaa Xaa Xaa Xaa Xaa Xaa Xaa Xaa Xaa Xaa Arg Xaa Xaa Xaa Xaa
            20                  25                  30

Xaa Xaa Xaa Xaa Xaa Xaa Xaa Gly Xaa Xaa Xaa Xaa Xaa Xaa
        35                  40                  45

Xaa Xaa Xaa Xaa Xaa Xaa Xaa Gly Xaa Xaa Xaa Xaa Xaa Xaa Xaa
    50                  55                  60

Xaa Xaa Xaa Xaa Xaa Xaa Xaa Xaa Xaa Trp Xaa Pro Asp Pro Val
65                  70                  75                  80

Thr Gly Xaa Tyr Arg Pro Xaa Asn Xaa Xaa Xaa Xaa Xaa Asp Pro Xaa
                85                  90                  95

Xaa Leu Arg Xaa Xaa Leu Leu Xaa Xaa Lys Xaa Xaa Ser
            100                 105

<210> SEQ ID NO 148
<211> LENGTH: 19
<212> TYPE: DNA
<213> ORGANISM: Artificial Sequence
<220> FEATURE:
<223> OTHER INFORMATION: Synthetic oligo(dT)18 primer

<400> SEQUENCE: 148
tttttttttt tttttttv                                              19

<210> SEQ ID NO 149
<211> LENGTH: 19
<212> TYPE: DNA
<213> ORGANISM: Artificial Sequence
<220> FEATURE:
<223> OTHER INFORMATION: Synthetic oligo dTV primer
<220> FEATURE:
<221> NAME/KEY: misc_feature
<222> LOCATION: (19)..(19)
<223> OTHER INFORMATION: n is a, c, or g

<400> SEQUENCE: 149
tttttttttt tttttttn                                              19
```